US012767960B2

(12) United States Patent
Cigan et al.

(10) Patent No.: US 12,767,960 B2
(45) **Date of Patent: *Oct. 20, 2026**

(54) METHODS AND COMPOSITIONS FOR MARKER-FREE GENOME MODIFICATION

(71) Applicant: PIONEER HI-BRED INTERNATIONAL, INC., Johnston, IA (US)

(72) Inventors: Andrew Mark Cigan, Madison, WI (US); Sergei Svitashev, Johnston, IA (US)

(73) Assignee: PIONEER HI-BRED INTERNATIONAL, INC., Johnston, IA (US)

( * ) Notice: Subject to any disclaimer, the term of this patent is extended or adjusted under 35 U.S.C. 154(b) by 59 days.

This patent is subject to a terminal disclaimer.

(21) Appl. No.: 15/763,758

(22) PCT Filed: Oct. 17, 2016

(86) PCT No.: PCT/US2016/057272

§ 371 (c)(1),
(2) Date: Mar. 27, 2018

(87) PCT Pub. No.: WO2017/070029

PCT Pub. Date: Apr. 27, 2017

(65) Prior Publication Data

US 2018/0273960 A1 Sep. 27, 2018

Related U.S. Application Data

(60) Provisional application No. 62/359,254, filed on Jul. 7, 2016, provisional application No. 62/309,033, filed on Mar. 16, 2016, provisional application No. 62/243,719, filed on Oct. 20, 2015.

(51) Int. Cl.

| | |
|---|---|
| ***C12N 15/90*** | (2006.01) |
| ***A01H 4/00*** | (2006.01) |
| ***C12N 9/22*** | (2006.01) |
| ***C12N 15/82*** | (2006.01) |
| *C12N 15/11* | (2006.01) |

(52) U.S. Cl.

CPC ........... *C12N 15/902* (2013.01); *A01H 4/008* (2013.01); *C12N 9/222* (2025.05); *C12N 15/8206* (2013.01); *C12N 15/8207* (2013.01); *C12N 15/8209* (2013.01); *C12N 15/8213* (2013.01); *C12N 15/8241* (2013.01); *C07K 2319/09* (2013.01); *C12N 2310/20* (2017.05); *C12N 2800/22* (2013.01); *C12N 2800/80* (2013.01)

(58) Field of Classification Search

None

See application file for complete search history.

(56) References Cited

U.S. PATENT DOCUMENTS 5,036,006 A * 7/1991 Sanford ............. C12N 15/8207 435/235.1
2009/0104700 A1 4/2009 Samuel et al.
2010/0159598 A1 6/2010 Jayakumar et al.
2010/0311168 A1 12/2010 Samuel et al.
2011/0035836 A1 2/2011 Eudes et al.
2011/0167516 A1* 7/2011 Gordon-Kamm et al. .................. C12N 15/8241 800/278
2011/0247100 A1 10/2011 Samboju et al.
2012/0023619 A1 1/2012 Samboju et al.
2012/0023620 A1 1/2012 Yau et al.
2012/0244569 A1 9/2012 Samuel et al.
2014/0096284 A1 4/2014 Martin-Ortigosa et al.
2014/0182012 A1 6/2014 Eudes et al.
2014/0242703 A1 8/2014 Samuel et al.
2014/0273232 A1 9/2014 Zhang et al.
2014/0273233 A1 9/2014 Chen et al.
2017/0022521 A1 1/2017 Samuel et al.

FOREIGN PATENT DOCUMENTS

EP 3279321 A1 2/2018
WO 2013/176772 A1 11/2013
WO 2014/071006 A1 † 5/2014
WO WO 2014/065596 * 5/2014
WO WO 2014/065596 A1 * 5/2014
WO 2014199358 A1 12/2014
WO 2015/026883 A1 2/2015
WO 2015/026885 A1 2/2015

(Continued)

OTHER PUBLICATIONS

Clouse et al. (1996) 111(3):671-78.*
Koornneef (2004) Annu Rev Plant Biol 55:141-72.*
Le Corre et al. (2002) Mol Biol Evol 19(8):1261-71.*
Meinke et al. (2003) Plant Physiol 131:409-18.*
Kanchiswamy et al. (2015) Trends Biotech 33(9):489-91.*
Abdullah et al. (1986) Nat Biotech 4:1087-90.*
Martin-Ortigosa & Wang (2014) Transgen Res 23:743-56.*
Lutz et al. (2015) Plant Cell Rep 34:1849-56.*
Daude et al. (2020) Biologia 75:1483-95.*
Kanchiswamy et al. (2015) Trends Biotech 33(1):1162-64.*
International Preliminary Report on Patentability (2018).*
Townsend et al. (2009) Nature 459:442-45.*

(Continued)

*Primary Examiner* — Russell T Boggs

(57) ABSTRACT

Compositions and methods are provided for modifying a nucleotide sequence in the genome of a plant cell, without the use of a selectable marker. The methods and compositions employ a guide polynucleotide/Cas endonuclease system to make a double strand break in a target site located in a nucleotide sequence and plant cells are obtained without the use of a selectable marker, and to provide an effective system for modifying target sites within the genome of a plant, plant cell or seed. Compositions and methods are also provided for producing a plant cell, callus tissue or plant having a modified nucleotide sequence in its genome, without the use of a selectable marker.

11 Claims, 7 Drawing Sheets

Figure 3:

Specification includes a Sequence Listing.

(56) References Cited

FOREIGN PATENT DOCUMENTS

| | | | |
|---|---|---|---|
| WO | 2015/026886 | A1 | 2/2015 |
| WO | 2015/026887 | A1 | 2/2015 |
| WO | 2015171894 | A1 | 11/2015 |

OTHER PUBLICATIONS

Klein et al. (1988) Bio/Tech 6:559-63.*
Woo et al. (2015) Nat Biotech 33(11):1162-64.*
Lowe et al. (2016) Plant Cell 28:1998-2015.*
Sanford (1990) Physiol. Plant., 79(1):206-209.*
Je Wook Woo et al: "DNA-free genome editing in plants with preassembled CRISPR-Cas9 ribonucleoproteins", Nature Biotechnology, vol. 33, No. 11, Oct. 19, 2015 (Oct. 19, 2015), pp. 1162-1164.
Kanchiswamy C N et al: "Non-GMO genetically edited crop plants", Trends in Biotechnology Sep. 1, 2015 Elsevier Ltd GBR, vol. 33, No. 9, Sep. 1, 2015 (Sep. 1, 2015), XP002765281, DOI: 10.1016/J. TIBTECH.2015.04.002 p. 490.
Luisa Bortesi et al: "The CRISPR/Cas9 system for plant genome editing and beyond", Biotechnology Advances, vol. 33, No. 1, Jan. 1, 2015 (Jan. 1, 2015), pp. 41-52.
Li Zhongsen et al: "Cas9-Guide RNA Directed Genome Editing in Soybean", Plant Physiology (Rockville), vol. 169, No. 2, Oct. 2015 (Oct. 2015), pp. 960-970.
Sojung Kim et al: "Highly efficient RNA-guided genome editing in human cells via delivery of purified Cas9 ribonucleoproteins", Genome Res, vol. 24, Apr. 2, 2014, pp. 1012-1019.
Steven Lin et al: "Enhanced homology-directed human genome engineering by controlled timing of CRISPR/Cas9 delivery", eLIFE, 3:e04766, Dec. 15, 2014.
Susana Martin-Ortigosa et al: "Proteolistics: a biolistic method for intracellular delivery of proteins", Transgenic Res, vol. 23, Aug. 5, 2014, pp. 743-756.
Song Luo, et al: "Non-transgenic Plant Genome Editing Using Purified Sequence-Specific Nucleases", Mol Plant, vol. 8, Jun. 11, 2015, pp. 1425-1427.
John A Zuris, et al: "Cationic lipid-mediated delivery of proteins enables efficient protein-based genome editing in vitro and in vivo", Nature Biotech, vol. 33 No. 1, Oct. 30, 2014, pp. 73-80.
Susana Martin-Ortigosa et al: "Mesoporous Silica Nanoparticle-Mediated Intracellular Cre Protein Delivery for Maize Genome Editing via loxP Site Excision", Plant Physiol, vol. 164, Issue 2, Feb. 2014, pp. 537-547.
International Search Report and Written Opinion, International Application No. PCT/US2016/057272 mailed Nov. 1, 2017.
International Preliminary Report on Patentability for International Application No. PCT/US2016/057272, mailed May 3, 2018, 9 Pages.
Asad, S., et al., "Silicon Carbide Whisker-mediated Plant Transformation," Properties and Applications of Silicon Carbide, 2011, 16 pages.
Barampuram, S., et al., "Recent Advances in Plant Transformation," Plant Chromosome Engineering. Methods in Molecular Biology, vol. 701, 2011, pp. 1-35.
Christou, P., et al., "Prediction of germ-line transformation events in chimeric Ro transgenic soybean plantlets using tissue-specific expression patterns," The Plant Journal, vol. 2(3), pp. 283-290 (1992).
Ji, Q., et al., "Genetic transformation of major cereal crops," International Journal of Developmental Biology, vol. 57, pp. 495-508 (2013).
Lusser, M., et al., "Comparative regulatory approaches for groups of new plant breeding techniques," New Biotechnology, vol. 30(5), pp. 437-446 (Jun. 2013).
Martin-Ortigosa, S., et al., "Gold Functionalized Mesoporous Silica Nanoparticle Mediated Protein and DNA Codelivery to Plant Cells Via the Biolistic Method" Advanced Function Materials, 2012, 7 pages.
Subburaj S., et al., "Site-Directed Mutagenesis in Petunia x Hybrida Protoplast System Using Direct Delivery of Purified Recombinant Cas9 Ribonucleoproteins," Plant Cell Reports, 2016, vol. 35, pp. 1535-1544.
Liang Z., et al., "Efficient DNA-free Genome Editing of Bread Wheat Using CRISPR/Cas9 Ribonucleoprotein Complexes," Nature Communications, Jan. 18, 2017, vol. 8, No. 14261, 5 Pages.
Rivera A.L., et al., "Physical Methods For Genetic Plant Transformation," Physics Of Life Reviews, Sep. 2012, vol. 09, No. 03, pp. 308-345.
Sanford J.C., "Biolistic Plant Transformation," Physiologia Plantarum, 1990, vol. 79, pp. 206-209.
Cho S.W., et al., "Heritable Gene Knockout in Caenorhabditis Elegans by Direct Injection of Cas9-sgRNA Ribonucleoproteins," Genetics, 2013, vol. 195, No. 3, pp. 1177-1180.
Vert M., et al., "Terminology for Biorelated Polymers and Applications (IUPAC Recommendations 2012)," Pure and Applied Chemistry, 2012, vol. 84, No. 2, pp. 377-410.
Woo, Nature Biotechnology, 2015, 33(11), pp. 1162-1165.†
Gaj, Trends Biotechnol., 2013, 31(7), pp. 397-405.†
Zhang, Plant Physiology, 2013, vol. 161, pp. 20-27.†

* cited by examiner
† cited by third party

FIGURE 1 cleavage site
PAM

| | Count | SEQID NO: |
|---|---|---|
| CACGTATATATAC**GCGTACGCGTACGTGTG**AGGTATATATATCCTCCGCCGGGGCACGTAC | | 48 |
| CACGTATATATAC**GCGTACGCGTACGT***t***GTG**AGGTATATATATCCTCCGCCGGGGCACGTAC | 16,861 | 49 |
| CACGTATATATAC**GCGTACGCGTACG**-**GTG**AGGTATATATATCCTCCGCCGGGGCACGTAC | 3,684 | 50 |
| CACGTATATATAC**GCGTACGCGTAC**-*t***GTG**AGGTATATATATCCTCCGCCGGGGCACGTAC | 2,263 | 51 |
| CACGTATATATAC**GCGTACGCGTACG**--**TG**AGGTATATATATCCTCCGCCGGGGCACGTAC | 2,132 | 52 |
| CACGTATATATA-----------------------------TCCTCCGCCGGGGCACGTAC | 1,181 | 53 |
| CACGTATATATAC**G**------------------------------------------CGTAC | 848 | 54 |
| CACGTATATATAC**GCGTACGCGT**----**GTG**AGGTATATATATCCTCCGCCGGGGCACGTAC | 327 | 55 |
| CACGTATATATAC**GCGTACGC**----------------------------CGGGGCACGTAC | 263 | 56 |
| CACGTATATAT-------------------------------CCTCCGCCGGGGCACGTAC | 227 | 57 |
| CACGTATATATAC**GCGTACGCGTA***t*--**GTG**AGGTATATATATCCTCCGCCGGGGCACGTAC | 209 | 58 |

FIGURE 2

```
                                ALS-CR4 TS     PAM                                  SEQ ID NO:
ALS1 (genomic)  GCGCTGCTCGATTCCGTCCCATGGTCGCCATCACGGGACAGGTGCCGCGACGC          59
                 A  L  L  D  S  V  P  M  V  A  I  T  G  Q  V  P  R  R         60
Oligo1          GCGTTGCTCGACTCCGTCCCATTGTCGCCATCACGGGACAGGTGTCGCGACGC          61
                 A  L  L  D  S  V  P  I  V  A  I  T  G  Q  V  S  R  R         62
Oligo2          GCGTTGCTGGACTCCGTGCCGATGGTCGCCATCACGGGACAGGTGTCCCGACGC         63
                 A  L  L  D  S  V  P  M  V  A  I  T  G  Q  V  S  R  R         64
```

Wild type plants

Plants with edited ALS2 allele

ALS-CR7 target site
cleavage site
Pro
PAM
SEQ ID NO:
ATGGCTCCCCCGGCCACCCCGCTCCGGCCGT 65
M A P P A T P L R P* 66 new ALS-CR7 target site
new cleavage site
PAM
ATGGCTCCCCCGGCCACCCCCCTCCGGCCGT 67
M A P P A T P P S G R 68

Pro
PAM
ATGGCTCCCCCGGCCACCCCNCTCCGGCCGT 69
M A P P A T P L R P 66

(SEQ ID NO: 70)

(SEQ ID NO: 71)

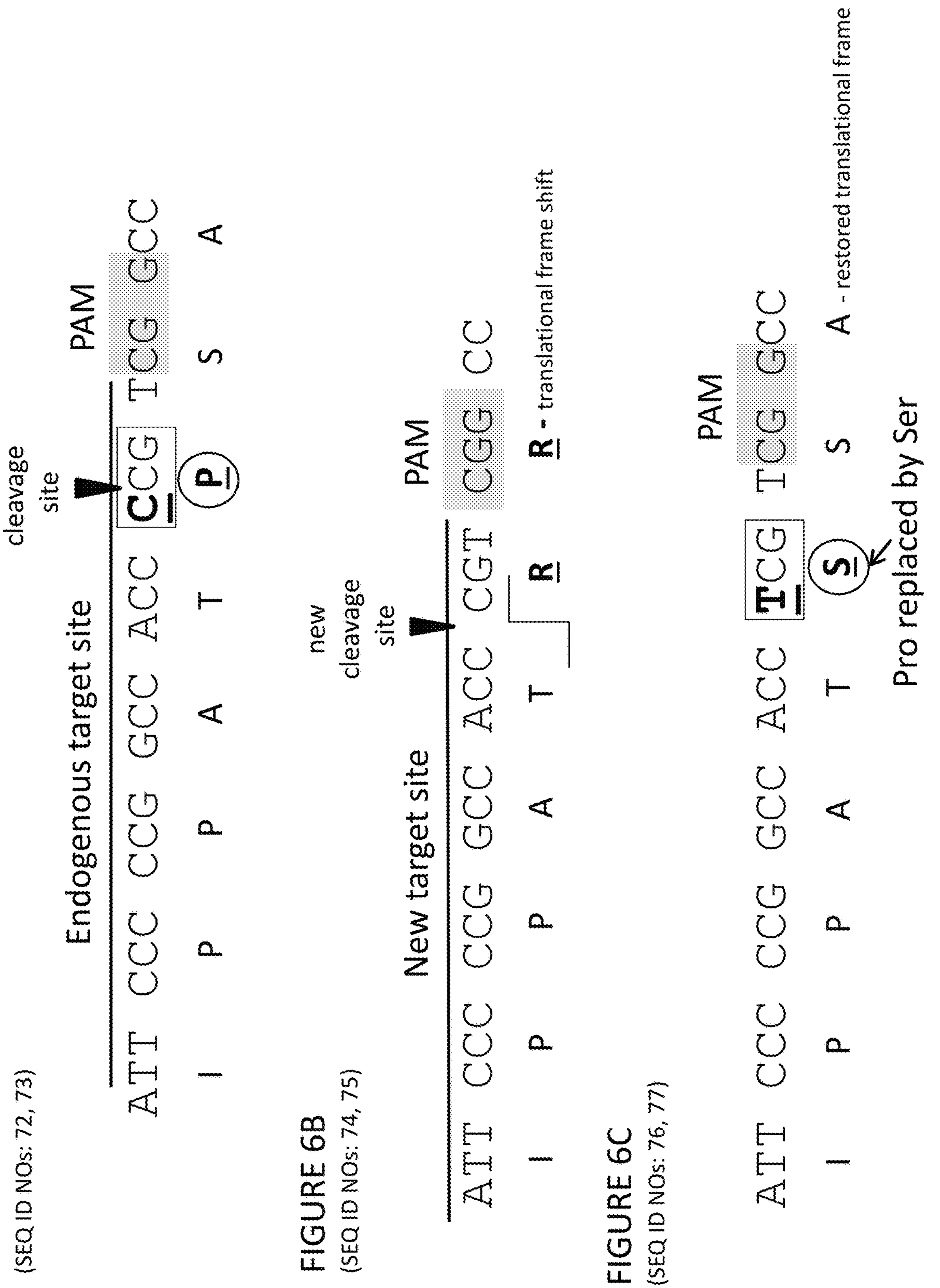
FIGURE 6A (SEQ ID NOs: 72, 73)
FIGURE 6B (SEQ ID NOs: 74, 75)
FIGURE 6C (SEQ ID NOs: 76, 77)

METHODS AND COMPOSITIONS FOR MARKER-FREE GENOME MODIFICATION

This application claims the benefit of U.S. Provisional Application No. 62/243,719, filed Oct. 20, 2015, U.S. Provisional Application No. 62/309,033, filed Mar. 16, 2016 and U.S. Provisional Application No. 62/359,254, filed Jul. 7, 2016, which are incorporated herein in their entirety by reference.

FIELD

The disclosure relates to the field of molecular biology, in particular, to methods for altering the genome of a cell.

REFERENCE TO SEQUENCE LISTING SUBMITTED ELECTRONICALLY

The official copy of the sequence listing is submitted electronically via EFS-Web as an ASCII formatted sequence listing with a file named 20161011_7158PCT_SeqLs.txt, created on Oct. 11, 2016 and having a size of 185 kilobytes and is filed concurrently with the specification. The sequence listing contained in this ASCII formatted document is part of the specification and is herein incorporated by reference in its entirety.

BACKGROUND

Recombinant DNA technology has made it possible to insert DNA sequences at targeted genomic locations and/or modify (edit) specific endogenous chromosomal sequences, thus altering the organism's phenotype. Site-specific integration techniques, which employ site-specific recombination systems, as well as other types of recombination technologies, have been used to generate targeted insertions of genes of interest in a variety of organism. Genome-editing techniques such as designer zinc finger nucleases (ZFNs) or transcription activator-like effector nucleases (TALENs), or homing meganucleases, are available for producing targeted genome perturbations, but these systems tends to have a low specificity and employ designed nucleases that need to be redesigned for each target site, which renders them costly and time-consuming to prepare.

Although several approaches have been developed to target a specific site for modification in the genome of an organism, there still remains a need for new genome engineering technologies that are affordable, easy to set up, scalable, and amenable to targeting multiple positions within the genome of an organism.

BRIEF SUMMARY

Compositions and methods are provided for modifying a nucleotide sequence in the genome of a plant cell, without the use of a selectable marker. The methods and compositions employ a guide polynucleotide/Cas endonuclease system to make a double strand break in a target site located in a nucleotide sequence and plant cells are obtained without the use of a selectable marker and to provide an effective system for modifying target sites within the genome of a plant, plant cell or seed. Compositions and methods are also provided for producing a plant cell, callus tissue or plant having a modified nucleotide sequence in its genome, without the use of a selectable marker.

In one embodiment of the disclosure, the method comprises a method for modifying a nucleotide sequence in the genome of a plant cell without the use of a selectable marker, the method comprising introducing into at least one plant cell a guide RNA/Cas endonuclease complex capable of making a double strand break in a target site located in said nucleotide sequence, and selecting a plant cell having a modification in said nucleotide sequence, wherein the selection occurs without the use of a selectable In one embodiment of the disclosure, the method comprises a method for producing a plant having a modified nucleotide sequence in its genome without the use of a selectable marker, the method comprising: introducing into at least one plant cell a guide polynucleotide/Cas endonuclease complex capable of making a double strand break in a target site located in a nucleotide sequence; obtaining a plant from said plant cell; and, selecting a plant having a modification in said nucleotide sequence, wherein the selection occurs without the use of a selectable marker.

In one embodiment of the disclosure, the method comprises a method for producing plant callus tissue having a modified nucleotide sequence in its genome without the use of a selectable marker, the method comprising: introducing into at least one plant cell a guide polynucleotide/Cas endonuclease complex capable of making a double strand break in a target site located in a nucleotide sequence; obtaining callus tissue from said plant cell; selecting callus tissue having a modification in said nucleotide sequence, wherein the selection occurs without the use of a selectable marker. The guide polynucleotide/Cas endonuclease complex can be a guide RNA/Cas endonuclease complex.

The methods of the present disclosure can further comprise introducing a polynucleotide template, wherein said polynucleotide modification template comprises at least one nucleotide modification of the nucleotide sequence comprising a target site in the genome of said cell, wherein said at least one nucleotide modification of said polynucleotide modification template is selected from the group consisting of (i) a replacement of at least one nucleotide, (ii) a deletion of at least one nucleotide, (iii) an insertion of at least one nucleotide, and (iv) any combination of (i)-(iii). The method can also further comprise introducing a donor DNA, wherein said donor DNA comprises at least one polynucleotide of interest. The introduction of the guide polynucleotide/Cas endonuclease complex into the cell can be via any method known in the art, such as but not limiting to a delivery system selected from the group consisting of particle mediated delivery, whisker mediated delivery, cell-penetrating peptide mediated delivery, electroporation, PEP-mediated transfection and nanoparticle mediated delivery.

The methods of the present disclosure can be used without the use of a phenotypic or selectable marker and with no application of a selective agent. The methods include the introduction into a plant cell of a guide polynucleotide/Cas endonuclease complex without also introducing a selectable marker into said plant cell, or wherein the introducing of said guide polynucleotide/Cas endonuclease complex is not accompanied by the restoration of a disrupted selectable marker gene into a non-disrupted selectable marker gene encoding a functional selectable marker protein, or wherein the introducing of said guide polynucleotide/Cas endonuclease complex does not result in the production of a selectable marker within said cell. The methods of the present disclosure can further include selecting a plant cell, callus tissue or plant comprising a modified nucleotide sequence in its genome, wherein the selection occurs without the use of a selectable marker.

Also provided are nucleic acid constructs, cells, plants, progeny plants, microorganisms, explants, seeds and grain produced by the methods described herein. Additional embodiments of the methods and compositions of the present disclosure are shown herein.

BRIEF DESCRIPTION OF THE DRAWINGS AND THE SEQUENCE LISTING

The disclosure can be more fully understood from the following detailed description and the accompanying drawings and Sequence Listing, which form a part of this application. The sequence descriptions and sequence listing attached hereto comply with the rules governing nucleotide and amino acid sequence disclosures in patent applications as set forth in 37 C.F.R. §§ 1.821-1.825. The sequence descriptions contain the three letter codes for amino acids as defined in 37 C.F.R. §§ 1.821-1.825, which are incorporated herein by reference.

FIGURES

FIG. 1 depicts an alignment and count of the top 10 most frequent NHEJ mutations induced by the maize optimized guide RNA/Cas endonuclease system described herein. The mutations were identified by deep sequencing. The reference sequence (SEQ ID NO: 48) represents the unmodified locus with each target site shown in bold. The PAM sequence (grey) and expected site of cleavage (arrow) are also indicated. Deletions or insertions as a result of imperfect NHEJ are shown by a "-" or an italicized underlined nucleotide, respectively. The reference and mutations 1-10 of the target site correspond to SEQ ID NOs: 49-58, respectively. In maize, for the majority of target sites, the most prevalent type of mutation generated by Cas9-gRNA system is a single nucleotide insertion (60%) (count shown as 16,861).

FIG. 2 depicts partial nucleotide sequences ((SEQ ID NOs: 59, 61, 63) and partial amino acid sequences (SEQ ID NOs: 60, 62, 64) of the ALS2 gene and two editing repair templates (Oligo1 and Oligo2); modified nucleotides are underlined and the codon sequence targeted for gene editing (Pro to Ser) is boxed.

FIG. 3 depicts maize plants having an edited ALS2 allele for resistance to chlorsulfuron (left) and wild type plants (right). Four-week old plants were sprayed with chlorsulfuron (100 mg/L). Plants are shown three weeks after the treatment.

Figures 4A, 4B, 4C:

FIG. 4A-4C shows a schematic of a fragment of the ALS2 gene (SEQ ID NOs: 65, 67, 69) selected for modification and use of ALS2 as a selectable marker. The encoded amino acid sequences are shown below each nucleotide sequence. (SEQ ID NOs: 66, 68). FIG. 4A: A single nucleotide (G) in position 165 (bold and underlined) can be removed in order to generate a specific knock-out version of the edited for chlorsulfuron resistance ALS2 gene. FIG. 4B depicts the new nucleotide sequence with a single nucleotide deletion (G removed) resulting in the translational frame shift and ALS2 gene knock-out. FIG. 4C: The ALS2 gene function and chlorsulfuron resistance are restored through insertion of a single nucleotide (N, bold and underlined) during the process of DSB repair via NHEJ pathway.

Figure 5A:
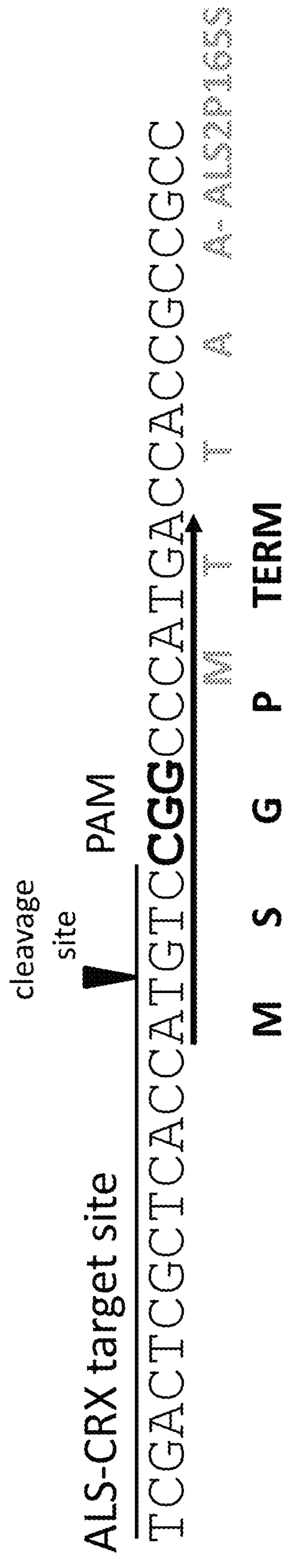
Figure 5B:
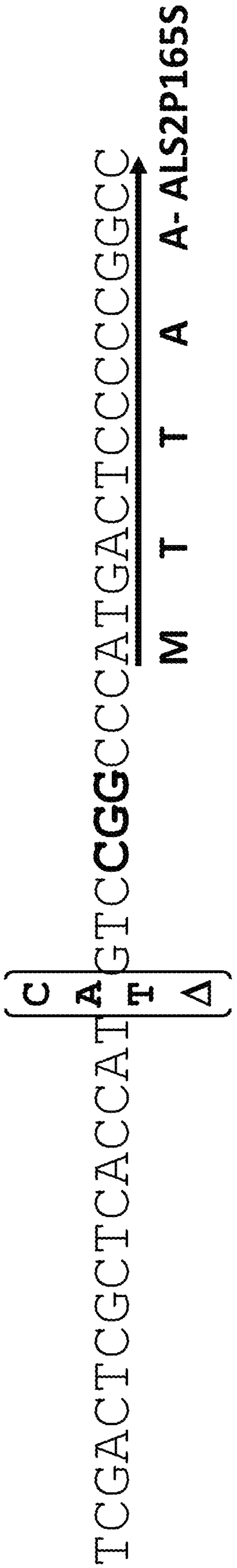

FIG. 5A-5B. Re-activation of inactivated ALS2P165S as selectable marker. FIG. 5A (SEQ ID NO: 70). A design of ALS 2P165S gene containing upstream out-of-frame translational start codon located 3 nucleotides 5' of PAM. Initiation of translation at the first AUG (depicted by arrow below sequence) encodes a 4 amino acid polypeptide which prevents the initiation of translation start codon of ALS2 (grey letters). FIG. 5B (SEQ ID NO: 71). Single nucleotide insertion (C, A or T) or deletion (or any combination) that results in the loss of the upstream AUG allows initiation of translation at the start codon of ALS2 (depicted by arrow below sequence) restoring translation of the full-length ALS2P165S herbicide resistance gene.

FIG. 6A-6C shows a schematic of a fragment of polynucleotide of interest (SEQ ID NO: 72) comprising an endogenous target site selected for modification. The encoded amino acid sequences are shown below each nucleotide sequence. (SEQ ID NOs: 73, 75, 77). FIG. 6A depicts single nucleotide (in this example C, shown in bold and underlined) located next to an endonuclease cleavage site (shown by arrow) can be removed through NHEJ. FIG. 6B depicts the resulting polynucleotide of interest (SEQ ID NO:74) having a single base deleted, resulting in the creation of a new cleavage site (indicated by arrow) and translational frameshift. FIG. 4C: A single nucleotide (in this example T, shown in bold and underlined) located next to an endonuclease cleavage site can be inserted through NHEJ without the use of a polynucleotide modification (repair) template, resulting in a single nucleotide edit of the polynucleotide of interest (SEQ ID NO:76). PAM sequences are highlighted in grey.

Figure 7:
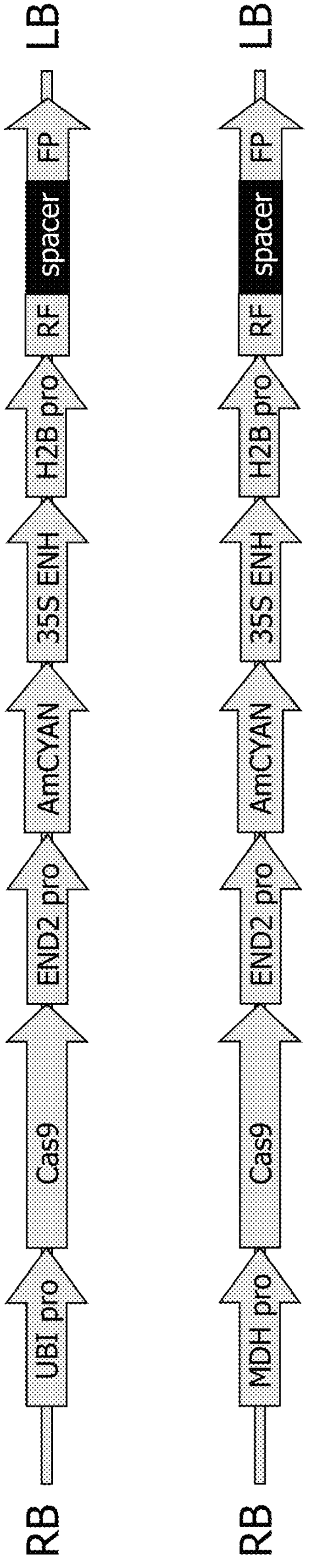

FIG. 7. Top: *Agrobacterium* vector for stable integration of the UBI:Cas9 into the maize genome. Bottom: *Agrobacterium* vector for stable integration of the MDH:Cas9 into the maize genome. MDH is a temperature regulated promoter, regulating expression of the Cas9. These vectors also contain visible marker gene (END2:AmCYAN), which was used for selection of stably transformed callus sectors. Sequence of the Red Fluorescent Protein (DsRED) contained duplicated in a direct orientation 369 bp fragments separated by a 343-bp spacer, which contained sequences for recognition and targeting by two gRNAs and LIG3:4 meganuclease. H2B refers to the histone H2B gene promoter.

SEQUENCES

TABLE 1

Summary of Nucleic Acid and Protein SEQ ID Numbers

| Description | Nucleic acid SEQ ID NO. | Protein SEQ ID NO. |
|---|---|---|
| Cas9 coding sequence | 1 | |
| potato ST-LS1 intron | 2 | |
| SV40 NLS | | 3 |
| VirD2 NLS | 4 | |
| Maize optimized Cas9 expression cassette | 5 | |
| Lig-CR3 guide RNA expression vector | 6 | |
| Maize genomic target site MS26Cas-1 plus PAM sequence | 7 | |
| Maize genomic target site MS26Cas-2 plus PAM sequence | 8 | |

TABLE 1-continued

Summary of Nucleic Acid and Protein SEQ ID Numbers

| Description | Nucleic acid SEQ ID NO. | Protein SEQ ID NO. |
|---|---|---|
| Maize genomic target site MS26Cas-3 plus PAM sequence | 9 | |
| Maize genomic target site LIGCas-1 plus PAM sequence | 10 | |
| Maize genomic target site LIGCas-2 plus PAM sequence | 11 | |
| Maize genomic target site LIGCas-3 plus PAM sequence | 12 | |
| Maize genomic target site MS45Cas-1 plus PAM sequence | 13 | |
| Maize genomic target site MS45Cas-2 plus PAM sequence | 14 | |
| Maize genomic target site MS45Cas-3 plus PAM sequence | 15 | |
| Maize genomic target site ALSCas-1 plus PAM sequence | 16 | |
| Maize genomic target site ALSCas-2 plus PAM sequence | 17 | |
| Maize genomic target site ALSCas-3 plus PAM sequence | 18 | |
| Primer sequences | 19-38 | |
| ALS1-DNA sequence | 39 | |
| ALS2-DNA sequence | 40 | |
| full length Zm-ALS2 protein | | 41 |
| Maize genomic target site ALSCas-4 plus PAM sequence | 42 | |
| 794 bp polynucleotide modification template | 43 | |
| 127 bp polynucleotide modification template, oligo1 | 44 | |
| 127 bp polynucleotide modification template, oligo2 | 45 | |
| *Agrobacterium* vector containing maize codon optimized Cas9 and maize UBI promoter | 46 | |
| *Agrobacterium* vector containing maize codon optimized Cas9 and maize MDH promoter | 47 | |
| Sequences shown in FIG. 1 | 48-58 | |
| Sequences shown in FIG. 2 | 59, 61, 63 | 60, 62, 64 |
| Sequences shown in FIG. 4A-4C | 65, 67, 69 | 66, 68 |
| Sequences shown in FIG. 5A-5B | 70-71 | |
| Sequences shown in FIG. 6A-6C | 72, 74, 76 | 73, 75, 77 |
| IN2 promoter | 78 | |
| ALSCas7 target site | 79 | |
| ALSCas7-1 target site which is the modified ALSCas7 target site | 80 | |
| maize off target site | 81 | |

DETAILED DESCRIPTION

Compositions and methods are provided for modifying a nucleotide sequence in the genome of a plant cell, without the use of a selectable marker. The methods and compositions employ a guide polynucleotide/Cas endonuclease system to make a double strand break in a target site located in a nucleotide sequence to be modified and plant cells are obtained without the use of a selectable marker. Compositions and methods are also provided for producing a plant cell, callus tissue or plant having a modified nucleotide sequence in its genome, without the use of a selectable marker. The methods described herein can further include introducing into at least one plant cell a guide polynucleotide/Cas endonuclease complex capable of making a double strand break in a target site located in a nucleotide sequence, and selecting a plant cell having a modification in said nucleotide sequence, wherein the selection occurs without the use of a selectable marker. The method can further include obtaining a callus tissue or a plant from the plant cell and selecting a callus tissue or plant having a modification in said nucleotide sequence, wherein the selection occurs without the use of a selectable marker.

One skilled in the art can appreciate that conventional genome modification methods and plant transformation methods have relied predominantly on introducing selectable marker genes into the cells to be modified to allow for selection schemes, in which for example, an antibiotic or herbicide (a selective agent) is used to inhibit or kill cells or tissues that do not comprise the selectable marker gene, and the cells or tissues that comprise the selectable marker gene continue to grow due to expression of the selectable marker (resistance) gene. In contrast, the methods of the present disclosure can be used without the use of a selectable marker and with no application of a selective agent.

CRISPR loci (Clustered Regularly Interspaced Short Palindromic Repeats) (also known as SPIDRs—SPacer Interspersed Direct Repeats) constitute a family of DNA loci. CRISPR loci consist of short and highly conserved DNA repeats (typically 24 to 40 bp, repeated from 1 to 140 times—also referred to as CRISPR-repeats) which are partially palindromic. The repeated sequences (usually specific to a species) are interspaced by variable sequences of constant length (typically 20 to 58 by depending on the CRISPR locus (WO2007/025097, published Mar. 1, 2007). Bacteria and archaea have evolved adaptive immune defenses termed clustered regularly interspaced short palindromic repeats (CRISPR)/CRISPR-associated (Cas) systems that use short RNA to direct degradation of foreign nucleic acids (WO2007/025097, published Mar. 1, 2007). Multiple CRISPR-Cas systems have been described including Class 1 systems, with multisubunit effector complexes, and Class 2 systems, with single protein effectors (such as but not limiting to Cas9, Cpf1, C2c1, C2c2, C2c3). (Zetsche et al., 2015, Cell 163, 1-13; Shmakov et al., 2015, Molecular_Cell 60, 1-13; Makarova et al. 2015, Nature Reviews Microbiology Vol. 13:1-15, WO 2013/176772 A1 published on Nov. 23, 2013 and incorporated by its entirety by reference herein).

The type II CRISPR/Cas system from bacteria employs a crRNA (CRISPR RNA) and tracrRNA (trans-activating CRISPR RNA) to guide the Cas endonuclease to its DNA target. The crRNA contains a spacer region complementary to one strand of the double strand DNA target and a region that base pairs with the tracrRNA (trans-activating CRISPR RNA) forming a RNA duplex that directs the Cas endonuclease to cleave the DNA target. Spacers are acquired through a not fully understood process involving Cas1 and Cas2 proteins. All type II CRISPR-Cas loci contain cas1 and cas2 genes in addition to the cas9 gene (Makarova et al. 2015, Nature Reviews Microbiology Vol. 13:1-15). Cas gene includes a gene that is generally coupled, associated or close to, or in the vicinity of flanking CRISPR loci. The terms "Cas gene", "CRISPR-associated (Cas) gene" are used interchangeably herein. A comprehensive review of the Cas protein family is presented in Haft et al. (2005) Computational Biology, PLoS Comput Biol 1(6): e60. doi:10.1371/journal.pcbi.0010060. As described therein, 41 CRISPR-associated (Cas) gene families are described, in addition to the four previously known gene families. It shows that CRISPR systems belong to different classes, with different repeat patterns, sets of genes, and species ranges. The number of Cas genes at a given CRISPR locus can vary between species (Haft et al., 2005, Computational Biology, PLoS Comput Biol 1(6): e60. doi:10.1371/journal.pcbi.0010060; Makarova et al. 2015, Nature Reviews Microbiology Vol. 13:1-15; WO 2013/176772 A1 published on Nov. 23, 2013 and incorporated by its entirety by reference herein).

The term "Cas endonuclease" herein refers to a protein encoded by a Cas (CRISPR-associated) gene. A Cas endonuclease, when in complex with a suitable polynucleotide component, is capable of recognizing, binding to, and optionally nicking or cleaving all or part of a specific DNA target sequence. A Cas endonuclease described herein comprises one or more nuclease domains. Cas endonucleases of the disclosure include those having a HNH or HNH-like nuclease domain and/or a RuvC or RuvC-like nuclease domain (Makarova et al. 2015, Nature Reviews Microbiology Vol. 13:1-15). A Cas includes a Cas9 protein, a Cpf1 protein, a C2c1 protein, a C2c2 protein, a C2c3 protein, Cas3, Cas3-HD, Cas 5, Cas7, Cas8, Cas10, or complexes of these.

As used herein, the terms "guide polynucleotide/Cas endonuclease complex", "guide polynucleotide/Cas endonuclease system", "guide polynucleotide/Cas complex", "guide polynucleotide/Cas system", "guided Cas system", "PGEN" are used interchangeably herein and refer to at least one guide polynucleotide and at least one Cas endonuclease protein that are capable of forming a polynucleotide-protein complex, wherein said guide polynucleotide/Cas endonuclease complex can direct the Cas endonuclease to a DNA target site, enabling the Cas endonuclease to recognize, bind to, and optionally nick or cleave (introduce a single or double strand break) the DNA target site. A guide polynucleotide/Cas endonuclease complex herein can comprise Cas protein(s) and suitable polynucleotide component(s) of any of the four known CRISPR systems (Horvath and Barrangou, Science 327:167-170) such as a type I, II, or III CRISPR system. A Cas endonuclease unwinds the DNA duplex at the target sequence and optionally cleaves at least one DNA strand, as mediated by recognition of the target sequence by a polynucleotide (such as, but not limited to, a crRNA or guide RNA) that is in complex with the Cas protein. Such recognition and cutting of a target sequence by a Cas endonuclease typically occurs if the correct protospacer-adjacent motif (PAM) is located at or adjacent to the 3' end of the DNA target sequence. Alternatively, a Cas protein herein may lack DNA cleavage or nicking activity, but can still specifically bind to a DNA target sequence when complexed with a suitable RNA component. (See also U.S. Patent Application US 2015-0082478 A1, published on Mar. 19, 2015 and US 2015-0059010 A1, published on Feb. 26, 2015, both are hereby incorporated in its entirety by reference).

A guide polynucleotide/Cas endonuclease complex can cleave one or both strands of a DNA target sequence. A guide polynucleotide/Cas endonuclease complex that can cleave both strands of a DNA target sequence typically comprises a Cas protein that has all of its endonuclease domains in a functional state (e.g., wild type endonuclease domains or variants thereof retaining some or all activity in each endonuclease domain). Thus, a wild type Cas protein (e.g., a Cas9 protein disclosed herein), or a variant thereof retaining some or all activity in each endonuclease domain of the Cas protein, is a suitable example of a Cas endonuclease that can cleave both strands of a DNA target sequence. A Cas9 protein comprising functional RuvC and HNH nuclease domains is an example of a Cas protein that can cleave both strands of a DNA target sequence. A guide polynucleotide/Cas endonuclease complex that can cleave one strand of a DNA target sequence can be characterized herein as having nickase activity (e.g., partial cleaving capability). A Cas nickase typically comprises one functional endonuclease domain that allows the Cas to cleave only one strand (i.e., make a nick) of a DNA target sequence. For example, a Cas9 nickase may comprise (i) a mutant, dysfunctional RuvC domain and (ii) a functional HNH domain (e.g., wild type HNH domain). As another example, a Cas9 nickase may comprise (i) a functional RuvC domain (e.g., wild type RuvC domain) and (ii) a mutant, dysfunctional HNH domain. Non-limiting examples of Cas9 nickases suitable for use herein are disclosed by Gasiunas et al. (Proc. Natl. Acad. Sci. U.S.A. 109:E2579-E2586), Jinek et al. (Science 337:816-821), Sapranauskas et al. (Nucleic Acids Res. 39:9275-9282) and in U.S. Patent Appl. Publ. No. 2014/0189896, which are incorporated herein by reference.

A pair of Cas9 nickases can be used to increase the specificity of DNA targeting. In general, this can be done by introducing two Cas9 nickases that, by virtue of being associated with RNA components with different guide sequences, target and nick nearby DNA sequences on opposite strands in the region for desired targeting. Such nearby cleavage of each DNA strand creates a double strand break (i.e., a DSB with single-stranded overhangs), which is then recognized as a substrate for non-homologous-end-joining, NHEJ (prone to imperfect repair leading to mutations) or homologous recombination, HR. Each nick in these embodiments can be at least about 5, 10, 15, 20, 30, 40, 50, 60, 70, 80, 90, or 100 (or any integer between 5 and 100) bases apart from each other, for example. One or two Cas9 nickase proteins herein can be used in a Cas9 nickase pair. For example, a Cas9 nickase with a mutant RuvC domain, but functioning HNH domain (i.e., Cas9 HNH+/RuvC−), could be used (e.g., *Streptococcus pyogenes* Cas9 HNH+/RuvC−). Each Cas9 nickase (e.g., Cas9 HNH+/RuvC−) would be directed to specific DNA sites nearby each other (up to 100 base pairs apart) by using suitable RNA components herein with guide RNA sequences targeting each nickase to each specific DNA site.

A Cas protein can be part of a fusion protein comprising one or more heterologous protein domains (e.g., 1, 2, 3, or more domains in addition to the Cas protein). Such a fusion protein may comprise any additional protein sequence, and optionally a linker sequence between any two domains, such as between Cas and a first heterologous domain. Examples of protein domains that may be fused to a Cas protein herein include, without limitation, epitope tags (e.g., histidine

[His], V5, FLAG, influenza hemagglutinin [HA], myc, VSV-G, thioredoxin [Trx]), reporters (e.g., glutathione-5-transferase [GST], horseradish peroxidase [HRP], chloramphenicol acetyltransferase [CAT], beta-galactosidase, beta-glucuronidase [GUS], luciferase, green fluorescent protein [GFP], HcRed, DsRed, cyan fluorescent protein [CFP], yellow fluorescent protein [YFP], blue fluorescent protein [BFP]), and domains having one or more of the following activities: methylase activity, demethylase activity, transcription activation activity (e.g., VP16 or VP64), transcription repression activity, transcription release factor activity, histone modification activity, RNA cleavage activity and nucleic acid binding activity. A Cas protein can also be in fusion with a protein that binds DNA molecules or other molecules, such as maltose binding protein (MBP), S-tag, Lex A DNA binding domain (DBD), GAL4A DNA binding domain, and herpes simplex virus (HSV) VP16.

A Cas protein herein can be from any of the following genera: Aeropyrum, *Pyrobaculum, Sulfolobus, Archaeoglobus, Haloarcula, Methanobacterium, Methanococcus, Methanosarcina, Methanopyrus, Pyrococcus, Picrophilus, Thernioplasnia, Corynebacterium, Mycobacterium, Streptomyces, Aquifrx, Porphvromonas, Chlorobium, Thermus, Bacillus, Listeria, Staphylococcus, Clostridium, Thermoanaerobacter, Mycoplasma, Fusobacterium, Azarcus, Chromobacterium, Neisseria, Nitrosomonas, Desulfovibrio, Geobacter, Myrococcus, Campylobacter, Wolinella, Acinetobacter, Erwinia, Escherichia, Legionella, Methylococcus, Pasteurella, Photobacterium, Salmonella, Xanthomonas, Yersinia, Streptococcus, Treponema, Francisella*, or *Thermotoga*. Alternatively, a Cas protein herein can be encoded, for example, by any of SEQ ID NOs:462-465, 467-472, 474-477, 479-487, 489-492, 494-497, 499-503, 505-508, 510-516, or 517-521 as disclosed in U.S. Appl. Publ. No. 2010/0093617, which is incorporated herein by reference.

A guide polynucleotide/Cas endonuclease complex in certain embodiments can bind to a DNA target site sequence, but does not cleave any strand at the target site sequence. Such a complex may comprise a Cas protein in which all of its nuclease domains are mutant, dysfunctional. For example, a Cas9 protein herein that can bind to a DNA target site sequence, but does not cleave any strand at the target site sequence, may comprise both a mutant, dysfunctional RuvC domain and a mutant, dysfunctional HNH domain. A Cas protein herein that binds, but does not cleave, a target DNA sequence can be used to modulate gene expression, for example, in which case the Cas protein could be fused with a transcription factor (or portion thereof) (e.g., a repressor or activator, such as any of those disclosed herein).

The Cas endonuclease gene can be a Type II Cas9 endonuclease, such as but not limited to, Cas9 genes listed in SEQ ID NOs: 462, 474, 489, 494, 499, 505, and 518 of WO2007/025097published Mar. 1, 2007, and incorporated herein by reference. In another embodiment, the Cas endonuclease gene is a plant, maize or soybean optimized Cas9 endonuclease gene. The Cas endonuclease gene herein can be a plant or microbial codon optimized Cas9 endonuclease gene. The Cas endonuclease gene can be operably linked to a SV40 nuclear targeting signal upstream of the Cas codon region and a bipartite VirD2 nuclear localization signal (Tinland et al. (1992) Proc. Natl. Acad. Sci. USA 89:7442-6) downstream of the Cas codon region.

"Cas9" (formerly referred to as Cas5, Csn1, or Csx12) herein refers to a Cas endonuclease of a type II CRISPR system that forms a complex with a crNucleotide and a tracrNucleotide, or with a single guide polynucleotide, for specifically recognizing and cleaving all or part of a DNA target sequence. A Cas9 protein comprises a RuvC nuclease domain and an HNH (H—N—H) nuclease domain, each of which can cleave a single DNA strand at a target sequence (the concerted action of both domains leads to DNA double-strand cleavage, whereas activity of one domain leads to a nick). In general, the RuvC domain comprises subdomains I, II and III, where domain I is located near the N-terminus of Cas9 and subdomains II and III are located in the middle of the protein, flanking the HNH domain (Hsu et al, Cell 157:1262-1278). A type II CRISPR system includes a DNA cleavage system utilizing a Cas9 endonuclease in complex with at least one polynucleotide component. For example, a Cas9 can be in complex with a CRISPR RNA (crRNA) and a trans-activating CRISPR RNA (tracrRNA). In another example, a Cas9 can be in complex with a single guide RNA.

The amino acid sequence of a Cas9 protein described herein, as well as certain other Cas proteins herein, may be derived from a *Streptococcus* (e.g., *S. pyogenes, S. pneumoniae, S. thermophilus, S. agalactiae, S. parasanguinis, S. oralis, S. salivarius, S. macacae, S. dysgalactiae, S. anginosus, S. constellatus, S. pseudoporcinus, S. mutans*), *Listeria* (e.g., *L. innocua*), *Spiroplasma* (e.g., *S. apis, S. syrphidicola*), Peptostreptococcaceae, *Atopobium, Porphyromonas* (e.g., *P. catoniae*), *Prevotella* (e.g., *P. intermedia*), *Veillonella, Treponema* (e.g., *T. socranskii, T. denticola*), *Capnocytophaga, Finegoldia* (e.g., *F. magna*), Coriobacteriaceae (e.g., *C. bacterium*), *Olsenella* (e.g., *O. profusa*), *Haemophilus* (e.g., *H. sputorum, H. pittmaniae*), *Pasteurella* (e.g., *P. bettyae*), *Olivibacter* (e.g., *O. sitiensis*), *Epilithonimonas* (e.g., *E. tenax*), *Mesonia* (e.g., *M. mobilis*), *Lactobacillus* (e.g., *L. plantarum*), *Bacillus* (e.g., *B. cereus*), *Aquimarina* (e.g., *A. muelleri*), *Chryseobacterium* (e.g., *C. palustre*), *Bacteroides* (e.g., *B. graminisolvens*), *Neisseria* (e.g., *N. meningitidis*), *Francisella* (e.g., *F. novicida*), or *Flavobacterium* (e.g., *F. frigidarium, F. soli*) species, for example. As another example, a Cas9 protein can be any of the Cas9 proteins disclosed in Chylinski et al. (RNA Biology 10:726-737 and U.S. patent application 62/162,377, filed May 15, 2015), which are incorporated herein by reference.

Accordingly, the sequence of a Cas9 protein herein can comprise, for example, any of the Cas9 amino acid sequences disclosed in GenBank Accession Nos. G3ECR1 (*S. thermophilus*), WP_026709422, WP_027202655, WP_027318179, WP_027347504, WP_027376815, WP_027414302, WP_027821588, WP_027886314, WP_027963583, WP_028123848, WP_028298935, Q03J16 (*S. thermophilus*), EGP66723, EGS38969, EGV05092, EH165578 (*S. pseudoporcinus*), EIC75614 (*S. oralis*), EID22027 (*S. constellatus*), EIJ69711, EJP22331 (*S. oralis*), EJP26004 (*S. anginosus*), EJP30321, EPZ44001 (*S. pyogenes*), EPZ46028 (*S. pyogenes*), EQL78043 (*S. pyogenes*), EQL78548 (*S. pyogenes*), ERL10511, ERL12345, ERL19088 (*S. pyogenes*), ESA57807 (*S. pyogenes*), ESA59254 (*S. pyogenes*), ESU85303 (*S. pyogenes*), ETS96804, UC75522, EGR87316 (*S. dysgalactiae*), EGS33732, EGV01468 (*S. oralis*), EHJ52063 (*S. macacae*), EID26207 (*S. oralis*), EID33364, EIG27013 (*S. parasanguinis*), EJF37476, EJ019166 (*Streptococcus* sp. BS35b), EJU16049, EJU32481, YP_006298249, ERF61304, ERK04546, ETJ95568 (*S. agalactiae*), TS89875, ETS90967 (*Streptococcus* sp. SR4), ETS92439, EUB27844 (*Streptococcus* sp. BS21), AFJ08616, EUC82735 (*Streptococcus* sp. CM6), EWC92088, EWC94390, EJP25691, YP_008027038, YP_008868573, AGM26527, AHK22391, AHB36273, Q927P4, G3ECR1, or Q99ZW2 (*S. pyogenes*), which are incorporated by reference. A variant of any of these Cas9 protein sequences may be used, but should have specific binding activity, and optionally endonucleolytic activity, toward DNA when associated with an RNA component herein. Such a variant may comprise an amino acid sequence that is at least about 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence of the reference Cas9.

Alternatively, a Cas9 protein herein can be encoded by any of SEQ ID NOs:462 (*S. thermophilus*), 474 (*S. thermophilus*), 489 (*S. agalactiae*), 494 (*S. agalactiae*), 499 (*S. mutans*), 505 (*S. pyogenes*), or 518 (*S. pyogenes*) as disclosed in U.S. Appl. Publ. No. 2010/0093617 (incorporated herein by reference), for example. Alternatively still, a Cas9 protein may comprise an amino acid sequence that is at least about 80%, 81%, 82%, 83%, 84%, 85%, 86%, 87%, 88%, 89%, 90%, 91%, 92%, 93%, 94%, 95%, 96%, 97%, 98%, or 99% identical to any of the foregoing amino acid sequences, for example. Such a variant Cas9 protein should have specific binding activity, and optionally cleavage or nicking activity, toward DNA when associated with an RNA component herein.

A Cas protein herein such as a Cas9 can comprise a heterologous nuclear localization sequence (NLS). A heterologous NLS amino acid sequence herein may be of sufficient strength to drive accumulation of a Cas protein in a detectable amount in the nucleus of a yeast cell herein, for example. An NLS may comprise one (monopartite) or more (e.g., bipartite) short sequences (e.g., 2 to 20 residues) of basic, positively charged residues (e.g., lysine and/or arginine), and can be located anywhere in a Cas amino acid sequence but such that it is exposed on the protein surface. An NLS may be operably linked to the N-terminus or C-terminus of a Cas protein herein, for example. Two or more NLS sequences can be linked to a Cas protein, for example, such as on both the N- and C-termini of a Cas protein. Non-limiting examples of suitable NLS sequences herein include those disclosed in U.S. Pat. Nos. 6,660,830 and 7,309,576 (e.g., Table 1 therein), which are both incorporated herein by reference.

The Cas endonuclease can comprise a modified form of the Cas9 polypeptide. The modified form of the Cas9 polypeptide can include an amino acid change (e.g., deletion, insertion, or substitution) that reduces the naturally-occurring nuclease activity of the Cas9 protein. For example, in some instances, the modified form of the Cas9 protein has less than 50%, less than 40%, less than 30%, less than 20%, less than 10%, less than 5%, or less than 1% of the nuclease activity of the corresponding wild-type Cas9 polypeptide (US patent application US20140068797 A1, published on Mar. 6, 2014). In some cases, the modified form of the Cas9 polypeptide has no substantial nuclease activity and is referred to as catalytically "inactivated Cas9" or "deactivated cas9 (dCas9)." Catalytically inactivated Cas9 variants include Cas9 variants that contain mutations in the HNH and RuvC nuclease domains. These catalytically inactivated Cas9 variants are capable of interacting with sgRNA and binding to the target site in vivo but cannot cleave either strand of the target DNA.

A catalytically inactive Cas9 can be fused to a heterologous sequence (US patent application US20140068797 A1, published on Mar. 6, 2014). Suitable fusion partners include, but are not limited to, a polypeptide that provides an activity that indirectly increases transcription by acting directly on the target DNA or on a polypeptide (e.g., a histone or other DNA-binding protein) associated with the target DNA. Additional suitable fusion partners include, but are not limited to, a polypeptide that provides for methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, or demyristoylation activity. Further suitable fusion partners include, but are not limited to, a polypeptide that directly provides for increased transcription of the target nucleic acid (e.g., a transcription activator or a fragment thereof, a protein or fragment thereof that recruits a transcription activator, a small molecule/drug-responsive transcription regulator, etc.). A catalytically inactive Cas9 can also be fused to a FokI nuclease to generate double strand breaks (Guilinger et al. Nature biotechnology, volume 32, number 6, June 2014).

The terms "functional fragment", "fragment that is functionally equivalent" and "functionally equivalent fragment" of a Cas endonuclease are used interchangeably herein, and refer to a portion or subsequence of a Cas endonuclease sequence in which the ability to recognize, bind to, and optionally nick or cleave (introduce a single or double strand break in) the target site is retained.

The terms "functional variant", "variant that is functionally equivalent" and "functionally equivalent variant" of a Cas endonuclease are used interchangeably herein, and refer to a variant of a Cas endonuclease in which the ability to recognize, bind to, and optionally nick or cleave (introduce a single or double strand break in) the target site is retained. Fragments and variants can be obtained via methods such as site-directed mutagenesis and synthetic construction.

The Cas endonuclease gene includes a plant codon optimized *Streptococcus pyogenes* Cas9 gene that can recognize any genomic sequence of the form N(12-30)NGG can in principle be targeted or a Cas9 endonuclease originated from an organism selected from the group consisting of *Brevibacillus laterosporus, Lactobacillus reuteri* Mlc3, *Lactobacillus rossiae* DSM 15814, *Pediococcus pentosaceus* SL4, *Lactobacillus nodensis* JCM 14932, *Sulfurospirillum* sp. SCADC, *Bifidobacterium thermophilum* DSM 20210, *Loktanella vestfoldensis, Sphingomonas sanxanigenens* NX02, *Epilithonimonas tenax* DSM 16811, *Sporocytophaga myxococcoides* and *Psychroflexus torquis* ATCC 700755, wherein said Cas9 endonuclease can form a guide RNA/Cas endonuclease complex capable of recognizing, binding to, and optionally nicking or cleaving all or part of a DNA target sequence. Other Cas endonuclease systems have been described in U.S. patent applications 62/162,377 filed May 15, 2015 and 62/162,353 filed May 15, 2015, both applications incorporated herein by reference.

Cas9 endonucleases can be used for targeted genome editing (via simplex and multiplex double-strand breaks and nicks) and targeted genome regulation (via tethering of epigenetic effector domains to either the Cas9 or sgRNA. Cas9 might also be engineered to function as an RNA-guided recombinase, and via RNA tethers could serve as a scaffold for the assembly of multiprotein and nucleic acid complexes (Mali et al. 2013 Nature Methods Vol. 10: 957-963).

As used herein, the term "guide polynucleotide", relates to a polynucleotide sequence that can form a complex with a Cas endonuclease and enables the Cas endonuclease to recognize, bind to, and optionally cleave a DNA target site. The guide polynucleotide can be a single molecule or a double molecule. The guide polynucleotide sequence can be a RNA sequence (referred to as guide RNA, gRNA), a DNA sequence, or a combination thereof (a RNA-DNA combination sequence). Optionally, the guide polynucleotide can comprise at least one nucleotide, phosphodiester bond or linkage modification such as, but not limited, to Locked Nucleic Acid (LNA), 5-methyl dC, 2,6-Diaminopurine, 2'-Fluoro A, 2'-Fluoro U, 2'-O-Methyl RNA, phosphorothioate bond, linkage to a cholesterol molecule, linkage to a polyethylene glycol molecule, linkage to a spacer 18 (hexaethylene glycol chain) molecule, or 5' to 3' covalent linkage resulting in circularization. A guide polynucleotide that solely comprises ribonucleic acids is also referred to as a “guide RNA” or “gRNA” (See also U.S. Patent Application US 2015-0082478 A1, published on Mar. 19, 2015 and US 2015-0059010 A1, published on Feb. 26, 2015, both are hereby incorporated in its entirety by reference).

The guide polynucleotide can be a double molecule (also referred to as duplex guide polynucleotide) comprising a crNucleotide sequence and a tracrNucleotide sequence. The crNucleotide includes a first nucleotide sequence domain (referred to as Variable Targeting domain or VT domain) that can hybridize to a nucleotide sequence in a target DNA and a second nucleotide sequence (also referred to as a tracr mate sequence) that is part of a Gas endonuclease recognition (CER) domain. The tracr mate sequence can hybridized to a tracrNucleotide along a region of complementarity and together form the Gas endonuclease recognition domain or CER domain. The CER domain is capable of interacting with a Cas endonuclease polypeptide. The crNucleotide and the tracrNucleotide of the duplex guide polynucleotide can be RNA, DNA, and/or RNA-DNA-combination sequences. In some embodiments, the crNucleotide molecule of the duplex guide polynucleotide is referred to as “crDNA” (when composed of a contiguous stretch of DNA nucleotides) or “crRNA” (when composed of a contiguous stretch of RNA nucleotides), or “crDNA-RNA” (when composed of a combination of DNA and RNA nucleotides). The crNucleotide can comprise a fragment of the crRNA naturally occurring in Bacteria and Archaea. The size of the fragment of the crRNA naturally occurring in Bacteria and Archaea that can be present in a crNucleotide disclosed herein can range from, but is not limited to, 2, 3, 4, 5, 6, 7, 8, 9, 10, 11, 12, 13, 14, 15, 16, 17, 18, 19, 20 or more nucleotides. In some embodiments the tracrNucleotide is referred to as “tracrRNA” (when composed of a contiguous stretch of RNA nucleotides) or “tracrDNA” (when composed of a contiguous stretch of DNA nucleotides) or “tracrDNA-RNA” (when composed of a combination of DNA and RNA nucleotides. In one embodiment, the RNA that guides the RNA/Cas9 endonuclease complex is a duplexed RNA comprising a duplex crRNA-tracrRNA. The tracrRNA (trans-activating CRISPR RNA) contains, in the 5'-to-3' direction, (i) a sequence that anneals with the repeat region of CRISPR type II crRNA and (ii) a stem loop-containing portion (Deltcheva et al., Nature 471:602-607). The duplex guide polynucleotide can form a complex with a Cas endonuclease, wherein said guide polynucleotide/Cas endonuclease complex (also referred to as a guide polynucleotide/Cas endonuclease system) can direct the Cas endonuclease to a genomic target site, enabling the Cas endonuclease to recognize, bind to, and optionally nick or cleave (introduce a single or double strand break) into the target site. (See also U.S. Patent Application US 2015-0082478 A1, published on Mar. 19, 2015 and US 2015-0059010 A1, published on Feb. 26, 2015, both are hereby incorporated in its entirety by reference.)

The guide polynucleotide can also be a single molecule (also referred to as single guide polynucleotide) comprising a crNucleotide sequence linked to a tracrNucleotide sequence. The single guide polynucleotide comprises a first nucleotide sequence domain (referred to as Variable Targeting domain or VT domain) that can hybridize to a nucleotide sequence in a target DNA and a Cas endonuclease recognition domain (CER domain), that interacts with a Cas endonuclease polypeptide. By “domain” it is meant a contiguous stretch of nucleotides that can be RNA, DNA, and/or RNA-DNA-combination sequence. The VT domain and/or the CER domain of a single guide polynucleotide can comprise a RNA sequence, a DNA sequence, or a RNA-DNA-combination sequence. The single guide polynucleotide being comprised of sequences from the crNucleotide and the tracrNucleotide may be referred to as “single guide RNA” (when composed of a contiguous stretch of RNA nucleotides) or “single guide DNA” (when composed of a contiguous stretch of DNA nucleotides) or “single guide RNA-DNA” (when composed of a combination of RNA and DNA nucleotides). The single guide polynucleotide can form a complex with a Cas endonuclease, wherein said guide polynucleotide/Cas endonuclease complex (also referred to as a guide polynucleotide/Cas endonuclease system) can direct the Cas endonuclease to a genomic target site, enabling the Cas endonuclease to recognize, bind to, and optionally nick or cleave (introduce a single or double strand break) the target site. (See also U.S. Patent Application US 2015-0082478 A1, published on Mar. 19, 2015 and US 2015-0059010 A1, published on Feb. 26, 2015, both are hereby incorporated in its entirety by reference.)

The term “variable targeting domain” or “VT domain” is used interchangeably herein and includes a nucleotide sequence that can hybridize (is complementary) to one strand (nucleotide sequence) of a double strand DNA target site. The % complementation between the first nucleotide sequence domain (VT domain) and the target sequence can be at least 50%, 51%, 52%, 53%, 54%, 55%, 56%, 57%, 58%, 59%, 60%, 61%, 62%, 63%, 63%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. The variable targeting domain can be at least 12, 13, 14, 15, 16, 17, 18, 19, 20, 21, 22, 23, 24, 25, 26, 27, 28, 29 or 30 nucleotides in length. In some embodiments, the variable targeting domain comprises a contiguous stretch of 12 to 30 nucleotides. The variable targeting domain can be composed of a DNA sequence, a RNA sequence, a modified DNA sequence, a modified RNA sequence, or any combination thereof.

The term “Cas endonuclease recognition domain” or “CER domain” (of a guide polynucleotide) is used interchangeably herein and includes a nucleotide sequence that interacts with a Cas endonuclease polypeptide. A CER domain comprises a tracrNucleotide mate sequence followed by a tracrNucleotide sequence. The CER domain can be composed of a DNA sequence, a RNA sequence, a modified DNA sequence, a modified RNA sequence (see for example US 2015-0059010 A1, published on Feb. 26, 2015, incorporated in its entirety by reference herein), or any combination thereof.

The nucleotide sequence linking the crNucleotide and the tracrNucleotide of a single guide polynucleotide can comprise a RNA sequence, a DNA sequence, or a RNA-DNA combination sequence. In one embodiment, the nucleotide sequence linking the crNucleotide and the tracrNucleotide of a single guide polynucleotide can be at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 78, 79, 80, 81, 82, 83, 84, 85, 86, 87, 88, 89, 90, 91, 92, 93, 94, 95, 96, 97, 98, 99 or 100 nucleotides in length. In another embodiment, the nucleotide sequence linking the crNucleotide and the tracrNucleotide of a single guide polynucleotide can comprise a tetraloop sequence, such as, but not limiting to a GAAA tetraloop sequence.

Nucleotide sequence modification of the guide polynucleotide, VT domain and/or CER domain can be selected from, but not limited to, the group consisting of a 5' cap, a 3' polyadenylated tail, a riboswitch sequence, a stability control sequence, a sequence that forms a dsRNA duplex, a modification or sequence that targets the guide poly nucleotide to a subcellular location, a modification or sequence that provides for tracking, a modification or sequence that provides a binding site for proteins, a Locked Nucleic Acid (LNA), a 5-methyl dC nucleotide, a 2,6-Diaminopurine nucleotide, a 2'-Fluoro A nucleotide, a 2'-Fluoro U nucleotide; a 2'-O-Methyl RNA nucleotide, a phosphorothioate bond, linkage to a cholesterol molecule, linkage to a polyethylene glycol molecule, linkage to a spacer 18 molecule, a 5' to 3' covalent linkage, or any combination thereof. These modifications can result in at least one additional beneficial feature, wherein the additional beneficial feature is selected from the group of a modified or regulated stability, a subcellular targeting, tracking, a fluorescent label, a binding site for a protein or protein complex, modified binding affinity to complementary target sequence, modified resistance to cellular degradation, and increased cellular permeability.

The terms "functional fragment", "fragment that is functionally equivalent" and "functionally equivalent fragment" of a guide RNA, crRNA or tracrRNA are used interchangeably herein, and refer to a portion or subsequence of a guide RNA, crRNA or tracrRNA, respectively, in which the ability to function as a guide RNA, crRNA or tracrRNA, respectively, is retained.

The terms "functional variant", "Variant that is functionally equivalent" and "functionally equivalent variant" of a guide RNA, crRNA or tracrRNA (respectively) are used interchangeably herein, and refer to a variant of the guide RNA, crRNA or tracrRNA, respectively, in which the ability to function as a guide RNA, crRNA or tracrRNA, respectively, is retained.

The terms "single guide RNA", "gRNA" and "sgRNA" are used interchangeably herein and relate to a synthetic fusion of two RNA molecules, a crRNA (CRISPR RNA) comprising a variable targeting domain (linked to a tracr mate sequence that hybridizes to a tracrRNA), fused to a tracrRNA (trans-activating CRISPR RNA). The single guide RNA can comprise a crRNA or crRNA fragment and a tracrRNA or tracrRNA fragment of the type II CRISPR/Cas system that can form a complex with a type II Cas endonuclease, wherein said guide RNA/Cas endonuclease complex can direct the Cas endonuclease to a DNA target site, enabling the Cas endonuclease to recognize, bind to, and optionally nick or cleave (introduce a single or double strand break) the DNA target site.

The terms "guide RNA/Cas endonuclease complex", "guide RNA/Cas endonuclease system", "guide RNA/Cas complex", "guide RNA/Cas system", "gRNA/Cas complex", "gRNA/Cas system", "RNA-guided endonuclease", "RGEN" are used interchangeably herein and refer to at least one RNA component and at least one Cas endonuclease protein that are capable of forming a complex, wherein said guide RNA/Cas endonuclease complex can direct the Cas endonuclease to a DNA target site, enabling the Cas endonuclease to recognize, bind to, and optionally nick or cleave (introduce a single or double strand break) the DNA target site. A guide RNA/Cas endonuclease complex herein can comprise Cas protein(s) and suitable RNA component(s) of any of the known CRISPR systems (Zetsche et al., 2015, Cell 163, 1-13; Shmakov et al., 2015, Molecular_Cell 60, 1-13; Makarova et al. 2015, Nature Reviews Microbiology Vol. 13:1-15; Horvath and Barrangou, Science 327:167-170) such as a type I, II, or III CRISPR system. A guide RNA/Cas endonuclease complex can comprise a Type II Cas9 endonuclease and at least one RNA component (e.g., a crRNA and tracrRNA, or a gRNA). (See also U.S. Patent Application US 2015-0082478 A1, published on Mar. 19, 2015 and US 2015-0059010 A1, published on Feb. 26, 2015, both are hereby incorporated in its entirety by reference).

The Cas endonuclease can be introduced into a cell (provided to a cell) by any method known in the art, for example, but not limited to transient introduction methods, transfection, microinjection, and/or topical application or indirectly via recombination constructs. Plant cells differ from human and animal cells in that plant cells contain a plant cell wall which may act as a barrier to the direct delivery of the Cas9 endonuclease into the plant cell. Recombinant DNA constructs encoding a Cas9 endonuclease have been successfully introduced into plant cells (Svitashev et al., Plant Physiology, 2015, Vol. 169, pp. 931-945) to allow for genome editing at a target site. One possible disadvantage of stably introducing recombinant DNA constructs in plant cells is that the continued presence of Cas9 endonucleases may increase off-target effects.

As described herein, direct delivery of the Cas endonuclease into plant cells can be achieved through particle mediated delivery. Based on the experiments described herein, a skilled artesian can now envision that any other direct method of delivery, such as but not limiting to, polyethylene glycol (PEG)-mediated transfection to protoplasts, whisker mediated delivery, electroporation, particle bombardment, cell-penetrating peptides, or mesoporous silica nanoparticle (MSN)-mediated direct protein delivery can be successfully used for delivering the Cas9 endonuclease in plant cells.

Direct delivery of the Cas endonuclease (also referred to as DNA free delivery off the Cas endonuclease) can be achieved by introducing the Cas protein, the mRNA encoding the Cas endonuclease, and/or the RNA guided endonuclease ribonucleotide-protein complex (RGEN) itself (as a ribonucleotide-protein complex), into a cell using any method known in the art. Direct delivery of the Cas endonuclease, either via mRNA encoding the Cas endonuclease or via a polypeptide molecule is also referred to herein as DNA free delivery of the Cas endonuclease, as no DNA molecule is involved in the production of the Cas endonuclease protein. Similarly, direct delivery of the guide RNA as an RNA molecule is also referred to herein as DNA free delivery of the guide RNA. Similarly, direct delivery of the guide RNA/endonuclease complex itself (RGEN) as a ribonucleotide-protein complex, is also referred to herein as DNA free delivery of the RGEN.

Directly introducing the Cas endonuclease as a protein, or as an mRNA molecule together with a gRNA, or as a RGEN ribonucleotide-protein itself, allows for genome editing at the target site followed by rapid degradation of the RGEN complex, and only a transient presence of the complex in the cell which leads to reduced off-target effects (as described in Example 12).

Direct delivery of these components can be accompanied by direct delivery (co-delivery) of other mRNAs that can promote the enrichment and/or visualization of cells receiving the RGEN components. For example, delivery of mRNAs encoding screenable visual markers such as fluorescence proteins (for example but not limited to Red, green, yellow, blue or combinations thereof) can also be used in lieu of, or coupled with, direct selection of a repaired disrupted, non-functional gene product.

Described herein are methods to restore the function of a non-functional gene product by restoring the nucleotide sequence of a disrupted gene such that the restored nucleotide sequence encodes the functional gene product.

A disrupted gene refers to a gene that has been modified (disrupted) such that its gene product loses its function (referred to as a non-functional gene product) or has a reduced function when compared to the product of the corresponding gene that does not have the disruption (also referred to as the undisrupted gene). For example, a gene encoding for a functional polypeptide or protein can be disrupted (modified) such that the translation product of the disrupted gene results in a polypeptide that has lost its function or has a reduced function.

A functional gene product includes a functional protein or polypeptide that has a biological or non-biological function.

A non-functional gene product includes reference to the gene product of a disrupted gene. The non-functional gene product includes polypeptides that have lost their function (absent function) or have a reduced function when compared to the gene product of the corresponding undisrupted gene.

Coincident with the restoration of gene function by NHEJ (through for example delivery of RGEN components or the RGEN complex itself to a cell), modification of other targets can be accomplished by the simultaneous addition of other guide-polynucleotides. Such other targets (other than the target for restoration of gene function by NHEJ) can be any target in the genome including a transgenic locus. The approach of simultaneous delivery of two or more gRNAs when one gRNA targets and activates a selectable marker through NHEJ, (such as but not limiting to conferring herbicide tolerance) and the other gRNA(s) promote DSB(s) at target site(s) different than the selectable marker (or other disrupted gene design) and can facilitate either targeted mutagenesis, deletion, gene editing, or site-specific trait gene insertions can allow for completely transient targeted genome modifications as all other necessary components (Cas9, gRNAs) can be delivered in a form of protein and/or in vitro transcribed RNA molecules.

A disrupted gene includes reference to a marker gene (such as, but not limited to, a phenotypic marker gene and a selectable marker gene) that has been modified (disrupted) such that its gene product loses its function (for example, in case of a herbicide disrupted selectable marker gene, the disrupted gene does not confer herbicide resistance anymore).

A selectable marker and screenable marker are used interchangeably herein and includes reference to a DNA segment (such as a selectable marker gene) that allows one to identify, or select for or against a molecule or a cell that contains it, often under particular conditions. These markers can encode an activity, such as, but not limited to, production of RNA, peptide, or protein, or can provide a binding site for RNA, peptides, proteins, inorganic and organic compounds or compositions and the like. A selectable marker further includes a gene that when modified or knocked-out generates a property in a cell that allows one to identify, or select for (or against) a cell that contains said property.

In one aspect, the selectable marker allows for the selection of cells by applying selection schemes, in which for example, a selective agent (such as, but not limited to an antibiotic or herbicide) is used to inhibit or kill cells or tissues that do not comprise the selectable marker, and the cells or tissues that comprise the selectable marker continue to grow due to expression of the selectable marker gene.

In one aspect, the selectable marker allows for the visual selection of cells by applying selection schemes, in which for example, a visible marker (such as a fluorescent molecule) is used to select cells that comprise the visible marker.

Selectable marker genes include, but are not limited to, chlorosulfuron resistance genes, phosphomannose isomerase genes (PMI), bialaphos resistance genes (BAR), phosphinothricin acetyltransferase (PAT) genes, hygromycin resistance genes (NPTII), glyphosate resistance genes, DNA segments that comprise restriction enzyme sites; DNA segments that encode products which provide resistance against otherwise toxic compounds including antibiotics, such as, spectinomycin, ampicillin, kanamycin, tetracycline, Basta, neomycin phosphotransferase II (NEO) and hygromycin phosphotransferase (HPT)); DNA segments that encode products which are otherwise lacking in the recipient cell (e.g., tRNA genes, auxotrophic markers); DNA segments that encode products which can be readily identified (referred to as visible marker genes). Visible marker genes include reference to fluorescent markers genes (such as red fluorescent marker genes, blue fluorescent marker genes, green fluorescent marker genes, yellow fluorescent marker genes), genes encoding DsRED, RFP, red fluorescent protein, CFP, GFP, green fluorescent protein) and genes encoding phenotypic markers such as β-galactosidase, GUS; fluorescent proteins such as green fluorescent protein (GFP), cyan (CFP), yellow (YFP), red (RFP), and cell surface proteins. Selectable marker genes further include the generation of new primer sites for PCR (e.g., the juxtaposition of two DNA sequence not previously juxtaposed), the inclusion of DNA sequences not acted upon or acted upon by a restriction endonuclease or other DNA modifying enzyme, chemical, etc.; and, the inclusion of a DNA sequences required for a specific modification (e.g., methylation) that allows its identification.

Additional selectable markers include genes that confer resistance to herbicidal compounds, such as glufosinate ammonium, bromoxynil, imidazolinones, and 2,4-dichlorophenoxyacetate (2,4-D). See for example, Yarranton, (1992) Curr Opin Biotech 3:506-11; Christopherson et al., (1992) Proc. Natl. Acad. Sci. USA 89:6314-8; Yao et al., (1992) Cell 71:63-72; Reznikoff, (1992) Mol Microbiol 6:2419-22; Hu et al., (1987) Cell 48:555-66; Brown et al., (1987) Cell 49:603-12; Figge et al., (1988) Cell 52:713-22; Deuschle et al., (1989) Proc. Natl. Acad. Sci. USA 86:5400-4; Fuerst et al., (1989) Proc. Natl. Acad. Sci. USA 86:2549-53; Deuschle et al., (1990) Science 248:480-3; Gossen, (1993) Ph.D. Thesis, University of Heidelberg; Reines et al., (1993) Proc. Natl. Acad. Sci. USA 90:1917-21; Labow et al., (1990) Mol Cell Biol 10:3343-56; Zambretti et al., (1992) Proc. Natl. Acad. Sci. USA 89:3952-6; Baim et al., (1991) Proc. Natl. Acad. Sci. USA 88:5072-6; Wyborski et al., (1991) Nucleic Acids Res 19:4647-53; Hillen and Wissman, (1989) Topics Mol Struc Biol 10:143-62; Degenkolb et al., (1991) Antimicrob Agents Chemother 35:1591-5; Kleinschnidt et al., (1988) Biochemistry 27:1094-104; Bonin, (1993) Ph.D. Thesis, University of Heidelberg; Gossen et al., (1992) Proc.

Natl. Acad. Sci. USA 89:5547-51; Oliva et al., (1992) Antimicrob Agents Chemother 36:913-9; Hlavka et al., (1985) Handbook of Experimental Pharmacology, Vol. 78 (Springer-Verlag, Berlin); Gill et al., (1988) Nature 334:721-4. J. Bacteriol. 170:5837-5847) facilitate expression of polyhyroxyalkanoates (PHAs).

Phenotypic marker genes include genes encoding a screenable or selectable marker that includes visual markers, whether it is a positive or negative selectable marker. Any phenotypic marker can be used.

As described herein, a phenotypic and selectable marker gene can be modified to be introduced into plant cells as a disrupted gene encoding a non-functional gene product and used as targets by double strand break inducing endonucleases for restoration back to the non-disrupted gene encoding a functional gene product, by guide RNA introduction and DNA repair.

Phenotypic or selectable marker genes to be disrupted can be marker genes that were previously introduced into the cell and are stably incorporated into the genome of the cell. Such pre-integrated selectable marker genes can also be complemented with other genes, for example, cell developmental enhancing genes (ZmODP2 and ZmWUS, see for example PCT/US16/49144, filed Aug. 26, 2016 and PCT/US16/49128 filed Aug. 26, 2016, incorporated herein by reference).

One skilled in the art can appreciate that conventional genome modification methods have relied predominantly on introducing selectable marker genes into the cells to be modified to allow for selection schemes, in which for example an antibiotic or herbicide (a selective agent) is used to inhibit or kill cells or tissues that do not comprise the selectable marker gene, and the cells or tissues that comprise the selectable marker gene continue to grow due to expression of the selectable marker (resistance) gene. In contrast, the methods of the present disclosure can be used without the use of a selectable marker and with no application of a selective agent.

In one embodiment of the disclosure, the method comprises a method for introducing into at least one plant cell a guide polynucleotide Cas endonuclease complex capable of making a double strand break in a target site located in a nucleotide sequence; and, selecting a plant cell having a modification in said nucleotide sequence, wherein the selection occurs without the use of a selectable marker. The guide polynucleotide/Cas endonuclease complex can be a guide RNA/Cas endonuclease complex.

In one embodiment of the disclosure, the method comprises a method for producing a plant having a modified nucleotide sequence in its genome without the use of a selectable marker, the method comprising: introducing into at least one plant cell a guide polynucleotide/Cas endonuclease complex capable of making a double strand break in a target site located in a nucleotide sequence; obtaining a plant from said plant cell; and, selecting a plant having a modification in said nucleotide sequence, wherein the selection occurs without the use of a selectable marker. The guide polynucleotide/Cas endonuclease complex can be a guide RNA/Cas endonuclease complex.

In one embodiment of the disclosure, the method comprises a method for producing plant callus tissue having a modified nucleotide sequence in its genome without the use of a selectable marker, the method comprising: introducing into at least one plant cell a guide polynucleotide/Cas endonuclease complex capable of making a double strand break in a target site located in a nucleotide sequence; obtaining callus tissue from said plant cell; selecting callus tissue having a modification in said nucleotide sequence, wherein the selection occurs without the use of a selectable marker. The guide polynucleotide/Cas endonuclease complex can be a guide RNA/Cas endonuclease complex.

The selection step in the methods described herein can include any selection (identification, obtaining) known to one skilled in the art that is not based on the use of a selectable marker, such as for example selecting a plant cell, callus or plant comprising the desired modification in its genome by genotypic means (such as but not limiting to DNA sequencing) or phenotypic means (such as plant morphological characteristics or selectable phenotype relating to the desired modification in its genome.

In one aspect, the method comprises a method for modifying a nucleotide sequence in the genome of a plant cell without the use of a selectable marker, the method comprising: introducing into at least one plant cell a guide RNA/Cas endonuclease complex capable of making a double strand break in a target site located in said nucleotide sequence, wherein the guide RNA/Cas endonuclease complex is introduced into the cell without the use of recombinant DNA constructs; obtaining a plant from the plant cel of (a); and, selecting a plant having a modification in said nucleotide sequence, wherein the selection occurs via sequencing of the DNA of said plant.

The methods described herein can further comprise introducing a polynucleotide template, wherein said polynucleotide modification template comprises at least one nucleotide modification of a nucleotide sequence in the genome of said cell, wherein said at least one nucleotide modification of said polynucleotide modification template is selected from the group consisting of (i) a replacement of at least one nucleotide, (ii) a deletion of at least one nucleotide, (iii) an insertion of at least one nucleotide, and (iv) any combination of (i)-(iii). The method can also further comprise introducing a donor DNA, wherein said donor DNA comprises at least one polynucleotide of interest. The introduction of the guide polynucleotide/Cas endonuclease complex into the cell can be via a delivery system selected from the group consisting of particle mediated delivery, whisker mediated delivery, cell-penetrating peptide mediated delivery, electroporation, PEP-mediated transfection and nanoparticle mediated delivery.

The methods of the present disclosure can be used without the use of a phenotypic or selectable marker and with no application of a selective agent. The methods include the introduction into a plant cell of a guide RNA/Cas endonuclease complex without also introducing a selectable marker into said plant cell, or wherein the introducing of said guide RNA/Cas endonuclease complex is not accompanied by the restoration of a disrupted selectable marker gene into a non-disrupted selectable marker gene encoding a functional selectable marker protein, or wherein the introducing of said guide RNA/Cas endonuclease complex does not result in the production of a selectable marker within said cell. The methods include selecting a plant cell, callus tissue or plant comprising a modified nucleotide sequence in its genome, wherein the selection occurs without the use of a selectable marker.

Any guided endonuclease can be used in the methods disclosed herein. Such endonucleases include, but are not limited to Cas and Cpf1 endonucleases. Many endonucleases have been described to date that can recognize specific PAM sequences (see for example—U.S. patent applications 62/162,377 filed May 15, 2015 and 62/162,353 filed May 15, 2015 and Zetsche B et al. 2015. Cell 163, 1013) and cleave the target DNA at a specific positions. It is understood that based on the methods and embodiments described herein utilizing a guided Cas system one can now tailor these methods such that they can utilize any guided endonuclease system. For example, one can envision adapting the method for modifying a nucleotide sequence in the genome of a plant cell without the use of a selectable marker, described herein to a method comprising introducing a guided Cpf1 endonuclease complex instead of a guided Cas endonuclease complex. Other guided endonucleases and nucleotide-protein complexes that find use in the methods disclosed herein include those described in WO 2013/088446.

Endonucleases are enzymes that cleave the phosphodiester bond within a polynucleotide chain, and include restriction endonucleases that cleave DNA at specific sites without damaging the bases. Restriction endonucleases include Type I, Type II, Type III, and Type IV endonucleases, which further include subtypes. In the Type I and Type III systems, both the methylase and restriction activities are contained in a single complex. Endonucleases also include meganucleases, also known as homing endonucleases (HEases), which like restriction endonucleases, bind and cut at a specific recognition site, however the recognition sites for meganucleases are typically longer, about 18 bp or more (patent application PCT/US12/30061, filed on Mar. 22, 2012). Meganucleases have been classified into four families based on conserved sequence motifs, the families are the LAGLIDADG, GIY-YIG, H—N—H, and His-Cys box families. These motifs participate in the coordination of metal ions and hydrolysis of phosphodiester bonds. HEases are notable for their long recognition sites, and for tolerating some sequence polymorphisms in their DNA substrates. The naming convention for meganuclease is similar to the convention for other restriction endonuclease. Meganucleases are also characterized by prefix F—, I—, or PI— for enzymes encoded by free-standing ORFs, introns, and inteins, respectively. One step in the recombination process involves polynucleotide cleavage at or near the recognition site. This cleaving activity can be used to produce a double-strand break. For reviews of site-specific recombinases and their recognition sites, see, Sauer (1994) Curr Op Biotechnol 5:521-7; and Sadowski (1993) FASEB 7:760-7. In some examples the recombinase is from the Integrase or Resolvase families.

TAL effector nucleases are a new class of sequence-specific nucleases that can be used to make double-strand breaks at specific target sequences in the genome of a plant or other organism. (Miller et al. (2011) *Nature Biotechnology* 29:143-148). Zinc finger nucleases (ZFNs) are engineered double-strand break inducing agents comprised of a zinc finger DNA binding domain and a double-strand-break-inducing agent domain. Recognition site specificity is conferred by the zinc finger domain, which typically comprising two, three, or four zinc fingers, for example having a C2H2 structure, however other zinc finger structures are known and have been engineered. Zinc finger domains are amenable for designing polypeptides which specifically bind a selected polynucleotide recognition sequence. ZFNs include an engineered DNA-binding zinc finger domain linked to a non-specific endonuclease domain, for example nuclease domain from a Type IIs endonuclease such as FokI. Additional functionalities can be fused to the zinc-finger binding domain, including transcriptional activator domains, transcription repressor domains, and methylases. In some examples, dimerization of nuclease domain is required for cleavage activity. Each zinc finger recognizes three consecutive base pairs in the target DNA. For example, a 3 finger domain recognized a sequence of 9 contiguous nucleotides, with a dimerization requirement of the nuclease, two sets of zinc finger triplets are used to bind an 18 nucleotide recognition sequence.

DNA double strand break (DSB) technologies (ZFNs, TALENs and CRISPR-Cas) have wide-ranging applications in academic research, gene therapy, and animal and plant breeding programs. These technologies have been successfully used to introduce genome modifications in multiple plant species, including major crops such as maize, wheat, soybean and rice. Plant genome editing is limited by current transformation and gene modification methods, efficiency of DNA delivery, and low frequencies of plant regeneration. In contrast to human and animal systems, the presence of a thick wall surrounding every plant cell fundamentally impacts plant transformation and plant gene modification protocols. This cell wall makes it impossible to use transfection or electroporation, which are broadly used for nucleic acid and/or protein delivery in mammalian genome editing experiments. For this reason, plant transformation and plant genome modification primarily relies on *Agrobacterium*-mediated and biolistic delivery (ballistic delivery) of guide RNA/Cas endonuclease reagents on DNA vectors. As a result, gRNA and Cas9 expression cassettes frequently integrate into the genome and potentially lead to gene disruption, plant mosaicism, and potential off-site cutting. Although these undesired secondary changes can be segregated away by several rounds of backcrossing to the wild type parent plant, this process can be time consuming especially for crops with complex polyploid genomes and long breeding cycles such as, but not limited to, soybean and wheat. As described herein, delivery of Cas endonuclease and gRNAs in the form of RGEN complexes into plant cells can mitigate many of these side effects (Example 11-12). An unexpected high frequency of NHEJ-mediated mutagenesis facilitated by delivery of RGEN complexes in plants is described in Example 10. Given this high frequency of mutagenesis using a RGEN complex, DNA-free and selectable marker-free gene modification may become a practical approach to generate gene knock-outs. This DNA- and selectable marker-free approach might be less practical for gene editing and gene insertion (as compared to gene mutations by NHEJ) applications due to the low frequency of the HDR pathway in somatic plant cells. Moreover, DNA molecules often integrate into the targeted DSB sites, decreasing the efficiency of gene editing, and especially, gene insertion. It has been demonstrated that DNA vectors encoding for genes delivered into the plant cell (for example, Cas9, gRNA, selectable marker genes and trait gene) have tendency to co-integrate into the same DSB site dramatically reducing frequency of usable events with site-specific trait gene insertions. Limiting delivered DNA molecules to donor DNA (for example, trait gene with homology arms) can increase the probability of events with desirable genotype. Therefore, the concept, described herein, of disrupted (inactive) endogenous or pre-integrated selectable marker genes that can be activated upon RGEN delivery, can make the DNA- and selectable marker-free approach for gene editing and gene insertion become very practical The guide polynucleotide can be introduced into a cell directly, as single stranded polynucleotide or a double stranded polynucleotide, using any method known in the art such as, but not limited to, particle bombardment, whiskers mediated transformation, *Agrobacterium* transformation or topical applications. The guide RNA can also be introduced indirectly into a cell by introducing a recombinant DNA molecule (via methods such as, but not limited to, particle bombardment or *Agrobacterium* transformation) comprising a heterologous nucleic acid fragment encoding a guide RNA, operably linked to a specific promoter that is capable of transcribing the guide RNA in said cell. The specific promoter can be, but is not limited to, a RNA polymerase III promoter, which allow for transcription of RNA with precisely defined, unmodified, 5'- and 3'-ends (DiCarlo et al., Nucleic Acids Res. 41: 4336-4343; Ma et al., Mol. Ther. Nucleic Acids 3:e161). As described herein, direct delivery of a sgRNA into plant cells can be achieved through particle mediated delivery. Based on the experiments described herein, a skilled artesian can now envision that any other direct method of delivery, such as but not limiting to, polyethylene glycol (PEG)-mediated transfection to protoplasts, whiskers mediated transformation, electroporation, particle bombardment, cell-penetrating peptides, or mesoporous silica nanoparticle (MSN)-mediated direct protein delivery can be successfully used for delivering gRNA in plant cells.

The guide polynucleotide can be produced by any method known in the art, including chemically synthesizing guide polynucleotides (such as but not limiting to Hendel et al. 2015, Nature Biotechnology 33, 985-989), in vitro generated guide polynucleotides, and/or self-splicing guide RNAs (such as but not limiting to Xie et al. 2015, PNAS 112: 3570-3575).

The terms "target site", "target sequence", "target site sequence, "target DNA", "target locus", "genomic target site", "genomic target sequence", "genomic target locus" and "protospacer", are used interchangeably herein and refer to a polynucleotide sequence such as, but not limited to, a nucleotide sequence on a chromosome, episome, a transgenic locus, or any other DNA molecule in the genome (including chromosomal, choloroplastic, mitochondrial DNA, plasmid DNA) of a cell, at which a guide polynucleotide/Cas endonuclease complex can recognize, bind to, and optionally nick or cleave. The target site can be an endogenous site in the genome of a cell, or alternatively, the target site can be heterologous to the cell and thereby not be naturally occurring in the genome of the cell, or the target site can be found in a heterologous genomic location compared to where it occurs in nature. As used herein, terms "endogenous target sequence" and "native target sequence" are used interchangeable herein to refer to a target sequence that is endogenous or native to the genome of a cell and is at the endogenous or native position of that target sequence in the genome of the cell. Cells include, but are not limited to, human, non-human, animal, bacterial, fungal, insect, yeast, non-conventional yeast, and plant cells as well as plants and seeds produced by the methods described herein. An "artificial target site" or "artificial target sequence" are used interchangeably herein and refer to a target sequence that has been introduced into the genome of a cell. Such an artificial target sequence can be identical in sequence to an endogenous or native target sequence in the genome of a cell but be located in a different position (i.e., a non-endogenous or non-native position) in the genome of a cell.

An "altered target site", "altered target sequence", "modified target site", "modified target sequence" are used interchangeably herein and refer to a target sequence as disclosed herein that comprises at least one alteration when compared to non-altered target sequence. Such "alterations" include, for example: (i) replacement of at least one nucleotide, (ii) a deletion of at least one nucleotide, (iii) an insertion of at least one nucleotide, or (iv) any combination of (i)-(iii).

The length of the target DNA sequence (target site) can vary, and includes, for example, target sites that are at least 12, 13, 14, 15, 16, 17, 18, 19, 20, 21, 22, 23, 24, 25, 26, 27, 28, 29, 30 or more nucleotides in length. It is further possible that the target site can be palindromic, that is, the sequence on one strand reads the same in the opposite direction on the complementary strand. The nick/cleavage site can be within the target sequence or the nick/cleavage site could be outside of the target sequence. In another variation, the cleavage could occur at nucleotide positions immediately opposite each other to produce a blunt end cut or, in other Cases, the incisions could be staggered to produce single-stranded overhangs, also called "sticky ends", which can be either 5' overhangs, or 3' overhangs. Active variants of genomic target sites can also be used. Such active variants can comprise at least 65%, 70%, 75%, 80%, 85%, 90%, 91%, 92%, 93%, 94%, 95%, 96%, 97%, 98%, 99% or more sequence identity to the given target site, wherein the active variants retain biological activity and hence are capable of being recognized and cleaved by an Cas endonuclease. Assays to measure the single or double-strand break of a target site by an endonuclease are known in the art and generally measure the overall activity and specificity of the agent on DNA substrates containing recognition sites.

A "protospacer adjacent motif" (PAM) herein refers to a short nucleotide sequence adjacent to a target sequence (protospacer) that is recognized (targeted) by a guide polynucleotide/Cas endonuclease system. The Cas endonuclease may not successfully recognize a target DNA sequence if the target DNA sequence is not followed by a PAM sequence. The sequence and length of a PAM herein can differ depending on the Cas protein or Cas protein complex used. The PAM sequence can be of any length but is typically 1, 2, 3, 4, 5, 6, 7, 8, 9, 10, 11, 12, 13, 14, 15, 16, 17, 18, 19 or 20 nucleotides long.

The terms "targeting", "gene targeting" and "DNA targeting" are used interchangeably herein. DNA targeting herein may be the specific introduction of a knock-out, edit, or knock-in at a particular DNA sequence, such as in a chromosome or plasmid of a cell. In general, DNA targeting can be performed herein by cleaving one or both strands at a specific DNA sequence in a cell with a Cas protein associated with a suitable polynucleotide component. Such DNA cleavage, if a double-strand break (DSB), can prompt NHEJ or HDR processes which can lead to modifications at the target site.

The terms "knock-out", "gene knock-out" and "genetic knock-out" are used interchangeably herein. A knock-out represents a DNA sequence of a cell that has been rendered partially or completely inoperative by targeting with a Cas protein, such a DNA sequence prior to knock-out could have encoded an amino acid sequence, or could have had a regulatory function (e.g., promoter), for example. A knock-out may be produced by an indel (insertion or deletion of nucleotide bases in a target DNA sequence through NHEJ), or by specific removal of sequence that reduces or completely destroys the function of sequence at or near the targeting site.

The guide polynucleotide/Cas endonuclease system can be used in combination with a co-delivered polynucleotide modification template to allow for editing (modification) of a genomic nucleotide sequence of interest. (See also U.S. Patent Application US 2015-0082478 A1, published on Mar. 19, 2015 and WO2015/026886 A1, published on Feb. 26, 2015, both are hereby incorporated in its entirety by reference.)

A "modified nucleotide" or "edited nucleotide" refers to a nucleotide sequence of interest that comprises at least one alteration when compared to its non-modified nucleotide sequence. Such "alterations" include, for example: (i) replacement of at least one nucleotide, (ii) a deletion of at least one nucleotide, (iii) an insertion of at least one nucleotide, or (iv) any combination of (i)-(iii).

The term "polynucleotide modification template" includes a polynucleotide that comprises at least one nucleotide modification when compared to the nucleotide sequence to be edited. A nucleotide modification can be at least one nucleotide substitution, addition or deletion. Optionally, the polynucleotide modification template can further comprise homologous nucleotide sequences flanking the at least one nucleotide modification, wherein the flanking homologous nucleotide sequences provide sufficient homology to the desired nucleotide sequence to be edited.

A polynucleotide modification template can be introduced into a cell by any method known in the art, such as, but not limited to, transient introduction methods, transfection, electroporation, microinjection, particle mediated delivery, topical application, whiskers mediated delivery, delivery via cell-penetrating peptides, or mesoporous silica nanoparticle (MSN)-mediated direct delivery.

The polynucleotide modification template can be introduced into a cell as a single stranded polynucleotide molecule, a double stranded polynucleotide molecule, or as part of a circular DNA (vector DNA). The polynucleotide modification template can also be tethered to the guide RNA and/or the Cas endonuclease. Tethered DNAs can allow for co-localizing target and template DNA, useful in genome editing and targeted genome regulation, and can also be useful in targeting post-mitotic cells where function of endogenous HR machinery is expected to be highly diminished (Mali et al. 2013 Nature Methods Vol. 10: 957-963.) The polynucleotide modification template may be present transiently in the cell or it can be introduced via a viral replicon.

The nucleotide to be edited can be located within or outside a target site recognized and cleaved by a Cas endonuclease. In one embodiment, the at least one nucleotide modification is not a modification at a target site recognized and cleaved by a Cas endonuclease. In another embodiment, there are at least 1, 2, 3, 4, 5, 6, 7, 8, 9, 10, 11, 12, 13, 14, 15, 16, 17, 18, 19, 20, 21, 22, 23, 24, 25, 26, 27, 30, 40, 50, 100, 200, 300, 400, 500, 600, 700, 900 or 1000 nucleotides between the at least one nucleotide to be edited and the genomic target site.

Genome editing can be accomplished using any method of gene editing available. For example, gene editing can be accomplished through the introduction into a host cell of a polynucleotide modification template (sometimes also referred to as a gene repair oligonucleotide) containing a targeted modification to a gene within the genome of the host cell. The polynucleotide modification template for use in such methods can be either single-stranded or double-stranded. Examples of such methods are generally described, for example, in US Publication No. 2013/0019349.

Based on the experiments described herein, a skilled artesian can now envision that any other direct method of delivery, such as but not limiting to, polyethylene glycol (PEG)-mediated transfection to protoplasts, whiskers mediated transformation, electroporation, particle bombardment, cell-penetrating peptides, or mesoporous silica nanoparticle (MSN)-mediated direct protein delivery can be successfully used for delivering a polynucleotide modification template in plant cells.

In some embodiments, gene editing may be facilitated through the induction of a double-stranded break (DSB) in a defined position in the genome near the desired alteration. DSBs can be induced using any DSB-inducing agent available, including, but not limited to, TALENs, meganucleases, zinc finger nucleases, nucleic acid guided-endonuclease systems, e.g. Cas9-gRNA systems (based on bacterial CRISPR-Cas systems), and the like. In some embodiments, the introduction of a DSB can be combined with the introduction of a polynucleotide modification template.

The process for editing a genomic sequence combining DSB and modification templates generally comprises: introducing to a host cell, a DSB-inducing agent, or a nucleic acid encoding a DSB-inducing agent, that recognizes a target sequence in the chromosomal sequence and is able to induce a DSB in the genomic sequence, and at least one polynucleotide modification template comprising at least one nucleotide alteration when compared to the nucleotide sequence to be edited. The polynucleotide modification template can further comprise nucleotide sequences flanking the at least one nucleotide alteration, in which the flanking sequences are substantially homologous to the chromosomal region flanking the DSB. Genome editing using DSB-inducing agents, such as Cas9-gRNA complexes, has been described, for example in U.S. Patent Application US 2015-0082478 A1, published on Mar. 19, 2015, WO2015/026886 A1, published on Feb. 26, 2015, U.S. application 62/023,246, filed on Jul. 7, 2014, and U.S. application 62/036,652, filed on Aug. 13, 2014, all of which are incorporated by reference herein.

The terms "knock-in", "gene knock-in, "gene insertion" and "genetic knock-in" are used interchangeably herein. A knock-in represents the replacement or insertion of a DNA sequence at a specific DNA sequence in a cell by targeting with a Cas protein (by HR, wherein a suitable donor DNA polynucleotide is also used). Examples of knock-ins are a specific insertion of a heterologous amino acid coding sequence in a coding region of a gene, or a specific insertion of a transcriptional regulatory element in a genetic locus.

Various methods and compositions can be employed to obtain a cell or organism having a polynucleotide of interest inserted in a target site for a Cas endonuclease. Such methods can employ homologous recombination to provide integration of the polynucleotide of Interest at the target site. In one method provided, a polynucleotide of interest is provided to the organism cell in a donor DNA construct.

As used herein, "donor DNA" includes reference to a DNA construct that comprises a polynucleotide of interest to be inserted into the target site of a Cas endonuclease. The donor DNA construct can further comprise a first and a second region of homology that flank the polynucleotide of Interest. The first and second regions of homology of the donor DNA share homology to a first and a second genomic region, respectively, present in or flanking the target site of the cell or organism genome. The donor DNA can be tethered to the guide polynucleotide and /or the Cas endonuclease. Tethered donor DNAs can allow for co-localizing target and donor DNA, useful in genome editing and targeted genome regulation, and can also be useful in targeting post-mitotic cells where function of endogenous HR machinery is expected to be highly diminished (Mali et al. 2013 Nature Methods Vol. 10: 957-963.)

By "homology" is meant DNA sequences that are similar. For example, a "region of homology to a genomic region" that is found on the donor DNA is a region of DNA that has a similar sequence to a given "genomic region" in the cell or organism genome. A region of homology can be of any length that is sufficient to promote homologous recombination at the cleaved target site. For example, the region of homology can comprise at least 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 5-100, 5-200, 5-300, 5-400, 5-500, 5-600, 5-700, 5-800, 5-900, 5-1000, 5-1100, 5-1200, 5-1300, 5-1400, 5-1500, 5-1600, 5-1700, 5-1800, 5-1900, 5-2000, 5-2100, 5-2200, 5-2300, 5-2400, 5-2500, 5-2600, 5-2700, 5-2800, 5-2900, 5-3000, 5-3100 or more bases in length such that the region of homology has sufficient homology to undergo homologous recombination with the corresponding genomic region. "Sufficient homology" indicates that two polynucleotide sequences have sufficient structural similarity to act as substrates for a homologous recombination reaction. The structural similarity includes overall length of each polynucleotide fragment, as well as the sequence similarity of the polynucleotides. Sequence similarity can be described by the percent sequence identity over the whole length of the sequences, and/or by conserved regions comprising localized similarities such as contiguous nucleotides having 100% sequence identity, and percent sequence identity over a portion of the length of the sequences.

The amount of homology or sequence identity shared by a target and a donor polynucleotide can vary and includes total lengths and/or regions having unit integral values in the ranges of about 1-20 bp, 20-50 bp, 50-100 bp, 75-150 bp, 100-250 bp, 150-300 bp, 200-400 bp, 250-500 bp, 300-600 bp, 350-750 bp, 400-800 bp, 450-900 bp, 500-1000 bp, 600-1250 bp, 700-1500 bp, 800-1750 bp, 900-2000 bp, 1-2.5 kb, 1.5-3 kb, 2-4 kb, 2.5-5 kb, 3-6 kb, 3.5-7 kb, 4-8 kb, 5-10 kb, or up to and including the total length of the target site. These ranges include every integer within the range, for example, the range of 1-20 bp includes 1, 2, 3, 4, 5, 6, 7, 8, 9, 10, 11, 12, 13, 14, 15, 16, 17, 18, 19 and 20 bps. The amount of homology can also described by percent sequence identity over the full aligned length of the two polynucleotides which includes percent sequence identity of about at least 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. Sufficient homology includes any combination of polynucleotide length, global percent sequence identity, and optionally conserved regions of contiguous nucleotides or local percent sequence identity, for example sufficient homology can be described as a region of 75-150 bp having at least 80% sequence identity to a region of the target locus. Sufficient homology can also be described by the predicted ability of two polynucleotides to specifically hybridize under high stringency conditions, see, for example, Sambrook et al., (1989) *Molecular Cloning: A Laboratory Manual*, (Cold Spring Harbor Laboratory Press, NY); *Current Protocols in Molecular Biology*, Ausubel et al., Eds (1994) Current Protocols, (Greene Publishing Associates, Inc. and John Wiley & Sons, Inc.); and, Tijssen (1993) *Laboratory Techniques in Biochemistry and Molecular Biology—Hybridization with Nucleic Acid Probes*, (Elsevier, New York).

As used herein, a "genomic region" is a segment of a chromosome in the genome of a cell that is present on either side of the target site or, alternatively, also comprises a portion of the target site. The genomic region can comprise at least 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 5-100, 5-200, 5-300, 5-400, 5-500, 5-600, 5-700, 5-800, 5-900, 5-1000, 5-1100, 5-1200, 5-1300, 5-1400, 5-1500, 5-1600, 5-1700, 5-1800, 5-1900, 5-2000, 5-2100, 5-2200, 5-2300, 5-2400, 5-2500, 5-2600, 5-2700, 5-2800. 5-2900, 5-3000, 5-3100 or more bases such that the genomic region has sufficient homology to undergo homologous recombination with the corresponding region of homology.

Polynucleotides of interest and/or traits can be stacked together in a complex trait locus as described in US-2013-0263324-A1, published 3 Oct. 2013 and in PCT/US13/22891, published Jan. 24, 2013, both applications are hereby incorporated by reference. The guide polynucleotide/Cas9 endonuclease system described herein provides for an efficient system to generate double strand breaks and allows for traits to be stacked in a complex trait locus.

The guide polynucleotide/Cas endonuclease system can be used for introducing one or more polynucleotides of interest or one or more traits of interest into one or more target sites by introducing one or more guide polynucleotides, one Cas endonuclease, and optionally one or more donor DNAs to a plant cell. ((as described in US patent application US-2015-0082478-A1, published on Mar. 19, 2015, incorporated by reference herein). A fertile plant can be produced from that plant cell that comprises an alteration at said one or more target sites, wherein the alteration is selected from the group consisting of (i) replacement of at least one nucleotide, (ii) a deletion of at least one nucleotide, (iii) an insertion of at least one nucleotide, and (iv) any combination of (i)-(iii). Plants comprising these altered target sites can be crossed with plants comprising at least one gene or trait of interest in the same complex trait locus, thereby further stacking traits in said complex trait locus. (see also US-2013-0263324-A1, published Oct. 3, 2013 and in PCT/US13/22891, published Jan. 24, 2013, incorporated by reference herein).

The structural similarity between a given genomic region and the corresponding region of homology found on the donor DNA can be any degree of sequence identity that allows for homologous recombination to occur. For example, the amount of homology or sequence identity shared by the "region of homology" of the donor DNA and the "genomic region" of the organism genome can be at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, such that the sequences undergo homologous recombination The region of homology on the donor DNA can have homology to any sequence flanking the target site. While in some embodiments the regions of homology share significant sequence homology to the genomic sequence immediately flanking the target site, it is recognized that the regions of homology can be designed to have sufficient homology to regions that may be further 5' or 3' to the target site. In still other embodiments, the regions of homology can also have homology with a fragment of the target site along with downstream genomic regions. In one embodiment, the first region of homology further comprises a first fragment of the target site and the second region of homology comprises a second fragment of the target site, wherein the first and second fragments are dissimilar.

Once a double-strand break is induced in the DNA, the cell's DNA repair mechanism is activated to repair the break. The Non-Homologous-End-Joining (NHEJ) pathways are the most common repair mechanism to bring the broken ends together (Bleuyard et al., (2006) DNA Repair 5:1-12). The structural integrity of chromosomes is typically preserved by the repair, but deletions, insertions, or other rearrangements are possible. The two ends of one double-strand break are the most prevalent substrates of NHEJ (Kirik et al., (2000) EMBO J 19:5562-6), however if two different double-strand breaks occur, the free ends from different breaks can be ligated and result in chromosomal deletions (Siebert and Puchta, (2002) Plant Cell 14:1121-31), or chromosomal translocations between different chromosomes (Pacher et al., (2007) Genetics 175:21-9). Error-prone DNA repair mechanisms can produce mutations at double-strand break sites. The Non-Homologous-End-Joining (NHEJ) pathways are the most common repair mechanism to bring the broken ends together (Bleuyard et al., (2006) DNA Repair 5:1-12).

Alternatively, the double-strand break can be repaired by homologous recombination (HR) between homologous DNA sequences. Once the sequence around the double-strand break is altered, for example, by exonuclease activities involved in the maturation of double-strand breaks, gene conversion pathways can restore the original structure if a homologous sequence is available, such as a homologous chromosome in non-dividing somatic cells, or a sister chromatid after DNA replication (Molinier et al., (2004) Plant Cell 16:342-52). Ectopic and/or epigenic DNA sequences may also serve as a DNA repair template for homologous recombination (Puchta, (1999) Genetics 152:1173-81). Episomal DNA molecules can also be ligated into the double-strand break, for example, integration of T-DNAs into chromosomal double-strand breaks (Chilton and Que, (2003) Plant Physiol 133:956-65; Salomon and Puchta, (1998) EMBO J 17:6086-95).

As used herein, "homologous recombination (HR)" includes the exchange of DNA fragments between two DNA molecules at the sites of homology. The frequency of homologous recombination is influenced by a number of factors. Different organisms vary with respect to the amount of homologous recombination and the relative proportion of homologous to non-homologous recombination. Generally, the length of the region of homology affects the frequency of homologous recombination events: the longer the region of homology, the greater the frequency. The length of the homology region needed to observe homologous recombination is also species-variable. In many cases, at least 5 kb of homology has been utilized, but homologous recombination has been observed with as little as 25-50 bp of homology. See, for example, Singer et al., (1982) Cell 31:25-33; Shen and Huang, (1986) Genetics 112:441-57; Watt et al., (1985) Proc. Natl. Acad. Sci. USA 82:4768-72, Sugawara and Haber, (1992) Mol Cell Biol 12:563-75, Rubnitz and Subramani, (1984) Mol Cell Biol 4:2253-8; Ayares et al., (1986) Proc. Natl. Acad. Sci. USA 83:5199-203; Liskay et al., (1987) Genetics 115:161-7.

Homology-directed repair (HDR) is a mechanism in cells to repair double-stranded and single stranded DNA breaks. Homology-directed repair includes homologous recombination (HR) and single-strand annealing (SSA) (Lieber. 2010 Annu. Rev. Biochem. 79:181-211).The most common form of HDR is called homologous recombination (HR), which has the longest sequence homology requirements between the donor and acceptor DNA. Other forms of HDR include single-stranded annealing (SSA) and breakage-induced replication, and these require shorter sequence homology relative to HR. Homology-directed repair at nicks (single-stranded breaks) can occur via a mechanism distinct from HDR at double-strand breaks (Davis and Maizels. PNAS (0027-8424), 111 (10), p. E924-E932.

Alteration of the genome of a plant cell, for example, through homologous homology-directed repair (HDR), is a powerful tool for genetic engineering. Despite the low frequency of homologous recombination in higher plants, there are a few examples of successful homologous recombination of plant endogenous genes. The parameters for homologous recombination in plants have primarily been investigated by rescuing introduced truncated selectable marker genes. In these experiments, the homologous DNA fragments were typically between 0.3 kb to 2 kb. Observed frequencies for homologous recombination were on the order of $10^{-4}$ to $10^{-5}$. See, for example, Halfter et al., (1992) Mol Gen Genet 231:186-93; Offringa et al., (1990) EMBO J 9:3077-84; Offringa et al., (1993) Proc. Natl. Acad. Sci. USA 90:7346-50; Paszkowski et al., (1988) EMBO J 7:4021-6; Hourda and Paszkowski, (1994) Mol Gen Genet 243:106-11; and Risseeuw et al., (1995) Plant J 7:109-19.

DNA double-strand breaks appear to be an effective factor to stimulate homologous recombination pathways (Puchta et al., (1995) Plant Mol Biol 28:281-92; Tzfira and White, (2005) Trends Biotechnol 23:567-9; Puchta, (2005) J Exp Bot 56:1-14). Using DNA-breaking agents, a two- to nine-fold increase of homologous recombination was observed between artificially constructed homologous DNA repeats in plants (Puchta et al., (1995) Plant Mol Biol 28:281-92). In maize protoplasts, experiments with linear DNA molecules demonstrated enhanced homologous recombination between plasmids (Lyznik et al., (1991) Mol Gen Genet 230:209-18).

The donor DNA may be introduced by any means known in the art. For example, a plant having a target site is provided. The donor DNA may be provided by any delivery method known in the art including, for example, *Agrobacterium*-mediated transformation, whiskers mediated transformation, or biolistic particle bombardment. The donor DNA may be present transiently in the cell or it can be introduced via a viral replicon. In the presence of the Cas endonuclease and the target site, the donor DNA is inserted into the plant's genome.

As described herein, direct delivery of a donor DNA into plant cells can be achieved through particle mediated delivery. Based on the experiments described herein, a skilled artesian can now envision that any other direct method of delivery, such as but not limiting to, polyethylene glycol (PEG)-mediated transfection to protoplasts, electroporation, particle bombardment, whiskers mediated delivery, cell-penetrating peptides, or mesoporous silica nanoparticle (MSN)-mediated direct protein delivery can be successfully used for delivering a donor DNA in plant cells.

Further uses for guide RNA/Cas endonuclease systems have been described (See U.S. Patent Application US 2015-0082478 A1, published on Mar. 19, 2015, WO2015/026886 A1, published on Feb. 26, 2015, US 2015-0059010 A1, published on Feb. 26, 2015, U.S. application 62/023,246, filed on Jul. 7, 2014, and U.S. application 62/036,652, filed on Aug. 13, 2014, all of which are incorporated by reference herein) and include but are not limited to modifying or replacing nucleotide sequences of interest (such as a regulatory elements), insertion of polynucleotides of interest, gene knock-out, gene-knock in, modification of splicing sites and/or introducing alternate splicing sites, modifications of nucleotide sequences encoding a protein of interest, amino acid and/or protein fusions, and gene silencing by expressing an inverted repeat into a gene of interest.

Polynucleotides of interest are further described herein and include polynucleotides reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increase, the choice of genes for genetic engineering will change accordingly.

Further provided are methods for identifying at least one plant cell, comprising in its genome, a polynucleotide of interest integrated at the target site. A variety of methods are available for identifying those plant cells with insertion into the genome at or near to the target site without using a screenable marker phenotype. Such methods can be viewed as directly analyzing a target sequence to detect any change in the target sequence, including but not limited to PCR methods, sequencing methods, nuclease digestion, Southern blots, and any combination thereof. See, for example, U.S. patent application Ser. No. 12/147,834, herein incorporated by reference to the extent necessary for the methods described herein. The method also comprises recovering a plant from the plant cell comprising a polynucleotide of Interest integrated into its genome. The plant may be sterile or fertile. It is recognized that any polynucleotide of interest can be provided, integrated into the plant genome at the target site, and expressed in a plant.

Polynucleotides/polypeptides of interest include, but are not limited to, herbicide-resistance coding sequences, insecticidal coding sequences, nematicidal coding sequences, antimicrobial coding sequences, antifungal coding sequences, antiviral coding sequences, abiotic and biotic stress tolerance coding sequences, or sequences modifying plant traits such as yield, grain quality, nutrient content, starch quality and quantity, nitrogen fixation and/or utilization, fatty acids, and oil content and/or composition. More specific polynucleotides of interest include, but are not limited to, genes that improve crop yield, polypeptides that improve desirability of crops, genes encoding proteins conferring resistance to abiotic stress, such as drought, nitrogen, temperature, salinity, toxic metals or trace elements, or those conferring resistance to toxins such as pesticides and herbicides, or to biotic stress, such as attacks by fungi, viruses, bacteria, insects, and nematodes, and development of diseases associated with these organisms. General categories of genes of interest include, for example, those genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, fertility or sterility, grain characteristics, and commercial products. Genes of interest include, generally, those involved in oil, starch, carbohydrate, or nutrient metabolism as well as those affecting kernel size, sucrose loading, and the like that can be stacked or used in combination with other traits, such as but not limited to herbicide resistance, described herein.

Agronomically important traits such as oil, starch, and protein content can be genetically altered in addition to using traditional breeding methods. Modifications include increasing content of oleic acid, saturated and unsaturated oils, increasing levels of lysine and sulfur, introducing essential amino acids, and also modification of starch. Hordothionin protein modifications are described in U.S. Pat. Nos. 5,703,049, 5,885,801, 5,885,802, and 5,990,389, herein incorporated by reference.

Polynucleotide sequences of interest may encode proteins involved in introducing disease or pest resistance. By "disease resistance" or "pest resistance" is intended that the plants avoid the harmful symptoms that are the outcome of the plant-pathogen interactions. Pest resistance genes may encode resistance to pests that have great yield drag such as rootworm, cutworm, European Corn Borer, and the like. Disease resistance and insect resistance genes such as lysozymes or cecropins for antibacterial protection, or proteins such as defensins, glucanases or chitinases for antifungal protection, or *Bacillus thuringiensis* endotoxins, protease inhibitors, collagenases, lectins, or glycosidases for controlling nematodes or insects are all examples of useful gene products. Genes encoding disease resistance traits include detoxification genes, such as against fumonisin (U.S. Pat. No. 5,792,931); avirulence (avr) and disease resistance (R) genes (Jones et al. (1994) Science 266:789; Martin et al. (1993) Science 262:1432; and Mindrinos et al. (1994) Cell 78:1089); and the like. Insect resistance genes may encode resistance to pests that have great yield drag such as rootworm, cutworm, European Corn Borer, and the like. Such genes include, for example, *Bacillus thuringiensis* toxic protein genes (U.S. Pat. Nos. 5,366,892; 5,747,450; 5,736,514; 5,723,756; 5,593,881; and Geiser et al. (1986) Gene 48:109); and the like.

An "herbicide resistance protein" or a protein resulting from expression of an "herbicide resistance-encoding nucleic acid molecule" includes proteins that confer upon a cell the ability to tolerate a higher concentration of an herbicide than cells that do not express the protein, or to tolerate a certain concentration of an herbicide for a longer period of time than cells that do not express the protein. Herbicide resistance traits may be introduced into plants by genes coding for resistance to herbicides that act to inhibit the action of acetolactate synthase (ALS also called AHAS), in particular the sulfonylurea-type (UK: sulphonylurea) herbicides, genes coding for resistance to herbicides that act to inhibit the action of glutamine synthase, such as phosphinothricin or basta (e.g., the bar gene), glyphosate (e.g., the EPSP synthase gene and the GAT gene), HPPD inhibitors (e.g, the HPPD gene) or other such genes known in the art. See, for example, U.S. Pat. Nos. 7,626,077, 5,310,667, 5,866,775, 6,225,114, 6,248,876, 7,169,970, 6,867,293, and U.S. Provisional Application No. 61/401,456, each of which is herein incorporated by reference. The bar gene encodes resistance to the herbicide basta, the nptII gene encodes resistance to the antibiotics kanamycin and geneticin, and the ALS-gene mutants encode resistance to the herbicide chlorsulfuron.

As used herein, a "sulfonylurea-tolerant polypeptide" comprises any polypeptide which when expressed in a plant confers tolerance to at least one sulfonylurea. Sulfonylurea herbicides inhibit growth of higher plants by blocking acetolactate synthase (ALS), also known as, acetohydroxy acid synthase (AHAS). Plants containing particular mutations in ALS (e.g., the S4 and/or HRA mutations) are tolerant to sulfonylurea herbicides. The production of sulfonylurea-tolerant plants is described more fully in U.S. Pat. Nos. 5,605,011; 5,013,659; 5,141,870; 5,767,361; 5,731,180; 5,304,732; 4,761,373; 5,331,107; 5,928,937; and 5,378,824; and international publication WO 96/33270, which are incorporated herein by reference in their entireties for all purposes, and in Tan et al. 2005. Imidazolinone-tolerant crops: history, current status and future. Pest Manag Sci 61:246-257. The sulfonylurea-tolerant polypeptide can be encoded by, for example, the SuRA or SuRB locus of ALS. In specific embodiments, the ALS inhibitor-tolerant polypeptide comprises the C3 ALS mutant, the HRA ALS mutant, the S4 mutant or the S4/HRA mutant or any combination thereof. Different mutations in ALS are known to confer tolerance to different herbicides and groups (and/or subgroups) of herbicides; see, e.g., Tranel and Wright (2002) Weed Science 50:700-712. See also, U.S. Pat. Nos. 5,605,011, 5,378,824, 5,141,870, and 5,013,659, each of which is herein incorporated by reference in their entirety. The HRA mutation in ALS finds particular use in one embodiment.

The mutation results in the production of an acetolactate synthase polypeptide which is resistant to at least one sulfonylurea compound in comparison to the wild-type protein.

A gene encoding a sulfonylurea-tolerant polypeptide is referred to as a sulfonyl tolerant gene or a sulfonyl resistant gene. The terms sulfonyl tolerant gene or sulfonyl resistant gene are used interchangeably herein.

A disrupted sulfonylurea resistant (ALS) gene refers to a disrupted gene, of which its corresponding undisrupted gene encodes a sulfonylurea-tolerant polypeptide, that is modified such that its gene product no longer encodes a functional sulfonylurea-tolerant polypeptide.

Components of a sulfonylurea-responsive repressor system (as described in U.S. Pat. No. 8,257,956, issued on Sep. 4, 2012) can also be introduced into plant genomes to generate a repressor/operator/inducer systems into said plant where polypeptides can specifically bind to an operator, wherein the specific binding is regulated by a sulfonylurea compound.

Sterility genes can also be encoded in an expression cassette and provide an alternative to physical detasseling. Examples of genes used in such ways include male fertility genes such as MS26 (see for example U.S. Pat. Nos. 7,098,388, 7,517,975, 7,612,251), MS45 (see for example U.S. Pat. Nos. 5,478,369, 6,265,640) or MSCA1 (see for example U.S. Pat. No. 7,919,676). Maize plants (*Zea mays* L.) can be bred by both self-pollination and cross-pollination techniques. Maize has male flowers, located on the tassel, and female flowers, located on the ear, on the same plant. It can self-pollinate ("selfing") or cross pollinate. Natural pollination occurs in maize when wind blows pollen from the tassels to the silks that protrude from the tops of the incipient ears. Pollination may be readily controlled by techniques known to those of skill in the art. The development of maize hybrids requires the development of homozygous inbred lines, the crossing of these lines, and the evaluation of the crosses. Pedigree breeding and recurrent selections are two of the breeding methods used to develop inbred lines from populations. Breeding programs combine desirable traits from two or more inbred lines or various broad-based sources into breeding pools from which new inbred lines are developed by selfing and selection of desired phenotypes. A hybrid maize variety is the cross of two such inbred lines, each of which may have one or more desirable characteristics lacked by the other or which complement the other. The new inbreds are crossed with other inbred lines and the hybrids from these crosses are evaluated to determine which have commercial potential. The hybrid progeny of the first generation is designated F1. The F1 hybrid is more vigorous than its inbred parents. This hybrid vigor, or heterosis, can be manifested in many ways, including increased vegetative growth and increased yield.

Hybrid maize seed can be produced by a male sterility system incorporating manual detasseling. To produce hybrid seed, the male tassel is removed from the growing female inbred parent, which can be planted in various alternating row patterns with the male inbred parent. Consequently, introducing that there is sufficient isolation from sources of foreign maize pollen, the ears of the female inbred will be fertilized only with pollen from the male inbred. The resulting seed is therefore hybrid (F1) and will form hybrid plants.

Field variation impacting plant development can result in plants tasseling after manual detasseling of the female parent is completed. Or, a female inbred plant tassel may not be completely removed during the detasseling process. In any event, the result is that the female plant will successfully shed pollen and some female plants will be self-pollinated. This will result in seed of the female inbred being harvested along with the hybrid seed which is normally produced. Female inbred seed does not exhibit heterosis and therefore is not as productive as F1 seed. In addition, the presence of female inbred seed can represent a germplasm security risk for the company producing the hybrid.

Alternatively, the female inbred can be mechanically detasseled by machine. Mechanical detasseling is approximately as reliable as hand detasseling, but is faster and less costly. However, most detasseling machines produce more damage to the plants than hand detasseling. Thus, no form of detasseling is presently entirely satisfactory, and a need continues to exist for alternatives which further reduce production costs and to eliminate self-pollination of the female parent in the production of hybrid seed.

Mutations that cause male sterility in plants have the potential to be useful in methods for hybrid seed production for crop plants such as maize and can lower production costs by eliminating the need for the labor-intensive removal of male flowers (also known as de-tasseling) from the maternal parent plants used as a hybrid parent. Mutations that cause male sterility in maize have been produced by a variety of methods such as X-rays or UV-irradiations, chemical treatments, or transposable element insertions (ms23, ms25, ms26, ms32) (Chaubal et al. (2000) Am J Bot 87:1193-1201). Conditional regulation of fertility genes through fertility/sterility "molecular switches" could enhance the options for designing new male-sterility systems for crop improvement (Unger et al. (2002) Transgenic Res 11:455-465).

Furthermore, it is recognized that the polynucleotide of interest may also comprise antisense sequences complementary to at least a portion of the messenger RNA (mRNA) for a targeted gene sequence of interest. Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, 80%, or 85% sequence identity to the corresponding antisense sequences may be used. Furthermore, portions of the antisense nucleotides may be used to disrupt the expression of the target gene. Generally, sequences of at least 50 nucleotides, 100 nucleotides, 200 nucleotides, or greater may be used.

In addition, the polynucleotide of interest may also be used in the sense orientation to suppress the expression of endogenous genes in plants. Methods for suppressing gene expression in plants using polynucleotides in the sense orientation are known in the art. The methods generally involve transforming plants with a DNA construct comprising a promoter that drives expression in a plant operably linked to at least a portion of a nucleotide sequence that corresponds to the transcript of the endogenous gene. Typically, such a nucleotide sequence has substantial sequence identity to the sequence of the transcript of the endogenous gene, generally greater than about 65% sequence identity, about 85% sequence identity, or greater than about 95% sequence identity. See, U.S. Pat. Nos. 5,283,184 and 5,034,323; herein incorporated by reference.

The polynucleotide of interest can also be a phenotypic marker.

The recombinant DNA molecules, DNA sequences of interest, and polynucleotides of interest can comprise one or more DNA sequences for gene silencing. Methods for gene silencing involving the expression of DNA sequences in plant are known in the art include, but are not limited to, cosuppression, antisense suppression, double-stranded RNA (dsRNA) interference, hairpin RNA (hpRNA) interference, intron-containing hairpin RNA (ihpRNA) interference, transcriptional gene silencing, and micro RNA (miRNA) interference As used herein, "nucleic acid" means a polynucleotide and includes a single or a double-stranded polymer of deoxyribonucleotide or ribonucleotide bases. Nucleic acids may also include fragments and modified nucleotides. Thus, the terms "polynucleotide", "nucleic acid sequence", "nucleotide sequence" and "nucleic acid fragment" are used interchangeably to denote a polymer of RNA and/or DNA that is single- or double-stranded, optionally containing synthetic, non-natural, or altered nucleotide bases. Nucleotides (usually found in their 5'-monophosphate form) are referred to by their single letter designation as follows: "A" for adenosine or deoxyadenosine (for RNA or DNA, respectively), "C" for cytosine or deoxycytosine, "G" for guanosine or deoxyguanosine, "U" for uridine, "T" for deoxythymidine, "R" for purines (A or G), "Y" for pyrimidines (C or T), "K" for G or T, "H" for A or C or T, "I" for inosine, and "N" for any nucleotide.

"Open reading frame" is abbreviated ORF.

The terms "subfragment that is functionally equivalent" and "functionally equivalent subfragment" are used interchangeably herein. These terms refer to a portion or subsequence of an isolated nucleic acid fragment in which the ability to alter gene expression or produce a certain phenotype is retained whether or not the fragment or subfragment encodes an active enzyme. For example, the fragment or subfragment can be used in the design of genes to produce the desired phenotype in a transformed plant. Genes can be designed for use in suppression by linking a nucleic acid fragment or subfragment thereof, whether or not it encodes an active enzyme, in the sense or antisense orientation relative to a plant promoter sequence.

The term "conserved domain" or "motif" means a set of amino acids conserved at specific positions along an aligned sequence of evolutionarily related proteins. While amino acids at other positions can vary between homologous proteins, amino acids that are highly conserved at specific positions indicate amino acids that are essential to the structure, the stability, or the activity of a protein. Because they are identified by their high degree of conservation in aligned sequences of a family of protein homologues, they can be used as identifiers, or "signatures", to determine if a protein with a newly determined sequence belongs to a previously identified protein family.

Polynucleotide and polypeptide sequences, variants thereof, and the structural relationships of these sequences can be described by the terms "homology", "homologous", "substantially identical", "substantially similar" and "corresponding substantially" which are used interchangeably herein. These refer to polypeptide or nucleic acid fragments wherein changes in one or more amino acids or nucleotide bases do not affect the function of the molecule, such as the ability to mediate gene expression or to produce a certain phenotype. These terms also refer to modification(s) of nucleic acid fragments that do not substantially alter the functional properties of the resulting nucleic acid fragment relative to the initial, unmodified fragment. These modifications include deletion, substitution, and/or insertion of one or more nucleotides in the nucleic acid fragment.

Substantially similar nucleic acid sequences encompassed may be defined by their ability to hybridize (under moderately stringent conditions, e.g., 0.5×SSC, 0.1% SDS, 60° C.) with the sequences exemplified herein, or to any portion of the nucleotide sequences disclosed herein and which are functionally equivalent to any of the nucleic acid sequences disclosed herein. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, or 90% sequence identity, up to and including 100% sequence identity (i.e., fully complementary) with each other.

The term "stringent conditions" or "stringent hybridization conditions" includes reference to conditions under which a probe will selectively hybridize to its target sequence in an in vitro hybridization assay. Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na ion, typically about 0.01 to 1.0 M Na ion concentration (or other salt(s)) at pH 7.0 to 8.3, and at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

"Sequence identity" or "identity" in the context of nucleic acid or polypeptide sequences refers to the nucleic acid bases or amino acid residues in two sequences that are the same when aligned for maximum correspondence over a specified comparison window.

The term "percentage of sequence identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. Useful examples of percent sequence identities include, but are not limited to, 50%, 55%, 60%, 65%, 70%, 75%, 80%, 85%, 90% or 95%, or any integer percentage from 50% 10 to 100%. These identities can be determined using any of the programs described herein.

Sequence alignments and percent identity or similarity calculations may be determined using a variety of comparison methods designed to detect homologous sequences including, but not limited to, the MegAlign™ program of the LASERGENE bioinformatics computing suite (DNASTAR Inc., Madison, WI). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

The "Clustal V method of alignment" corresponds to the alignment method labeled Clustal V (described by Higgins and Sharp, (1989) *CABIOS* 5:151-153; Higgins et al., (1992) *Comput Appl Biosci* 8:189-191) and found in the MegAlign™ program of the LASERGENE bioinformatics computing suite (DNASTAR Inc., Madison, WI). For multiple alignments, the default values correspond to GAP PENALTY=10 and GAP LENGTH PENALTY=10. Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program.

The "Clustal W method of alignment" corresponds to the alignment method labeled Clustal W (described by Higgins and Sharp, (1989) *CABIOS* 5:151-153; Higgins et al., (1992) *Comput Appl Biosci* 8:189-191) and found in the MegAlign™ v6.1 program of the LASERGENE bioinformatics computing suite (DNASTAR Inc., Madison, WI). Default parameters for multiple alignment (GAP PENALTY=10, GAP LENGTH PENALTY=0.2, Delay Divergen Seqs (%)=30, DNA Transition Weight=0.5, Protein Weight Matrix=Gonnet Series, DNA Weight Matrix=IUB). After alignment of the sequences using the Clustal W program, it is possible to obtain a "percent identity" by viewing the "sequence distances" table in the same program.

Unless otherwise stated, sequence identity/similarity values provided herein refer to the value obtained using GAP Version 10 (GCG, Accelrys, San Diego, CA) using the following parameters: % identity and % similarity for a nucleotide sequence using a gap creation penalty weight of 50 and a gap length extension penalty weight of 3, and the nwsgapdna.cmp scoring matrix; % identity and % similarity for an amino acid sequence using a GAP creation penalty weight of 8 and a gap length extension penalty of 2, and the BLOSUM62 scoring matrix (Henikoff and Henikoff, (1989) *Proc. Natl. Acad. Sci. USA* 89:10915). GAP uses the algorithm of Needleman and Wunsch, (1970) *J Mol Biol* 48:443-53, to find an alignment of two complete sequences that maximizes the number of matches and minimizes the number of gaps. GAP considers all possible alignments and gap positions and creates the alignment with the largest number of matched bases and the fewest gaps, using a gap creation penalty and a gap extension penalty in units of matched bases.

"BLAST" is a searching algorithm provided by the National Center for Biotechnology Information (NCBI) used to find regions of similarity between biological sequences. The program compares nucleotide or protein sequences to sequence databases and calculates the statistical significance of matches to identify sequences having sufficient similarity to a query sequence such that the similarity would not be predicted to have occurred randomly. BLAST reports the identified sequences and their local alignment to the query sequence.

It is well understood by one skilled in the art that many levels of sequence identity are useful in identifying polypeptides from other species or modified naturally or synthetically wherein such polypeptides have the same or similar function or activity. Useful examples of percent identities include, but are not limited to, 50%, 55%, 60%, 65%, 70%, 75%, 80%, 85%, 90% or 95%, or any integer percentage from 50% to 100%. Indeed, any integer amino acid identity from 50% to 100% may be useful in describing the present disclosure, such as 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%.

"Gene" includes a nucleic acid fragment that expresses a functional molecule such as, but not limited to, a specific protein, including regulatory sequences preceding (5' non-coding sequences) and following (3' non-coding sequences) the coding sequence. "Native gene" refers to a gene as found in nature with its own regulatory sequences.

A "mutated gene" is a gene that has been altered through human intervention. Such a "mutated gene" has a sequence that differs from the sequence of the corresponding non-mutated gene by at least one nucleotide addition, deletion, or substitution. In certain embodiments of the disclosure, the mutated gene comprises an alteration that results from a guide polynucleotide/Cas endonuclease system as disclosed herein. A mutated plant is a plant comprising a mutated gene.

As used herein, a "targeted mutation" is a mutation in a native gene that was made by altering a target sequence within the native gene using a method involving a double-strand-break-inducing agent that is capable of inducing a double-strand break in the DNA of the target sequence as disclosed herein or known in the art.

The guide RNA/Cas endonuclease induced targeted mutation can occur in a nucleotide sequence that is located within or outside a genomic target site that is recognized and cleaved by a Cas endonuclease.

The term "genome" as it applies to a plant cells encompasses not only chromosomal DNA found within the nucleus, but organelle DNA found within subcellular components (e.g., mitochondria, or plastid) of the cell.

A "codon-modified gene" or "codon-preferred gene" or "codon-optimized gene" is a gene having its frequency of codon usage designed to mimic the frequency of preferred codon usage of the host cell.

An "allele" is one of several alternative forms of a gene occupying a given locus on a chromosome. When all the alleles present at a given locus on a chromosome are the same, that plant is homozygous at that locus. If the alleles present at a given locus on a chromosome differ, that plant is heterozygous at that locus.

"Coding sequence" refers to a polynucleotide sequence which codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to: promoters, translation leader sequences, 5' untranslated sequences, 3' untranslated sequences, introns, polyadenylation target sequences, RNA processing sites, effector binding sites, and stem-loop structures.

"A plant-optimized nucleotide sequence" is nucleotide sequence that has been optimized for increased expression in plants. For example, a plant-optimized nucleotide sequence can be synthesized by modifying a nucleotide sequence encoding a protein such as, for example, double-strand-break-inducing agent (e.g., an endonuclease) as disclosed herein, using one or more plant-preferred codons for improved expression. See, for example, Campbell and Gowri (1990) Plant Physiol. 92:1-11 for a discussion of host-preferred codon usage.

Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference. Additional sequence modifications are known to enhance gene expression in a plant host. These include, for example, elimination of: one or more sequences encoding spurious polyadenylation signals, one or more exon-intron splice site signals, one or more transposon-like repeats, and other such well-characterized sequences that may be deleterious to gene expression. The G-C content of the sequence may be adjusted to levels average for a given plant host, as calculated by reference to known genes expressed in the host plant cell. When possible, the sequence is modified to avoid one or more predicted hairpin secondary mRNA structures. Thus, "a plant-optimized nucleotide sequence" of the present disclosure comprises one or more of such sequence modifications.

A promoter is a region of DNA involved in recognition and binding of RNA polymerase and other proteins to initiate transcription. The promoter sequence consists of proximal and more distal upstream elements, the latter elements often referred to as enhancers. An "enhancer" is a DNA sequence that can stimulate promoter activity, and may be an innate element of the promoter or a heterologous element inserted to enhance the level or tissue-specificity of a promoter. Promoters may be derived in their entirety from a native gene, or be composed of different elements derived from different promoters found in nature, and/or comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity. Promoters that cause a gene to be expressed in most cell types at most times are commonly referred to as "constitutive promoters".

It has been shown that certain promoters are able to direct RNA synthesis at a higher rate than others. These are called "strong promoters". Certain other promoters have been shown to direct RNA synthesis at higher levels only in particular types of cells or tissues and are often referred to as "tissue specific promoters", or "tissue-preferred promoters" if the promoters direct RNA synthesis preferably in certain tissues but also in other tissues at reduced levels. Since patterns of expression of a chimeric gene (or genes) introduced into a plant are controlled using promoters, there is an ongoing interest in the isolation of novel promoters which are capable of controlling the expression of a chimeric gene or (genes) at certain levels in specific tissue types or at specific plant developmental stages.

A plant promoter can include a promoter capable of initiating transcription in a plant cell, for a review of plant promoters, see, Potenza et al., (2004) *In Vitro Cell Dev Biol* 40:1-22. Constitutive promoters include, for example, the core promoter of the Rsyn7 promoter and other constitutive promoters disclosed in WO99/43838 and U.S. Pat. No. 6,072,050; the core CaMV 35S promoter (Odell et al., (1985) *Nature* 313:810-2); rice actin (McElroy et al., (1990) *Plant Cell* 2:163-71); ubiquitin (Christensen et al., (1989) *Plant Mol Biol* 12:619-32; Christensen et al., (1992) *Plant Mol Biol* 18:675-89); pEMU (Last et al., (1991) *Theor Appl Genet* 81:581-8); MAS (Velten et al., (1984) *EMBO J* 3:2723-30); ALS promoter (U.S. Pat. No. 5,659,026), and the like. Other constitutive promoters are described in, for example, U.S. Pat. Nos. 5,608,149; 5,608,144; 5,604,121; 5,569,597; 5,466,785; 5,399,680; 5,268,463; 5,608,142 and 6,177,611. In some examples an inducible promoter may be used. Pathogen-inducible promoters induced following infection by a pathogen include, but are not limited to those regulating expression of PR proteins, SAR proteins, beta-1,3-glucanase, chitinase, etc.

Chemical-regulated promoters can be used to modulate the expression of a gene in a plant through the application of an exogenous chemical regulator. The promoter may be a chemical-inducible promoter, where application of the chemical induces gene expression, or a chemical-repressible promoter, where application of the chemical represses gene expression. Chemical-inducible promoters include, but are not limited to, the maize ln2-2 promoter, activated by benzene sulfonamide herbicide safeners (De Veylder et al., (1997) *Plant Cell Physiol* 38:568-77), the maize GST promoter (GST-II-27, WO93/01294), activated by hydrophobic electrophilic compounds used as pre-emergent herbicides, and the tobacco PR-1a promoter (Ono et al., (2004) *Biosci Biotechnol Biochem* 68:803-7) activated by salicylic acid. Other chemical-regulated promoters include steroid-responsive promoters (see, for example, the glucocorticoid-inducible promoter (Schena et al., (1991) *Proc. Natl. Acad. Sci. USA* 88:10421-5; McNellis et al., (1998) *Plant J* 14:247-257); tetracycline-inducible and tetracycline-repressible promoters (Gatz et al., (1991) *Mol Gen Genet* 227:229-37; U.S. Pat. Nos. 5,814,618 and 5,789,156).

Tissue-preferred promoters can be utilized to target enhanced expression within a particular plant tissue. Tissue-preferred promoters include, for example, Kawamata et al., (1997) *Plant Cell Physiol* 38:792-803; Hansen et al., (1997) *Mol Gen Genet* 254:337-43; Russell et al., (1997) *Transgenic Res* 6:157-68; Rinehart et al., (1996) *Plant Physiol* 112:1331-41; Van Camp et al., (1996) *Plant Physiol* 112:525-35; Canevascini et al., (1996) *Plant Physiol* 112:513-524; Lam, (1994) *Results Probl Cell Differ* 20:181-96; and Guevara-Garcia et al., (1993) *Plant J* 4:495-505. Leaf-preferred promoters include, for example, Yamamoto et al., (1997) *Plant J* 12:255-65; Kwon et al., (1994) *Plant Physiol* 105:357-67; Yamamoto et al., (1994) *Plant Cell Physiol* 35:773-8; Gotor et al., (1993) *Plant J* 3:509-18; Orozco et al., (1993) *Plant Mol Biol* 23:1129-38; Matsuoka et al., (1993) *Proc. Natl. Acad. Sci. USA* 90:9586-90; Simpson et al., (1958) *EMBO J* 4:2723-9; Timko et al., (1988) *Nature*

318:57-8. Root-preferred promoters include, for example, Hire et al., (1992) *Plant Mol Biol* 20:207-18 (soybean root-specific glutamine synthase gene); Miao et al., (1991) *Plant Cell* 3:11-22 (cytosolic glutamine synthase (GS)); Keller and Baumgartner, (1991) *Plant Cell* 3:1051-61 (root-specific control element in the GRP 1.8 gene of French bean); Sanger et al., (1990) *Plant Mol Biol* 14:433-43 (root-specific promoter of *A. tumefaciens* mannopine synthase (MAS)); Bogusz et al., (1990) *Plant Cell* 2:633-41 (root-specific promoters isolated from *Parasponia andersonii* and *Trema tomentosa*); Leach and Aoyagi, (1991) *Plant Sci* 79:69-76 (*A. rhizogenes* rolC and rolD root-inducing genes); Teeri et al., (1989) *EMBO J* 8:343-50 (*Agrobacterium* wound-induced TR1' and TR2' genes); VfENOD-GRP3 gene promoter (Kuster et al., (1995) *Plant Mol Biol* 29:759-72); and rolB promoter (Capana et al., (1994) *Plant Mol Biol* 25:681-91; phaseolin gene (Murai et al., (1983) *Science* 23:476-82; Sengopta-Gopalen et al., (1988) *Proc. Natl. Acad. Sci. USA* 82:3320-4). See also, U.S. Pat. Nos. 5,837,876; 5,750,386; 5,633,363; 5,459,252; 5,401,836; 5,110,732 and 5,023,179.

Seed-preferred promoters include both seed-specific promoters active during seed development, as well as seed-germinating promoters active during seed germination. See, Thompson et al., (1989) *BioEssays* 10:108. Seed-preferred promoters include, but are not limited to, Cim1 (cytokinin-induced message); cZ19B1 (maize 19 kDa zein); and milps (myo-inositol-1-phosphate synthase); (WO00/11177; and U.S. Pat. No. 6,225,529). For dicots, seed-preferred promoters include, but are not limited to, bean β-phaseolin, napin, β-conglycinin, soybean lectin, cruciferin, and the like. For monocots, seed-preferred promoters include, but are not limited to, maize 15 kDa zein, 22 kDa zein, 27 kDa gamma zein, waxy, shrunken 1, shrunken 2, globulin 1, oleosin, and nuc1. See also, WO00/12733, where seed-preferred promoters from END1 and END2 genes are disclosed.

The term “inducible promoter” refers to promoters that selectively express a coding sequence or functional RNA in response to the presence of an endogenous or exogenous stimulus, for example by chemical compounds (chemical inducers) or in response to environmental, hormonal, chemical, and/or developmental signals. Inducible or regulated promoters include, for example, promoters induced or regulated by light, heat, stress, flooding or drought, salt stress, osmotic stress, phytohormones, wounding, or chemicals such as ethanol, abscisic acid (ABA), jasmonate, salicylic acid, or safeners.

An example of a stress-inducible is RD29A promoter (Kasuga et al. (1999) Nature Biotechnol. 17:287-91). One of ordinary skill in the art is familiar with protocols for simulating drought conditions and for evaluating drought tolerance of plants that have been subjected to simulated or naturally-occurring drought conditions. For example, one can simulate drought conditions by giving plants less water than normally required or no water over a period of time, and one can evaluate drought tolerance by looking for differences in physiological and/or physical condition, including (but not limited to) vigor, growth, size, or root length, or in particular, leaf color or leaf area size. Other techniques for evaluating drought tolerance include measuring chlorophyll fluorescence, photosynthetic rates and gas exchange rates. Also, one of ordinary skill in the art is familiar with protocols for simulating stress conditions such as osmotic stress, salt stress and temperature stress and for evaluating stress tolerance of plants that have been subjected to simulated or naturally-occurring stress conditions.

Another example of an inducible promoter useful in plant cells has been described in US patent application, US 2013-0312137A1, published on Nov. 21, 2013, incorporated by reference herein. US patent application US 2013-0312137A1 describes a ZmCAS1 promoter from a CBSU-Anther_Subtraction library (CAS1) gene encoding a mannitol dehydrogenase from maize, and functional fragments thereof. The ZmCAS1 promoter (also referred to as “CAS1 promoter”, “mannitol dehydrogenase promoter”, “mdh promoter”) can be induced by a chemical or stress treatment. The chemical can be a safener such as, but not limited to, N-(aminocarbonyl)-2-chlorobenzenesulfonamide (2-CBSU). The stress treatment can be a heat treatment such as, but not limited to, a heat shock treatment (see also U.S. provisional patent application, 62/120,421, filed on Feb. 25, 2015, and incorporated by reference herein.

New promoters of various types useful in plant cells are constantly being discovered; numerous examples may be found in the compilation by Okamuro and Goldberg, (1989) In *The Biochemistry of Plants*, Vol. 115, Stumpf and Conn, eds (New York, NY: Academic Press), pp. 1-82.

“Translation leader sequence” refers to a polynucleotide sequence located between the promoter sequence of a gene and the coding sequence. The translation leader sequence is present in the mRNA upstream of the translation start sequence. The translation leader sequence may affect processing of the primary transcript to mRNA, mRNA stability or translation efficiency. Examples of translation leader sequences have been described (e.g., Turner and Foster, (1995) *Mol Biotechnol* 3:225-236).

“3' non-coding sequences”, “transcription terminator” or “termination sequences” refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., (1989) *Plant Cell* 1:671-680.

“RNA transcript” refers to the product resulting from RNA polymerase-catalyzed transcription of a DNA sequence. When the RNA transcript is a perfect complimentary copy of the DNA sequence, it is referred to as the primary transcript or pre-mRNA. A RNA transcript is referred to as the mature RNA or mRNA when it is a RNA sequence derived from post-transcriptional processing of the primary transcript pre mRNA. “Messenger RNA” or “mRNA” refers to the RNA that is without introns and that can be translated into protein by the cell. “crDNA” refers to a DNA that is complementary to, and synthesized from, an mRNA template using the enzyme reverse transcriptase. The cDNA can be single-stranded or converted into double-stranded form using the Klenow fragment of DNA polymerase I. “Sense” RNA refers to RNA transcript that includes the mRNA and can be translated into protein within a cell or in vitro. “Antisense RNA” refers to an RNA transcript that is complementary to all or part of a target primary transcript or mRNA, and that blocks the expression of a target gene (see, e.g., U.S. Pat. No. 5,107,065). The complementarity of an antisense RNA may be with any part of the specific gene transcript, i.e., at the 5' non-coding sequence, 3' non-coding sequence, introns, or the coding sequence. “Functional RNA” refers to antisense RNA, ribozyme RNA, or other RNA that may not be translated but yet has an effect on cellular processes. The terms “complement” and “reverse complement” are used interchangeably herein with respect to mRNA transcripts, and are meant to define the antisense RNA of the message.

The term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., the coding sequence is under the transcriptional control of the promoter). Coding sequences can be operably linked to regulatory sequences in a sense or antisense orientation. In another example, the complementary RNA regions can be operably linked, either directly or indirectly, 5' to the target mRNA, or 3' to the target mRNA, or within the target mRNA, or a first complementary region is 5' and its complement is 3' to the target mRNA.

Standard recombinant DNA and molecular cloning techniques used herein are well known in the art and are described more fully in Sambrook et al., *Molecular Cloning: A Laboratory Manual; Cold Spring Harbor Laboratory*: Cold Spring Harbor, NY (1989). Transformation methods are well known to those skilled in the art and are described infra.

"PCR" or "polymerase chain reaction" is a technique for the synthesis of specific DNA segments and consists of a series of repetitive denaturation, annealing, and extension cycles. Typically, a double-stranded DNA is heat denatured, and two primers complementary to the 3' boundaries of the target segment are annealed to the DNA at low temperature, and then extended at an intermediate temperature. One set of these three consecutive steps is referred to as a "cycle".

The term "recombinant" refers to an artificial combination of two otherwise separated segments of sequence, e.g., by chemical synthesis, or manipulation of isolated segments of nucleic acids by genetic engineering techniques.

The terms "plasmid", "vector" and "cassette" refer to an extra chromosomal element often carrying genes that are not part of the central metabolism of the cell, and usually in the form of double-stranded DNA. Such elements may be autonomously replicating sequences, genome integrating sequences, phage, or nucleotide sequences, in linear or circular form, of a single- or double-stranded DNA or RNA, derived from any source, in which a number of nucleotide sequences have been joined or recombined into a unique construction which is capable of introducing a polynucleotide of interest into a cell. "Transformation cassette" refers to a specific vector containing a gene and having elements in addition to the gene that facilitates transformation of a particular host cell. "Expression cassette" refers to a specific vector containing a gene and having elements in addition to the gene that allow for expression of that gene in a host.

The terms "recombinant DNA molecule", "recombinant construct", "expression construct", "construct", "construct", and "recombinant DNA construct" are used interchangeably herein. A recombinant construct comprises an artificial combination of nucleic acid fragments, e.g., regulatory and coding sequences that are not all found together in nature. For example, a construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells. The skilled artisan will also recognize that different independent transformation events may result in different levels and patterns of expression (Jones et al., (1985) *EMBO J* 4:2411-2418; De Almeida et al., (1989) *Mol Gen Genetics* 218:78-86), and thus that multiple events are typically screened in order to obtain lines displaying the desired expression level and pattern. Such screening may be accomplished standard molecular biological, biochemical, and other assays including Southern analysis of DNA, Northern analysis of mRNA expression, PCR, real time quantitative PCR (qPCR), reverse transcription PCR (RT-PCR), immunoblotting analysis of protein expression, enzyme or activity assays, and/or phenotypic analysis.

The term "expression", as used herein, refers to the production of a functional end-product (e.g., an mRNA, guide RNA, or a protein) in either precursor or mature form.

The term "introducing" includes reference to introducing, providing, contacting a compound, such as but not limited to, a nucleic acid (e.g., expression construct) or peptide, polypeptide or protein into a cell. Introducing includes the direct delivery of polynucleotides (such as RNA, DNA, RNA-DNA hybrids, single or double stranded oligonucleotides, linear or circular polynucleotides) and/or includes the direct delivery of proteins (polypeptides). Introducing includes reference to the incorporation of a nucleic acid or polypeptide into a eukaryotic or prokaryotic cell where the nucleic acid may be incorporated into the genome of the cell, and includes reference to the transient introduction of a nucleic acid or protein into the cell. Introducing includes reference to stable or transient transformation methods, transfection, transduction, microinjection, electroporation, viral methods, *Agrobacterium*-mediated transformation, ballistic particle acceleration, whiskers mediated transformation, as well as sexually crossing. Thus, "introducing" in the context of inserting a nucleic acid fragment (e.g., a recombinant DNA construct/expression construct, guide RNA, guide DNA, template DNA, donor DNA) into a cell, includes "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid, or mitochondrial DNA), converted into an autonomous replicon, or transiently expressed (e.g., transfected mRNA).

A variety of methods are known for introducing, contacting and/or providing a composition into an organisms including stable transformation methods, transient transformation methods, virus-mediated methods, sexual crossing and sexual breeding. Stable transformation indicates that the introduced polynucleotide integrates into the genome of the organism and is capable of being inherited by progeny thereof. Transient transformation indicates that the introduced composition is only temporarily expressed or present in the organism.

Protocols for contacting, providing, introducing polynucleotides and polypeptides into cells or organisms are known and include microinjection (Crossway et al., (1986) *Biotechniques* 4:320-34 and U.S. Pat. No. 6,300,543), meristem transformation (U.S. Pat. No. 5,736,369), electroporation (Riggs et al., (1986) *Proc. Natl. Acad. Sci. USA* 83:5602-6, *Agrobacterium*-mediated transformation (U.S. Pat. Nos. 5,563,055 and 5,981,840), whiskers mediated transformation (Ainley et al. 2013, *Plant Biotechnology Journal* 11:1126-1134; Shaheen A. and M. Arshad 2011 Properties and Applications of Silicon Carbide (2011), 345-358 Editor(s): Gerhardt, Rosario. Publisher: InTech, Rijeka, Croatia. CODEN: 69PQBP; ISBN: 978-953-307-201-2) direct gene transfer (Paszkowski et al., (1984) *EMBO J* 3:2717-22), and ballistic particle acceleration (U.S. Pat. Nos. 4,945,050; 5,879,918; 5,886,244; 5,932,782; Tomes et al., (1995) "Direct DNA Transfer into Intact Plant Cells via Microprojectile Bombardment" in *Plant Cell, Tissue, and Organ Culture: Fundamental Methods*, ed. Gamborg & Phillips (Springer-Verlag, Berlin); McCabe et al., (1988) *Biotechnology* 6:923-6; Weissinger et al., (1988) *Ann Rev Genet* 22:421-77; Sanford et al., (1987) *Particulate Science and Technology* 5:27-37 (onion); Christou et al., (1988) *Plant Physiol* 87:671-4 (soybean); Finer and McMullen, (1991) *In Vitro Cell Dev Biol* 27P:175-82 (soybean); Singh et al., (1998) *Theor Appl Genet* 96:319-24 (soybean); Datta et al., (1990) *Biotechnology* 8:736-40 (rice); Klein et al., (1988) *Proc. Natl. Acad. Sci. USA* 85:4305-9 (maize); Klein et al., (1988) *Biotechnology* 6:559-63 (maize); U.S. Pat. Nos. 5,240,855; 5,322,783 and 5,324,646; Klein et al., (1988) *Plant Physiol* 91:440-4 (maize); Fromm et al., (1990) *Biotechnology* 8:833-9 (maize); Hooykaas-Van Slogteren et al., (1984) *Nature* 311:763-4; U.S. Pat. No. 5,736,369 (cereals); Bytebier et al., (1987) *Proc. Natl. Acad. Sci. USA* 84:5345-9 (Liliaceae); De Wet et al., (1985) in *The Experimental Manipulation of Ovule Tissues*, ed. Chapman et al., (Longman, New York), pp. 197-209 (pollen); Kaeppler et al., (1990) *Plant Cell Rep* 9:415-8) and Kaeppler et al., (1992) *Theor Appl Genet* 84:560-6 (whisker-mediated transformation); D'Halluin et al., (1992) *Plant Cell* 4:1495-505 (electroporation); Li et al., (1993) *Plant Cell Rep* 12:250-5; Christou and Ford (1995) *Annals Botany* 75:407-13 (rice) and Osjoda et al., (1996) *Nat Biotechnol* 14:745-50 (maize via *Agrobacterium tumefaciens*).

Alternatively, polynucleotides may be introduced into cells or organisms by contacting cells or organisms with a virus or viral nucleic acids. Generally, such methods involve incorporating a polynucleotide within a viral DNA or RNA molecule. In some examples a polypeptide of interest may be initially synthesized as part of a viral polyprotein, which is later processed by proteolysis in vivo or in vitro to produce the desired recombinant protein. Methods for introducing polynucleotides into plants and expressing a protein encoded therein, involving viral DNA or RNA molecules, are known, see, for example, U.S. Pat. Nos. 5,889,191, 5,889,190, 5,866,785, 5,589,367 and 5,316,931. Transient transformation methods include, but are not limited to, the introduction of polypeptides, such as a double-strand break inducing agent, directly into the organism, the introduction of polynucleotides such as DNA and/or RNA polynucleotides, and the introduction of the RNA transcript, such as an mRNA encoding a double-strand break inducing agent, into the organism. Such methods include, for example, microinjection or particle bombardment. See, for example Crossway et al., (1986) *Mol Gen Genet* 202:179-85; Nomura et al., (1986) *Plant Sci* 44:53-8; Hepler et al., (1994) *Proc. Natl. Acad. Sci. USA* 91:2176-80; and, Hush et al., (1994) *J Cell Sci* 107:775-84.

Nucleic acids and proteins can be provided to a cell by any method including methods using molecules to facilitate the uptake of anyone or all components of a guided Cas system (protein and/or nucleic acids), such as cell-penetrating peptides and nanocarriers. See also US20110035836 Nanocarrier based plant transfection and transduction, and EP 2821486 A1 Method of introducing nucleic acid into plant cells, incorporated herein by reference.

Introducing a guide RNA/Cas endonuclease complex into a cell includes introducing the individual components of said complex either separately or combined into the cell, and either directly (direct delivery as RNA for the guide and protein for the Cas endonuclease) or via recombination constructs expressing the components (guide RNA, Cas endonuclease). Introducing a guide RNA/Cas endonuclease complex into a cell includes introducing the guide RNA/Cas endonuclease complex as a ribonucleotide-protein into the cell. The ribonucleotide-protein can be assembled prior to being introduced into the cell as described herein.

Plant cells differ from human and animal cells in that plant cells contain a plant cell wall which may act as a barrier to the direct delivery of the RGEN ribonucleoproteins and/or of the direct delivery of the RGEN components.

As described herein, direct delivery of the RGEN ribonucleoproteins into plant cells can be achieved through particle mediated delivery (particle bombardment. Based on the experiments described herein, a skilled artesian can now envision that any other direct method of delivery, such as but not limiting to, polyethylene glycol (PEG)-mediated transfection to protoplasts, electroporation, cell-penetrating peptides, or mesoporous silica nanoparticle (MSN)-mediated direct protein delivery, can be successfully used for delivering RGEN ribonucleoproteins into plant cells.

Direct delivery of the RGEN ribonucleoprotein, as described herein, allows for genome editing at a target site in the genome of a cell which can be followed by rapid degradation of the complex, and only a transient presence of the complex in the cell. This transient presence of the RGEN complex may lead to reduced off-target effects. In contrast, delivery of RGEN components (guide RNA, Cas9 endonuclease) via plasmid DNA sequences can result in constant expression of RGENs from these plasmids which can intensify off target effects (Cradick, T. J. et al (2013) Nucleic Acids Res 41:9584-9592; Fu, Y et al (2014) Nat. Biotechnol. 31:822-826.

Direct delivery can be achieved by combining any one component of the RNA guided endonuclease (guide RNA, Cas protein, mRNA encoding the gRNA or Cas endonuclease) or the RGEN complex itself, with a particle delivery matrix comprising a microparticle such as but not limited to of a gold particle, tungsten particle, and silicon carbide whisker particle. Examples of combination methods described herein for combining microparticles to plasmid DNA and DNA of interest can also be used for coating guide RNA molecules, mRNA molecules, Cas proteins and RGEN complexes to the microparticles.

These coated microparticles can be introduced into the cells by any direct method known in the art such as the particle bombardment method described in Example 8. Microparticles and RGEN components or RGEN complex can be combined (mixed) in any matter to allow for coating of the RGEN components to the micro particles. For example, RGEN components can be precipitated onto gold pellets of a diameter ranging from at least 0.1 μm, 0.2 μm, 0.3 μm, 0.4 μm, 0.5 μm, 0.6 μm, 0.7 μm, 0.8 μm, 0.9 μm or 1.0 μm in diameter using any suitable buffer (such as but not limiting to a water-soluble cationic lipid such as but not limiting to TransIT-2020 Transfection Reagent (Cat #MIR 5404, Mirus, USA). RGEN component solutions can prepared on ice (or at any temperature suitable to enable mircoparticle bounding) using at least 0.1 μg, 0.2 μg, 0.3 μg, 0.4 μg, 0.5 μg, 0.6 μg, 0.7 μg, 0.8 μg, 0.9 μg, 1.0 μg, 2.0 μg, 3.0 μg, 4.0 μg, 5.0 μg, 6.0 μg, 7.0 μg, 8.0 μg 9.0 μg or 10 μg of RNA (guided RNA or mRNA) or Cas endonuclease protein. To the pre-mixed RGEN components of RGEN complexes, at least 1 μl to 20 μl of prepared microparticles can be added and mixed carefully.

Methods of introducing a guide RNA/Cas endonuclease complex into a cell, include methods comprising combining at least one guide RNA molecule and at least one Cas endonuclease protein to form a ribonucleotide-protein and combining said ribonucleotide-protein with a particle delivery matrix to allow for said ribonucleotide-protein and matrix to bind and form a ribonucleotide-protein-matrix complex; and, introducing said ribonucleotide-protein-matrix complex into said cell. The particle delivery matrix can comprise microparticles combined with a cationic lipid.

The term "cationic lipid" includes reference to a water soluble cationic lipid, such as but not limiting to TransIT-2020, or a cationic lipid solution such as but not limiting to a cationic lipid solution comprising N,N,N',N'-tetramethyl-N, N'-bis(2-hydroxylethyl)-2,3-di(oleoyloxy)-1,4-butanediammonium iodide, and L-dioleoyl phosphatidylethanolamine (DOPE). (see also US2007/0178593, published on Aug. 2, 2007, incorporated herein by reference), 5. The method of claim.

The particle delivery matrix can comprise microparticles selected from the group consisting of gold particles, tungsten particles, and silicon carbide whisker particles.

The particle delivery matrix can further comprise a compound selected from the group consisting of Tfx-10™, Tfx-20™, Tfx-50™, Lipofectin™, Lipofectamine™ Cellfectin™, Effectene™, Cytofectin GSV™, Perfect Lipids™, DOTAP™, DMRIE-C™, FuGENE-6™, Superfect™, Polyfeet™, polyethyleneimine, chitosan, protamine CI, histone H1, histone CENH3, poly-L lysine, and DMSA. (US2007/0178593, published on Aug. 2, 2007, incorporated herein by reference)

RGEN components can also be combined prior to be coated on microparticles by combining least 0.1 μg, 0.2 μg, 0.3 μg, 0.4 μg, 0.5 μg, 0.6 μg, 0.7 μg, 0.8 μg, 0.9 μg, 1.0 μg, 2.0 μg, 3.0 μg, 4.0 μg, 5.0 μg, 6.0 μg, 7.0 μg, 8.0 μg 9.0 μg or 10 μg of guide RNA with at least 0.1 μg, 0.2 μg, 0.3 μg, 0.4 μg, 0.5 μg, 0.6 μg, 0.7 μg, 0.8 μg, 0.9 μg, 1.0 μg, 2.0 μg, 3.0 μg, 4.0 μg, 5.0 μg, 6.0 μg, 7.0 μg, 8.0 μg 9.0 μg or 10 μg of Cas endonuclease in a solution suitable to allow for complex formation (such as but not limiting to a Cas9 buffer (NEB)), at any temperature to allow for complex formation such as a temperature ranging from 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23.0° C., 24° C., 25° C., 26° C., 27° C., 28° C., 29° C., 30° C., 31° C., 32° C., 33.0° C., 34° C., 35° C., 36° C., 37° C., 38° C., 39° C. and 40° C.

Methods of introducing a guide RNA/Cas endonuclease complex into a cell, include methods of introducing at least one guide RNA molecule and at least one Cas endonuclease protein into a cell, and growing said cell under suitable conditions to allow said guide RNA and said Cas endonuclease protein to form a complex inside said cell.

Methods of introducing a guide RNA/Cas endonuclease complex into a cell, include methods of introducing at least one guide RNA molecule and at least one mRNA encoding a Cas endonuclease protein into a cell, and growing said cell under suitable conditions to allow said mRNA to translate said Cas endonuclease protein and form a complex with said guide RNA Methods of introducing a guide RNA/Cas endonuclease complex into a cell, include methods of combining at least one guide RNA molecule and at least one Cas endonuclease protein to form a ribonucleotide-protein and combining said ribonucleotide-protein with a particle delivery matrix to allow for said ribonucleotide-protein and matrix to bind and form a ribonucleotide-protein-matrix complex; and, introducing said ribonucleotide-protein-matrix complex together with at least one a polynucleotide template into said cell, wherein said polynucleotide modification template comprises at least one nucleotide modification of a nucleotide sequence in the genome of said cell, wherein said at least one nucleotide modification of said polynucleotide modification template is selected from the group consisting of (i) a replacement of at least one nucleotide, (ii) a deletion of at least one nucleotide, (iii) an insertion of at least one nucleotide, and (iv) any combination of (i)-(iii).

Methods of introducing a guide RNA/Cas endonuclease complex into a cell, include methods of combining at least one guide RNA molecule and at least one Cas endonuclease protein to form a ribonucleotide-protein and combining said ribonucleotide-protein with a particle delivery matrix to allow for said ribonucleotide-protein and matrix to bind and form a ribonucleotide-protein-matrix complex; and, introducing said ribonucleotide-protein-matrix complex together with a donor DNA into said cell, wherein said donor DNA comprises at least one polynucleotide of interest.

Suitable conditions for growing cells are well known in the art and the skilled artesian can use any growing condition based on the type of cell (such as conditions suitable for plant cells). As described in Example 8, plant embryos or cells can be incubated in any plant maintenance medium known in the art (such as, but not limiting to 560P, Example 8) for 12 to 48 hours at temperatures ranging from 26° C. to 37° C., and then placed at 26° C. After 5 to 7 days the embryos/cells are transferred to any selection medium known in the art (such as, but not limiting to 560R, Example 8), and subcultured thereafter.

RGEN components (including guide RNA, Cas endonuclease protein) can be combined to form a ribonucleotide-protein complex (RNP) prior to be coated on (combined with) microparticles by combining least 0.1 μg, 0.2 μg, 0.3 μg, 0.4 μg, 0.5 μg, 0.6 μg, 0.7 μg, 0.8 μg, 0.9 μg, 1.0 μg, 2.0 μg, 3.0 μg, 4.0 μg, 5.0 μg, 6.0 μg, 7.0 μg, 8.0 μg, 9.0 μg or 10 μg of guide RNA with at least 0.1 μg, 0.2 μg, 0.3 μg, 0.4 μg, 0.5 μg, 0.6 μg, 0.7 μg, 0.8 μg, 0.9 μg, 1.0 μg, 2.0 μg, 3.0 μg, 4.0 μg, 5.0 μg, 6.0 μg, 7.0 μg, 8.0 μg, 9.0 μg or 10 μg of Cas endonuclease in a solution suitable to allow for complex formation (such as but not limiting to a Cas9 buffer (NEB)), at any temperature to allow for complex formation such as a temperature ranging from 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C. and 40° C.

"Mature" protein refers to a post-translationally processed polypeptide (i.e., one from which any pre- or propeptides present in the primary translation product have been removed). "Precursor" protein refers to the primary product of translation of mRNA (i.e., with pre- and propeptides still present). Pre- and propeptides may be but are not limited to intracellular localization signals.

"Stable transformation" refers to the transfer of a nucleic acid fragment into a genome of a host organism, including both nuclear and organellar genomes, resulting in genetically stable inheritance. In contrast, "transient transformation" refers to the transfer of a nucleic acid fragment into the nucleus, or other DNA-containing organelle, of a host organism resulting in gene expression without integration or stable inheritance. Host organisms containing the transformed nucleic acid fragments are referred to as "transgenic" organisms.

The commercial development of genetically improved germplasm has also advanced to the stage of introducing multiple traits into crop plants, often referred to as a gene stacking approach. In this approach, multiple genes conferring different characteristics of interest can be introduced into a plant. Gene stacking can be accomplished by many means including but not limited to co-transformation, retransformation, and crossing lines with different genes of interest.

Cells include, but are not limited to, human, non-human, animal, bacterial, fungal, insect, yeast, and plant cells as well as plants and seeds produced by the methods described herein. Plant cells include cells selected from the group consisting of maize, rice, sorghum, rye, barley, wheat, millet, oats, sugarcane, turfgrass, or switchgrass, soybean, canola, alfalfa, sunflower, cotton, tobacco, peanut, potato, tomato, tobacco, *Arabidopsis*, and safflower cells.

The term "plant" includes reference to whole plants, plant organs, plant tissues, seeds, and plant cells, and progeny of the same. Plant cells include, without limitation, cells from seeds, suspension cultures, embryos, meristematic regions, callus tissue, leaves, roots, shoots, gametophytes, sporophytes, pollen and microspores. Plant parts include differentiated and undifferentiated tissues including, but not limited to roots, stems, shoots, leaves, pollens, seeds, tumor tissue and various forms of cells and culture (e.g., single cells, protoplasts, embryos, and callus tissue). The plant tissue may be in plant or in a plant organ, tissue or cell culture. The term "plant organ" refers to plant tissue or a group of tissues that constitute a morphologically and functionally distinct part of a plant. The term "genome" refers to the entire complement of genetic material (genes and non-coding sequences) that is present in each cell of an organism, or virus or organelle; and/or a complete set of chromosomes inherited as a (haploid) unit from one parent. "Progeny" comprises any subsequent generation of a plant.

A transgenic plant includes, for example, a plant which comprises within its genome a heterologous polynucleotide introduced by a transformation step. The heterologous polynucleotide can be stably integrated within the genome such that the polynucleotide is passed on to successive generations. The heterologous polynucleotide may be integrated into the genome alone or as part of a recombinant DNA construct. A transgenic plant can also comprise more than one heterologous polynucleotide within its genome. Each heterologous polynucleotide may confer a different trait to the transgenic plant. A heterologous polynucleotide can include a sequence that originates from a foreign species, or, if from the same species, can be substantially modified from its native form. Transgenic can include any cell, cell line, callus, tissue, plant part or plant, the genotype of which has been altered by the presence of heterologous nucleic acid including those transgenics initially so altered as well as those created by sexual crosses or asexual propagation from the initial transgenic. The alterations of the genome (chromosomal or extra-chromosomal) by conventional plant breeding methods, by the genome editing procedure described herein that does not result in an insertion of a foreign polynucleotide, or by naturally occurring events such as random cross-fertilization, non-recombinant viral infection, non-recombinant bacterial transformation, non-recombinant transposition, or spontaneous mutation are not intended to be regarded as transgenic.

In certain embodiments of the disclosure, a fertile plant is a plant that produces viable male and female gametes and is self-fertile. Such a self-fertile plant can produce a progeny plant without the contribution from any other plant of a gamete and the genetic material contained therein. Other embodiments of the disclosure can involve the use of a plant that is not self-fertile because the plant does not produce male gametes, or female gametes, or both, that are viable or otherwise capable of fertilization. As used herein, a "male sterile plant" is a plant that does not produce male gametes that are viable or otherwise capable of fertilization. As used herein, a "female sterile plant" is a plant that does not produce female gametes that are viable or otherwise capable of fertilization. It is recognized that male-sterile and female-sterile plants can be female-fertile and male-fertile, respectively. It is further recognized that a male fertile (but female sterile) plant can produce viable progeny when crossed with a female fertile plant and that a female fertile (but male sterile) plant can produce viable progeny when crossed with a male fertile plant.

Non-conventional yeast herein refers to any yeast that is not a *Saccharomyces* (e.g., *S. cerevisiae*) or *Schizosaccharomyces* yeast species. Non-conventional yeast are described in Non-Conventional Yeasts in Genetics, Biochemistry and Biotechnology: Practical Protocols (K. Wolf, K. D. Breunig, G. Barth, Eds., Springer-Verlag, Berlin, Germany, 2003), which is incorporated herein by reference. Non-conventional yeast in certain embodiments may additionally (or alternatively) be yeast that favor non-homologous end-joining (NHEJ) DNA repair processes over repair processes mediated by homologous recombination (HR). Definition of a non-conventional yeast along these lines—preference of NHEJ over HR—is further disclosed by Chen et al. (*PLoS ONE* 8:e57952), which is incorporated herein by reference. Preferred non-conventional yeast herein are those of the genus *Yarrowia* (e.g., *Yarrowia lipolytica*). The term "yeast" herein refers to fungal species that predominantly exist in unicellular form. Yeast can alternative be referred to as "yeast cells" herein (see also U.S. provisional application 62/036,652, filed on Aug. 13, 2014, which is incorporated by reference herein).

A "centimorgan" (cM) or "map unit" is the distance between two linked genes, markers, target sites, loci, or any pair thereof, wherein 1% of the products of meiosis are recombinant. Thus, a centimorgan is equivalent to a distance equal to a 1% average recombination frequency between the two linked genes, markers, target sites, loci, or any pair thereof.

The present disclosure finds use in the breeding of plants comprising one or more introduced traits. Most commonly, transgenic traits are randomly inserted throughout the plant genome as a consequence of transformation systems based on *Agrobacterium*, biolistics, or other commonly used procedures. More recently, gene targeting protocols have been developed that enable directed transgene insertion. One important technology, site-specific integration (SSI) enables the targeting of a transgene to the same chromosomal location as a previously inserted transgene. Custom-designed meganucleases and custom-designed zinc finger meganucleases allow researchers to design nucleases to target specific chromosomal locations, and these reagents allow the targeting of transgenes at the chromosomal site cleaved by these nucleases.

The currently used systems for precision genetic engineering of eukaryotic genomes, e.g. plant genomes, rely upon homing endonucleases, meganucleases, zinc finger nucleases, and transcription activator-like effector nucleases (TALENs), which require de novo protein engineering for every new target locus. The highly specific, RNA-directed DNA nuclease, guide RNA/Cas9 endonuclease system described herein, is more easily customizable and therefore more useful when modification of many different target sequences is the goal.

The guide RNA/Cas system described herein is especially useful for genome engineering, especially plant genome engineering, in circumstances where nuclease off-target cutting can be toxic to the targeted cells. In one embodiment of the guide RNA/Cas system described herein, an expression-optimized Cas9 gene, is stably integrated into the target genome, e.g. plant genome. Expression of the Cas9 gene is under control of a promoter, e.g. plant promoter, which can be a constitutive promoter, tissue-specific promoter or inducible promoter, e.g. temperature-inducible, stress-inducible, developmental stage inducible, or chemically inducible promoter. In the absence of the guide RNA or crRNA, the Cas9 protein is not able to cut DNA and therefore its presence in the plant cell should have little or no consequence. Hence a key advantage of the guide RNA/Cas system described herein is the ability to create and maintain a cell line or transgenic organism capable of efficient expression of the Cas9 protein with little or no consequence to cell viability. In order to induce cutting at desired genomic sites to achieve targeted genetic modifications, guide RNAs or crRNAs can be introduced by a variety of methods into cells containing the stably-integrated and expressed cas9 gene. For example, guide RNAs or crRNAs can be chemically or enzymatically synthesized, and introduced into the Cas9 expressing cells via direct delivery methods such a particle bombardment or electroporation. Alternatively, genes capable of efficiently expressing guide RNAs or crRNAs in the target cells can be synthesized chemically, enzymatically or in a biological system, and these genes can be introduced into the Cas9 expressing cells via direct delivery methods such a particle bombardment, electroporation or biological delivery methods such as *Agrobacterium* mediated DNA delivery.

A guide RNA/Cas system mediating gene targeting can be used in methods for directing transgene insertion and/or for producing complex transgenic trait loci comprising multiple transgenes in a fashion similar as disclosed in WO2013/0198888 (published Aug. 1, 2013) where instead of using a double strand break inducing agent to introduce a gene of interest, a guide RNA/Cas system as disclosed herein is used. A complex trait locus includes a genomic locus that has multiple transgenes genetically linked to each other. By inserting independent transgenes within 0.1, 0.2, 0.3, 0.4, 0.5, 1.0, 2, or even 5 centimorgans (cM) from each other, the transgenes can be bred as a single genetic locus (see, for example, U.S. patent application Ser. No. 13/427,138) or PCT application PCT/US2012/030061. After selecting a plant comprising a transgene, plants containing (at least) one transgenes can be crossed to form an F1 that contains both transgenes. In progeny from these F1 (F2 or BC1) 1/500 progeny would have the two different transgenes recombined onto the same chromosome. The complex locus can then be bred as single genetic locus with both transgene traits. This process can be repeated to stack as many traits as desired.

Chromosomal intervals that correlate with a phenotype or trait of interest can be identified. A variety of methods well known in the art are available for identifying chromosomal intervals. The boundaries of such chromosomal intervals are drawn to encompass markers that will be linked to the gene controlling the trait of interest. In other words, the chromosomal interval is drawn such that any marker that lies within that interval (including the terminal markers that define the boundaries of the interval) can be used as a marker for northern leaf blight resistance. In one embodiment, the chromosomal interval comprises at least one QTL, and furthermore, may indeed comprise more than one QTL. Close proximity of multiple QTLs in the same interval may obfuscate the correlation of a particular marker with a particular QTL, as one marker may demonstrate linkage to more than one QTL. Conversely, e.g., if two markers in close proximity show co-segregation with the desired phenotypic trait, it is sometimes unclear if each of those markers identifies the same QTL or two different QTL. The term "quantitative trait locus" or "QTL" refers to a region of DNA that is associated with the differential expression of a quantitative phenotypic trait in at least one genetic background, e.g., in at least one breeding population. The region of the QTL encompasses or is closely linked to the gene or genes that affect the trait in question. An "allele of a QTL" can comprise multiple genes or other genetic factors within a contiguous genomic region or linkage group, such as a haplotype. An allele of a QTL can denote a haplotype within a specified window wherein said window is a contiguous genomic region that can be defined, and tracked, with a set of one or more polymorphic markers. A haplotype can be defined by the unique fingerprint of alleles at each marker within the specified window.

A variety of methods are available to identify those cells having an altered genome at or near a target site without using a screenable marker phenotype. Such methods can be viewed as directly analyzing a target sequence to detect any change in the target sequence, including but not limited to PCR methods, sequencing methods, nuclease digestion, Southern blots, and any combination thereof.

Proteins may be altered in various ways including amino acid substitutions, deletions, truncations, and insertions. Methods for such manipulations are generally known. For example, amino acid sequence variants of the protein(s) can be prepared by mutations in the DNA. Methods for mutagenesis and nucleotide sequence alterations include, for example, Kunkel, (1985) *Proc. Natl. Acad. Sci. USA* 82:488-92; Kunkel et al., (1987) *Meth Enzymol* 154:367-82; U.S. Pat. No. 4,873,192; Walker and Gaastra, eds. (1983) *Techniques in Molecular Biology* (MacMillan Publishing Company, New York) *and the references* cited therein. Guidance regarding amino acid substitutions not likely to affect biological activity of the protein is found, for example, in the model of Dayhoff et al., (1978) *Atlas of Protein Sequence and Structure* (Natl Biomed Res Found, Washington, D.C.). Conservative substitutions, such as exchanging one amino acid with another having similar properties, may be preferable. Conservative deletions, insertions, and amino acid substitutions are not expected to produce radical changes in the characteristics of the protein, and the effect of any substitution, deletion, insertion, or combination thereof can be evaluated by routine screening assays. Assays for double-strand-break-inducing activity are known and generally measure the overall activity and specificity of the agent on DNA substrates containing target sites.

The term "dicot" refers to the subclass of angiosperm plants also knows as "dicotyledoneae" and includes reference to whole plants, plant organs (e.g., leaves, stems, roots, etc.), seeds, plant cells, and progeny of the same. Plant cell, as used herein includes, without limitation, seeds, suspension cultures, embryos, meristematic regions, callus tissue, leaves, roots, shoots, gametophytes, sporophytes, pollen, and microspores.

The term "crossed" or "cross" or "crossing" in the context of this disclosure means the fusion of gametes via pollination to produce progeny (i.e., cells, seeds, or plants). The term encompasses both sexual crosses (the pollination of one plant by another) and selfing (self-pollination, i.e., when the pollen and ovule (or microspores and megaspores) are from the same plant or genetically identical plants).

The term "introgression" refers to the transmission of a desired allele of a genetic locus from one genetic background to another. For example, introgression of a desired allele at a specified locus can be transmitted to at least one progeny plant via a sexual cross between two parent plants, where at least one of the parent plants has the desired allele within its genome. Alternatively, for example, transmission of an allele can occur by recombination between two donor genomes, e.g., in a fused protoplast, where at least one of the donor protoplasts has the desired allele in its genome. The desired allele can be, e.g., a transgene, a modified (mutated or edited) native allele, or a selected allele of a marker or QTL.

Standard DNA isolation, purification, molecular cloning, vector construction, and verification/characterization methods are well established, see, for example Sambrook et al., (1989) *Molecular Cloning: A Laboratory Manual*, (Cold Spring Harbor Laboratory Press, NY). Vectors and constructs include circular plasmids, and linear polynucleotides, comprising a polynucleotide of interest and optionally other components including linkers, adapters, regulatory or analysis. In some examples a recognition site and/or target site can be contained within an intron, coding sequence, 5' UTRs, 3' UTRs, and/or regulatory regions.

The present disclosure further provides expression constructs for expressing in a plant, plant cell, or plant part a guide RNA/Cas system that is capable of binding to and creating a double strand break in a target site. In one embodiment, the expression constructs of the disclosure comprise a promoter operably linked to a nucleotide sequence encoding a Cas gene and a promoter operably linked to a guide RNA of the present disclosure. The promoter is capable of driving expression of an operably linked nucleotide sequence in a plant cell.

Any plant can be used, including monocot and dicot plants. Examples of monocot plants that can be used include, but are not limited to, corn (*Zea mays*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), wheat (*Triticum aestivum*), sugarcane (*Saccharum* spp.), oats (*Avena*), barley (*Hordeum*), switchgrass (*Panicum virgatum*), pineapple (*Ananas comosus*), banana (*Musa* spp.), palm, ornamentals, turfgrasses, and other grasses. Examples of dicot plants that can be used include, but are not limited to, soybean (*Glycine max*), canola (*Brassica napus* and *B. campestris*), alfalfa (*Medicago sativa*), tobacco (*Nicotiana tabacum*), *Arabidopsis* (*Arabidopsis thaliana*), sunflower (*Helianthus annuus*), cotton (*Gossypium arboreum*), and peanut (*Arachis hypogaea*), tomato (*Solanum lycopersicum*), potato (*Solanum tuberosum*) etc.

The meaning of abbreviations is as follows: "sec" means second(s), "min" means minute(s), "h" means hour(s), "d" means day(s), "µL" means microliter(s), "mL" means milliliter(s), "L" means liter(s), "µM" means micromolar, "mM" means millimolar, "M" means molar, "mmol" means millimole(s), "µmole" mean micromole(s), "g" means gram(s), "µg" means microgram(s), "ng" means nanogram(s), "U" means unit(s), "bp" means base pair(s) and "kb" means kilobase(s).

Non-limiting examples of compositions and methods disclosed herein are as follows:

1. A method for modifying a nucleotide sequence in the genome of a plant cell without the use of a selectable marker, the method comprising: introducing into at least one plant cell a guide polynucleotide/Cas endonuclease complex capable of making a double strand break in a target site located in a nucleotide sequence; and, selecting a plant cell having a modification in said nucleotide sequence, wherein the selection occurs without the use of a selectable marker.

1b. A method for modifying a nucleotide sequence in the genome of a plant cell without the use of a selectable marker, the method comprising: introducing into at least one plant cell a guide RNA/Cas endonuclease complex capable of making a double strand break in a target site located in said nucleotide sequence; and, selecting a plant cell having a modification in said nucleotide sequence, wherein the selection occurs without the use of a selectable marker.

2. A method for producing a plant having a modified nucleotide sequence in its genome without the use of a selectable marker, the method comprising: introducing into at least one plant cell a guide polynucleotide/Cas endonuclease complex capable of making a double strand break in a target site located in a nucleotide sequence; obtaining a plant from said plant cell; and, selecting a plant having a modification in said nucleotide sequence, wherein the selection occurs without the use of a selectable marker.

2b. A method for producing a plant having a modified nucleotide sequence in its genome without the use of a selectable marker, the method comprising: introducing into at least one plant cell a guide RNA/Cas endonuclease complex capable of making a double strand break in a target site located in a nucleotide sequence; obtaining a plant from said plant cell; and, selecting a plant having a modification in said nucleotide sequence, wherein the selection occurs without the use of a selectable marker.

3. A method for producing plant callus tissue having a modified nucleotide sequence in its genome without the use of a selectable marker, the method comprising: introducing into at least one plant cell a guide polynucleotide/Cas endonuclease complex capable of making a double strand break in a target site located in a nucleotide sequence; obtaining callus tissue from said plant cell; and, selecting callus tissue having a modification in said nucleotide sequence, wherein the selection occurs without the use of a selectable marker.

3b. A method for producing plant callus tissue having a modified nucleotide sequence in its genome without the use of a selectable marker, the method comprising: introducing into at least one plant cell a guide RNA/Cas endonuclease complex capable of making a double strand break in a target site located in a nucleotide sequence; obtaining callus tissue from said plant cell; and, selecting callus tissue having a modification in said nucleotide sequence, wherein the selection occurs without the use of a selectable marker.

4. The method of embodiments 1-3b, wherein the modification is selected from the group consisting of an insertion of at least one nucleotide, a deletion of at least one nucleotide, or a substitution of at least one nucleotide in said target site.

5. The method of embodiments 1-3b, further comprising introducing a polynucleotide modification template into said plant cell, wherein said polynucleotide modification template comprises at least one nucleotide modification of said nucleotide sequence.

6. The method of embodiment 5, wherein the at least one nucleotide modification of said polynucleotide modification template is selected from the group consisting of (i) a replacement of at least one nucleotide, (ii) a deletion of at least one nucleotide, (iii) an insertion of at least one nucleotide, and (iv) any combination of (i)-(iii).

7. The method of embodiments 1-3b, further comprising introducing a donor DNA to the plant cell of (a) wherein said donor DNA comprises at least one polynucleotide of interest to be inserted into said target site.

8. The method of embodiments 1-3b, wherein the introducing does not comprise the introduction of a selectable marker into said cell.

9. The method of embodiments 1-3b, wherein the introducing does not comprise the restoration of a disrupted selectable marker gene into a non-disrupted selectable marker gene encoding a functional selectable marker protein.

10. The method of embodiments 1-3b, wherein the introducing does not result in the production of a selectable marker within said cell.

11. The method of embodiments 1-3b, wherein the selecting does not comprise the identification or use of a selectable marker.

12. The method of embodiments 1-3b, wherein the selecting occurs via sequencing of the isolated DNA of said plant.

13. The method of embodiments 1-3b, wherein the guide RNA/Cas endonuclease complex is assemble in vitro and introduced as a ribonucleotide-protein complex.

13b. The method of embodiments 1-3b, wherein the guide RNA/Cas endonuclease complex is introduced as a ribonucleotide-protein complex.

13c. The method of embodiments 1-3b, wherein the guide RNA/Cas endonuclease complex is-introduced into the cell without the use of recombinant DNA constructs.

14. The method of embodiments 1-3b, wherein components of the guide RNA/Cas endonuclease complex are introduced as guide RNA and Cas endonuclease protein, capable of forming said guide RNA/Cas endonuclease complex.

15. The method of embodiments 1-3b, wherein components of the guide RNA/Cas endonuclease complex are introduced as mRNA encoding the Cas endonuclease and as RNA comprising guide RNA.

16. The method of embodiments 1-3b, wherein components of the guide RNA/Cas endonuclease complex are introduced as recombinant DNA molecules encoding guide RNA and Cas endonuclease protein.

17. The method of embodiments 1-3b, wherein the guide RNA/Cas endonuclease complex is assembled inside the cell.

18. The method of embodiment 13, wherein said ribonucleotide-protein complex is coated onto or combined with a particle delivery matrix to form a ribonucleotide-protein-matrix complex, wherein said ribonucleotide-protein-matrix complex is introduced into said cell.

18b. The method of embodiment 18, wherein said particle delivery matrix comprises at least one microparticle.

18c. The method of embodiment 18, wherein the particle delivery matrix comprises at least one microparticle combined with a cationic lipid.

18d. The method of embodiments 18c-18c, wherein said microparticle is selected from the group consisting of a gold particle, a tungsten particle, and a silicon carbide whisker particle 18e. The method of embodiments 1-3b, wherein the plant cell is a somatic embryo cell.

19. The method of embodiments 1-3b, wherein the plant cell in not a protoplast.

20. The method of embodiments 1-3b, wherein the plant cell is selected from the group consisting of a monocot and a dicot cell.

21. The method of embodiment 21, wherein the plant cell is selected from the group consisting of a maize, rice, sorghum, rye, barley, wheat, millet, oats, sugarcane, turfgrass, or switchgrass, soybean, canola, alfalfa, sunflower, cotton, tobacco, peanut, potato, tomato, tobacco, *Arabidopsis*, and safflower cell.

22. The method of embodiments 1-3b, further comprising regenerating a plant from the plant cell.

23. A plant produced by the method of embodiment 22.

24. A progeny plant of the plant of embodiment 23, wherein said progeny plant is void of any components selected from the group consisting of a guide RNA, a Cas endonucleases, a polynucleotide modification template and a donor DNA.

EXAMPLES

In the following Examples, unless otherwise stated, parts and percentages are by weight and degrees are Celsius. It should be understood that these Examples, while indicating embodiments of the disclosure, are given by way of illustration only. From the above discussion and these Examples, one skilled in the art can make various changes and modifications of the disclosure to adapt it to various usages and conditions. Such modifications are also intended to fall within the scope of the appended claims.

Example 1

Modifying Target DNA Sequences in the Genome of a Plant Cell by Delivering Cas9 Endonuclease and Guide RNA Expression Cassettes The Cas9 gene from *Streptococcus pyogenes* M1 GAS (SF370) (SEQ ID NO: 1) was maize codon optimized using standard techniques known in the art and the potato ST-LS1 intron (SEQ ID NO: 2) was introduced in order to eliminate its expression in *E. coli* and *Agrobacterium*. To facilitate nuclear localization of the Cas9 protein in maize cells, Simian virus 40 (SV40) monopartite amino terminal nuclear localization signal (MAPKKKRKV, SEQ ID NO: 3) and *Agrobacterium tumefaciens* bipartite VirD2 T-DNA border endonuclease carboxyl terminal nuclear localization signal (KRPRDRHDGELGGRKRAR, SEQ ID NO: 4) were incorporated at the amino and carboxyl-termini of the Cas9 open reading frame, respectively. The maize optimized Cas9 gene was operably linked to a maize constitutive promoter (Ubiquitin) by standard molecular biology techniques. Transcription is terminated by the addition of the 3' sequences from the potato proteinase inhibitor II gene (PinII) to generate UBI:Cas9:PinII vector. The sequence of the Ubiquitin driven maize optimized Cas9 expression cassette is shown in SEQ ID NO: 5.

Single guide RNAs (gRNAs) were designed using the methods described by Mali et al., 2013 (*Science* 339:823-26). A maize U6 polymerase III promoter and terminator were isolated and used to direct initiation and termination of gRNAs, respectively. Two BbsI restriction endonuclease sites were introduced in an inverted tandem orientation with cleavage orientated in an outward direction as described in Cong et al., 2013 (*Science* 339:819-23) to facilitate the rapid introduction of maize genomic DNA target sequences into the gRNA expression constructs. Only target sequences starting with a G nucleotide were used to promote favorable polymerase III expression of the gRNA. The gRNA expression cassettes were subcloned into Bluescript SK vector (SEQ ID NO: 6).

To test whether the maize optimized Cas9-gRNA complex could recognize, cleave, and facilitate targeted mutations in maize chromosomal DNA through non-homologous end joining (NHEJ) repair pathway, 5 maize loci (three different genomic sequences in each locus) were targeted for cleavage (see Table 2) and examined by amplicon deep sequencing for the presence of mutations.

TABLE 2

Maize genomic sites targeted by the Cas9-gRNA system

| Locus | Location | Target Site Designation | Maize Genomic Target Site Sequence | PAM Sequence | SEQ ID NO: |
|---|---|---|---|---|---|
| MS26 | Chr. 1: | MS26Cas-1 | GTACTCCATCCGCCCCATCGAGTA | GGG | 7 |
| | 51.81 cM | MS26Cas-2 | GCACGTACGTCACCATCCCGC | CGG | 8 |
| | | MS26Cas-3 | GACGTACGTGCCCTACTCGAT | GGG | 9 |
| LIG | Chr. 2: | LIGCas-1 | GTACCGTACGTGCCCCGGCGG | AGG | 10 |
| | 28.45 cM | LIGCas-2 | GGAATTGTACCGTACGTGCCC | CGG | 11 |
| | | LIGCas-3 | GCGTACGCGTACGTGTG | AGG | 12 |
| MS45 | Chr. 9: | MS45Cas-1 | GCTGGCCGAGGTCGACTAC | CGG | 13 |
| | 119.15 cM | MS45Cas-2 | GGCCGAGGTCGACTACCGGC | CGG | 14 |
| | | MS45Cas-3 | GGCGCGAGCTCGTGCTTCAC | CGG | 15 |
| ALS1 | 1- Chr. 4: | ALSCas-1 | GGTGCCAATCATGCGTCG | CGG | 16 |
| and | 107.73 cM | ALSCas-2 | GGTCGCCATCACGGGAC | AGG | 17 |
| ALS2 | 2- Chr. 5: | ALSCas-3 | GTCGCGGCACCTGTCCCGTGA | TGG | 18 |
| | 115.49 cM | | | | |

MS26 = Male Sterility Gene 26,
LIG = Liguleless-1 Gene Promoter,
MS45 = Male Sterility Gene 45,
ALS1 = Acetolactate Synthase Gene 1 (Chr.4),
ALS1 = Acetolactate Synthase Gene 2 (Chr.5).

The maize optimized Cas9 endonuclease and gRNA expression cassettes containing the specific maize variable targeting domains were co-delivered to 60-90 Hi-II immature maize embryos by particle bombardment (see Example 8) with selectable and visible marker (UBI:MoPAT:DsRED fusion) and developmental genes ZmODP-2 (BBM) and ZmWUS2 (WUS) (see Example 9). Hi-II maize embryos transformed with only the Cas9 or gRNA expression cassette served as negative controls. After 7 days, 20-30 most uniformly transformed embryos from each treatment (based on transient expression of the DsRED fluorescent protein) were pooled and total genomic DNA was extracted. The region surrounding the intended target site was PCR amplified with Phusion® High Fidelity PCR Master Mix (New England Biolabs, M0531 L) adding sequences necessary for amplicon-specific barcodes and Illumina sequencing using "tailed" primers through two rounds of PCR. The primers used in the primary PCR reaction are shown in Table 3.

TABLE 3

PCR primer sequences

| Target Site | Primer | Primary PCR Primer Sequence | SEQ ID NO: |
|---|---|---|---|
| MS26Cas-1 | Forward | CTACACTCTTTCCCTACACGA CGCTCTTCCGATCTAGGACCG GAAGCTCGCCGCGT | 19 |
| MS26Cas-1 | Reverse | CAAGCAGAAGACGGCATACGA GCTCTTCCGATCTTCCTGGAG GACGACGTGCTG | 20 |
| MS26Cas-2 | Forward | CTACACTCTTTCCCTACACGA CGCTCTTCCGATCTAAGGTCC TGGAGGACGACGTGCTG | 21 |

TABLE 3-continued

PCR primer sequences

| Target Site | Primer | Primary PCR Primer Sequence | SEQ ID NO: |
|---|---|---|---|
| MS26Cas-2 | Reverse | CAAGCAGAAGACGGCATACGA GCTCTTCCGATCTCCGGAAGC TCGCCGCGT | 22 |
| MS26Cas-3 | Forward | CTACACTCTTTCCCTACACGA CGCTCTTCCGATCTTCCTCCG GAAGCTCGCCGCGT | 23 |
| MS26Cas-3 | Reverse | CAAGCAGAAGACGGCATACGA GCTCTTCCGATCTTCCTGGAG GACGACGTGCTG | 20 |
| LIGCas-1 | Forward | CTACACTCTTTCCCTACACGA CGCTCTTCCGATCTAGGACTG TAACGATTTACGCACCTGCTG | 24 |
| LIGCas-1 | Reverse | CAAGCAGAAGACGGCATACGA GCTCTTCCGATCTGCAAATGA GTAGCAGCGCACGTAT | 25 |
| LIGCas-2 | Forward | CTACACTCTTTCCCTACACGA CGCTCTTCCGATCTTCCTCTG TAACGATTTACGCACCTGCTG | 26 |
| LIGCas-2 | Reverse | CAAGCAGAAGACGGCATACGA GCTCTTCCGATCTGCAAATGA GTAGCAGCGCACGTAT | 25 |
| LIGCas-3 | Forward | CTACACTCTTTCCCTACACGA CGCTCTTCCGATCTAAGGCGC AAATGAGTAGCAGCGCAC | 27 |
| LIGCas-3 | Reverse | CAAGCAGAAGACGGCATACGA GCTCTTCCGATCTCACCTGCT GGGAATTGTACCGTA | 28 |

TABLE 3-continued

| PCR primer sequences | | | |
|---|---|---|---|
| Target Site | Primer | Primary PCR Primer Sequence | SEQ ID NO: |
| MS45Cas-1 | Forward | CTACACTCTTTCCCTACACGA CGCTCTTCCGATCTAGGAGGA CCCGTTCGGCCTCAGT | 29 |
| MS45Cas-1 | Reverse | CAAGCAGAAGACGGCATACGA GCTCTTCCGATCTGCCGGCTG GCATTGTCTCTG | 30 |
| MS45Cas-2 | Forward | CTACACTCTTTCCCTACACGA CGCTCTTCCGATCTTCCTGGA CCCGTTCGGCCTCAGT | 31 |
| MS45Cas-2 | Reverse | CAAGCAGAAGACGGCATACGA GCTCTTCCGATCTGCCGGCTG GCATTGTCTCTG | 30 |
| MS45Cas-3 | Forward | CTACACTCTTTCCCTACACGA CGCTCTTCCGATCTGAAGGGA CCCGTTCGGCCTCAGT | 32 |
| MS45Cas-3 | Reverse | CAAGCAGAAGACGGCATACGA GCTCTTCCGATCTGCCGGCTG GCATTGTCTCTG | 30 |
| ALSCas-1 | Forward | CTACACTCTTTCCCTACACGA CGCTCTTCCGATCTAAGGCGA CGATGGGCGTCTCCTG | 33 |
| ALSCas-1 | Reverse | CAAGCAGAAGACGGCATACGA GCTCTTCCGATCTGCGTCTGC ATCGCCACCTC | 34 |
| ALSCas-2 | Forward | CTACACTCTTTCCCTACACGA CGCTCTTCCGATCTTTCCCGA CGATGGGCGTCTCCTG | 35 |
| ALSCas-2 | Reverse | CAAGCAGAAGACGGCATACGA GCTCTTCCGATCTGCGTCTGC ATCGCCACCTC | 34 |
| ALSCas-3 | Forward | CTACACTCTTTCCCTACACGA CGCTCTTCCGATCTGGAACGA CGATGGGCGTCTCCTG | 36 |
| ALSCas-3 | Reverse | CAAGCAGAAGACGGCATACGA GCTCTTCCGATCTGCGTCTGC ATCGCCACCTC | 34 |

Primers used in the secondary PCR reaction were

```
(forward, SEQ ID NO: 37)
AATGATACGGCGACCACCGAGATCTACACTCTTTCCCTACACG
and

(reverse, SEQ ID NO: 38)
CAAGCAGAAGACGGCATA.
```

The resulting PCR amplifications were purified with a Qiagen PCR purification spin column, concentration measured with a Hoechst dye-based fluorometric assay, combined in an equimolar ratio, and single read 100 nucleotide-length deep sequencing was performed on Illumina's MiSeq Personal Sequencer with a 30-40% (v/v) spike of PhiX control v3 (Illumina, FC-110-3001) to off-set sequence bias. Only those reads with a ≥1 nucleotide indel arising within the 10 nucleotide window centered over the expected site of cleavage and not found in a similar level in the negative control were classified as mutations. Mutant reads with the same mutation were counted and collapsed into a single group and the top 10 most prevalent mutations were visually confirmed as arising within the expected site of cleavage. The total numbers of mutations were then used to calculate the percentage of mutant reads based on the total number of reads of an appropriate length containing a perfect match to the barcode and forward primer.

The mutation frequencies revealed by amplicon deep sequencing for the Cas9-gRNA system targeting all 15 sites are shown in Table 4.

TABLE 4

| Percent of mutant reads at 5 target loci (15 target sites) | | | | |
|---|---|---|---|---|
| Target | DSB Reagents | Total Number of Reads | Number of Mutant Target Gene Reads | Percentage of Mutant Reads in Target Gene |
| LIG (Chr. 2) | LIG-CR1 gRNA + Cas9 | 716,854 | 33,050 | 4.61% |
| | LIG-CR2 gRNA + Cas9 | 711,047 | 16,675 | 2.35% |
| | LIG-CR3 gRNA + Cas9 | 713,183 | 27,959 | 3.92% |
| MS26 (Chr. 1) | MS26-CR1 gRNA + Cas9 | 575,671 | 10,073 | 1.75% |
| | MS26-CR2 gRNA + Cas9 | 543,856 | 16,930 | 3.11% |
| | MS26-CR3 gRNA + Cas9 | 538,141 | 13,879 | 2.58% |
| MS45 (Chr. 9) | MS45-CR1 gRNA + Cas9 | 812,644 | 3,795 | 0.47% |
| | MS45-CR2 gRNA + Cas9 | 785,183 | 14,704 | 1.87% |
| | MS45-CR3 gRNA + Cas9 | 728,023 | 9,203 | 1.26% |
| ALS1 (Chr. 4) and ALS2 (Chr. 5) | ALS-CR1 gRNA + Cas9 | 434,452 | 9,669 | 2.23% |
| | ALS-CR2 gRNA + Cas9 | 472,351 | 6,352 | 1.35% |
| | ALS-CR3 gRNA + Cas9 | 497,786 | 8,535 | 1.72% |
| Controls | Cas9 only | 640,063 | 1 | 0.00% |
| | LIG-CR1 gRNA only | 646,774 | 1 | 0.00% |

Further analysis demonstrated, that the most common type of mutations promoted by Cas9-gRNA system was single nucleotide insertions (for example, see FIG. 1, SEQ ID NOs: 49-58). Similar results were observed for the majority of gRNAs tested (Table 5).

TABLE 5

| Frequency of a single nucleotide insertions and deletions in 15 target sites promoted by the Cas9-gRNA system This example demonstrates that RNA guided Cas9 generates double strand | | | |
|---|---|---|---|
| Target Locus | DSB Reagents | % Single nt Insertion of Total Number of Mutant Reads | % Single nt Deletion of Total Number of Mutant Reads |
| LIG | LIG-CR1 gRNA + Cas9 | 86% | 5% |
| | LIG-CR2 gRNA + Cas9 | 49% | 25% |
| | LIG-CR3 gRNA + Cas9 | 62% | 20% |
| MS26 | MS26-CR1 gRNA + Cas9 | 46% | 16% |
| | MS26-CR2 gRNA + Cas9 | 78% | 8% |
| | MS26-CR3 gRNA + Cas9 | 45% | 18% |
| MS45 | MS45-CR1 gRNA + Cas9 | 45% | 17% |

TABLE 5-continued

Frequency of a single nucleotide insertions and deletions in 15 target sites promoted by the Cas9-gRNA system
This example demonstrates that RNA guided Cas9 generates double strand

| Target Locus | DSB Reagents | % Single nt Insertion of Total Number of Mutant Reads | % Single nt Deletion of Total Number of Mutant Reads |
|---|---|---|---|
| | MS45-CR2 gRNA + Cas9 | 41% | 23% |
| | MS45-CR3 gRNA + Cas9 | 20% | 24% |
| ALS1 (Chr. 4) | ALS-CR1 gRNA + Cas9 | 22% | 76% |
| and | ALS-CR2 gRNA + Cas9 | 60% | 27% |
| ALS2 (Chr. 5) | ALS-CR3 gRNA + Cas9 | 84% | 12% |

breaks resulting in high frequency of mutations. Analysis of mutations in multiple target sites showed that although various size deletions and/or insertions were observed, a single nucleotide insertion and a single nucleotide deletion were the most prevalent types of mutations generated by the Cas9-gRNA technology for the majority of the target sites tested in maize.

Example 2

Edited Acetolactate Synthase Gene Confers Resistance to Chlorsulfuron

This example demonstrates that specific change(s) introduced into the nucleotide sequence of the native maize acetolactate synthase (ALS) gene result in resistance to sulfonylurea class herbicides, specifically, chlorsulfuron.

There are two ALS genes in maze, ALS1 (SEQ ID NO: 39) and ALS2 (SEQ ID NO: 40), located on chromosomes 4 and 5, respectively, with 94% sequence identity at the DNA level.

The ALS protein contains N-terminal transit and the mature protein is formed following transport into the chloroplast and subsequent cleavage of the transit peptide. The mature protein starts at residue S41, resulting in a mature protein of 598 amino acids with a predicted molecular weight of 65 kDa (SEQ ID NO: 41).

Modification of a nucleotide sequence of either ALS1 or ALS2 resulting in a single amino acid residue (P165A or P165S, boxed in grey) change in comparison to the endogenous maize acetolactate synthase protein provides resistance to herbicides in maize.

As acetolactate synthase is a critical enzyme for cell function in plants, simultaneous bi-allelic knockouts of ALS1 and ALS2 genes would not be expected to survive. Therefore, based on polymorphism between ALS1 and ALS2 nucleotide sequences, ALS2-specific ALSCas-4 target site was identified and tested. ALSCas-1 guide RNA expressing construct targeting both ALS1 and ALS2 genes was used as control. Table 6 presents information about ALSCas-1 and ALSCas-4 target sites.

TABLE 6

ALSCas-1 and ALSCas-4 (ALS2-specific) target sites

| Loci | Location | Target Site Designation | Maize Genomic Target Site Sequence | PAM Sequence | SEQ ID NO: |
|---|---|---|---|---|---|
| ALS1 and ALS2 | Chr. 4: 107.73 cM and Chr. 5: 115.49 cM | ALSCas-1 | GGTGCCAATC ATGCGTCG | CGG | 16 |
| | | ALSCas-4 | GCTGCTCGAT TCCGTCCCCA | TGG | 42 |

Underlined nucleotides in the ALSCas-4 target site and PAM are different in the ALS1 gene.

Mutation frequencies at the ALSCas-1 and ALSCas-4 were determined by amplicon deep sequencing as described in Example 1 and shown in Table 7.

TABLE 7

Frequencies of mutations at ALSCas-1 and ALSCas-4 target sites recovered by amplicon deep sequencing.

| Target Site | Total Reads | Mutant reads (ALS1) | Mutant reads (ALS2) |
|---|---|---|---|
| ALSCas-1 | 204,230 | 2704 (1.3%) | 5072 (2.5%) |
| ALSCas-4 | 120,766 | 40 (0.03%) | 3294 (2.7%) |

These results demonstrated that ALSCas-4 gRNA/Cas9 system mutated the ALS2 gene with approximately 90 times higher efficiency than the ALS1 gene. Therefore, the ALSCas-4 target site and the corresponding ALS-CR4 gRNA were selected for the ALS gene editing experiment.

To generate ALS2 edited alleles, a 794 bp polynucleotide modification template comprising a fragment of homology (SEQ ID NO: 43) was cloned into a plasmid vector and two 127 nt single-stranded polynucleotide modification templates (also referred to as DNA oligos, Oligo1, SEQ ID NO: 44, and Oligo2, SEQ ID NO: 45) were tested as polynucleotide modification templates (FIG. 2). The 794 bp fragment had the same sequence modifications as Oligo1. The polynucleotide modification templates (repair templates) contained several nucleotide changes in comparison to the native sequence. Single-stranded Oligo1 and the 794 bp repair templates included a single nucleotide change which would direct editing of DNA sequences corresponding to the proline at amino acid position 165 to a serine (P165S), as well as three additional changes within the ALS-CR4 target site and PAM sequence. Modification of the PAM sequence within the repair template altered the methionine codon (AUG) to isoleucine (AUU), which naturally occurs in the ALS1 gene. A second 127 nt single-stranded oligo repair template (Oligo2) was also tested which preserved the methionine at position 157 but contained three additional single nucleotide changes in the sequence which would influence base pairing with the ALS-CR4 gRNA (FIG. 2).

Approximately 1,000 immature embryos per treatment were bombarded with the two oligo or single plasmid repair templates, Cas9, ALS-CR4 gRNA, and MoPAT-DsRED in DNA expression cassettes and placed on media to select for bialaphos resistance conferred by PAT. Five weeks post-transformation, two hundred (per treatment) randomly selected independent young callus sectors growing on selective media were separated from the embryos and transferred to fresh bialaphos plates. The remaining embryos (>800 per treatment) with developing callus events were transferred to the plates containing 100 ppm of chlorosulfuron as direct selection for an edited ALS2 gene. A month later, a total of 384 randomly picked callus sectors growing on bialaphos (approximately 130 events for each repair template) and 7 callus sectors that continued growing on media with chlorsulfuron were analyzed by PCR amplification and sequencing. Edited ALS2 alleles were detected in nine callus sectors: two derived from the callus sectors growing on bialaphos and generated using the 794 bp repair DNA template, and the remaining 7 derived from chlorosulfuron resistant callus sectors edited using the 127 nt single-stranded oligos, three by Oligo1 and four by Oligo2. The second ALS2 allele in these callus sectors was mutated as a result of NHEJ repair. Analysis of the ALS1 gene revealed only wild-type sequence confirming high specificity of the ALS-CR4 gRNA.

Plants were regenerated from 7 out of 9 callus sectors containing edited ALS2 alleles for additional molecular analysis and progeny testing. DNA sequence analysis of ALS2 alleles confirmed the presence of the P165S modifications (ALS2-P165S) as well as the other nucleotide changes associated with the respective repair templates. T1 and T2 progeny of two TO plants generated from different callus events (794 bp repair DNA and Oligo2) were analyzed to evaluate the inheritance of the edited ALS2 alleles. Progeny plants derived from crosses using pollen from wild type Hi-II plants were analyzed by sequencing and demonstrated sexual transmission of the edited alleles observed in the parent plant with expected 1:1 segregation ratio (57:56 and 47:49, respectively). To test whether the edited ALS sequence confers herbicide resistance, selected four-week old segregating T1 plants with edited and wild-type ALS2 alleles were sprayed with four different concentrations of chlorsulfuron (50, 100 (1×), 200, and 400 mg/liter). Three weeks after treatment, plants with an edited allele showed normal phenotype (FIG. 3—left), while plants with only wild-type alleles demonstrated strong signs of senescence (FIG. 3—right).

In addition to resistance to sulfonylurea class herbicides (specifically, chlorsulfuron), ALS genes can be modified to confer resistance to other classes of AHAS inhibitors including triazolopy-rimidines, pyrimidinylthio-benzoates, and Imidazolinone herbicides (Tan S, Evans R R, Dahmer M L, Singh B K, Shaner D L (2005) Imidazolinone-tolerant crops: history, current status and future. Pest Management Science 61: 246-257). Thus, modifications to ALS genes should not be limited to changes describe herein and conferring chlorsulfuron resistance.

These experiments demonstrate that Cas9-gRNA can stimulate HDR-dependent targeted sequence modifications in maize resulting in plants with an edited endogenous gene which properly transmits to subsequent generations. The data also indicate that a single edited ALS2 allele under endogenous promoter provides herbicide resistance in maize.

Example 3

ALS2 as Endogenous Selectable Marker Gene

This example demonstrates how specifically edited ALS2 gene can be used to generate a selectable marker in a cell replacing delivery of exogenous marker genes currently used in plant transformation.

Due to the relatively low frequencies of plant transformation (transgenic event recovery), selectable marker genes providing resistance to various herbicides are routinely co-delivered with trait genes. To confer resistance, these selectable marker genes need to be stably integrated into the plant genome and have to be excised or bred out in consecutive generations. Some native plant genes can be specifically modified (edited) to confer resistance to herbicides. As described in Example 2, the ALS2 gene with a single amino acid change provides resistance to chlorsulfuron. Therefore, it may be anticipated that gene mutagenesis, gene editing or co-delivery of a trait gene and coincident ALS2 gene editing can be used without an exogenously supplied marker gene. Giving high mutation frequency as the result of NHEJ repair of DSB generated by Cas9-gRNA system (Example 1), this approach might be useful for gene mutagenesis. In this case, the frequency of mutated events would be anticipated to be dependent on HDR-mediated ALS gene editing. With respect to gene editing, it is likely that the combination of two low frequency HDR-dependent genome editing processes (one for ALS gene repair for selection and another for endogenous gene editing or trait gene integration) in plant cells would make the approach using coincident ALS2 gene editing rather impractical.

The following example describes a method that allows overcoming this low efficiency (and impracticality) and improving the likelihood of selecting for plant cells resistant to selective agents. The method does not rely on HDR-dependent gene editing but rather relies on the restoration of the gene function by targeted mutagenesis through NHEJ DNA repair, which is more common (than HDR) in plant somatic cells. As described in Example 2, there are two ALS genes in maize, ALS1 and ALS2, located on chromosomes 4 and 5, respectively. Specific editing of either one of the two ALS genes will confer herbicide resistance. These genes play an essential role in plant metabolism, consequently, targeting and mutating both of them at the same time leads to the cell death. Therefore, in this example, modifications only involve the ALS2 gene by using an ALS2-specific gRNA that does not target the ALS1 gene, hence ALS1 remains wild type. Specifically, two modifications are introduced into the ALS2 gene; first, specific nucleotide(s) change, for example, C to T at the nucleotide position 493 (FIG. 2, oligo1) or C to T and C to G at the nucleotide positions 493 and 495, respectively (FIG. 2, oligo2) to convert Proline to Serine at amino acid position 165 (named ALS2-P165S) conferring resistance to chlorsulfuron (see Example 2 for details). Second, removal of a single nucleotide, for example a G at the nucleotide position 165 (FIG. 4A-4B) resulting in the translational frameshift (FIG. 4B) and, hence, loss of ALS2-mediated chlorsulfuron resistance (named ALS2-P165S-CCA). While many designs are anticipated, for the highest frequency of ALS2 gene repair, the single nucleotide position (example shown in FIG. 4A-4C) should preferably be: i) the $4^{th}$ nucleotide upstream (5') from the PAM sequence in a gRNA/Cas endonuclease target site, and ii) the $3^{rd}$ nucleotide in the codon (FIG. 4A). This $3^{rd}$ position is flexible for most amino acids and can be occupied by any of the four nucleotides in 8 out of 20 amino acids (Table 8). Given such flexibility, a higher frequency of proper repair is anticipated at the $3^{rd}$ position, when compared to the $1^{st}$ or $2^{nd}$ position.

TABLE 8

Genetic code.

| Amino Acid | Codons | Compressed Codons |
|---|---|---|
| Alanine/Ala | GCU, GCC, GCA, GCG | GCN |
| Arginine/Arg | CGU, CGC, CGA, CGG, AGA, AGG | CGN, MGR |
| Glycine/Gly | GGU, GGC, GGA, GGG | GGN |
| Leucine/Leu | CUU, CUC, CUA, CUG, UUA, UUG | CUN,YUR |
| Proline/Pro | CCU, CCC, CCA, CCG | CCN |
| Serine/Ser | UCU, UCC, UCA, UCG, AGU, AGC | UCN, AGY |
| Threonine/Thr | ACU, ACC, ACA, ACG | ACN |
| Valine/Val | GUU, GUC, GUA, GUG | GUN |
| Isoleucine/Ile | AUU, AUC, AUA | AUH |
| Asparagine/Asn | AAU, AAC | AAY |
| Aspartic Acid/Asp | GAU, GAC | GAY |
| Cysteine/Cys | UGU, UGC | UGY |
| Glutamine/Gln | CAA, CAG | CAR |
| Glutamic Acid/Glu | GAA, GAG | GAR |
| Histidine/His | CAU, CAC | CAY |
| Lysine/Lys | AAA, AAG | AAR |
| Phenylalanine/Phe | UUU, UUC | UUY |
| Tyrosine/Tyr | UAU, UAC | UAY |
| Methionine/Met | AUG | — |
| Tryptophan/Trp | UGG | — |

Four different target sites satisfying the above criteria and the corresponding gRNAs were selected. Besides the above stated preferred single nucleotide position, the corresponding gRNA should promote high frequency of mutations with high percentage of mutations representing a single nucleotide insertion at the cleavage site. Only one of the four target sites tested satisfied all the described preferences and, therefore, suitable for this experiment, was identified (referred to as ALSCas-7; Table 9).

TABLE 9

ALS2-specific ALSCas-7 target site and ALS-CR7- gRNA evaluation by amplicon deep sequencing.

| Target | Target Site Sequence | % of Mutant Reads | % of Mutant Reads with 1 bp Insertion | % of Mutant Reads with 1 bp Deletion | SEQ ID NO: |
|---|---|---|---|---|---|
| ALSCas-4 (control) | GCTGCTCGAT TCCGTCCCCA | 2.73% | — | — | 42 |
| ALSCas-7 | GCTCCCCCGG CCACCCCGCT C | 2.99% | 2.23% (75%) | 0.14% (5%) | 79 |

Then, the ALS2-P165S gene conferring resistance to chlorsulfuron was further modified (resulting in a disrupted gene): the proline codon encoded by CCG (underlined in Table 9) in the ALSCas-7 target site was altered by removal of the G nucleotide at the wobble position ($3^{rd}$ nucleotide position in the codon) resulting in the translational frameshift and a disrupted gene (referred to as ALS2-P165S-CCA; FIG. 4 A-4B). As demonstrated in Example 1, repair of DSBs generated by Cas9-gRNA system in maize, and repaired through NHEJ, often results in a single nucleotide insertion at the cleavage site. Therefore, the function of the ALS2-P165S-CCA gene, and consecutively, cell resistance to chlorsulfuron, can be restored by generating a double strand break (DSB) at the modified ALSCas-7 site, referred to as ALSCas-7-1 (GCTCCCCCGGCCACCCCCTC; SEQ ID NO: 80) and its repair through NHEJ (see FIG. 4B-4C).

Based on this disclosure, one can envision simultaneous delivery of two or more gRNAs when one gRNA targets and activates the disrupted ALS2-P165S-CCA gene through NHEJ (thus conferring herbicide resistance) and the other gRNA(s) promote DSB(s) at a site(s) different than ALS2 and facilitate desired genome modifications, for example, targeted mutagenesis, deletion, gene editing, or site-specific trait gene insertions. This approach can allow for completely transient targeted genome modifications as all other necessary components (Cas9, gRNAs) can be delivered in a form of protein and/or in vitro transcribed RNA molecules.

To test this approach, maize plants (Hi-II genotype) with specifically modified the ALS2 gene described above were generated. First, ALS2 sequence was modified at the amino acid position 165 to confer resistance to chlorsulfuron as described in Example 2. Immature embryos from plants homozygous for the edit were then bombarded with Cas9 and ALS-CR7 gRNA targeting ALSCas-7 target site, selectable marker (UBI:MoPAT-DSRED fusion) and cell developmental enhancing genes (for details, see Examples 8 and 9). Regenerants from bialaphos resistant callus sectors were analyzed by sequencing. Several TO plants with a single nucleotide deletion (a G in the nucleotide position 165) were identified (FIG. 4A-4B). This deletion resulted in the translational frameshift (FIG. 4B) and, hence, loss of ALS2-P165S-mediated chlorsulfuron resistance. Plants homozygous for both edits (ALS2-P165S-CCA) were regenerated, confirmed by sequencing and tested for the loss of herbicide resistance by spraying with chlorsulfuron.

Embryos from homozygous plants with specifically modified endogenous ALS2 gene (ALS2-P165S-CCA) were used in a prove-of-concept experiment. In order to demonstrate that an edited disrupted ALS2-P165S-CCA gene can be repaired as described above (so that it encodes a functional protein) and work as selectable marker, DNA vectors encoding for Cas9, gRNA targeting the ALSCas-7-1 site (refed as ALS-CR7-1), cell development enhancing genes (ZmODP2 and ZmWUS), and MS45-CR2 gRNA were co-delivered into maize (Hi-II) immature embryo cells. One week after bombardment, embryos were transferred to the media with 100 ppm chlorsulfuron for selection. Approximately 30% of embryos (84 out of 290) developed herbicide resistant callus events, which were analyzed by sequencing. The vast majority of the events (79 events) demonstrated a single nucleotide insertion at the expected ALSCas-7-1 DSB site (FIG. 4C) and complete restoration of the ALS2-P165S gene. Four events had no insertion but either 2 or 5 bp deletions putting the gene back in frame, and a single event that seemed to be an escape. Fifty out of 83 events (60%) also demonstrated mutations at the MS45Cas-2 target site.

This example demonstrates prove-of-concept and utility of a specifically modified, inactive ALS2 as endogenous selectable marker gene by the use of a guided Cas endonuclease system. Based on the results described herein, one skilled in the art can use and expand the described approach to any similarly modified endogenous or pre-integrated exogenous gene(s) replacing co-delivery of a selectable marker gene currently used in plant genome editing experiments.

Example 4

Alternative Designs to Restore Function to a Non-Functional Protein Encoded by a Disrupted Gene.

In the previous example, sequence alterations were incorporated within the coding region or ALS2-P165S. It is anticipated that other sequence changes which create a disrupted gene (that does not encode a functional protein) can also be designed to be used as re-activation sequences. This example describes generation of a re-activation sequence that does not depend upon the restoration of a codon within a coding sequence, but rather the elimination of a start codon which is upstream and out-of-frame of the primary translational start codon of ALS2-P165S.

According to a scanning model of eukaryotic translation initiation the first AUG codon relative to the 5' cap of an mRNAs is used to initiate protein synthesis (Kozak M. 1989. The scanning model for translation: an update. The Journal of Cell Biology 108: 229-241). Thus, if an AUG codon within the non-coding leader of the RNA transcript is upstream and out-of-frame of the primary start codon, protein synthesis of the polypeptide encoded by the mRNA is abolished. To take advantage of this rule and apply to a strategy of reactivation of gene expression or function, an endogenous ALS2-P165S allele can be generated to contain an upstream out-of-frame translational start codon (FIG. 5A-5B). This allele contains a Cas9 PAM recognition site and an ALS-CRX targeting spacer. Cutting by Cas9 between nucleotides 3 and 4, located 5' of the PAM site in this example can promote nucleotide deletion(s) or addition(s) which can result in the loss of the ATG codon. Loss of this upstream out-of-frame ATG by any combination of deletion or addition due to NHEJ repair can result in translation initiation at the primary ALS2-P165S start codon conferring herbicide resistance.

It is anticipated that the re-activation strategy using an upstream out-of-frame ATG not be limited to the design in FIG. 5A-5B. PAM and targeting spacer can also be placed at various positions relative to the upstream out-of-frame ATG, as long as targeted cutting by Cas9 results in the loss of this start codon. For example, the PAM can be present on the antisense strand, 5' of the start codon. Other designs can be contemplated; the out-of-frame ATG start codon can also be placed at different positions within the 5' leader sequence. The PAM sequence can be recognized by other Cas9 proteins like *Streptococcus pyogenes* which recognize nGG PAMs or non-nGG PAM sequences for example *Streptococcus* thermophiles CR1 (PAM sequence recognition nnAGAAn) and others having PAM sequences. The utility of other Cas9 proteins would satisfy the re-activation design of this example as well as Example 3 described above.

Other designs for gene activation are anticipated. As mentioned earlier, in addition to chlorosulfuron resistance, modifications to the ALS gene which confer resistance to other herbicides can be used for reactivation. Furthermore, the phosphomannose isomerase gene (PMI), bialaphos resistance gene (BAR), phosphinothricin acetyltransferase (PAT), hygromycin resistance gene (NPTII), selectable marker genes, fluorescent marker genes (such as but not limiting to RFP, red fluorescent protein, CFP, GFP, green fluorescent protein) and glyphosate resistance genes can be modified to be introduced into plant cells as inactive forms and used as targets for re-activation by guide RNA introduction and repair by NHEJ as described in Example 3. It would be also anticipated that having multiple inactive genes can serve as targets. For example, guide RNA multiplexing has been demonstrated to simultaneously modify multiple genes in a single experiment, thus targeted reactivation of chlorsulfuron and bialaphos resistance, but not limited to these genes, can be an additionally designed for this approach. As described above, coincident with restoration of gene function by NHEJ, modification of other targets would be accomplished simultaneously by the addition of other guide-polynucleotides.

In addition, it would be anticipated that similar approach can be applied to any native or introduced gene sequence and used as an efficient gene switch mechanism.

Example 5

Specific Gene Editing without Introducing Polynucleotide Modification Templates for Homology Directed Repair.

Example 2 described sequence alterations within the coding region of the ALS2 gene (P165S) using specifically designed polynucleotide modification templates (repair templates). The example below describes a different approach to generating an edited gene of interest that does not depend upon the HDR mechanism, but rather on NHEJ.

As described in Example 1, two of the most prevalent types of mutations facilitated by NHEJ repair of DSBs generated by Cas9 nuclease are 1 bp insertion and 1 bp deletion (Table 4). Based on these observations described herein, methods were developed for gene editing that can be accomplished in two consecutive steps or into a single step, as described below.

The first step includes targeting a gene or polynucleotide of interest, containing a target site that is recognized by a Cas endonuclease, using the RNA guided Cas nuclease system described herein, resulting in the generation of a cell or an organism with a specific nucleotide deletion due to NHEJ repair of the cleaved DNA (illustrated in FIG. 6A). The second step requires re-targeting the mutated site and selecting events with insertion of a desired nucleotide (without the use of a polynucleotide modification template (repair template), hence, specifically changing the corresponding amino acid and the gene function. In general, the idea is illustrated in FIG. 6A-6C. This method can also be used to edit non-coding DNA fragments.

Alternatively, both steps can be combined into a single step. Two different gRNAs, one recognizing the original target site and the second one the same site but with a 1 bp deletion can be used. In this case, one can envision a consecutive cutting and repair of the endogenous site resulting in a 1 bp deletion followed by cutting of the altered site and its repair with a 1 bp insertion. Then, an event with an insertion of a desired nucleotide can be selected. In the case of editing coding DNA sequences, this process accomplishes two goals—restoring the translational reading frame and replacement of an amino acid of interest. It would be anticipated that combinations of different endonuclease could be used in this two-step or one-step system. For example, the introduction of a first double strand break leading to a single base deletion in a polynucleotide of interest can be accomplished by a first endonuclease, whereas the introduction of a second double strand break leading to a single base insertion (and editing of the polynucleotide of interest) can be accomplished by a second endonuclease that is different from the first endonuclease. The differences between the endonucleases may include, but are not limited to, different PAM recognition sequences, different target recognition sequences, different cleavage activity (blunt-end, 5' or 3' overhang, single strand, double strand), different DNA or amino acid sequences, originating from different organism, or any one combination thereof.

The ability to edit a specific nucleotide in a genome of interest may depend on the endonuclease system of choice and its ability to recognize and cut a particular target site. The discovery of novel guided endonucleases (See for example U.S. patent application 62/162,377 filed May 15 2015), and/or modifications of guided endonucleases with various PAM sequences, will further increase the density of target sites that can be recognized and/or cleaved by these endonuclease ultimately resulting in the ability to target any given nucleotide position in the genome using the methods described herein.

Example 6

Maize Lines with Stably Integrated Cas9 Endonuclease

This example describes generation and validation of maize lines with stably integrated Cas9 expression cassette.

Two *Agrobacterium* vectors (FIG. 7, containing maize-codon optimized Cas9 under the transcriptional control of a constitutive (maize UBI, SEQ ID NO: 46) or a temperature regulated (maize MDH, SEQ ID NO: 47) promoter were introduced into Hi-II embryo cells to establish lines containing pre-integrated genomic copies of Cas9 endonuclease. These vectors also contained an embryo-preferred END2 promoter regulating the expression of a blue-fluorescence gene (AmCYAN) as a visible marker and an interrupted copy of the DsRED gene transcriptionally regulated by a maize Histone 2B promoter. Part of the DsRED sequence was duplicated in a direct orientation (369 bp fragment) and consisted of two fragments of the DsRED (RF-FP) gene which were separated by a 347 bp spacer that could be targeted by gRNAs. DSBs within the spacer region promote intramolecular recombination restoring function to the disrupted DsRED gene which results in red fluorescing cells. Maize plants with single-copy T-DNA inserts containing either UBI:Cas9 or MDH:Cas9 were used as a source of immature embryos. Blue-fluorescing embryos containing pre-integrated Cas9 were excised and incubated at 28° C. (UBI:Cas9) or at 37° C. (MDH:Cas9) for 24 hours. Post-bombardment, embryos with MDH:Cas9 were incubated at 37° C. for 24 hours and then moved to 28° C. In contrast to control (no gRNA), UBI:Cas9 and MDH:Cas9 containing embryos bombarded with two DNA-expressed gRNAs that targeted sequences within the 347 bp spacer, readily produced red fluorescing foci.

These results demonstrate that described above maize lines poses single copies of functional Cas9 endonuclease.

Example 7

Transient gRNA Delivery into Embryo Cells with Pre-Integrated Cas9 Generates Mutations in Maize This Example demonstrates that delivery of gRNA in a form of in vitro transcribed RNA molecules into maize immature embryo cells with pre-integrated Cas 9 generates mutations at targeted sites.

Maize plants described in Example 6 containing either UBI:Cas9 or MDH:Cas9 were used as a source of immature embryos for delivery of gRNAs as in vitro transcribed RNA or as DNA expression cassettes as control. To measure mutation frequencies at the LIG and MS26 endogenous target sites, LIG-CR3 and MS26-CR2 gRNAs as RNA molecules (100 ng/shot) or as DNA vectors (25 ng/shot) were delivered into UBI:Cas9 and MDH:Cas9 containing embryo cells with temperature treatments described in Example 6. In these experiments, embryos were harvested two days post-bombardment and analyzed by amplicon deep sequencing. Similar frequencies were detected for gRNAs delivered as DNA vectors and as RNA molecules, particularly in the case of Cas9 regulated by the Ubiquitin promoter (Table 10).

TABLE 10

Percentage of mutant reads at maize LIG and MS26 target sites produced by transient gRNA delivery into embryos with pre-integrated Cas9 under constitutive (UBI) or regulated (MDH) promoters

| Target Site | Embryos | Transformation | Percentage of Mutant Reads (2 days post-bombardment) |
|---|---|---|---|
| LIG | UBI:Cas9 | gRNA (DNA) | 1.22% |
| | | gRNA (RNA) | 1.86% |
| | MDH:Cas9 | gRNA (DNA) | 0.25% |
| | event 1 | gRNA (RNA) | 0.12% |
| | MDH:Cas9 | gRNA (DNA) | 0.57% |
| | event 2 | gRNA (RNA) | 0.26% |
| | MDH:Cas9 | gRNA (DNA) | 0.46% |
| | event 3 | gRNA (RNA) | 0.35% |
| MS26 | MDH:Cas9 | gRNA (DNA) | 0.58% |
| | event 2 | gRNA (RNA) | 0.17% |

Together, these data demonstrate that delivery of gRNA in the form of RNA directly into maize cells containing pre-integrated Cas9 is a viable alternative to DNA delivery for the generation of mutations in plant cells.

Example 8

Transformation of Maize Immature Embryos

Transformation can be accomplished by various methods known to be effective in plants, including particle-mediated delivery, *Agrobacterium*-mediated transformation, PEG-mediated delivery, and electroporation.

a. Particle-Mediated Delivery

Transformation of maize immature embryos using particle delivery is performed as follows. Media recipes follow below.

The ears are husked and surface sterilized in 30% Clorox bleach plus 0.5% Micro detergent for 20 minutes, and rinsed two times with sterile water. The immature embryos are isolated and placed embryo axis side down (scutellum side up), 25 embryos per plate, on 560Y medium for 4 hours and then aligned within the 2.5-cm target zone in preparation for bombardment. Alternatively, isolated embryos are placed on 560 L (Initiation medium) and placed in the dark at temperatures ranging from 26° C. to 37° C. for 8 to 24 hours prior to placing on 560Y for 4 hours at 26° C. prior to bombardment as described above.

Plasmids containing the double strand brake inducing agent and template or donor DNA are constructed using standard molecular biology techniques and co-bombarded with plasmids containing the developmental genes ODP2 (AP2 domain transcription factor ODP2 (Ovule development protein 2); US20090328252 A1) and WUSCHEL (US2011/0167516).

The plasmids and DNA of interest are precipitated onto 0.6 μm (average diameter) gold pellets using a water-soluble cationic lipid TransIT-2020 Transfection Reagent (Cat #MIR 5404, Mirus, USA) as follows. DNA or DNA and RNA solution is prepared on ice using a total of 1 μg of DNA and/or RNA constructs (10 shots). To the pre-mixed DNA, 20 μl of prepared gold particles (15 mg/ml) and 1 μl TransIT-2020 are added and mixed carefully. Gold particles are pelleted in a microfuge at 10,000 rpm for 1 min and supernatant is removed. 105 μl of 100% EtOH is added and the particles are resuspended by brief sonication. Then, 10 μl is spotted onto the center of each macrocarrier and allowed to dry before bombardment. The sample plates are bombarded using Biorad Helium Gun (shelf #3) at 425 PSI.

Following bombardment, the embryos are incubated on 560P (maintenance medium) for 12 to 48 hours at temperatures ranging from 26 C to 37 C, and then placed at 26 C. After 5 to 7 days the embryos are transferred to 560R selection medium containing 3 mg/liter Bialaphos, and subcultured every 2 weeks at 26 C. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to a lighted culture room. Approximately 7-10 days later, developing plantlets are transferred to 272V hormone-free medium in tubes for 7-10 days until plantlets are well established. Plants are then transferred to inserts in flats (equivalent to a 2.5" pot) containing potting soil and grown for 1 week in a growth chamber, subsequently grown an additional 1-2 weeks in the greenhouse, then transferred to Classic 600 pots (1.6 gallon) and grown to maturity. Plants are monitored and scored for transformation efficiency, and/or modification of regenerative capabilities.

Initiation medium (560 L) comprises 4.0 g/l N6 basal salts (SIGMA C-1416), 1.0 ml/l Eriksson's Vitamin Mix (1000× SIGMA-1511), 0.5 mg/l thiamine HCl, 20.0 g/l sucrose, 1.0 mg/l 2,4-D, and 2.88 g/l L-proline (brought to volume with D-I H2O following adjustment to pH 5.8 with KOH); 2.0 g/l Gelrite (added after bringing to volume with D-I H2O); and 8.5 mg/l silver nitrate (added after sterilizing the medium and cooling to room temperature).

Maintenance medium (560P) comprises 4.0 g/l N6 basal salts (SIGMA C-1416), 1.0 ml/l Eriksson's Vitamin Mix (1000×SIGMA-1511), 0.5 mg/l thiamine HCl, 30.0 g/l sucrose, 2.0 mg/l 2,4-D, and 0.69 g/l L-proline (brought to volume with D-I H2O following adjustment to pH 5.8 with KOH); 3.0 g/l Gelrite (added after bringing to volume with D-I H2O); and 0.85 mg/l silver nitrate (added after sterilizing the medium and cooling to room temperature).

Bombardment medium (560Y) comprises 4.0 g/l N6 basal salts (SIGMA C-1416), 1.0 ml/l Eriksson's Vitamin Mix (1000×SIGMA-1511), 0.5 mg/l thiamine HCl, 120.0 g/l sucrose, 1.0 mg/l 2,4-D, and 2.88 g/l L-proline (brought to volume with D-I H2O following adjustment to pH 5.8 with KOH); 2.0 g/l Gelrite (added after bringing to volume with D-I H2O); and 8.5 mg/l silver nitrate (added after sterilizing the medium and cooling to room temperature).

Selection medium (560R) comprises 4.0 g/l N6 basal salts (SIGMA C-1416), 1.0 ml/l Eriksson's Vitamin Mix (1000× SIGMA-1511), 0.5 mg/l thiamine HCl, 30.0 g/l sucrose, and 2.0 mg/l 2,4-D (brought to volume with D-I H2O following adjustment to pH 5.8 with KOH); 3.0 g/l Gelrite (added after bringing to volume with D-I H2O); and 0.85 mg/l silver nitrate and 3.0 mg/l bialaphos (both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I H2O) (Murashige and Skoog (1962) Physiol. Plant. 15:473), 100 mg/l myo-inositol, 0.5 mg/l zeatin, 60 g/l sucrose, and 1.0 ml/l of 0.1 mM abscisic acid (brought to volume with polished D-I H2O after adjusting to pH 5.6); 3.0 g/l Gelrite (added after bringing to volume with D-I H2O); and 1.0 mg/l indoleacetic acid and 3.0 mg/l bialaphos (added after sterilizing the medium and cooling to 60° C.).

Hormone-free medium (272V) comprises 4.3 g/l MS salts (GIBCO 11117-074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I H2O), 0.1 g/l myo-inositol, and 40.0 g/l sucrose (brought to volume with polished D-I H2O after adjusting pH to 5.6); and 6 g/l bacto-agar (added after bringing to volume with polished D-I H2O), sterilized and cooled to 60° C.

b. *Agrobacterium*-Mediated Transformation

*Agrobacterium*-mediated transformation was performed essentially as described in Djukanovic et al. (2006) Plant Biotech J 4:345-57. Briefly, 10-12 day old immature embryos (0.8-2.5 mm in size) were dissected from sterilized kernels and placed into liquid medium (4.0 g/L N6 Basal Salts (Sigma C-1416), 1.0 ml/L Eriksson's Vitamin Mix (Sigma E-1511), 1.0 mg/L thiamine HCl, 1.5 mg/L 2, 4-D, 0.690 g/L L-proline, 68.5 g/L sucrose, 36.0 g/L glucose, pH 5.2). After embryo collection, the medium was replaced with 1 ml *Agrobacterium* at a concentration of 0.35-0.45 OD550. Maize embryos were incubated with *Agrobacterium* for 5 min at room temperature, then the mixture was poured onto a media plate containing 4.0 g/L N6 Basal Salts (Sigma C-1416), 1.0 ml/L Eriksson's Vitamin Mix (Sigma E-1511), 1.0 mg/L thiamine HCl, 1.5 mg/L 2, 4-D, 0.690 g/L L-proline, 30.0 g/L sucrose, 0.85 mg/L silver nitrate, 0.1 nM acetosyringone, and 3.0 g/L Gelrite, pH 5.8. Embryos were incubated axis down, in the dark for 3 days at 20° C., then incubated 4 days in the dark at 28° C., then transferred onto new media plates containing 4.0 g/L N6 Basal Salts (Sigma C-1416), 1.0 ml/L Eriksson's Vitamin Mix (Sigma E-1511), 1.0 mg/L thiamine HCl, 1.5 mg/L 2, 4-D, 0.69 g/L L-proline, 30.0 g/L sucrose, 0.5 g/L MES buffer, 0.85 mg/L silver nitrate, 3.0 mg/L Bialaphos, 100 mg/L carbenicillin, and 6.0 g/L agar, pH 5.8. Embryos were subcultured every three weeks until transgenic events were identified. Somatic embryogenesis was induced by transferring a small amount of tissue onto regeneration medium (4.3 g/L MS salts (Gibco 11117), 5.0 ml/L MS Vitamins Stock Solution, 100 mg/L myo-inositol, 0.1 μM ABA, 1 mg/L IAA, 0.5 mg/L zeatin, 60.0 g/L sucrose, 1.5 mg/L Bialaphos, 100 mg/L carbenicillin, 3.0 g/L Gelrite, pH 5.6) and incubation in the dark for two weeks at 28° C. All material with visible shoots and roots were transferred onto media containing 4.3 g/L MS salts (Gibco 11117), 5.0 ml/L MS Vitamins Stock Solution, 100 mg/L myo-inositol, 40.0 g/L sucrose, 1.5 g/L Gelrite, pH 5.6, and incubated under artificial light at 28° C. One week later, plantlets were moved into glass tubes containing the same medium and grown until they were sampled and/or transplanted into soil.

Example 9

Transient Expression of ZmODP-2 and ZmWUS Enhances Transformation

Parameters of the transformation protocol can be modified to ensure that the BBM activity is transient. One such method involves precipitating the BBM-containing plasmid in a manner that allows for transcription and expression, but precludes subsequent release of the DNA, for example, by using the chemical PEI.

In one example, the BBM plasmid is precipitated onto gold particles with PEI, while the transgenic expression cassette (UBI:MoPAT-GFPm:PinII; MoPAT is the maize optimized PAT gene) to be integrated is precipitated onto gold particles using the standard calcium chloride method.

Briefly, gold particles were coated with PEI as follows. First, the gold particles were washed. Thirty-five mg of gold particles, 1.0 in average diameter (A.S.I. #162-0010), were weighed out in a microcentrifuge tube, and 1.2 ml absolute EtOH was added and vortexed for one minute. The tube was incubated for 15 minutes at room temperature and then centrifuged at high speed using a microfuge for 15 minutes at 4° C. The supernatant was discarded and a fresh 1.2 ml aliquot of ethanol (EtOH) was added, vortexed for one minute, centrifuged for one minute, and the supernatant again discarded (this is repeated twice). A fresh 1.2 ml aliquot of EtOH was added, and this suspension (gold particles in EtOH) was stored at −20° C. for weeks. To coat particles with polyethylimine (PEI; Sigma #P3143), 250 μl of the washed gold particle/EtOH mix was centrifuged and the EtOH discarded. The particles were washed once in 100 μl ddH2O to remove residual ethanol, 250 μl of 0.25 mM PEI was added, followed by a pulse-sonication to suspend the particles and then the tube was plunged into a dry ice/EtOH bath to flash-freeze the suspension, which was then lyophilized overnight. At this point, dry, coated particles could be stored at −80° C. for at least 3 weeks. Before use, the particles were rinsed 3 times with 250 μl aliquots of 2.5 mM HEPES buffer, pH 7.1, with 1× pulse-sonication, and then a quick vortex before each centrifugation. The particles were then suspended in a final volume of 250 μl HEPES buffer. A 25 μl aliquot of the particles was added to fresh tubes before attaching DNA. To attach uncoated DNA, the particles were pulse-sonicated, then 1 μg of DNA (in 5 μl water) was added, followed by mixing by pipetting up and down a few times with a Pipetteman and incubated for 10 minutes. The particles were spun briefly (i.e. 10 seconds), the supernatant removed, and 60 μl EtOH added. The particles with PEI-precipitated DNA-1 were washed twice in 60 μl of EtOH. The particles were centrifuged, the supernatant discarded, and the particles were resuspended in 45 μl water. To attach the second DNA (DNA-2), precipitation using TransIT-2020 was used. The 45 μl of particles/DNA-1 suspension was briefly sonicated, and then 5 μl of 100 ng/μl of DNA-2 and 1 μl of TransIT-2020 were added. The solution was placed on a rotary shaker for 10 minutes, centrifuged at 10,000 g for 1 minute. The supernatant was removed, and the particles resuspended in 60 μl of EtOH. The solution was spotted onto macrocarriers and the gold particles onto which DNA-1 and DNA-2 had been sequentially attached were delivered into scutellar cells of 10 DAP Hi-II immature embryos using a standard protocol for the PDS-1000. For this experiment, the DNA-1 plasmid contained a UBI:RFP:PinII expression cassette, and DNA-2 contained a UBI:CFP:PinII expression cassette. Two days after bombardment, transient expression of both the CFP and RFP fluorescent markers was observed as numerous red & blue cells on the surface of the immature embryo. The embryos were then placed on non-selective culture medium and allowed to grow for 3 weeks before scoring for stable colonies. After this 3-week period, 10 multicellular, stably-expressing blue colonies were observed, in comparison to only one red colony. This demonstrated that PEI-precipitation could be used to effectively introduce DNA for transient expression while dramatically reducing integration of the PEI-introduced DNA and thus reducing the recovery of RFP-expressing transgenic events. In this manner, PEI-precipitation can be used to deliver transient expression of BBM and/or WUS2.

For example, the particles are first coated with UBI:BBM:PinII using PEI, then coated with UBI:MoPAT-YFP using TransIT-2020, and then bombarded into scutellar cells on the surface of immature embryos. PEI-mediated precipitation results in a high frequency of transiently expressing cells on the surface of the immature embryo and extremely low frequencies of recovery of stable transformants (relative to the TransIT-2020 method). Thus, it is expected that the PEI-precipitated BBM cassette expresses transiently and stimulates a burst of embryogenic growth on the bombarded surface of the tissue (i.e. the scutellar surface), but this plasmid will not integrate. The MoPAT-GFP plasmid released from the Ca++/gold particles is expected to integrate and express the selectable marker at a frequency that results in substantially improved recovery of transgenic events. As a control treatment, PEI-precipitated particles containing a UBI:GUS:PinII (instead of BBM) are mixed with the MoPAT-GFP/Ca++ particles. Immature embryos from both treatments are moved onto culture medium containing 3 mg/l bialaphos. After 6-8 weeks, it is expected that GFP+, bialaphos-resistant calli will be observed in the PEI/BBM treatment at a much higher frequency relative to the control treatment (PEI/GUS).

As an alternative method, the BBM plasmid is precipitated onto gold particles with PEI, and then introduced into scutellar cells on the surface of immature embryos, and subsequent transient expression of the BBM gene elicits a rapid proliferation of embryogenic growth. During this period of induced growth, the explants are treated with *Agrobacterium* using standard methods for maize (see Example 1), with T-DNA delivery into the cell introducing a transgenic expression cassette such as UBI:MoPAT-GFPm:PinII. After co-cultivation, explants are allowed to recover on normal culture medium, and then are moved onto culture medium containing 3 mg/l bialaphos. After 6-8 weeks, it is expected that GFP+, bialaphos-resistant calli will be observed in the PEI/BBM treatment at a much higher frequency relative to the control treatment (PEI/GUS).

It may be desirable to "kick start" callus growth by transiently expressing the BBM and/or WUS2 polynucleotide products. This can be done by delivering BBM and WUS2 5-capped polyadenylated RNA, expression cassettes containing BBM and WUS2 DNA, or BBM and/or WUS2 proteins. All of these molecules can be delivered using a biolistics particle gun. For example 5-capped polyadenylated BBM and/or WUS2 RNA can easily be made in vitro using Ambion's mMessage mMachine kit. RNA is co-delivered along with DNA containing a polynucleotide of interest and a marker used for selection/screening such as UBI:MoPAT-GFPm:PinII. It is expected that the cells receiving the RNA will immediately begin dividing more rapidly and a large portion of these will have integrated the agronomic gene. These events can further be validated as being transgenic clonal colonies because they will also express the PAT-GFP fusion protein (and thus will display green fluorescence under appropriate illumination). Plants regenerated from these embryos can then be screened for the presence of the polynucleotide of interest.

Example 10

Direct Delivery of gRNA and Cas9 as a Guide RNA/Cas Endonuclease Ribonucleotide-Protein Complex (RGEN) into Embryo Cells Generates Mutations in Maize This example demonstrates that direct delivery of Cas9 in the form of protein and gRNA in the form of in vitro transcribed or chemically synthesized RNA molecules, into maize immature embryo cells generates mutations at the corresponding targeted sites.

To generate gRNA in the form of RNA molecules, the maize-optimized U6 polymerase III gRNA expression cassettes were amplified by PCR using a 5' oligonucleotide primer that also contained the sequence of the T7 polymerase promoter and transcriptional initiation signal just 5' of the spacer to gene. T7 in vitro transcription was carried out with the AmpliScribe T7-Flash Kit (Epicentre) according to the manufacturer's recommendations, and products were purified using NucAway Spin Columns (Invitrogen; Life Technologies Inc) followed by ethanol precipitation.

To generate a guide RNA/Cas9 endonuclease protein complex (RGEN) (also referred to as a guide RNA/Cas9 endonuclease ribonucleotide-protein), 7 μg of Cas9 (*Streptococcus pyogenes* Cas9) protein and 3 μg of gRNA molecules (1:2 molar ratio) were mixed in 1×Cas9 buffer (NEB) in a total volume of 20 μl and incubated at room temperature for 15 minutes. Together with the RGEN, plasmids containing Ubiquitin promoter regulated selectable and visible markers (MoPAT-DsRed fusion), Ubiquitin promoter regulated mays Ovule development protein 2, ZmODP2 (see US20090328252, published Dec. 31, 2009) and maize IN2 promoter (Hershey et al. 1991, Plant Mol. Biol 17:679-690) regulated WUSCHEL, ZmWUS (see US20110167516, published Jul. 7, 2011) were mixed with a particle delivery matrix comprising commercially available gold particles (0.6 μm, Bio-Rad) and a water soluble cationic lipid TransIT-2020 (Mirus, USA). The particle delivery matrix comprising the guide RNA/Cas endonuclease ribonucleotide-protein complexes were delivered into maize embryo cells using particle mediated delivery (see Particle-mediated delivery described in Example 8) with some modifications. Specifically, after gold particles were pelleted in a microfuge at 10,000 rpm for 1 min and supernatant was removed, the particles were resuspended in 105 μl of sterile water instead of 100% ethanol. Then, 10 μl was spotted onto the center of each macrocarrier and allowed to dry before bombardment.

Wild type maize plants were used as a source of immature embryos for co-delivery of Cas9 and gRNA in the form of a guide RNA/Cas endonuclease ribonucleotide-protein complexes (RGEN) along with selectable and visible marker (UBI:MoPAT-DsRED) and developmental genes (UBI:ZmODP2 and IN2:ZmWUS). To measure mutation frequencies at the LIGCas-3, MS26Cas-2, MS45Cas-2 and ALS-Cas-4 endogenous target sites, embryos were harvested two days post-bombardment and analyzed by amplicon deep sequencing. Untreated embryos and embryos bombarded with the Cas9 protein only served as negative controls while embryos bombarded with DNA vectors expressing Cas9 and gRNA were used as positive controls. Similar frequencies were detected for Cas9-gRNA components delivered as DNA vectors and as guide RNA/Cas endonuclease ribonucleotide-protein complexes (Table 11).

TABLE 11

Percentage of mutant reads at LIG, MS26, MS45, and ALS target sites produced by direct delivery of RGEN complexes into maize embryo cells.

| Target Sites | Molecules delivered | Total Number of Reads | Number of Mutant Reads | Percentage of Mutant Reads |
|---|---|---|---|---|
| LIGCas-3 (Chr. 2) | Untreated embryos (control 1) | 915,198 | 38 | 0.004% |
| | Cas9 protein only (control 2) | 408,348 | 17 | 0.004% |
| | Cas9-Lig-CR3 RGEN | 439,827 | 2,510 | 0.57% |
| | Cas9 (DNA) + Lig-CR3 (DNA) | 369,443 | 2,058 | 0.56% |
| MS26Cas-2 (Chr. 1) | Untreated embryos (control 1) | 245,476 | 8 | 0.003% |
| | Cas9 protein only (control 2) | 429,388 | 20 | 0.004% |
| | Cas9-MS26-CR2 RGEN | 252,519 | 533 | 0.21% |
| | Cas9 (DNA) + MS26-CR2 (DNA) | 186,857 | 812 | 0.43% |
| MS45Cas-2 (Chr. 9) | Untreated embryos (control 1) | 255,877 | 12 | 0.005% |
| | Cas9 protein only (control 2) | 487,876 | 12 | 0.002% |
| | Cas9-MS45-CR2 RGEN | 241,287 | 2,075 | 0.86% |
| | Cas9 (DNA) + MS45-CR2 (DNA) | 304,622 | 1591 | 0.52% |
| ALS2Cas-4 (Chr. 5) | Cas9 protein only (control 2) | 807,014 | 125 | 0.02% |
| | Cas9-ALS-CR4 RGEN | 791,084 | 3,613 | 0.45% |
| | Cas9 (DNA) + ALS-CR4 (DNA) | 833,130 | 4251 | 0.51% |

To measure the mutation frequency at the plant level, 60 embryos co-bombarded with Cas9-MS45-gRNA complex, ZmODP2, ZmWUS and MOPAT-DSRED were placed on media containing bialaphos as selective agent. Multiple plants were regenerated from each of the 36 herbicide-resistant callus sectors and screened for mutations. Out of the 36 events, 17 (47%) contained mutant alleles (10 single and 7 biallelic) while 19 (53%) revealed only wild type MS45 alleles. Among plants with mutations, the number of sequencing reads for each allele was similar indicating plants were not chimeric.

To demonstrate that direct RGEN delivery is also sufficient to generate specific edits in endogenous genes in plants, the maize ALS2 gene was targeted (ALS2-specific ALSCas-4 target site) as described in Example 2. A 127 nt single-stranded DNA Oligo2, (SEQ ID NO: 45) as a repair template was co-delivered with Cas9/ALS-CR4 RGEN complex in a similar manner as described above. Embryos were harvested two days post-bombardment and analyzed by amplicon deep sequencing (Table 12).

TABLE 12

Percentage of mutant reads and reads with edits at ALS target site produced by delivery of RGEN complex and donor DNA template into maize embryo cells.

| Target Site | Molecules delivered | Total Number of Reads | Number of Mutant Reads | % of Mutant Reads | Number of Reads with Edits | % of Reads with Edits |
|---|---|---|---|---|---|---|
| ALS2 | Cas9 protein only | 807,014 | 105 | 0.01% | — | — |
| | Cas9-ALS-CR4 RGEN + ss Oligo2 | 791,084 | 3,613 | 0.45% | 209 | 0.02% |

In addition, in two independent experiments, 40 to 50 bombarded embryos were transferred to plates containing 100 ppm of chlorsulfuron as direct selection for an edited ALS2 gene. Six weeks later, two callus sectors (one from each experiment) that continued growing on media with chlorsulfuron were analyzed by sequencing. In both events, one ALS2 allele was specifically edited while the 10 second allele remained wild type. Plants regenerated from these callus sectors contained edited ALS2 alleles and were resistant to chlorsulfuron when sprayed with the herbicide.

These data demonstrate that direct delivery of Cas9 and gRNA, in the form of a guide RNA/Cas endonuclease ribonucleotide-protein complex (with or without a polynucleotide modification template DNA) into maize immature embryo cells, is a viable alternative to DNA delivery (such as recombinant DNA, plasmid DNA) for targeted mutagenesis and gene editing in plants.

Example 11

Direct Delivery of Cas9 in the Form of mRNA and gRNA into Embryo Cells Generates Mutations in Maize This example demonstrates that direct delivery of Cas9, in the form of mRNA molecules and gRNA in the form of in vitro transcribed or chemically synthesized RNA molecules, into maize immature embryo cells generates mutations at the corresponding targeted sites.

In our previous experiment (Svitashev et al., Plant Physiology, 2015, Vol. 169, pp. 931-945), co-delivery of gRNA in the form of in vitro synthesized RNA molecules with the Cas9 expressing DNA vector yielded approximately 100-fold lower mutation frequency then in experiments where both Cas9 and gRNA were delivered as DNA vectors. One possible explanation for this difference may be that the requirement for coincident function of Cas9 and gRNA was not met when gRNA was delivered as RNA and Cas9 was delivered as a DNA vector. To overcome this problem, Cas9 can be delivered as mRNA molecules that will shorten the time from the moment of delivery to functional Cas9 protein expression. Commercially available Cas9 mRNA (TriLink Biotechnologies) was used in the experiment.

To test this idea, maize embryo cells were co-bombarded with Cas9 mRNA (200 ng), gRNA in the form of in vitro synthesized RNA molecules (100 ng), DNA vectors containing Ubiquitin regulated MoPAT-DsRED fusion (25 ng) and developmental genes, Ubiquitin promoter regulated ODP2 and IN2 promoter regulated WUS (12 ng each) per shot. Commercially available Cas9 mRNA (TriLink Biotechnologies) and RNA molecules, in vitro synthesized as described above, were used in the experiment. Analysis for mutation frequency was performed by amplicon deep sequencing on embryos collected 2 days post-transformation (Table 13).

TABLE 13

Percentage of mutant reads at MS45 target site produced by transient delivery of Cas9 as mRNA and gRNA as RNA molecules into maize embryo cells.

| Target Sites | Molecules delivered | Total Number of Reads | Number of Mutant Reads | Percentage of Mutant Reads |
|---|---|---|---|---|
| MS45 | Cas9 mRNA only | 1,097,279 | 799 | 0.07% |
| | Cas9 mRNA + Ms45 CR2 gRNA | 1,260,332 | 2,304 | 0.18% |
| | Cas9 (DNA) + Ms45 CR2 (DNA) | 1,106,125 | 3,490 | 0.31% |

These data demonstrate that delivery of both Cas9 and gRNA, in the form of RNA molecules, improves frequencies of targeted mutations and, along with Cas9-gRNA delivery as the RGEN complex, is a viable alternative to DNA delivery for targeted mutagenesis and gene editing in plants.

Example 12

Direct Delivery of Cas9 and gRNA as a Guide RNA/Cas Endonuclease Ribonucleotide-Protein Complex (RGEN) into Embryo Cells without the Use of a Selectable Marker Generates Mutations in Maize This example demonstrates that delivery of Cas9 in the form of protein and gRNA in the form of in vitro transcribed or chemically synthesized RNA molecules, into maize immature embryo cells without co-delivery of selectable marker gene(s) is sufficient to regenerate plants with mutations at the corresponding targeted sites with practical frequencies.

The necessity of selectable markers to provide a growth advantage to transformed or modified cells has been the long standing paradigm in plant transformation and genome modification protocols. Therefore, in all mutation, gene editing and gene integration experiments, selectable markers are used to select for genome edited events. Taking into consideration the unexpected high activity (mutation frequency) of RGEN complexes in the experiments described in Example 10, a completely DNA-free (vector free) genome editing without a selectable marker was attempted. Maize embryo cells were bombarded with guide RNA/Cas endonuclease ribonucleotide-protein (RGEN) complexes targeting three different genes: liguleless1 (LIG), MS26 and MS45. Cas9 endonuclease and MS45-gRNA on DNA vectors were delivered in parallel experiments which served as controls. Plants were regenerated and analyzed by sequencing for targeted mutations. In all experiments, mutant plants were recovered at surprisingly high frequencies ranging from 2.4 to 9.7% (Table 14).

TABLE 14

Mutation frequencies at LIG, MS26 and MS45 target sites upon delivery of Cas9 and gRNAs in the form of DNA vectors and direct delivery of RGEN complexes into maize immature embryo cells. Analysis was performed on T0 plants regenerated without selection (without use of selectable markers).

| Target site | Cas9 and gRNA delivery method | Plants analyzed | Plants with mutated alleles | SEQ ID NO: |
|---|---|---|---|---|
| LIGCas-3 | RGEN | 756 | 73 (9.7%) | 12 |
| MS26Cas-2 | RGEN | 756 | 18 (2.4%) | 14 |
| MS45 Cas-2 | RGEN | 1,880 | 70 (3.7%) | 8 |
| MS45 Cas-2 | Vector DNA | 940 | 38 (4.0%) | 8 |

Further, regenerated TO plants were crossed with wild type Hi-II plants and the progeny plants were used for segregation analysis. Sexual transmission of mutated ms45 alleles at the expected Mendelian segregation (1:1) was demonstrated in all progeny plants analyzed.

To assess the potential of RGEN delivery to reduce off-target cleavage in maize, the mutation frequency at the MS45 off-site was evaluated using DNA vectors and RGEN delivery. Searches for a site with close homology to the on-target site were performed by aligning the protospacer region of the MS45Cas-2 target site (the region of the target site that base pairs with the guide RNA spacer) with the maize B73 reference genome (B73 RefGen_v3, Maize Genetics and Genomics Database) using Bowtie sequence aligner (Langmead, B., Trapnell, C., Pop, M. & Salzberg, S. L. Ultrafast and memory-efficient alignment of short DNA sequences to the human genome. Genome Biol. 10:R25, 2009) permitting up to two mismatches with the on-target sequence. Potential off-target sites were then examined for the presence of a NGG protospacer adjacent motif (PAM) sequence immediately 3' of the identified protospacer off-target. Only a single off-target site (5'-CGCCGAGGGCGACTACCGGC-3', SEQ ID NO:81) was identified using these search criteria. It contained a 2 bp mismatch with the MS45 protospacer target and an AGG PAM (Table 15). To confirm the site was cleaved in vivo, it was analyzed by deep sequencing for the presence of mutations in maize embryos transformed with DNA vectors expressing Cas9 and MS45-CR2 gRNA. As shown in Table 15, mutational activity of the off-target site was at a frequency of 2% compared to a 4% frequency observed for the on-target site. As shown in Table 15, RGEN off-target activity was greatly reduced relative to Cas9 and gRNA delivery on DNA vectors (from 2% to 0%).

TABLE 15

Mutation frequencies at the MS45 off-target site upon delivery of Cas9 and gRNAs in the form of DNA vectors and RGEN complexes into maize immature embryo cells. Analysis performed on T0 plants regenerated without selection.

| Target Site | Cas9 and gRNA delivery method | Target site sequence with PAM* | Plants Analyzed | Plants with Mutations (number) | Plants with Mutations (%) | SEQ ID NO: |
|---|---|---|---|---|---|---|
| MS45Cas-2 | | GGCCGAGGTCGA CTACCGGC<u>CGG</u> | 904 | 38 | 4% | 14 |
| MS45 off-site | DNA | **C**GCCGAGG**G**CGA CTACCGGC**A**GG | 940 | 19 | 2.0% | 82 |
| MS45 off-site | RGEN | **C**GCCGAGG**G**CGA CTACCGGC**A**GG | 1,880 | 0 | 0.0% | 82 |

*PAM- protospacer adjacent motif is a 3 nt sequence immediately 3' of the target site. Two nucleotides different in the MS45 off-target site in comparison to the intended site are shown in bold and underlined.

This example demonstrates that generation of plants with targeted mutations using RNA-guided endonucleases, does not require co-delivery of selectable or screenable marker genes, thus increasing specificity and exactness of the introduced modifications. Regenerated plants contained only targeted mutations or targeted gene edits (if a repair template was included to modify DNA sequence) without random integration of DNA vectors. This method of delivery provides an approach to gene mutagenesis in plant cells of major crop species including but not limited to maize, soybean, wheat, rice, millet, sorghum and canola.

That which is claimed:

1. A method for modifying a target site of a nucleotide sequence in the genome of a plant embryo cell and selecting the plant embryo cell, the method comprising:

(a) introducing into the plant embryo cell a guide RNA/Cas endonuclease complex coated onto or combined with a first particle delivery matrix using a precipitation method that allows for release of the guide RNA/Cas endonuclease complex from the first particle delivery matrix when introduced into the plant embryo cell;

(b) delivering the guide RNA/Cas endonuclease complex to the plant embryo cell as (i) a Cas endonuclease and (ii) a guide RNA that guides the Cas endonuclease to the target site, wherein the guide RNA/Cas endonuclease complex is assembled in the plant embryo cell;

(c) introducing into the plant embryo cell a DNA plasmid comprising a ZmWUS gene and a ZmODP gene coated onto or combined with a second particle delivery matrix using a precipitation method that does not allow for release of the DNA plasmid comprising the ZmWUS gene and the ZmODP gene when introduced into the plant embryo cell;

(d) delivering the DNA plasmid comprising the ZmWUS gene and the ZmODP gene to the plant embryo cell;

(e) making a double strand break in the target site of the plant embryo cell, wherein the guide RNA/Cas endonuclease complex does not comprise the restoration of a disrupted selectable marker gene into a non-disrupted selectable marker gene encoding a functional selectable marker protein of the plant embryo cell; and, (f) selecting the plant embryo cell having a modification in said nucleotide sequence to identify the modified target site in the genome of the plant embryo cell, wherein the selection of the plant embryo cell does not include the use of a selectable marker.

2. The method of claim 1, wherein the modification is selected from the group consisting of an insertion of at least one nucleotide, a deletion of at least one nucleotide, a substitution of at least one nucleotide in said target site, and any combination thereof.

3. The method of claim 1, further comprising introducing a donor DNA to the plant embryo cell of (a) wherein said donor DNA comprises at least one heterologous polynucleotide of interest to be inserted into a genomic nucleotide sequence other than said target site.

4. The method of claim 1, wherein the guide RNA/Cas endonuclease complex is introduced as a ribonucleotide-protein complex.

5. The method of claim 1, wherein components of the guide RNA/Cas endonuclease complex are introduced as guide RNA and Cas endonuclease protein, capable of forming said guide RNA/Cas endonuclease complex.

6. The method of claim 1, wherein components of the guide RNA/Cas endonuclease complex are introduced as mRNA encoding the Cas endonuclease and as RNA comprising guide RNA.

7. The method of claim 1, wherein components of the guide RNA/Cas endonuclease complex are introduced as recombinant DNA molecules encoding guide RNA and Cas endonuclease protein.

8. The method of claim 1, wherein the guide RNA/Cas endonuclease complex is assembled inside the cell.

9. The method of claim 1, wherein plant embryo cell is selected from the group consisting of a monocot and a dicot cell.

10. The method of claim 1, wherein the plant embryo cell is selected from the group consisting of a maize, rice, sorghum, rye, barley, wheat, millet, oats, sugarcane, turfgrass, or switchgrass, soybean, canola, alfalfa, sunflower, cotton, peanut, potato, tomato, tobacco, *Arabidopsis*, and safflower cell.

11. The method of claim 1, further comprising regenerating a plant from the plant embryo cell, wherein the plant retains the nucleotide modification at the target site; wherein the nucleotide modification is selected from the group consisting of (i) a replacement of at least one nucleotide, (ii) a deletion of at least one nucleotide, (iii) an insertion of at least one nucleotide, and (iv) any combination of (i)-(iii).

* * * * *

SEQUENCE LISTING

<160> NUMBER OF SEQ ID NOS: 82

<210> SEQ ID NO 1
<211> LENGTH: 4107
<212> TYPE: DNA

<213> ORGANISM: Streptococcus pyogenes M1 GAS (SF370)

<400> SEQUENCE: 1

```
atggataaga aatactcaat aggcttagat atcggcacaa atagcgtcgg atgggcggtg     60
atcactgatg aatataaggt tccgtctaaa aagttcaagg ttctgggaaa tacagaccgc    120
cacagtatca aaaaaaatct tataggggct cttttatttg acagtggaga gacagcggaa    180
gcgactcgtc tcaaacggac agctcgtaga aggtatacac gtcggaagaa tcgtatttgt    240
tatctacagg agattttttc aaatgagatg gcgaaagtag atgatagttt ctttcatcga    300
cttgaagagt cttttttggt ggaagaagac aagaagcatg aacgtcatcc tatttttgga    360
aatatagtag atgaagttgc ttatcatgag aaatatccaa ctatctatca tctgcgaaaa    420
aaattggtag attctactga taaagcggat ttgcgcttaa tctatttggc cttagcgcat    480
atgattaagt ttcgtggtca tttttttgatt gagggagatt taaatcctga taatagtgat    540
gtggacaaac tatttatcca gttggtacaa acctacaatc aattatttga agaaaaccct    600
attaacgcaa gtggagtaga tgctaaagcg attctttctg cacgattgag taaatcaaga    660
cgattagaaa atctcattgc tcagctcccc ggtgagaaga aaaatggctt atttgggaat    720
ctcattgctt tgtcattggg tttgacccct aattttaaat caaattttga tttggcagaa    780
gatgctaaat tacagctttc aaaagatact tacgatgatg atttagataa tttattggcg    840
caaattggag atcaatatgc tgatttgttt ttggcagcta agaatttatc agatgctatt    900
ttactttcag atatcctaag agtaaatact gaaataacta aggctcccct atcagcttca    960
atgattaaac gctacgatga acatcatcaa gacttgactc ttttaaaagc tttagttcga   1020
caacaacttc cagaaaagta taaagaaatc ttttttgatc aatcaaaaaa cggatatgca   1080
ggttatattg atgggggagc tagccaagaa gaattttata aatttatcaa accaatttta   1140
gaaaaaatgg atggtactga ggaattattg gtgaaactaa atcgtgaaga tttgctgcgc   1200
aagcaacgga cctttgacaa cggctctatt ccccatcaaa ttcacttggg tgagctgcat   1260
gctattttga gaagacaaga agacttttat ccatttttaa aagacaatcg tgagaagatt   1320
gaaaaaatct tgacttttcg aattccttat tatgttggtc cattggcgcg tggcaatagt   1380
cgttttgcat ggatgactcg gaagtctgaa gaaacaatta ccccatggaa ttttgaagaa   1440
gttgtcgata aaggtgcttc agctcaatca tttattgaac gcatgacaaa ctttgataaa   1500
aatcttccaa atgaaaaagt actaccaaaa catagtttgc tttatgagta ttttacggtt   1560
tataacgaat tgacaaaggt caaatatgtt actgaaggaa tgcgaaaacc agcatttctt   1620
tcaggtgaac agaagaaagc cattgttgat ttactcttca aaacaaatcg aaaagtaacc   1680
gttaagcaat taaaagaaga ttatttcaaa aaaatagaat gttttgatag tgttgaaatt   1740
tcaggagttg aagatagatt taatgcttca ttaggtacct accatgattt gctaaaaatt   1800
attaaagata aagatttttt ggataatgaa gaaaatgaag atatcttaga ggatattgtt   1860
ttaacattga ccttatttga agatagggag atgattgagg aaagacttaa aacatatgct   1920
cacctctttg atgataaggt gatgaaacag cttaaacgtc gccgttatac tggttgggga   1980
cgtttgtctc gaaaattgat taatggtatt agggataagc aatctggcaa aacaatatta   2040
gatttttttga aatcagatgg ttttgccaat cgcaatttta tgcagctgat ccatgatgat   2100
agtttgacat ttaaagaaga cattcaaaaa gcacaagtgt ctggacaagg cgatagttta   2160
catgaacata ttgcaaattt agctggtagc cctgctatta aaaaaggtat tttacagact   2220
gtaaaagttg ttgatgaatt ggtcaaagta atggggcggc ataagccaga aaatatcgtt   2280
```

```
attgaaatgg cacgtgaaaa tcagacaact caaaagggcc agaaaaattc gcgagagcgt   2340
atgaaacgaa tcgaagaagg tatcaaagaa ttaggaagtc agattcttaa agagcatcct   2400
gttgaaaata ctcaattgca aaatgaaaag ctctatctct attatctcca aaatggaaga   2460
gacatgtatg tggaccaaga attagatatt aatcgtttaa gtgattatga tgtcgatcac   2520
attgttccac aaagtttcct taaagacgat tcaatagaca ataaggtctt aacgcgttct   2580
gataaaaatc gtggtaaatc ggataacgtt ccaagtgaag aagtagtcaa aaagatgaaa   2640
aactattgga gacaacttct aaacgccaag ttaatcactc aacgtaagtt tgataattta   2700
acgaaagctg aacgtggagg tttgagtgaa cttgataaag ctggttttat caaacgccaa   2760
ttggttgaaa ctcgccaaat cactaagcat gtggcacaaa ttttggatag tcgcatgaat   2820
actaaatacg atgaaaatga taaacttatt cgagaggtta aagtgattac cttaaaatct   2880
aaattagttt ctgacttccg aaaagatttc caattctata aagtacgtga gattaacaat   2940
taccatcatg cccatgatgc gtatctaaat gccgtcgttg gaactgcttt gattaagaaa   3000
tatccaaaac ttgaatcgga gtttgtctat ggtgattata aagtttatga tgttcgtaaa   3060
atgattgcta agtctgagca agaaataggc aaagcaaccg caaaatattt cttttactct   3120
aatatcatga acttcttcaa aacagaaatt acacttgcaa atggagagat tcgcaaacgc   3180
cctctaatcg aaactaatgg ggaaactgga gaaattgtct gggataaagg gcgagatttt   3240
gccacagtgc gcaaagtatt gtccatgccc caagtcaata ttgtcaagaa aacagaagta   3300
cagacaggcg gattctccaa ggagtcaatt ttaccaaaaa gaaattcgga caagcttatt   3360
gctcgtaaaa aagactggga tccaaaaaaa tatggtggtt ttgatagtcc aacggtagct   3420
tattcagtcc tagtggttgc taaggtggaa aaagggaaat cgaagaagtt aaaatccgtt   3480
aaagagttac tagggatcac aattatggaa agaagttcct ttgaaaaaaa tccgattgac   3540
tttttagaag ctaaaggata taaggaagtt aaaaaagact taatcattaa actacctaaa   3600
tatagtcttt ttgagttaga aaacggtcgt aaacggatgc tggctagtgc cggagaatta   3660
caaaaaggaa atgagctggc tctgccaagc aaatatgtga atttttttata tttagctagt   3720
cattatgaaa agttgaaggg tagtccagaa gataacgaac aaaaacaatt gtttgtggag   3780
cagcataagc attatttaga tgagattatt gagcaaatca gtgaattttc taagcgtgtt   3840
attttagcag atgccaattt agataaagtt cttagtgcat ataacaaaca tagagacaaa   3900
ccaatacgtg aacaagcaga aaatattatt catttattta cgttgacgaa tcttggagct   3960
cccgctgctt ttaaatattt tgatacaaca attgatcgta aacgatatac gtctacaaaa   4020
gaagttttag atgccactct tatccatcaa tccatcactg gtctttatga aacacgcatt   4080
gatttgagtc agctaggagg tgactga                                        4107
```

<210> SEQ ID NO 2
<211> LENGTH: 189
<212> TYPE: DNA
<213> ORGANISM: Solanum tuberosum

<400> SEQUENCE: 2

```
gtaagtttct gcttctacct ttgatatata tataataatt atcattaatt agtagtaata     60
taatatttca aatatttttt tcaaaataaa agaatgtagt atatagcaat tgcttttctg    120
tagtttataa gtgtgtatat tttaatttat aacttttcta atatatgacc aaaacatggt    180
gatgtgcag                                                            189
```

<210> SEQ ID NO 3
<211> LENGTH: 9
<212> TYPE: PRT
<213> ORGANISM: Simian virus 40

<400> SEQUENCE: 3

Met Ala Pro Lys Lys Lys Arg Lys Val
1 5

<210> SEQ ID NO 4
<211> LENGTH: 18
<212> TYPE: PRT
<213> ORGANISM: Agrobacterium tumefaciens

<400> SEQUENCE: 4

Lys Arg Pro Arg Asp Arg His Asp Gly Glu Leu Gly Gly Arg Lys Arg
1 5 10 15

Ala Arg

<210> SEQ ID NO 5
<211> LENGTH: 6717
<212> TYPE: DNA
<213> ORGANISM: Artificial Sequence
<220> FEATURE:
<223> OTHER INFORMATION: Maize optimized Cas9 expression cassette

<400> SEQUENCE: 5
gtgcagcgtg acccggtcgt gcccctctct agagataatg agcattgcat gtctaagtta 60
taaaaaatta ccacatattt tttttgtcac acttgtttga agtgcagttt atctatcttt 120
atacatatat ttaaacttta ctctacgaat aatataatct atagtactac aataatatca 180
gtgttttaga gaatcatata aatgaacagt tagacatggt ctaaaggaca attgagtatt 240
ttgacaacag gactctacag ttttatcttt ttagtgtgca tgtgttctcc tttttttttg 300
caaatagctt cacctatata atacttcatc cattttatta gtacatccat ttagggttta 360
gggttaatgg tttttataga ctaatttttt tagtacatct attttattct attttagcct 420
ctaaattaag aaaactaaaa ctctatttta gtttttttat ttaataattt agatataaaa 480
tagaataaaa taaagtgact aaaaattaaa caaataccct ttaagaaatt aaaaaaacta 540
aggaaacatt tttcttgttt cgagtagata atgccagcct gttaaacgcc gtcgacgagt 600
ctaacggaca ccaaccagcg aaccagcagc gtcgcgtcgg gccaagcgaa gcagacggca 660
cggcatctct gtcgctgcct ctggacccct ctcgagagtt ccgctccacc gttggacttg 720
ctccgctgtc ggcatccaga aattgcgtgg cggagcggca gacgtgagcc ggcacggcag 780
gcggcctcct cctcctctca cggcaccggc agctacgggg gattcctttc ccaccgctcc 840
ttcgctttcc cttcctcgcc cgccgtaata aatagacacc ccctccacac cctctttccc 900
caacctcgtg ttgttcggag cgcacacaca cacaaccaga tctcccccaa atccacccgt 960
cggcacctcc gcttcaaggt acgccgctcg tcctcccccc ccccccctctc taccttctct 1020 agatcggcgt tccggtccat gcatggttag ggcccggtag ttctacttct gttcatgttt 1080
gtgttagatc cgtgtttgtg ttagatccgt gctgctagcg ttcgtacacg gatgcgacct 1140
gtacgtcaga cacgttctga ttgctaactt gccagtgttt ctctttgggg aatcctggga 1200
tggctctagc cgttccgcag acgggatcga tttcatgatt ttttttgttt cgttgcatag 1260
ggtttggttt gccctttcc tttatttcaa tatatgccgt gcacttgttt gtcgggtcat 1320
cttttcatgc ttttttttgt cttggttgtg atgatgtggt ctggttgggc ggtcgttcta 1380

```
gatcggagta gaattctgtt tcaaactacc tggtggattt attaattttg gatctgtatg   1440
tgtgtgccat acatattcat agttacgaat tgaagatgat ggatggaaat atcgatctag   1500
gataggtata catgttgatg cgggttttac tgatgcatat acagagatgc tttttgttcg   1560
cttggttgtg atgatgtggt gtggttgggc ggtcgttcat tcgttctaga tcggagtaga   1620
atactgtttc aaactacctg gtgtatttat taattttgga actgtatgtg tgtgtcatac   1680
atcttcatag ttacgagttt aagatggatg gaaatatcga tctaggatag gtatacatgt   1740
tgatgtgggt tttactgatg catatacatg atggcatatg cagcatctat tcatatgctc   1800
taaccttgag tacctatcta ttataataaa caagtatgtt ttataattat tttgatcttg   1860
atatacttgg atgatggcat atgcagcagc tatatgtgga ttttttagc cctgccttca   1920
tacgctattt atttgcttgg tactgtttct tttgtcgatg ctcaccctgt tgtttggtgt   1980
tacttctgca ggtcgactct agaggatcca tggcaccgaa gaagaagcgc aaggtgatgg   2040
acaagaagta cagcatcggc ctcgacatcg gcaccaactc ggtgggctgg gccgtcatca   2100
cggacgaata taaggtcccg tcgaagaagt tcaaggtcct cggcaataca gaccgccaca   2160
gcatcaagaa aaacttgatc ggcgccctcc tgttcgatag cggcgagacc gcggaggcga   2220
ccaggctcaa gaggaccgcc aggagacggt acactaggcg caagaacagg atctgctacc   2280
tgcaggagat cttcagcaac gagatggcga aggtggacga ctccttcttc caccgcctgg   2340
aggaatcatt cctggtggag gaggacaaga agcatgagcg gcacccaatc ttcggcaaca   2400
tcgtcgacga ggtaagtttc tgcttctacc tttgatatat atataataat tatcattaat   2460
tagtagtaat ataatatttc aaatattttt ttcaaaataa aagaatgtag tatatagcaa   2520
ttgcttttct gtagtttata agtgtgtata ttttaattta taacttttct aatatatgac   2580
caaaacatgg tgatgtgcag gtggcctacc acgagaagta cccgacaatc taccacctcc   2640
ggaagaaact ggtggacagc acagacaagg cggacctccg gctcatctac cttgccctcg   2700
cgcatatgat caagttccgc ggccacttcc tcatcgaggg cgacctgaac ccggacaact   2760
ccgacgtgga caagctgttc atccagctcg tgcagacgta caatcaactg ttcgaggaga   2820
accccataaa cgctagcggc gtggacgcca aggccatcct ctcggccagg ctctcgaaat   2880
caagaaggct ggagaacctt atcgcgcagt tgccaggcga aaagaagaac ggcctcttcg   2940
gcaaccttat tgcgctcagc ctcggcctga cgccgaactt caaatcaaac ttcgacctcg   3000
cggaggacgc caagctccag ctctcaaagg acacctacga cgacgacctc gacaacctcc   3060
tggcccagat aggagaccag tacgcggacc tcttcctcgc cgccaagaac ctctccgacg   3120
ctatcctgct cagcgacatc cttcgggtca acaccgaaat taccaaggca ccgctgtccg   3180
ccagcatgat taaacgctac gacgagcacc atcaggacct cacgctgctc aaggcactcg   3240
tccgccagca gctccccgag aagtacaagg agatcttctt cgaccaatca aaaaacggct   3300
acgcgggata tatcgacggc ggtgccagcc aggaagagtt ctacaagttc atcaaaccaa   3360
tcctggagaa gatggacggc accgaggagt tgctggtcaa gctcaacagg gaggacctcc   3420
tcaggaagca gaggaccttc gacaacggct ccatcccgca tcagatccac ctgggcgaac   3480
tgcatgccat cctgcggcgc caggaggact tctacccgtt cctgaaggat aaccgggaga   3540
agatcgagaa gatcttgacg ttccgcatcc catactacgt gggcccgctg gctcgcggca   3600
actcccggtt cgcctggatg acccggaagt cggaggagac catcacaccc tggaactttg   3660
aggaggtggt cgataagggc gctagcgctc agagcttcat cgagcgcatg accaacttcg   3720
```

```
ataaaaacct gcccaatgaa aaagtcctcc ccaagcactc gctgctctac gagtacttca   3780
ccgtgtacaa cgagctcacc aaggtcaaat acgtcaccga gggcatgcgg aagccggcgt   3840
tcctgagcgg cgagcagaag aaggcgatag tggacctcct cttcaagacc aacaggaagg   3900
tgaccgtgaa gcaattaaaa gaggactact tcaagaaaat agagtgcttc gactccgtgg   3960
agatctcggg cgtggaggat cggttcaacg cctcactcgg cacgtatcac gacctcctca   4020
agatcattaa agacaaggac ttcctcgaca acgaggagaa cgaggacatc ctcgaggaca   4080
tcgtcctcac cctgaccctg ttcgaggacc gcgaaatgat cgaggagagg ctgaagacct   4140
acgcgcacct gttcgacgac aaggtcatga aacagctcaa gaggcgccgc tacactggtt   4200
ggggaaggct gtcccgcaag ctcattaatg gcatcaggga caagcagagc ggcaagacca   4260
tcctggactt cctcaagtcc gacgggttcg ccaaccgcaa cttcatgcag ctcattcacg   4320
acgactcgct cacgttcaag gaagacatcc agaaggcaca ggtgagcggg cagggtgact   4380
ccctccacga acacatcgcc aacctggccg gctcgccggc cattaaaaag ggcatcctgc   4440
agacggtcaa ggtcgtcgac gagctcgtga aggtgatggg ccggcacaag cccgaaaata   4500
tcgtcataga gatggccagg gagaaccaga ccacccaaaa agggcagaag aactcgcgcg   4560
agcggatgaa acggatcgag gagggcatta aagagctcgg gtcccagatc ctgaaggagc   4620
accccgtgga aaatacccag ctccagaatg aaaagctcta cctctactac ctgcagaacg   4680
gccgcgacat gtacgtggac caggagctgg acattaatcg gctatcggac tacgacgtcg   4740
accacatcgt gccgcagtcg ttcctcaagg acgatagcat cgacaacaag gtgctcaccc   4800
ggtcggataa aaatcggggc aagagcgaca acgtgcccag cgaggaggtc gtgaagaaga   4860
tgaaaaacta ctggcgccag ctcctcaacg cgaaactgat cacccagcgc aagttcgaca   4920
acctgacgaa ggcggaacgc ggtggcttga gcgaactcga taaggcgggc ttcataaaaa   4980
ggcagctggt cgagacgcgc cagatcacga agcatgtcgc ccagatcctg gacagccgca   5040
tgaatactaa gtacgatgaa aacgacaagc tgatccggga ggtgaaggtg atcacgctga   5100
agtccaagct cgtgtcggac ttccgcaagg acttccagtt ctacaaggtc cgcgagatca   5160
acaactacca ccacgcccac gacgcctacc tgaatgcggt ggtcgggacc gccctgatca   5220
agaagtaccc gaagctggag tcggagttcg tgtacggcga ctacaaggtc tacgacgtgc   5280
gcaaaatgat cgccaagtcc gagcaggaga tcggcaaggc cacggcaaaa tacttcttct   5340
actcgaacat catgaacttc ttcaagaccg agatcaccct cgcgaacggc gagatccgca   5400
agcgcccgct catcgaaacc aacggcgaga cgggcgagat cgtctgggat aagggccggg   5460
atttcgcgac ggtccgcaag gtgctctcca tgccgcaagt caatatcgtg aaaaagacgg   5520
aggtccagac gggcgggttc agcaaggagt ccatcctccc gaagcgcaac tccgacaagc   5580
tcatcgcgag gaagaaggat tgggacccga aaaaatatgg cggcttcgac agcccgaccg   5640
tcgcatacag cgtcctcgtc gtggcgaagg tggagaaggg caagtcaaag aagctcaagt   5700
ccgtgaagga gctgctcggg atcacgatta tggagcggtc ctccttcgag aagaacccga   5760
tcgacttcct agaggccaag ggatataagg aggtcaagaa ggacctgatt attaaactgc   5820
cgaagtactc gctcttcgag ctggaaaacg gccgcaagag gatgctcgcc tccgcaggcg   5880
agttgcagaa gggcaacgag ctcgccctcc cgagcaaata cgtcaatttc ctgtacctcg   5940
ctagccacta tgaaaagctc aagggcagcc cggaggacaa cgagcagaag cagctcttcg   6000
tggagcagca caagcattac ctggacgaga tcatcgagca gatcagcgag ttctcgaagc   6060
gggtgatcct cgccgacgcg aacctggaca aggtgctgtc ggcatataac aagcaccgcg   6120
```

acaaaccaat acgcgagcag gccgaaaata tcatccacct cttcaccctc accaacctcg 6180
gcgctccggc agccttcaag tacttcgaca ccacgattga ccggaagcgg tacacgagca 6240
cgaaggaggt gctcgatgcg acgctgatcc accagagcat cacagggctc tatgaaacac 6300
gcatcgacct gagccagctg ggcggagaca agagaccacg ggaccgccac gatggcgagc 6360
tgggaggccg caagcgggca aggtaggtac cgttaaccta gacttgtcca tcttctggat 6420
tggccaactt aattaatgta tgaaataaaa ggatgcacac atagtgacat gctaatcact 6480
ataatgtggg catcaaagtt gtgtgttatg tgtaattact agttatctga ataaaagaga 6540
aagagatcat ccatatttct tatcctaaat gaatgtcacg tgtctttata attctttgat 6600
gaaccagatg catttcatta accaaatcca tatacatata aatattaatc atatataatt 6660
aatatcaatt gggttagcaa aacaaatcta gtctaggtgt gttttgcgaa tgcggcc 6717

<210> SEQ ID NO 6
<211> LENGTH: 4437
<212> TYPE: DNA
<213> ORGANISM: Artificial sequence
<220> FEATURE:
<223> OTHER INFORMATION: Lig-CR3 guide RNA expression vector

<400> SEQUENCE: 6
aaattgtaag cgttaatatt ttgttaaaat tcgcgttaaa tttttgttaa atcagctcat 60
tttttaacca ataggccgaa atcggcaaaa tcccttataa atcaaaagaa tagaccgaga 120
tagggttgag tgttgttcca gtttggaaca agagtccact attaaagaac gtggactcca 180
acgtcaaagg gcgaaaaacc gtctatcagg gcgatggccc actacgtgaa ccatcaccct 240
aatcaagttt tttggggtcg aggtgccgta aagcactaaa tcggaaccct aaagggagcc 300
cccgatttag agcttgacgg ggaaagccgg cgaacgtggc gagaaaggaa gggaagaaag 360
cgaaaggagc gggcgctagg gcgctggcaa gtgtagcggt cacgctgcgc gtaaccacca 420
cacccgccgc gcttaatgcg ccgctacagg gcgcgtccca ttcgccattc aggctgcgca 480
actgttggga agggcgatcg gtgcgggcct cttcgctatt acgccagctg gcgaaagggg 540
gatgtgctgc aaggcgatta agttgggtaa cgccagggtt ttcccagtca cgacgttgta 600
aaacgacggc cagtgaattg taatacgact cactataggg cgaattgggt accgggcccc 660
ccctcgaggt cgacggtatc gataagcttt gagagtacaa tgatgaacct agattaatca 720
atgccaaagt ctgaaaaatg caccctcagt ctatgatcca gaaaatcaag attgcttgag 780
gccctgttcg gttgttccgg attagagccc cggattaatt cctagccgga ttacttctct 840
aatttatata gattttgatg agctggaatg aatcctggct tattccggta caaccgaaca 900
ggccctgaag gataccagta atcgctgagc taaattggca tgctgtcaga gtgtcagtat 960
tgcagcaagg tagtgagata accggcatca tggtgccagt ttgatggcac cattagggtt 1020
agagatggtg gccatgggcg catgtcctgg ccaactttgt atgatatatg gcagggtgaa 1080
taggaaagta aaattgtatt gtaaaaaggg atttcttctg tttgttagcg catgtacaag 1140
gaatgcaagt tttgagcgag gggcatcaa agatctggct gtgtttccag ctgtttttgt 1200
tagccccatc gaatccttga cataatgatc ccgcttaaat aagcaacctc gcttgtatag 1260
ttccttgtgc tctaacacac gatgatgata agtcgtaaaa tagtggtgtc caaagaattt 1320
ccaggcccag ttgtaaaagc taaaatgcta ttcgaatttc tactagcagt aagtcgtgtt 1380
tagaaattat ttttttatat acctttttc cttctatgta cagtaggaca cagtgtcagc 1440
gccgcgttga cggagaatat ttgcaaaaaa gtaaaagaga aagtcatagc ggcgtatgtg 1500
ccaaaaactt cgtcacagag agggccataa gaaacatggc ccacggccca atacgaagca 1560
ccgcgacgaa gcccaaacag cagtccgtag gtggagcaaa gcgctgggta atacgcaaac 1620
gttttgtccc accttgacta atcacaagag tggagcgtac cttataaacc gagccgcaag 1680
caccgaattg cgtacgcgta cgtgtggttt tagagctaga aatagcaagt taaaataagg 1740
ctagtccgtt atcaacttga aaaagtggca ccgagtcggt gctttttttt tgcggccgcg 1800
aattcctgca gggccctctt gtcggaccag ttgcccacca cgttggtgag ctcggtgagg 1860
cccttcattg agaggaagga ggtcatgagg tgcctaccga tgtgggactt ggggccgttc 1920
ttgatggcga agatggagta gggggcgttc ttcttgaggg ccttgttgta ggacctcacg 1980
aggttgtcct tgaggagctg gtactcctgc ttgttggagg aggagttgcc ggtcctgttc 2040
accctcttga gcacgggctc tgagttcctg aggaactcgt cgaggtacac gagggggtcg 2100
atcctgccgc gagcggagaa gaagtagatg tgcctggaca cggaggtctt ggtctcggtc 2160
acgaggcact ggatgatcac gccgaggtac ttgttctgac tagttctaga gcggccgcca 2220
ccgcggtgga gctccagctt ttgttccctt tagtgagggt taatttcgag cttggcgtaa 2280
tcatggtcat agctgtttcc tgtgtgaaat tgttatccgc tcacaattcc acacaacata 2340
cgagccggaa gcataaagtg taaagcctgg ggtgcctaat gagtgagcta actcacatta 2400
attgcgttgc gctcactgcc cgctttccag tcgggaaacc tgtcgtgcca gctgcattaa 2460
tgaatcggcc aacgcgcggg gagaggcggt ttgcgtattg ggcgctcttc cgcttcctcg 2520
ctcactgact cgctgcgctc ggtcgttcgg ctgcggcgag cggtatcagc tcactcaaag 2580
gcggtaatac ggttatccac agaatcaggg gataacgcag gaaagaacat gtgagcaaaa 2640
ggccagcaaa aggccaggaa ccgtaaaaag gccgcgttgc tggcgttttt ccataggctc 2700
cgcccccctg acgagcatca caaaaatcga cgctcaagtc agaggtggcg aaacccgaca 2760
ggactataaa gataccaggc gtttccccct ggaagctccc tcgtgcgctc tcctgttccg 2820
accctgccgc ttaccggata cctgtccgcc tttctccctt cgggaagcgt ggcgctttct 2880
catagctcac gctgtaggta tctcagttcg gtgtaggtcg ttcgctccaa gctgggctgt 2940
gtgcacgaac cccccgttca gcccgaccgc tgcgccttat ccggtaacta tcgtcttgag 3000
tccaacccgg taagacacga cttatcgcca ctggcagcag ccactggtaa caggattagc 3060
agagcgaggt atgtaggcgg tgctacagag ttcttgaagt ggtggcctaa ctacggctac 3120
actagaagga cagtatttgg tatctgcgct ctgctgaagc cagttacctt cggaaaaaga 3180
gttggtagct cttgatccgg caaacaaacc accgctggta gcggtggttt ttttgtttgc 3240
aagcagcaga ttacgcgcag aaaaaaagga tctcaagaag atcctttgat cttttctacg 3300
gggtctgacg ctcagtggaa cgaaaactca cgttaaggga ttttggtcat gagattatca 3360
aaaaggatct tcacctagat ccttttaaat taaaaatgaa gttttaaatc aatctaaagt 3420
atatatgagt aaacttggtc tgacagttac caatgcttaa tcagtgaggc acctatctca 3480
gcgatctgtc tatttcgttc atccatagtt gcctgactcc ccgtcgtgta gataactacg 3540
atacgggagg gcttaccatc tggccccagt gctgcaatga taccgcgaga cccacgctca 3600
ccggctccag atttatcagc aataaaccag ccagccggaa gggccgagcg cagaagtggt 3660
cctgcaactt tatccgcctc catccagtct attaattgtt gccgggaagc tagagtaagt 3720
agttcgccag ttaatagttt gcgcaacgtt gttgccattg ctacaggcat cgtggtgtca 3780
cgctcgtcgt ttggtatggc ttcattcagc tccggttccc aacgatcaag gcgagttaca 3840
tgatccccca tgttgtgcaa aaaagcggtt agctccttcg gtcctccgat cgttgtcaga 3900
agtaagttgg ccgcagtgtt atcactcatg gttatggcag cactgcataa ttctcttact 3960
gtcatgccat ccgtaagatg cttttctgtg actggtgagt actcaaccaa gtcattctga 4020
gaatagtgta tgcggcgacc gagttgctct tgcccggcgt caatacggga taataccgcg 4080
ccacatagca gaactttaaa agtgctcatc attggaaaac gttcttcggg gcgaaaactc 4140
tcaaggatct taccgctgtt gagatccagt tcgatgtaac ccactcgtgc acccaactga 4200
tcttcagcat cttttacttt caccagcgtt tctgggtgag caaaaacagg aaggcaaaat 4260
gccgcaaaaa agggaataag ggcgacacgg aaatgttgaa tactcatact cttccttttt 4320
caatattatt gaagcattta tcagggttat tgtctcatga gcggatacat atttgaatgt 4380
atttagaaaa ataaacaaat aggggttccg cgcacatttc cccgaaaagt gccacct 4437

<210> SEQ ID NO 7
<211> LENGTH: 27
<212> TYPE: DNA
<213> ORGANISM: Zea mays

<400> SEQUENCE: 7
gtactccatc cgccccatcg agtaggg 27

<210> SEQ ID NO 8
<211> LENGTH: 24
<212> TYPE: DNA
<213> ORGANISM: Zea mays

<400> SEQUENCE: 8
gcacgtacgt caccatcccg ccgg 24

<210> SEQ ID NO 9
<211> LENGTH: 24
<212> TYPE: DNA
<213> ORGANISM: Zea mays

<400> SEQUENCE: 9
gacgtacgtg ccctactcga tggg 24

<210> SEQ ID NO 10
<211> LENGTH: 24
<212> TYPE: DNA
<213> ORGANISM: Zea mays

<400> SEQUENCE: 10
gtaccgtacg tgccccggcg gagg 24

<210> SEQ ID NO 11
<211> LENGTH: 24
<212> TYPE: DNA
<213> ORGANISM: Zea mays

<400> SEQUENCE: 11
ggaattgtac cgtacgtgcc ccgg 24

<210> SEQ ID NO 12
<211> LENGTH: 20
<212> TYPE: DNA
<213> ORGANISM: Zea mays

<400> SEQUENCE: 12
gcgtacgcgt acgtgtgagg 20

<210> SEQ ID NO 13
<211> LENGTH: 22
<212> TYPE: DNA
<213> ORGANISM: Zea mays

<400> SEQUENCE: 13
gctggccgag gtcgactacc gg 22

<210> SEQ ID NO 14
<211> LENGTH: 23
<212> TYPE: DNA
<213> ORGANISM: Zea mays

<400> SEQUENCE: 14
ggccgaggtc gactaccggc cgg 23

<210> SEQ ID NO 15
<211> LENGTH: 23
<212> TYPE: DNA
<213> ORGANISM: Zea mays

<400> SEQUENCE: 15
ggcgcgagct cgtgcttcac cgg 23

<210> SEQ ID NO 16
<211> LENGTH: 21
<212> TYPE: DNA
<213> ORGANISM: Zea mays

<400> SEQUENCE: 16
ggtgccaatc atgcgtcgcg g 21

<210> SEQ ID NO 17
<211> LENGTH: 20
<212> TYPE: DNA
<213> ORGANISM: Zea mays

<400> SEQUENCE: 17
ggtcgccatc acgggacagg 20

<210> SEQ ID NO 18
<211> LENGTH: 24
<212> TYPE: DNA
<213> ORGANISM: Zea mays

<400> SEQUENCE: 18
gtcgcggcac ctgtcccgtg atgg 24

<210> SEQ ID NO 19
<211> LENGTH: 56
<212> TYPE: DNA
<213> ORGANISM: Artificial Sequence
<220> FEATURE:
<223> OTHER INFORMATION: MS26Cas-1 forward primer

<400> SEQUENCE: 19
ctacactctt tccctacacg acgctcttcc gatctaggac cggaagctcg ccgcgt 56

<210> SEQ ID NO 20

<211> LENGTH: 54
<212> TYPE: DNA
<213> ORGANISM: Artificial Sequence
<220> FEATURE:
<223> OTHER INFORMATION: MS26Cas-1 and MS26Cas-3 reverse primer

<400> SEQUENCE: 20
caagcagaag acggcatacg agctcttccg atcttcctgg aggacgacgt gctg 54

<210> SEQ ID NO 21
<211> LENGTH: 59
<212> TYPE: DNA
<213> ORGANISM: Artificial Sequence
<220> FEATURE:
<223> OTHER INFORMATION: MS26Cas-2 forward primer

<400> SEQUENCE: 21
ctacactctt tccctacacg acgctcttcc gatctaaggt cctggaggac gacgtgctg 59

<210> SEQ ID NO 22
<211> LENGTH: 51
<212> TYPE: DNA
<213> ORGANISM: Artificial Sequence
<220> FEATURE:
<223> OTHER INFORMATION: MS26Cas-2 reverse primer

<400> SEQUENCE: 22
caagcagaag acggcatacg agctcttccg atctccggaa gctcgccgcg t 51

<210> SEQ ID NO 23
<211> LENGTH: 56
<212> TYPE: DNA
<213> ORGANISM: Artificial Sequence
<220> FEATURE:
<223> OTHER INFORMATION: MS26Cas-3 forward primer

<400> SEQUENCE: 23
ctacactctt tccctacacg acgctcttcc gatcttcctc cggaagctcg ccgcgt 56

<210> SEQ ID NO 24
<211> LENGTH: 63
<212> TYPE: DNA
<213> ORGANISM: Artificial Sequence
<220> FEATURE:
<223> OTHER INFORMATION: LIGCas-1 forward primer

<400> SEQUENCE: 24
ctacactctt tccctacacg acgctcttcc gatctaggac tgtaacgatt tacgcacctg 60
ctg 63

<210> SEQ ID NO 25
<211> LENGTH: 58
<212> TYPE: DNA
<213> ORGANISM: Artificial Sequence
<220> FEATURE:
<223> OTHER INFORMATION: LIGCas-1 and LIGCas-2 reverse primer

<400> SEQUENCE: 25
caagcagaag acggcatacg agctcttccg atctgcaaat gagtagcagc gcacgtat 58

<210> SEQ ID NO 26
<211> LENGTH: 63
<212> TYPE: DNA
<213> ORGANISM: Artificial Sequence
<220> FEATURE:
<223> OTHER INFORMATION: LIGCas-2 forward primer

<400> SEQUENCE: 26
ctacactctt tccctacacg acgctcttcc gatcttcctc tgtaacgatt tacgcacctg 60
ctg 63

<210> SEQ ID NO 27
<211> LENGTH: 60
<212> TYPE: DNA
<213> ORGANISM: Artificial Sequence
<220> FEATURE:
<223> OTHER INFORMATION: LIGCas-3 forward primer

<400> SEQUENCE: 27
ctacactctt tccctacacg acgctcttcc gatctaaggc gcaaatgagt agcagcgcac 60

<210> SEQ ID NO 28
<211> LENGTH: 57
<212> TYPE: DNA
<213> ORGANISM: Artificial Sequence
<220> FEATURE:
<223> OTHER INFORMATION: LIGCas-3 reverse primer

<400> SEQUENCE: 28
caagcagaag acggcatacg agctcttccg atctcacctg ctgggaattg taccgta 57

<210> SEQ ID NO 29
<211> LENGTH: 58
<212> TYPE: DNA
<213> ORGANISM: Artificial Sequence
<220> FEATURE:
<223> OTHER INFORMATION: MS45Cas-1 forward primer

<400> SEQUENCE: 29
ctacactctt tccctacacg acgctcttcc gatctaggag gacccgttcg gcctcagt 58

<210> SEQ ID NO 30
<211> LENGTH: 54
<212> TYPE: DNA
<213> ORGANISM: Artificial Sequence
<220> FEATURE:
<223> OTHER INFORMATION: S45Cas-1, MS45Cas-2 and MS45Cas-3 reverse primer

<400> SEQUENCE: 30
caagcagaag acggcatacg agctcttccg atctgccggc tggcattgtc tctg 54

<210> SEQ ID NO 31
<211> LENGTH: 58
<212> TYPE: DNA
<213> ORGANISM: Artificial Sequence
<220> FEATURE:
<223> OTHER INFORMATION: MS45Cas-2 forward primer

<400> SEQUENCE: 31
ctacactctt tccctacacg acgctcttcc gatcttcctg gacccgttcg gcctcagt 58

<210> SEQ ID NO 32
<211> LENGTH: 58
<212> TYPE: DNA
<213> ORGANISM: Artificial Sequence
<220> FEATURE:
<223> OTHER INFORMATION: MS45Cas-3 forward primer

<400> SEQUENCE: 32
ctacactctt tccctacacg acgctcttcc gatctgaagg gacccgttcg gcctcagt 58

<210> SEQ ID NO 33
<211> LENGTH: 58
<212> TYPE: DNA
<213> ORGANISM: Artificial Sequence
<220> FEATURE:
<223> OTHER INFORMATION: ALSCas-1 forward primer

<400> SEQUENCE: 33
ctacactctt tccctacacg acgctcttcc gatctaaggc gacgatgggc gtctcctg 58

<210> SEQ ID NO 34
<211> LENGTH: 53
<212> TYPE: DNA
<213> ORGANISM: Artificial Sequence
<220> FEATURE:
<223> OTHER INFORMATION: ALSCas-1, ALSCas-2 and ALSCas-3 reverse primer

<400> SEQUENCE: 34
caagcagaag acggcatacg agctcttccg atctgcgtct gcatcgccac ctc 53

<210> SEQ ID NO 35
<211> LENGTH: 58
<212> TYPE: DNA
<213> ORGANISM: Artificial Sequence
<220> FEATURE:
<223> OTHER INFORMATION: ALSCas-2 forward primer

<400> SEQUENCE: 35
ctacactctt tccctacacg acgctcttcc gatctttccc gacgatgggc gtctcctg 58

<210> SEQ ID NO 36
<211> LENGTH: 58
<212> TYPE: DNA
<213> ORGANISM: Artificial Sequence
<220> FEATURE:
<223> OTHER INFORMATION: ALSCas-3 forward primer

<400> SEQUENCE: 36
ctacactctt tccctacacg acgctcttcc gatctggaac gacgatgggc gtctcctg 58

<210> SEQ ID NO 37
<211> LENGTH: 43
<212> TYPE: DNA
<213> ORGANISM: Artificial Sequence
<220> FEATURE:
<223> OTHER INFORMATION: forward primer for secondary PCR

<400> SEQUENCE: 37
aatgatacgg cgaccaccga gatctacact ctttccctac acg 43

<210> SEQ ID NO 38
<211> LENGTH: 18
<212> TYPE: DNA
<213> ORGANISM: Artificial Sequence
<220> FEATURE:
<223> OTHER INFORMATION: reverse primer for secondary PCR;

<400> SEQUENCE: 38
caagcagaag acggcata 18

<210> SEQ ID NO 39
<211> LENGTH: 1910
<212> TYPE: DNA
<213> ORGANISM: Zea mays
<220> FEATURE:

<221> NAME/KEY: misc_feature
<222> LOCATION: (1)..(1910)
<223> OTHER INFORMATION: ALS1-DNA sequence

<400> SEQUENCE: 39

```
atggccaccg ccgccaccgc ggccgccgcg ctcaccggcg ccactaccgc tacgcccaag     60
tcgaggcgcc gagcccacca cttggccacc cggcgcgccc tcgccgcgcc catcaggtgc    120
tcagcgttgt cacgcgccac gccgacggct cccccggcca ctccgctacg tccgtggggc    180
cccaacgagc cccgcaaggg ctccgacatc ctcgtcgagg ctctcgagcg ctgtggcgtc    240
cgtgacgtct tcgcctaccc cggcggcgca tccatggaga tccaccaggc actcacccgc    300
tcccccgtca tcgccaacca cctcttccgc cacgaacaag gggaggcctt cgccgcctcc    360
ggctacgcgc gctcctcggg ccgcgttggc gtctgcatcg ccacctccgg ccccggcgcc    420
accaacctag tctctgcgct cgcagacgcg ttgctcgact ccgtccccat tgtcgccatc    480
acgggacagg tgccgcgacg catgattggc accgacgcct ttcaggagac gcccatcgtc    540
gaggtcaccc gctccatcac caagcacaac tacctggtcc tcgacgtcga cgacatcccc    600
cgcgtcgtgc aggaggcctt cttcctcgca tcctctggtc gcccggggcc ggtgcttgtt    660
gacatcccca aggacatcca gcagcagatg gcggtgccgg cctgggacac gcccatgagt    720
ctgcctgggt acatcgcgcg ccttcccaag cctcccgcga ctgaatttct tgagcaggtg    780
ctgcgtcttg ttggtgaatc acggcgccct gttctttatg ttggcggtgg ctgtgcagca    840
tcaggtgagg agttgtgccg ctttgtggag ttgactggaa tcccagtcac aactactctt    900
atgggccttg gcaacttccc cagcgacgac ccactgtcac tgcgcatgct tggtatgcat    960
ggcacagtgt atgcaaatta tgcagtggat aaggccgatc tgttgcttgc atttggtgtg   1020
cggtttgatg atcgtgtgac agggaaaatt gaggcttttg caggcagagc taagattgtg   1080
cacattgata ttgatcctgc tgagattggc aagaacaagc agccacatgt gtccatctgt   1140
gcagatgtta agcttgcttt gcagggcatg aatactcttc tggaaggaag cacatcaaag   1200
aagagctttg acttcggctc atggcatgat gaattggatc agcaaaagcg ggagtttccc   1260
cttgggtata aaatcttcaa tgaggaaatc cagccacaat atgctattca ggttcttgat   1320
gagttgacga aggggaaggc catcattgcc acaggtgttg ggcagcacca gatgtgggcg   1380
gcacagtatt acacttacaa gcggccaagg cagtggctgt cttcagctgg tcttggggct   1440
atgggatttg gtttgccggc tgctgctggt gctgctgtgg ccaacccagg tgtcactgtt   1500
gttgacatcg acggagatgg tagcttcctc atgaacattc aggagctagc tatgatccgt   1560
attgagaacc tcccagtcaa ggtctttgtg ctaaacaacc agcacctcgg gatggtggtg   1620
cagtgggagg acaggttcta taaggccaat agagcacaca cattcttggg aaacccagag   1680
aacgaaagtg agatatatcc agattttgtg gcaattgcca aagggttcaa cattccagca   1740
gtccgtgtga caaagaagag cgaagtccat gcagcaatca agaagatgct tgaggctcca   1800
gggccgtacc tcttggatat aatcgtcccg caccaggagc atgtgttgcc tatgatccct   1860
agtggtgggg ctttcaagga tatgatcctg gatggtgatg gcaggactgt              1910
```

<210> SEQ ID NO 40
<211> LENGTH: 1910
<212> TYPE: DNA
<213> ORGANISM: Zea mays
<220> FEATURE:
<221> NAME/KEY: misc_feature
<222> LOCATION: (1)..(1910)
<223> OTHER INFORMATION: ALS2-DNA sequence

<400> SEQUENCE: 40

```
atggccaccg ccgccgccgc gtctaccgcg ctcactggcg ccactaccgc tgcgcccaag     60
gcgaggcgcc gggcgcacct cctggccacc cgccgcgccc tcgccgcgcc catcaggtgc    120
tcagcggcgt cacccgccat gccgatggct cccccggcca ccccgctccg gccgtggggc    180
cccaccgatc cccgcaaggg cgccgacatc ctcgtcgagt ccctcgagcg ctgcggcgtc    240
cgcgacgtct tcgcctaccc cggcggcgcg tccatggaga tccaccaggc actcacccgc    300
tcccccgtca tcgccaacca cctcttccgc cacgagcaag gggaggcctt tgcggcctcc    360
ggctacgcgc gctcctcggg ccgcgtcggc gtctgcatcg ccacctccgg ccccggcgcc    420
accaaccttg tctccgcgct cgccgacgcg ctgctcgatt ccgtccccat ggtcgccatc    480
acgggacagg tgccgcgacg catgattggc accgacgcct tccaggagac gcccatcgtc    540
gaggtcaccc gctccatcac caagcacaac tacctggtcc tcgacgtcga cgacatcccc    600
cgcgtcgtgc aggaggcttt cttcctcgcc tcctctggtc gaccggggcc ggtgcttgtc    660
gacatcccca aggacatcca gcagcagatg gcggtgcctg tctgggacaa gcccatgagt    720
ctgcctgggt acattgcgcg ccttcccaag ccccctgcga ctgagttgct tgagcaggtg    780
ctgcgtcttg ttggtgaatc ccggcgccct gttctttatg ttggcggtgg ctgcgcagca    840
tctggtgagg agttgcgacg ctttgtggag ctgactggaa tcccggtcac aactactctt    900
atgggcctcg gcaacttccc cagcgacgac ccactgtctc tgcgcatgct aggtatgcat    960
ggcacggtgt atgcaaatta tgcagtggat aaggccgatc tgttgcttgc acttggtgtg   1020
cggtttgatg atcgtgtgac agggaagatt gaggcttttg caagcagggc taagattgtg   1080
cacgttgata ttgatccggc tgagattggc aagaacaagc agccacatgt gtccatctgt   1140
gcagatgtta agcttgcttt gcagggcatg aatgctcttc ttgaaggaag cacatcaaag   1200
aagagctttg actttggctc atggaacgat gagttggatc agcagaagag ggaattcccc   1260
cttgggtata aaacatctaa tgaggagatc cagccacaat atgctattca ggttcttgat   1320
gagctgacga aaggcgaggc catcatcggc acaggtgttg ggcagcacca gatgtgggcg   1380
gcacagtact acacttacaa gcggccaagg cagtggttgt cttcagctgg tcttggggct   1440
atgggatttg gtttgccggc tgctgctggt gcttctgtgg ccaacccagg tgttactgtt   1500
gttgacatcg atggagatgg tagctttctc atgaacgttc aggagctagc tatgatccga   1560
attgagaacc tcccggtgaa ggtctttgtg ctaaacaacc agcacctggg gatggtggtg   1620
cagtgggagg acaggttcta taaggccaac agagcgcaca catacttggg aaacccagag   1680
aatgaaagtg agatatatcc agatttcgtg acgatcgcca aagggttcaa cattccagcg   1740
gtccgtgtga caaagaagaa cgaagtccgc gcagcgataa agaagatgct cgagactcca   1800
gggccgtacc tcttggatat aatcgtccca caccaggagc atgtgttgcc tatgatccct   1860
agtggtgggg ctttcaagga tatgatcctg gatggtgatg gcaggactgt              1910
```

<210> SEQ ID NO 41
<211> LENGTH: 638
<212> TYPE: PRT
<213> ORGANISM: Zea mays
<220> FEATURE:
<221> NAME/KEY: MISC_FEATURE
<222> LOCATION: (1)..(638)
<223> OTHER INFORMATION: full length Zm-ALS2 protein

<400> SEQUENCE: 41

Met Ala Thr Ala Ala Ala Ala Ser Thr Ala Leu Thr Gly Ala Thr Thr
1 5 10 15

Ala Ala Pro Lys Ala Arg Arg Arg Ala His Leu Leu Ala Thr Arg Arg
20 25 30

Ala Leu Ala Ala Pro Ile Arg Cys Ser Ala Ala Ser Pro Ala Met Pro
35 40 45

Met Ala Pro Pro Ala Thr Pro Leu Arg Pro Trp Gly Pro Thr Glu Pro
50 55 60

Arg Lys Gly Ala Asp Ile Leu Val Glu Ser Leu Glu Arg Cys Gly Val
65 70 75 80

Arg Asp Val Phe Ala Tyr Pro Gly Gly Ala Ser Met Glu Ile His Gln
85 90 95

Ala Leu Thr Arg Ser Pro Val Ile Ala Asn His Leu Phe Arg His Glu
100 105 110

Gln Gly Glu Ala Phe Ala Ala Ser Gly Tyr Ala Arg Ser Ser Gly Arg
115 120 125

Val Gly Val Cys Ile Ala Thr Ser Gly Pro Gly Ala Thr Asn Leu Val
130 135 140

Ser Ala Leu Ala Asp Ala Leu Leu Asp Ser Val Pro Met Val Ala Ile
145 150 155 160

Thr Gly Gln Val Pro Arg Arg Met Ile Gly Thr Asp Ala Phe Gln Glu
165 170 175

Thr Pro Ile Val Glu Val Thr Arg Ser Ile Thr Lys His Asn Tyr Leu
180 185 190

Val Leu Asp Val Asp Asp Ile Pro Arg Val Val Gln Glu Ala Phe Phe
195 200 205

Leu Ala Ser Ser Gly Arg Pro Gly Pro Val Leu Val Asp Ile Pro Lys
210 215 220

Asp Ile Gln Gln Gln Met Ala Val Pro Val Trp Asp Lys Pro Met Ser
225 230 235 240

Leu Pro Gly Tyr Ile Ala Arg Leu Pro Lys Pro Pro Ala Thr Glu Leu
245 250 255

Leu Glu Gln Val Leu Arg Leu Val Gly Glu Ser Arg Arg Pro Val Leu
260 265 270

Tyr Val Gly Gly Gly Cys Ala Ala Ser Gly Glu Glu Leu Arg Arg Phe
275 280 285

Val Glu Leu Thr Gly Ile Pro Val Thr Thr Thr Leu Met Gly Leu Gly
290 295 300

Asn Phe Pro Ser Asp Asp Pro Leu Ser Leu Arg Met Leu Gly Met His
305 310 315 320

Gly Thr Val Tyr Ala Asn Tyr Ala Val Asp Lys Ala Asp Leu Leu Leu
325 330 335

Ala Leu Gly Val Arg Phe Asp Asp Arg Val Thr Gly Lys Ile Glu Ala
340 345 350

Phe Ala Ser Arg Ala Lys Ile Val His Val Asp Ile Asp Pro Ala Glu
355 360 365

Ile Gly Lys Asn Lys Gln Pro His Val Ser Ile Cys Ala Asp Val Lys
370 375 380

Leu Ala Leu Gln Gly Met Asn Ala Leu Leu Glu Gly Ser Thr Ser Lys
385 390 395 400

```
Lys Ser Phe Asp Phe Gly Ser Trp Asn Asp Glu Leu Asp Gln Gln Lys
                405                 410                 415

Arg Glu Phe Pro Leu Gly Tyr Lys Thr Ser Asn Glu Glu Ile Gln Pro
            420                 425                 430

Gln Tyr Ala Ile Gln Val Leu Asp Glu Leu Thr Lys Gly Glu Ala Ile
        435                 440                 445

Ile Gly Thr Gly Val Gly Gln His Gln Met Trp Ala Ala Gln Tyr Tyr
    450                 455                 460

Thr Tyr Lys Arg Pro Arg Gln Trp Leu Ser Ser Ala Gly Leu Gly Ala
465                 470                 475                 480

Met Gly Phe Gly Leu Pro Ala Ala Ala Gly Ala Ser Val Ala Asn Pro
                485                 490                 495

Gly Val Thr Val Val Asp Ile Asp Gly Asp Gly Ser Phe Leu Met Asn
            500                 505                 510

Val Gln Glu Leu Ala Met Ile Arg Ile Glu Asn Leu Pro Val Lys Val
        515                 520                 525

Phe Val Leu Asn Asn Gln His Leu Gly Met Val Val Gln Trp Glu Asp
    530                 535                 540

Arg Phe Tyr Lys Ala Asn Arg Ala His Thr Tyr Leu Gly Asn Pro Glu
545                 550                 555                 560

Asn Glu Ser Glu Ile Tyr Pro Asp Phe Val Thr Ile Ala Lys Gly Phe
                565                 570                 575

Asn Ile Pro Ala Val Arg Val Thr Lys Lys Asn Glu Val Arg Ala Ala
            580                 585                 590

Ile Lys Lys Met Leu Glu Thr Pro Gly Pro Tyr Leu Leu Asp Ile Ile
        595                 600                 605

Val Pro His Gln Glu His Val Leu Pro Met Ile Pro Ser Gly Gly Ala
    610                 615                 620

Phe Lys Asp Met Ile Leu Asp Gly Asp Gly Arg Thr Val Tyr
625                 630                 635
```

<210> SEQ ID NO 42
<211> LENGTH: 23
<212> TYPE: DNA
<213> ORGANISM: Zea mays

<400> SEQUENCE: 42
gctgctcgat tccgtcccca tgg 23

<210> SEQ ID NO 43
<211> LENGTH: 794
<212> TYPE: DNA
<213> ORGANISM: Artificial sequence
<220> FEATURE:
<223> OTHER INFORMATION: 794 bp polynucleotide modification template

<400> SEQUENCE: 43

```
ttctgctcaa gcaactcagt cgcagggggc ttgggaaggc gcgcaatgta cccaggcaga     60

ctcatgggct tgtcccagac aggcaccgcc atctgctgct ggatgtcctt ggggatgtcg    120

acaagcaccg gccctggtcg accagaggag gcgaggaaga aagcctcctg cacgacgcgg    180

gggatgtcgt cgacgtcgag gaccaggtag ttgtgcttgg tgatggagcg ggtgacctcg    240

acgatgggcg tctcctggaa ggcgtcggtg ccaatcatgc gtcgcgacac ttggccggta    300

atcgccacca tggggacgga atcgagcagc gcgtcggcga gcgcggagac aaggttggtg    360

gcgccggggc cggaggtggc gatgcagacg ccgacgcggc ccgaggagcg cgcgtagccg    420
```

gaggccgcaa aggcctcccc ttgctcgtgg cggaagaggt ggttggcgat gacgggggag 480
cgggtgagtg cctggtggat ctccatggac gcgccgccgg ggtaggcgaa gacgtcgcgg 540
acgccgcagc gctcgaggga ctcgacgagg atgtcggcgc ccttgcgggg atcggtgggg 600
ccccacggcc ggagcggggt ggccggggga gccatcggca tggcgggtga cgccgctgag 660
cacctgatgg gcgcggcgag ggcgcggcgg gtggccagga ggtgcgcccg gcgcctcgcc 720
ttgggcgcag cggtagtggc gccagtgagc gcggtagacg cggcggcggc ggtggccatg 780
gttgcggcgg ctgt 794

<210> SEQ ID NO 44
<211> LENGTH: 127
<212> TYPE: DNA
<213> ORGANISM: Artificial sequence
<220> FEATURE:
<223> OTHER INFORMATION: 127 bp polynucleotide modification template oligo -1

<400> SEQUENCE: 44
aaccttgtct ccgcgctcgc cgacgcgttg ctcgactccg tccccattgt cgccatcacg 60
ggacaggtgt cgcgacgcat gattggcacc gacgccttcc aggagacgcc catcgtcgag 120
gtcaccc 127

<210> SEQ ID NO 45
<211> LENGTH: 127
<212> TYPE: DNA
<213> ORGANISM: artificial sequence
<220> FEATURE:
<223> OTHER INFORMATION: 127 bp polynucleotide modification template oligo-2

<400> SEQUENCE: 45
aaccttgtct ccgcgctcgc cgacgcgttg ctggactccg tgccgatggt cgccatcacg 60
ggacaggtgt cccgacgcat gattggcacc gacgccttcc aggagacgcc catcgtcgag 120
gtcaccc 127

<210> SEQ ID NO 46
<211> LENGTH: 56493
<212> TYPE: DNA
<213> ORGANISM: Artificial sequence
<220> FEATURE:
<223> OTHER INFORMATION: Agrobacterium vector containing maize codon optimized Cas9 and maize UBI promoter

<400> SEQUENCE: 46
gtcggatcac cggaaaggac ccgtaaagtg ataatgatta tcatctacat atcacaacgt 60
gcgtggaggc catcaaacca cgtcaaataa tcaattatga cgcaggtatc gtattaattg 120
atctgcatca acttaacgta aaaacaactt cagacaatac aaatcagcga cactgaatac 180
ggggcaacct catgtccccc cccccccccc ccctgcaggc atcgtggtgt cacgctcgtc 240
gtttggtatg gcttcattca gctccggttc ccaacgatca aggcgagtta catgatcccc 300
catgttgtgc aaaaaagcgg ttagctcctt cggtcctccg atcgttgtca gaagtaagtt 360
ggccgcagtg ttatcactca tggttatggc agcactgcat aattctctta ctgtcatgcc 420
atccgtaaga tgcttttctg tgactggtga gtactcaacc aagtcattct gagaatagtg 480
tatgcggcga ccgagttgct cttgcccggc gtcaacacgg gataataccg cgccacatag 540
cagaacttta aaagtgctca tcattggaaa acgttcttcg gggcgaaaac tctcaaggat 600

-continued

```
cttaccgctg ttgagatcca gttcgatgta acccactcgt gcacccaact gatcttcagc    660
atcttttact ttcaccagcg tttctgggtg agcaaaaaca ggaaggcaaa atgccgcaaa    720
aaagggaata agggcgacac ggaaatgttg aatactcata ctcttccttt ttcaatatta    780
ttgaagcatt tatcagggtt attgtctcat gagcggatac atatttgaat gtatttagaa    840
aaataaacaa ataggggttc cgcgcacatt tccccgaaaa gtgccacctg acgtctaaga    900
aaccattatt atcatgacat taacctataa aaataggcgt atcacgaggc cctttcgtct    960
tcaagaattc ggagcttttg ccattctcac cggattcagt cgtcactcat ggtgatttct   1020
cacttgataa ccttattttt gacgagggga aattaatagg ttgtattgat gttggacgag   1080
tcggaatcgc agaccgatac caggatcttg ccatcctatg gaactgcctc ggtgagtttt   1140
ctccttcatt acagaaacgg ctttttcaaa aatatggtat tgataatcct gatatgaata   1200
aattgcagtt tcatttgatg ctcgatgagt ttttctaatc agaattggtt aattggttgt   1260
aacactggca gagcattacg ctgacttgac gggacggcgg ctttgttgaa taaatcgaac   1320
ttttgctgag ttgaaggatc agatcacgca tcttcccgac aacgcagacc gttccgtggc   1380
aaagcaaaag ttcaaaatca ccaactggtc cacctacaac aaagctctca tcaaccgtgg   1440
ctccctcact ttctggctgg atgatggggc gattcaggcc tggtatgagt cagcaacacc   1500
ttcttcacga ggcagacctc agcgccagaa ggccgccaga gaggccgagc gcggccgtga   1560
ggcttggacg ctagggcagg gcatgaaaaa gcccgtagcg ggctgctacg ggcgtctgac   1620
gcggtggaaa gggggagggg atgttgtcta catggctctg ctgtagtgag tgggttgcgc   1680
tccggcagcg gtcctgatca atcgtcaccc tttctcggtc cttcaacgtt cctgacaacg   1740
agcctccttt tcgccaatcc atcgacaatc accgcgagtc cctgctcgaa cgctgcgtcc   1800
ggaccggctt cgtcgaaggc gtctatcgcg gcccgcaaca gcggcgagag cggagcctgt   1860
tcaacggtgc cgccgcgctc gccggcatcg ctgtcgccgg cctgctcctc aagcacggcc   1920
ccaacagtga agtagctgat tgtcatcagc gcattgacgg cgtccccggc cgaaaaaccc   1980
gcctcgcaga ggaagcgaag ctgcgcgtcg gccgtttcca tctgcggtgc gcccggtcgc   2040
gtgccggcat ggatgcgcgc gccatcgcgg taggcgagca gcgcctgcct gaagctgcgg   2100
gcattcccga tcagaaatga gcgccagtcg tcgtcggctc tcggcaccga atgcgtatga   2160
ttctccgcca gcatggcttc ggccagtgcg tcgagcagcg cccgcttgtt cctgaagtgc   2220
cagtaaagcg ccggctgctg aacccccaac cgttccgcca gtttgcgtgt cgtcagaccg   2280
tctacgccga cctcgttcaa caggtccagg gcggcacgga tcactgtatt cggctgcaac   2340
tttgtcatgc ttgacacttt atcactgata aacataatat gtccaccaac ttatcagtga   2400
taaagaatcc gcgcgttcaa tcggaccagc ggaggctggt ccggaggcca gacgtgaaac   2460
ccaacatacc cctgatcgta attctgagca ctgtcgcgct cgacgctgtc ggcatcggcc   2520
tgattatgcc ggtgctgccg ggcctcctgc gcgatctggt tcactcgaac gacgtcaccg   2580
cccactatgg cattctgctg gcgctgtatg cgttggtgca atttgcctgc gcacctgtgc   2640
tgggcgcgct gtcggatcgt ttcgggcggc ggccaatctt gctcgtctcg ctggccggcg   2700
ccactgtcga ctacgccatc atggcgacag cgcctttcct ttgggttctc tatatcgggc   2760
ggatcgtggc cggcatcacc ggggcgactg gggcggtagc cggcgcttat attgccgata   2820
tcactgatgg cgatgagcgc gcgcggcact tcggcttcat gagcgcctgt ttcgggttcg   2880
ggatggtcgc gggacctgtg ctcggtgggc tgatgggcgg tttctccccc cacgctccgt   2940
```

```
tcttcgccgc ggcagccttg aacggcctca atttcctgac gggctgtttc cttttgccgg   3000
agtcgcacaa aggcgaacgc cggccgttac gccgggaggc tctcaacccg ctcgcttcgt   3060
tccggtgggc ccggggcatg accgtcgtcg ccgccctgat ggcggtcttc ttcatcatgc   3120
aacttgtcgg acaggtgccg gccgcgcttt gggtcatttt cggcgaggat cgctttcact   3180
gggacgcgac cacgatcggc atttcgcttg ccgcatttgg cattctgcat tcactcgccc   3240
aggcaatgat caccggccct gtagccgccc ggctcggcga aaggcgggca ctcatgctcg   3300
gaatgattgc cgacggcaca ggctacatcc tgcttgcctt cgcgacacgg ggatggatgg   3360
cgttcccgat catggtcctg cttgcttcgg gtggcatcgg aatgccggcg ctgcaagcaa   3420
tgttgtccag gcaggtggat gaggaacgtc aggggcagct gcaaggctca ctggcggcgc   3480
tcaccagcct gacctcgatc gtcggacccc tcctcttcac ggcgatctat gcggcttcta   3540
taacaacgtg gaacgggtgg gcatggattg caggcgctgc cctctacttg ctctgcctgc   3600
cggcgctgcg tcgcgggctt tggagcggcg cagggcaacg agccgatcgc tgatcgtgga   3660
aacgataggc ctatgccatg cgggtcaagg cgacttccgg caagctatac gcgccctagg   3720
agtgcggttg gaacgttggc ccagccagat actcccgatc acgagcagga cgccgatgat   3780
ttgaagcgca ctcagcgtct gatccaagaa caaccatcct agcaacacgg cggtccccgg   3840
gctgagaaag cccagtaagg aaacaactgt aggttcgagt cgcgagatcc cccggaacca   3900
aaggaagtag gttaaacccg ctccgatcag gccgagccac gccaggccga gaacattggt   3960
tcctgtaggc atcgggattg gcggatcaaa cactaaagct actggaacga gcagaagtcc   4020
tccggccgcc agttgccagg cggtaaaggt gagcagaggc acgggaggtt gccacttgcg   4080
ggtcagcacg gttccgaacg ccatggaaac cgcccccgcc aggcccgctg cgacgccgac   4140
aggatctagc gctgcgtttg gtgtcaacac caacagcgcc acgcccgcag ttccgcaaat   4200
agcccccagg accgccatca atcgtatcgg gctacctagc agagcggcag agatgaacac   4260
gaccatcagc ggctgcacag cgcctaccgt cgccgcgacc ccgcccggca ggcggtagac   4320
cgaaataaac aacaagctcc agaatagcga aatattaagt gcgccgagga tgaagatgcg   4380
catccaccag attcccgttg gaatctgtcg gacgatcatc acgagcaata aacccgccgg   4440
caacgcccgc agcagcatac cggcgacccc tcggcctcgc tgttcgggct ccacgaaaac   4500
gccggacaga tgcgccttgt gagcgtcctt ggggccgtcc tcctgtttga agaccgacag   4560
cccaatgatc tcgccgtcga tgtaggcgcc gaatgccacg gcatctcgca accgttcagc   4620
gaacgcctcc atgggctttt tctcctcgtg ctcgtaaacg gacccgaaca tctctggagc   4680
tttcttcagg gccgacaatc ggatctcgcg gaaatcctgc acgtcggccg ctccaagccg   4740
tcgaatctga gccttaatca caattgtcaa ttttaatcct ctgtttatcg gcagttcgta   4800
gagcgcgccg tgcgtcccga gcgatactga gcgaagcaag tgcgtcgagc agtgcccgct   4860
tgttcctgaa atgccagtaa agcgctggct gctgaacccc cagccggaac tgaccccaca   4920
aggccctagc gtttgcaatg caccaggtca tcattgaccc aggcgtgttc caccaggccg   4980
ctgcctcgca actcttcgca ggcttcgccg acctgctcgc gccacttctt cacgcgggtg   5040
gaatccgatc cgcacatgag gcggaaggtt tccagcttga gcgggtacgg ctcccggtgc   5100
gagctgaaat agtcgaacat ccgtcgggcc gtcggcgaca gcttgcggta cttctcccat   5160
atgaatttcg tgtagtggtc gccagcaaac agcacgacga tttcctcgtc gatcaggacc   5220
tggcaacggg acgttttctt gccacggtcc aggacgcgga agcggtgcag cagcgacacc   5280
gattccaggt gcccaacgcg gtcggacgtg aagcccatcg ccgtcgcctg taggcgcgac   5340
```

aggcattcct cggccttcgt gtaataccgg ccattgatcg accagcccag gtcctggcaa 5400
agctcgtaga acgtgaaggt gatcggctcg ccgatagggg tgcgcttcgc gtactccaac 5460
acctgctgcc acaccagttc gtcatcgtcg gcccgcagct cgacgccggt gtaggtgatc 5520
ttcacgtcct tgttgacgtg gaaaatgacc ttgttttgca gcgcctcgcg cgggattttc 5580
ttgttgcgcg tggtgaacag ggcagagcgg gccgtgtcgt ttggcatcgc tcgcatcgtg 5640
tccggccacg gcgcaatatc gaacaaggaa agctgcattt ccttgatctg ctgcttcgtg 5700
tgtttcagca acgcggcctg cttggcctcg ctgacctgtt ttgccaggtc ctcgccggcg 5760
gtttttcgct tcttggtcgt catagttcct cgcgtgtcga tggtcatcga cttcgccaaa 5820
cctgccgcct cctgttcgag acgacgcgaa cgctccacgg cggccgatgg cgcgggcagg 5880
gcagggggag ccagttgcac gctgtcgcgc tcgatcttgg ccgtagcttg ctggaccatc 5940
gagccgacgg actggaaggt ttcgcggggc gcacgcatga cggtgcggct tgcgatggtt 6000
tcggcatcct cggcggaaaa ccccgcgtcg atcagttctt gcctgtatgc cttccggtca 6060
aacgtccgat tcattcaccc tccttgcggg attgccccga ctcacgccgg ggcaatgtgc 6120
ccttattcct gatttgaccc gcctggtgcc ttggtgtcca gataatccac cttatcggca 6180
atgaagtcgg tcccgtagac cgtctggccg tccttctcgt acttggtatt ccgaatcttg 6240
ccctgcacga ataccagcga ccccttgccc aaatacttgc cgtgggcctc ggcctgagag 6300
ccaaaacact tgatgcggaa gaagtcggtg cgctcctgct tgtcgccggc atcgttgcgc 6360
cactcttcat taaccgctat atcgaaaatt gcttgcggct tgttagaatt gccatgacgt 6420
acctcggtgt cacgggtaag attaccgata aactggaact gattatggct catatcgaaa 6480
gtctccttga gaaaggagac tctagtttag ctaaacattg gttccgctgt caagaacttt 6540
agcggctaaa attttgcggg ccgcgaccaa aggtgcgagg ggcggcttcc gctgtgtaca 6600
accagatatt tttcaccaac atccttcgtc tgctcgatga gcggggcatg acgaaacatg 6660
agctgtcgga gagggcaggg gtttcaattt cgtttttatc agacttaacc aacggtaagg 6720
ccaacccctc gttgaaggtg atggaggcca ttgccgacgc cctggaaact cccctacctc 6780
ttctcctgga gtccaccgac cttgaccgcg aggcactcgc ggagattgcg ggtcatcctt 6840
tcaagagcag cgtgccgccc ggatacgaac gcatcagtgt ggttttgccg tcacataagg 6900
cgtttatcgt aaagaaatgg ggcgacgaca cccgaaaaaa gctgcgtgga aggctctgac 6960
gccaagggtt agggcttgca cttccttctt tagccgctaa aacggcccct tctctgcggg 7020
ccgtcggctc gcgcatcata tcgacatcct caacggaagc cgtgccgcga atggcatcgg 7080
gcgggtgcgc tttgacagtt gttttctatc agaaccccta cgtcgtgcgg ttcgattagc 7140
tgtttgtctt gcaggctaaa cactttcggt atatcgtttg cctgtgcgat aatgttgcta 7200
atgatttgtt gcgtaggggt tactgaaaag tgagcgggaa agaagagttt cagaccatca 7260
aggagcgggc caagcgcaag ctggaacgcg acatgggtgc ggacctgttg gccgcgctca 7320
acgacccgaa aaccgttgaa gtcatgctca acgcggacgg caaggtgtgg cacgaacgcc 7380
ttggcgagcc gatgcggtac atctgcgaca tgcggcccag ccagtcgcag gcgattatag 7440
aaacggtggc cggattccac ggcaaagagg tcacgcggca ttcgcccatc ctggaaggcg 7500
agttcccctt ggatggcagc cgctttgccg gccaattgcc gccggtcgtg gccgcgccaa 7560
cctttgcgat ccgcaagcgc gcggtcgcca tcttcacgct ggaacagtac gtcgaggcgg 7620
gcatcatgac ccgcgagcaa tacgaggtca ttaaaagcgc cgtcgcggcg catcgaaaca 7680

```
tcctcgtcat tggcggtact ggctcgggca agaccacgct cgtcaacgcg atcatcaatg   7740
aaatggtcgc cttcaacccg tctgagcgcg tcgtcatcat cgaggacacc ggcgaaatcc   7800
agtgcgccgc agagaacgcc gtccaatacc acaccagcat cgacgtctcg atgacgctgc   7860
tgctcaagac aacgctgcgt atgcgccccg accgcatcct ggtcggtgag gtacgtggcc   7920
ccgaagccct tgatctgttg atggcctgga acaccgggca tgaaggaggt gccgccaccc   7980
tgcacgcaaa caaccccaaa gcgggcctga gccggctcgc catgcttatc agcatgcacc   8040
cggattcacc gaaacccatt gagccgctga ttggcgaggc ggttcatgtg gtcgtccata   8100
tcgccaggac ccctagcggc cgtcgagtgc aagaaattct cgaagttctt ggttacgaga   8160
acggccagta catcaccaaa accctgtaag gagtatttcc aatgacaacg gctgttccgt   8220
tccgtctgac catgaatcgc ggcattttgt tctaccttgc cgtgttcttc gttctcgctc   8280
tcgcgttatc cgcgcatccg gcgatggcct cggaaggcac cggcggcagc ttgccatatg   8340
agagctggct gacgaacctg cgcaactccg taaccggccc ggtggccttc gcgctgtcca   8400
tcatcggcat cgtcgtcgcc ggcggcgtgc tgatcttcgg cggcgaactc aacgccttct   8460
tccgaaccct gatcttcctg gttctggtga tggcgctgct ggtcggcgcg cagaacgtga   8520
tgagcacctt cttcggtcgt ggtgccgaaa tcgcggccct cggcaacggg gcgctgcacc   8580
aggtgcaagt cgcggcggcg gatgccgtgc gtgcggtagc ggctggacgg ctcgcctaat   8640
catggctctg cgcacgatcc ccatccgtcg cgcaggcaac cgagaaaacc tgttcatggg   8700
tggtgatcgt gaactggtga tgttctcggg cctgatggcg tttgcgctga ttttcagcgc   8760
ccaagagctg cgggccaccg tggtcggtct gatcctgtgg ttcggggcgc tctatgcgtt   8820
ccgaatcatg gcgaaggccg atccgaagat gcggttcgtg tacctgcgtc accgccggta   8880
caagccgtat tacccggccc gctcgacccc gttccgcgag aacaccaata gccaagggaa   8940
gcaataccga tgatccaagc aattgcgatt gcaatcgcgg gcctcggcgc gcttctgttg   9000
ttcatcctct ttgcccgcat ccgcgcggtc gatgccgaac tgaaactgaa aaagcatcgt   9060
tccaaggacg ccggcctggc cgatctgctc aactacgccg ctgtcgtcga tgacggcgta   9120
atcgtgggca agaacggcag ctttatggct gcctggctgt acaagggcga tgacaacgca   9180
agcagcaccg accagcagcg cgaagtagtg tccgcccgca tcaaccaggc cctcgcgggc   9240
ctgggaagtg ggtggatgat ccatgtggac gccgtgcggc gtcctgctcc gaactacgcg   9300
gagcggggcc tgtcggcgtt ccctgaccgt ctgacggcag cgattgaaga agagcgctcg   9360
gtcttgcctt gctcgtcggt gatgtacttc accagctccg cgaagtcgct cttcttgatg   9420
gagcgcatgg ggacgtgctt ggcaatcacg cgcacccccc ggccgtttta gcggctaaaa   9480
aagtcatggc tctgccctcg ggcggaccac gcccatcatg accttgccaa gctcgtcctg   9540
cttctcttcg atcttcgcca gcagggcgag gatcgtggca tcaccgaacc gcgccgtgcg   9600
cgggtcgtcg gtgagccaga gtttcagcag gccgcccagg cggcccaggt cgccattgat   9660
gcgggccagc tcgcggacgt gctcatagtc cacgacgccc gtgattttgt agccctggcc   9720
gacggccagc aggtaggccg acaggctcat gccggccgcc gccgcctttt cctcaatcgc   9780
tcttcgttcg tctggaaggc agtacacctt gataggtggg ctgcccttcc tggttggctt   9840
ggtttcatca gccatccgct tgccctcatc tgttacgccg gcggtagccg gccagcctcg   9900
cagagcagga ttcccgttga gcaccgccag gtgcgaataa gggacagtga agaaggaaca   9960
cccgctcgcg ggtgggccta cttcacctat cctgcccggc tgacgccgtt ggatacacca  10020
aggaaagtct acacgaaccc tttggcaaaa tcctgtatat cgtgcgaaaa aggatggata  10080
```

```
taccgaaaaa atcgctataa tgaccccgaa gcagggttat gcagcggaaa agcgctgctt  10140
ccctgctgtt ttgtggaata tctaccgact ggaaacaggc aaatgcagga aattactgaa  10200
ctgaggggac aggcgagaga cgatgccaaa gagctacacc gacgagctgg ccgagtgggt  10260
tgaatcccgc gcggccaaga agcgccggcg tgatgaggct gcggttgcgt tcctggcggt  10320
gagggcggat gtcgaggcgg cgttagcgtc cggctatgcg ctcgtcacca tttgggagca  10380
catgcgggaa acggggaagg tcaagttctc ctacgagacg ttccgctcgc acgccaggcg  10440
gcacatcaag gccaagcccg ccgatgtgcc cgcaccgcag gccaaggctg cggaacccgc  10500
gccggcaccc aagacgccgg agccacggcg gccgaagcag gggggcaagg ctgaaaagcc  10560
ggcccccgct gcggccccga ccggcttcac cttcaaccca acaccggaca aaaaggatct  10620
actgtaatgg cgaaaattca catggttttg cagggcaagg gcggggtcgg caagtcggcc  10680
atcgccgcga tcattgcgca gtacaagatg gacaaggggc agacaccctt gtgcatcgac  10740
accgacccgg tgaacgcgac gttcgagggc tacaaggccc tgaacgtccg ccggctgaac  10800
atcatggccg gcgacgaaat taactcgcgc aacttcgaca ccctggtcga gctgattgcg  10860
ccgaccaagg atgacgtggt gatcgacaac ggtgccagct cgttcgtgcc tctgtcgcat  10920
tacctcatca gcaaccaggt gccggctctg ctgcaagaaa tggggcatga gctggtcatc  10980
cataccgtcg tcaccggcgg ccaggctctc ctggacacgg tgagcggctt cgcccagctc  11040
gccagccagt tcccggccga agcgcttttc gtggtctggc tgaacccgta ttgggggcct  11100
atcgagcatg agggcaagag ctttgagcag atgaaggcgt acacggccaa caaggcccgc  11160
gtgtcgtcca tcatccagat tccggccctc aaggaagaaa cctacggccg cgatttcagc  11220
gacatgctgc aagagcggct gacgttcgac caggcgctgg ccgatgaatc gctcacgatc  11280
atgacgcggc aacgcctcaa gatcgtgcgg cgcggcctgt ttgaacagct cgacgcggcg  11340
gccgtgctat gagcgaccag attgaagagc tgatccggga gattgcggcc aagcacggca  11400
tcgccgtcgg ccgcgacgac ccggtgctga tcctgcatac catcaacgcc cggctcatgg  11460
ccgacagtgc ggccaagcaa gaggaaatcc ttgccgcgtt caaggaagag ctggaaggga  11520
tcgcccatcg ttggggcgag gacgccaagg ccaaagcgga gcggatgctg aacgcggccc  11580
tggcggccag caaggacgca atggcgaagg taatgaagga cagcgccgcg caggcggccg  11640
aagcgatccg cagggaaatc gacgacggcc ttggccgcca gctcgcggcc aaggtcgcgg  11700
acgcgcggcg cgtggcgatg atgaacatga tcgccggcgg catggtgttg ttcgcggccg  11760
ccctggtggt gtgggcctcg ttatgaatcg cagaggcgca gatgaaaaag cccggcgttg  11820
ccgggctttg tttttgcgtt agctgggctt gtttgacagg cccaagctct gactgcgccc  11880
gcgctcgcgc tcctgggcct gtttcttctc ctgctcctgc ttgcgcatca gggcctggtg  11940
ccgtcgggct gcttcacgca tcgaatccca gtcgccggcc agctcgggat gctccgcgcg  12000
catcttgcgc gtcgccagtt cctcgatctt gggcgcgtga atgcccatgc cttccttgat  12060
ttcgcgcacc atgtccagcc gcgtgtgcag ggtctgcaag cgggcttgct gttgggcctg  12120
ctgctgctgc caggcggcct ttgtacgcgg cagggacagc aagccggggg cattggactg  12180
tagctgctgc aaacgcgcct gctgacggtc tacgagctgt tctaggcggt cctcgatgcg  12240
ctccacctgg tcatgctttg cctgcacgta gagcgcaagg gtctgctggt aggtctgctc  12300
gatgggcgcg gattctaaga gggcctgctg ttccgtctcg gcctcctggg ccgcctgtag  12360
caaatcctcg ccgctgttgc cgctggactg ctttactgcc ggggactgct gttgccctgc  12420
```

```
tcgcgccgtc gtcgcagttc ggcttgcccc cactcgattg actgcttcat ttcgagccgc  12480
agcgatgcga tctcggattg cgtcaacgga cggggcagcg cggaggtgtc cggcttctcc  12540
ttgggtgagt cggtcgatgc catagccaaa ggtttccttc caaaatgcgt ccattgctgg  12600
accgtgtttc tcattgatgc ccgcaagcat cttcggcttg accgccaggt caagcgcgcc  12660
ttcatgggcg gtcatgacgg acgccgccat gaccttgccg ccgttgttct cgatgtagcc  12720
gcgtaatgag gcaatggtgc cgcccatcgt cagcgtgtca tcgacaacga tgtacttctg  12780
gccggggatc acctccccct cgaaagtcgg gttgaacgcc aggcgatgat ctgaaccggc  12840
tccggttcgg gcgaccttct cccgctgcac aatgtccgtt tcgacctcaa ggccaaggcg  12900
gtcggccaga acgaccgcca tcatggccgg aatcttgttg ttccccgccg cctcgacggc  12960
gaggactgga acgatgcggg gcttgtcgtc gccgatcagc gtcttgagct gggcaacagt  13020
gtcgtccgaa atcaggcgct cgaccaaatt aagcgccgct tccgcgtcgc cctgcttcgc  13080
agcctggtat tcaggctcgt tggtcaaaga accaaggtcg ccgttgcgaa ccaccttcgg  13140
gaagtctccc cacggtgcgc gctcggctct gctgtagctg ctcaagacgc ctcccttttt  13200
agccgctaaa actctaacga gtgcgcccgc gactcaactt gacgctttcg gcacttacct  13260
gtgccttgcc acttgcgtca taggtgatgc ttttcgcact cccgatttca ggtactttat  13320
cgaaatctga ccgggcgtgc attacaaagt tcttccccac ctgttggtaa atgctgccgc  13380
tatctgcgtg gacgatgctg ccgtcgtggc gctgcgactt atcggccttt tgggccatat  13440
agatgttgta aatgccaggt ttcagggccc cggctttatc taccttctgg ttcgtccatg  13500
cgccttggtt ctcggtctgg acaattcttt gcccattcat gaccaggagg cggtgtttca  13560
ttgggtgact cctgacggtt gcctctggtg ttaaacgtgt cctggtcgct tgccggctaa  13620
aaaaaagccg acctcggcag ttcgaggccg gctttcccta gagccgggcg cgtcaaggtt  13680
gttccatcta ttttagtgaa ctgcgttcga tttatcagtt actttcctcc cgctttgtgt  13740
ttcctcccac tcgtttccgc gtctagccga cccctcaaca tagcggcctc ttcttgggct  13800
gcctttgcct cttgccgcgc ttcgtcacgc tcggcttgca ccgtcgtaaa gcgctcggcc  13860
tgcctggccg cctcttgcgc cgccaacttc ctttgctcct ggtgggcctc ggcgtcggcc  13920
tgcgccttcg ctttcaccgc tgccaactcc gtgcgcaaac tctccgcttc gcgcctggtg  13980
gcgtcgcgct cgccgcgaag cgcctgcatt tcctggttgg ccgcgtccag ggtcttgcgg  14040
ctctcttctt tgaatgcgcg ggcgtcctgg tgagcgtagt ccagctcggc gcgcagctcc  14100
tgcgctcgac gctccacctc gtcggcccgc tgcgtcgcca gcgcggcccg ctgctcggct  14160
cctgccaggg cggtgcgtgc ttcggccagg gcttgccgct ggcgtgcggc cagctcggcc  14220
gcctcggcgg cctgctgctc tagcaatgta acgcgcgcct gggcttcttc cagctcgcgg  14280
gcctgcgcct cgaaggcgtc ggccagctcc ccgcgcacgg cttccaactc gttgcgctca  14340
cgatcccagc cggcttgcgc tgcctgcaac gattcattgg caagggcctg ggcggcttgc  14400
cagagggcgg ccacggcctg gttgccggcc tgctgcaccg cgtccggcac ctggactgcc  14460
agcggggcgg cctgcgccgt gcgctggcgt cgccattcgc gcatgccggc gctggcgtcg  14520
ttcatgttga cgcgggcggc cttacgcact gcatccacgg tcgggaagtt ctcccggtcg  14580
ccttgctcga acagctcgtc cgcagccgca aaaatgcggt cgcgcgtctc tttgttcagt  14640
tccatgttgg ctccggtaat tggtaagaat aataatactc ttacctacct tatcagcgca  14700
agagtttagc tgaacagttc tcgacttaac ggcaggtttt ttagcggctg aagggcaggc  14760
aaaaaaagcc ccgcacggtc ggcgggggca aagggtcagc gggaagggga ttagcgggcg  14820
```

tcgggcttct tcatgcgtcg gggccgcgct tcttgggatg gagcacgacg aagcgcgcac 14880
gcgcatcgtc ctcggcccta tcggcccgcg tcgcggtcag gaacttgtcg cgcgctaggt 14940
cctccctggt gggcaccagg ggcatgaact cggcctgctc gatgtaggtc cactccatga 15000
ccgcatcgca gtcgaggccg cgttccttca ccgtctcttg caggtcgcgg tacgcccgct 15060
cgttgagcgg ctggtaacgg gccaattggt cgtaaatggc tgtcggccat gagcggcctt 15120
tcctgttgag ccagcagccg acgacgaagc cggcaatgca ggcccctggc acaaccaggc 15180
cgacgccggg ggcaggggat ggcagcagct cgccaaccag gaaccccgcc gcgatgatgc 15240
cgatgccggt caaccagccc ttgaaactat ccggccccga aacacccctg cgcattgcct 15300
ggatgctgcg ccggatagct tgcaacatca ggagccgttt cttttgttcg tcagtcatgg 15360
tccgccctca ccagttgttc gtatcggtgt cggacgaact gaaatcgcaa gagctgccgg 15420
tatcggtcca gccgctgtcc gtgtcgctgc tgccgaagca cggcgagggg tccgcgaacg 15480
ccgcagacgg cgtatccggc cgcagcgcat cgcccagcat ggccccggtc agcgagccgc 15540
cggccaggta gcccagcatg gtgctgttgg tcgccccggc caccagggcc gacgtgacga 15600
aatcgccgtc attccctctg gattgttcgc tgctcggcgg ggcagtgcgc cgcgccggcg 15660
gcgtcgtgga tggctcgggt tggctggcct gcgacggccg gcgaaaggtg cgcagcagct 15720
cgttatcgac cggctgcggc gtcggggccg ccgccttgcg ctgcggtcgg tgttccttct 15780
tcggctcgcg cagcttgaac agcatgatcg cggaaaccag cagcaacgcc gcgcctacgc 15840
ctcccgcgat gtagaacagc atcggattca ttcttcggtc ctccttgtag cggaaccgtt 15900
gtctgtgcgg cgcgggtggc ccgcgccgct gtctttgggg atcagccctc gatgagcgcg 15960
accagtttca cgtcggcaag gttcgcctcg aactcctggc cgtcgtcctc gtacttcaac 16020
caggcatagc cttccgccgg cggccgacgg ttgaggataa ggcgggcagg gcgctcgtcg 16080
tgctcgacct ggacgatggc ctttttcagc ttgtccgggt ccggctcctt cgcgcccttt 16140
tccttggcgt ccttaccgtc ctggtcgccg tcctcgccgt cctggccgtc gccggcctcc 16200
gcgtcacgct cggcatcagt ctggccgttg aaggcatcga cggtgttggg atcgcggccc 16260
ttctcgtcca ggaactcgcg cagcagcttg accgtgccgc gcgtgatttc ctgggtgtcg 16320
tcgtcaagcc acgcctcgac ttcctccggg cgcttcttga aggccgtcac cagctcgttc 16380
accacggtca cgtcgcgcac gcggccggtg ttgaacgcat cggcgatctt ctccggcagg 16440
tccagcagcg tgacgtgctg ggtgatgaac gccggcgact tgccgatttc cttggcgata 16500
tcgcctttct tcttgccctt cgccagctcg cggccaatga agtcggcaat ttcgcgcggg 16560
gtcagctcgt tgcgttgcag gttctcgata acctggtcgg cttcgttgta gtcgttgtcg 16620
atgaacgccg ggatggactt cttgccggcc cacttcgagc cacggtagcg gcgggcgccg 16680
tgattgatga tatagcggcc cggctgctcc tggttctcgc gcaccgaaat gggtgacttc 16740
accccgcgct ctttgatcgt ggcaccgatt tccgcgatgc tctccgggga aaagccgggg 16800
ttgtcggccg tccgcggctg atgcggatct tcgtcgatca ggtccaggtc cagctcgata 16860
gggccggaac cgccctgaga cgccgcagga gcgtccagga ggctcgacag gtcgccgatg 16920
ctatccaacc ccaggccgga cggctgcgcc gcgcctgcgg cttcctgagc ggccgcagcg 16980
gtgtttttct tggtggtctt ggcttgagcc gcagtcattg ggaaatctcc atcttcgtga 17040
acacgtaatc agccagggcg cgaacctctt tcgatgcctt gcgcgcggcc gttttcttga 17100
tcttccagac cggcacaccg gatgcgaggg catcggcgat gctgctgcgc aggccaacgg 17160
tggccggaat catcatcttg gggtacgcgg ccagcagctc ggcttggtgg cgcgcgtggc 17220
gcggattccg cgcatcgacc ttgctgggca ccatgccaag gaattgcagc ttggcgttct 17280
tctggcgcac gttcgcaatg gtcgtgacca tcttcttgat gccctggatg ctgtacgcct 17340
caagctcgat gggggacagc acatagtcgg ccgcgaagag ggcggccgcc aggccgacgc 17400
caagggtcgg ggccgtgtcg atcaggcaca cgtcgaagcc ttggttcgcc agggccttga 17460
tgttcgcccc gaacagctcg cgggcgtcgt ccagcgacag ccgttcggcg ttcgccagta 17520
ccgggttgga ctcgatgagg gcgaggcgcg cggcctggcc gtcgccggct gcgggtgcgg 17580
tttcggtcca gccgccggca gggacagcgc cgaacagctt gcttgcatgc aggccggtag 17640
caaagtcctt gagcgtgtag gacgcattgc cctgggggtc caggtcgatc acggcaaccc 17700
gcaagccgcg ctcgaaaaag tcgaaggcaa gatgcacaag ggtcgaagtc ttgccgacgc 17760
cgcctttctg gttggccgtg accaaagttt tcatcgtttg gtttcctgtt ttttcttggc 17820
gtccgcttcc cacttccgga cgatgtacgc ctgatgttcc ggcagaaccg ccgttacccg 17880
cgcgtacccc tcgggcaagt tcttgtcctc gaacgcggcc cacacgcgat gcaccgcttg 17940
cgacactgcg cccctggtca gtcccagcga cgttgcgaac gtcgcctgtg gcttcccatc 18000
gactaagacg ccccgcgcta tctcgatggt ctgctgcccc acttccagcc cctggatcgc 18060
ctcctggaac tggctttcgg taagccgttt cttcatggat aacacccata atttgctccg 18120
cgccttggtt gaacatagcg gtgacagccg ccagcacatg agagaagttt agctaaacat 18180
ttctcgcacg tcaacacctt tagccgctaa aactcgtcct tggcgtaaca aaacaaaagc 18240
ccggaaaccg ggctttcgtc tcttgccgct tatggctctg cacccggctc catcaccaac 18300
aggtcgcgca cgcgcttcac tcggttgcgg atcgacactg ccagcccaac aaagccggtt 18360
gccgccgccg ccaggatcgc gccgatgatg ccggccacac cggccatcgc ccaccaggtc 18420
gccgccttcc ggttccattc ctgctggtac tgcttcgcaa tgctggacct cggctcacca 18480
taggctgacc gctcgatggc gtatgccgct tctccccttg gcgtaaaacc cagcgccgca 18540
ggcggcattg ccatgctgcc cgccgctttc ccgaccacga cgcgcgcacc aggcttgcgg 18600
tccagacctt cggccacggc gagctgcgca aggacataat cagccgccga cttggctcca 18660
cgcgcctcga tcagctcttg cactcgcgcg aaatccttgg cctccacggc cgccatgaat 18720
cgcgcacgcg gcgaaggctc cgcagggccg gcgtcgtgat cgccgccgag aatgcccttc 18780
accaagttcg acgacacgaa aatcatgctg acggctatca ccatcatgca gacggatcgc 18840
acgaacccgc tgaattgaac acgagcacgg cacccgcgac cactatgcca agaatgccca 18900
aggtaaaaat tgccggcccc gccatgaagt ccgtgaatgc cccgacggcc gaagtgaagg 18960
gcaggccgcc acccaggccg ccgccctcac tgcccggcac ctggtcgctg aatgtcgatg 19020
ccagcacctg cggcacgtca atgcttccgg gcgtcgcgct cgggctgatc gcccatcccg 19080
ttactgcccc gatcccggca atggcaagga ctgccagcgc tgccattttt ggggtgaggc 19140
cgttcgcggc cgaggggcgc agcccctggg gggatgggag gcccgcgtta gcgggccggg 19200
agggttcgag aagggggggc accccccttc ggcgtgcgcg gtcacgcgca cagggcgcag 19260
ccctggttaa aaacaaggtt tataaatatt ggtttaaaag caggttaaaa gacaggttag 19320
cggtggccga aaaacgggcg gaaacccttg caaatgctgg attttctgcc tgtggacagc 19380
ccctcaaatg tcaataggtg cgcccctcat ctgtcagcac tctgcccctc aagtgtcaag 19440
gatcgcgccc ctcatctgtc agtagtcgcg cccctcaagt gtcaataccg cagggcactt 19500
atccccaggc ttgtccacat catctgtggg aaactcgcgt aaaatcaggc gttttcgccg 19560

```
atttgcgagg ctggccagct ccacgtcgcc ggccgaaatc gagcctgccc ctcatctgtc  19620
aacgccgcgc cgggtgagtc ggcccctcaa gtgtcaacgt ccgcccctca tctgtcagtg  19680
agggccaagt tttccgcgag gtatccacaa cgccggcggc cgcggtgtct cgcacacggc  19740
ttcgacggcg tttctggcgc gtttgcaggg ccatagacgg ccgccagccc agcggcgagg  19800
gcaaccagcc cggtgagcgt cggaaaggcg ctggaagccc cgtagcgacg cggagagggg  19860
cgagacaagc caagggcgca ggctcgatgc gcagcacgac atagccggtt ctcgcaagga  19920
cgagaatttc cctgcggtgc ccctcaagtg tcaatgaaag tttccaacgc gagccattcg  19980
cgagagcctt gagtccacgc tagatgagag ctttgttgta ggtggaccag ttggtgattt  20040
tgaacttttg ctttgccacg gaacggtctg cgttgtcggg aagatgcgtg atctgatcct  20100
tcaactcagc aaaagttcga tttattcaac aaagccacgt tgtgtctcaa aatctctgat  20160
gttacattgc acaagataaa aatatatcat catgaacaat aaaactgtct gcttacataa  20220
acagtaatac aaggggtgtt atgagccata ttcaacggga aacgtcttgc tcgactctag  20280
agctcgttcc tcgaggcctc gaggcctcga ggaacggtac ctgcggggaa gcttacaata  20340
atgtgtgttg ttaagtcttg ttgcctgtca tcgtctgact gactttcgtc ataaatcccg  20400
gcctccgtaa cccagctttg ggcaagctca cggatttgat ccggcggaac gggaatatcg  20460
agatgccggg ctgaacgctg cagttccagc tttccctttc gggacaggta ctccagctga  20520
ttgattatct gctgaagggt cttggttcca cctcctggca caatgcgaat gattacttga  20580
gcgcgatcgg gcatccaatt ttctcccgtc aggtgcgtgg tcaagtgcta caaggcacct  20640
ttcagtaacg agcgaccgtc gatccgtcgc cgggatacgg acaaaatgga gcgcagtagt  20700
ccatcgaggg cggcgaaagc ctcgccaaaa gcaatacgtt catctcgcac agcctccaga  20760
tccgatcgag ggtcttcggc gtaggcagat agaagcatgg atacattgct tgagagtatt  20820
ccgatggact gaagtatggc ttccatcttt tctcgtgtgt ctgcatctat ttcgagaaag  20880
cccccgatgc ggcgcaccgc aacgcgaatt gccatactat ccgaaagtcc cagcaggcgc  20940
gcttgatagg aaaaggtttc atactcggcc gatcgcagac gggcactcac gaccttgaac  21000
ccttcaactt tcagggatcg atgctggttg atggtagtct cactcgacgt ggctctggtg  21060
tgttttgaca tagcttcctc caaagaaagc ggaaggtctg gatactccag cacgaaatgt  21120
gcccgggtag acggatggaa gtctagccct gctcaatatg aaatcaacag tacatttaca  21180
gtcaatactg aatatacttg ctacatttgc aattgtctta taacgaatgt gaaataaaaa  21240
tagtgtaaca acgcttttac tcatcgataa tcacaaaaac atttatacga acaaaaatac  21300
aaatgcactc cggtttcaca ggataggcgg gatcagaata tgcaactttt gacgttttgt  21360
tctttcaaag gggtgctgg caaaaccacc gcactcatgg gcctttgcgc tgctttggca  21420
aatgacggta aacgagtggc cctctttgat gccgacgaaa accggcctct gacgcgatgg  21480
agagaaaacg ccttacaaag cagtactggg atcctcgctg tgaagtctat tccgccgacg  21540
aaatgcccct tcttgaagca gcctatgaaa atgccgagct cgaaggattt gattatgcgt  21600
tggccgatac gcgtggcggc tcgagcgagc tcaacaacac aatcatcgct agctcaaacc  21660
tgcttctgat ccccaccatg ctaacgccgc tcgacatcga tgaggcacta tctacctacc  21720
gctacgtcat cgagctgctg ttgagtgaaa atttggcaat tcctacagct gttttgcgcc  21780
aacgcgtccc ggtcggccga ttgacaacat cgcaacgcag gatgtcagag acgctagaga  21840
gccttccagt tgtaccgtct cccatgcatg aaagagatgc atttgccgcg atgaaagaac  21900
```

-continued gcggcatgtt gcatcttaca ttactaaaca cgggaactga tccgacgatg cgcctcatag 21960
agaggaatct tcggattgcg atggaggaag tcgtggtcat ttcgaaactg atcagcaaaa 22020
tcttggaggc ttgaagatgg caattcgcaa gcccgcattg tcggtcggcg aagcacggcg 22080
gcttgctggt gctcgacccg agatccacca tcccaacccg acacttgttc cccagaagct 22140
ggacctccag cacttgcctg aaaaagccga cgagaaagac cagcaacgtg agcctctcgt 22200
cgccgatcac atttacagtc ccgatcgaca acttaagcta actgtggatg cccttagtcc 22260
acctccgtcc ccgaaaaagc tccaggtttt tctttcagcg cgaccgcccg cgcctcaagt 22320
gtcgaaaaca tatgacaacc tcgttcggca atacagtccc tcgaagtcgc tacaaatgat 22380
tttaaggcgc gcgttggacg atttcgaaag catgctggca gatggatcat ttcgcgtggc 22440
cccgaaaagt tatccgatcc cttcaactac agaaaaatcc gttctcgttc agacctcacg 22500
catgttcccg gttgcgttgc tcgaggtcgc tcgaagtcat tttgatccgt tggggttgga 22560
gaccgctcga gctttcggcc acaagctggc taccgccgcg ctcgcgtcat tctttgctgg 22620
agagaagcca tcgagcaatt ggtgaagagg gacctatcgg aacccctcac caaatattga 22680
gtgtaggttt gaggccgctg gccgcgtcct cagtcacctt ttgagccaga taattaagag 22740
ccaaatgcaa ttggctcagg ctgccatcgt ccccccgtgc gaaacctgca cgtccgcgtc 22800
aaagaaataa ccggcacctc ttgctgtttt tatcagttga gggcttgacg gatccgcctc 22860
aagtttgcgg cgcagccgca aaatgagaac atctatactc ctgtcgtaaa cctcctcgtc 22920
gcgtactcga ctggcaatga gaagttgctc gcgcgataga acgtcgcggg gtttctctaa 22980
aaacgcgagg agaagattga actcacctgc cgtaagtttc acctcaccgc cagcttcgga 23040
catcaagcga cgttgcctga gattaagtgt ccagtcagta aaacaaaaag accgtcggtc 23100
tttggagcgg acaacgttgg ggcgcacgcg caaggcaacc cgaatgcgtg caagaaactc 23160
tctcgtacta aacggcttag cgataaaatc acttgctcct agctcgagtg caacaacttt 23220
atccgtctcc tcaaggcggt cgccactgat aattatgatt ggaatatcag actttgccgc 23280
cagatttcga acgatctcaa gcccatcttc acgacctaaa tttagatcaa caaccacgac 23340
atcgaccgtc gcggaagaga gtactctagt gaactgggtg ctgtcggcta ccgcggtcac 23400
tttgaaggcg tggatcgtaa ggtattcgat aataagatgc cgcatagcga catcgtcatc 23460
gataagaaga acgtgtttca acggctcacc tttcaatcta aaatctgaac ccttgttcac 23520
agcgcttgag aaattttcac gtgaaggatg tacaatcatc tccagctaaa tgggcagttc 23580
gtcagaattg cggctgaccg cggatgacga aaatgcgaac caagtatttc aattttatga 23640
caaaagttct caatcgttgt tacaagtgaa acgcttcgag gttacagcta ctattgatta 23700
aggagatcgc ctatggtctc gccccggcgt cgtgcgtccg ccgcgagcca gatctcgcct 23760
acttcataaa cgtcctcata ggcacggaat ggaatgatga catcgatcgc cgtagagagc 23820
atgtcaatca gtgtgcgatc ttccaagcta gcaccttggg cgctactttt gacaagggaa 23880
aacagtttct tgaatccttg gattggattc gcgccgtgta ttgttgaaat cgatcccgga 23940
tgtcccgaga cgacttcact cagataagcc catgctgcat cgtcgcgcat ctcgccaagc 24000
aatatccggt ccggccgcat acgcagactt gcttggagca agtgctcggc gctcacagca 24060
cccagcccag caccgttctt ggagtagagt agtctaacat gattatcgtg tggaatgacg 24120
agttcgagcg tatcttctat ggtgattagc ctttcctggg gggggatggc gctgatcaag 24180
gtcttgctca ttgttgtctt gccgcttccg gtagggccac atagcaacat cgtcagtcgg 24240
ctgacgacgc atgcgtgcag aaacgcttcc aaatccccgt tgtcaaaatg ctgaaggata 24300

```
gcttcatcat cctgattttg gcgtttcctt cgtgtctgcc actggttcca cctcgaagca  24360
tcataacggg aggagacttc tttaagacca gaaacacgcg agcttggccg tcgaatggtc  24420
aagctgacgg tgcccgaggg aacggtcggc ggcagacaga tttgtagtcg ttcaccacca  24480
ggaagttcag tggcgcagag ggggttacgt ggtccgacat cctgctttct cagcgcgccc  24540
gctaaaatag cgatatcttc aagatcatca taagagacgg gcaaaggcat cttggtaaaa  24600
atgccggctt ggcgcacaaa tgcctctcca ggtcgattga tcgcaatttc ttcagtcttc  24660
gggtcatcga gccattccaa aatcggcttc agaagaaagc gtagttgcgg atccacttcc  24720
atttacaatg tatcctatct ctaagcggaa atttgaattc attaagagcg gcggttcctc  24780
ccccgcgtgg cgccgccagt caggcggagc tggtaaacac caaagaaatc gaggtcccgt  24840
gctacgaaaa tggaaacggt gtcaccctga ttcttcttca gggttggcgg tatgttgatg  24900
gttgccttaa gggctgtctc agttgtctgc tcaccgttat tttgaaagct gttgaagctc  24960
atcccgccac ccgagctgcc ggcgtaggtg ctagctgcct ggaaggcgcc ttgaacaaca  25020
ctcaagagca tagctccgct aaaacgctgc cagaagtggc tgtcgaccga gcccggcaat  25080
cctgagcgac cgagttcgtc cgcgcttggc gatgttaacg agatcatcgc atggtcaggt  25140
gtctcggcgc gatcccacaa cacaaaaacg cgcccatctc cctgttgcaa gccacgctgt  25200
atttcgccaa caacggtggt gccacgatca agaagcacga tattgttcgt tgttccacga  25260
atatcctgag gcaagacaca ctttacatag cctgccaaat ttgtgtcgat tgcggtttgc  25320
aagatgcacg gaattattgt cccttgcgtt accataaaat cggggtgcgg caagagcgtg  25380
gcgctgctgg gctgcagctc ggtgggtttc atacgtatcg acaaatcgtt ctcgccggac  25440
acttcgccat tcggcaagga gttgtcgtca cgcttgcctt cttgtcttcg gcccgtgtcg  25500
ccctgaatgg cgcgtttgct gaccccttga tcgccgctgc tatatgcaaa aatcggtgtt  25560
tcttccggcc gtggctcatg ccgctccggt tcgcccctcg gcggtagagg agcagcaggc  25620
tgaacagcct cttgaaccgc tggaggatcc ggcggcacct caatcggagc tggatgaaat  25680
ggcttggtgt ttgttgcgat caaagttgac ggcgatgcgt tctcattcac cttcttttgg  25740
cgcccaccta gccaaatgag gcttaatgat aacgcgagaa cgacacctcc gacgatcaat  25800
ttctgagacc ccgaaagacg ccggcgatgt ttgtcggaga ccagggatcc agatgcatca  25860
acctcatgtg ccgcttgctg actatcgtta ttcatccctt cgccccccttc aggacgcgtt  25920
tcacatcggg cctcaccgtg cccgtttgcg gcctttggcc aacgggatcg taagcggtgt  25980
tccagataca tagtactgtg tggccatccc tcagacgcca acctcgggaa accgaagaaa  26040
tctcgacatc gctcccttta actgaatagt tggcaacagc ttccttgcca tcaggattga  26100
tggtgtagat ggagggtatg cgtacattgc ccggaaagtg gaataccgtc gtaaatccat  26160
tgtcgaagac ttcgagtggc aacagcgaac gatcgccttg ggcgacgtag tgccaattac  26220
tgtccgccgc accaagggct gtgacaggct gatccaataa attctcagct ttccgttgat  26280
attgtgcttc cgcgtgtagt ctgtccacaa cagccttctg ttgtgcctcc cttcgccgag  26340
ccgccgcatc gtcggcgggg taggcgaatt ggacgctgta atagagatcg ggctgctctt  26400
tatcgaggtg ggacagagtc ttggaactta tactgaaaac ataacggcgc atcccggagt  26460
cgcttgcggt tagcacgatt actggctgag gcgtgaggac ctggcttgcc ttgaaaaata  26520
gataatttcc ccgcggtagg gctgctagat ctttgctatt tgaaacggca accgctgtca  26580
ccgtttcgtt cgtggcgaat gttacgacca aagtagctcc aaccgccgtc gagaggcgca  26640
```

```
ccacttgatc gggattgtaa gccaaataac gcatgcgcgg atctagcttg cccgccattg  26700
gagtgtcttc agcctccgca ccagtcgcag cggcaaataa acatgctaaa atgaaaagtg  26760
cttttctgat catggttcgc tgtggcctac gtttgaaacg gtatcttccg atgtctgata  26820
ggaggtgaca accagacctg ccgggttggt tagtctcaat ctgccgggca agctggtcac  26880
cttttcgtag cgaactgtcg cggtccacgt actcaccaca ggcattttgc cgtcaacgac  26940
gagggtcctt ttatagcgaa tttgctgcgt gcttggagtt acatcatttg aagcgatgtg  27000
ctcgacctcc accctgccgc gtttgccaag aatgacttga ggcgaactgg gattgggata  27060
gttgaagaat tgctggtaat cctggcgcac tgttggggca ctgaagttcg ataccaggtc  27120
gtaggcgtac tgagcggtgt cggcatcata actctcgcgc aggcgaacgt actcccacaa  27180
tgaggcgtta acgacggcct cctcttgagt tgcaggcaat cgcgagacag acacctcgct  27240
gtcaacggtg ccgtccggcc gtatccatag atatacgggc acaagcctgc tcaacggcac  27300
cattgtggct atagcgaacg cttgagcaac atttcccaaa atcgcgatag ctgcgacagc  27360
tgcaatgagt ttggagagac gtcgcgccga tttcgctcgc gcggtttgaa aggcttctac  27420
ttccttatag tgctcggcaa ggctttcgcg cgccactagc atggcatatt caggccccgt  27480
catagcgtcc acccgaattg ccgagctgaa gatctgacgg agtaggctgc catcgcccca  27540
cattcagcgg gaagatcggg cctttgcagc tcgctaatgt gtcgtttgtc tggcagccgc  27600
tcaaagcgac aactaggcac agcaggcaat acttcataga attctccatt gaggcgaatt  27660
tttgcgcgac ctagcctcgc tcaacctgag cgaagcgacg gtacaagctg ctggcagatt  27720
gggttgcgcc gctccagtaa ctgcctccaa tgttgccggc gatcgccggc aaagcgacaa  27780
tgagcgcatc ccctgtcaga aaaaacatat cgagttcgta aagaccaatg atcttggccg  27840
cggtcgtacc ggcgaaggtg attacaccaa gcataagggt gagcgcagtc gcttcggtta  27900
ggatgacgat cgttgccacg aggtttaaga ggagaagcaa gagaccgtag gtgataagtt  27960
gcccgatcca cttagctgcg atgtcccgcg tgcgatcaaa aatatatccg acgaggatca  28020
gaggcccgat cgcgagaagc actttcgtga gaattccaac ggcgtcgtaa actccgaagg  28080
cagaccagag cgtgccgtaa aggacccact gtgccccttg gaaagcaagg atgtcctggt  28140
cgttcatcgg accgatttcg gatgcgattt tctgaaaaac ggcctgggtc acggcgaaca  28200
ttgtatccaa ctgtgccgga acagtctgca gaggcaagcc ggttacacta aactgctgaa  28260
caaagtttgg gaccgtcttt tcgaagatgg aaaccacata gtcttggtag ttagcctgcc  28320
caacaattag agcaacaacg atggtgaccg tgatcacccg agtgataccg ctacgggtat  28380
cgacttcgcc gcgtatgact aaaataccct gaacaataat ccaaagagtg acacaggcga  28440
tcaatggcgc actcaccgcc tcctggatag tctcaagcat cgagtccaag cctgtcgtga  28500
aggctacatc gaagatcgta tgaatggccg taaacggcgc cggaatcgtg aaattcatcg  28560
attggacctg aacttgactg gtttgtcgca taatgttgga taaaatgagc tcgcattcgg  28620
cgaggatgcg ggcggatgaa caaatcgccc agccttaggg gagggcacca aagatgacag  28680
cggtcttttg atgctccttg cgttgagcgg ccgcctcttc cgcctcgtga aggccggcct  28740
gcgcggtagt catcgttaat aggcttgtcg cctgtacatt ttgaatcatt gcgtcatgga  28800
tctgcttgag aagcaaacca ttggtcacgg ttgcctgcat gatattgcga gatcgggaaa  28860
gctgagcaga cgtatcagca ttcgccgtca agcgtttgtc catcgtttcc agattgtcag  28920
ccgcaatgcc agcgctgttt gcggaaccgg tgatctgcga tcgcaacagg tccgcttcag  28980
catcactacc cacgactgca cgatctgtat cgctggtgat cgcacgtgcc gtggtcgaca  29040
```

ttggcattcg cggcgaaaac atttcattgt ctaggtcctt cgtcgaagga tactgatttt 29100
tctggttgag cgaagtcagt agtccagtaa cgcccgtaggc cgacgtcaac atcgtaacca 29160
tcgctatagt ctgagtgaga ttctccgcag tcgcgagcgc agtcgcgagc gtctcagcct 29220
ccgttgccgg gtcgctaaca acaaactgcg cccgcgcggg ctgaatatat agaaagctgc 29280
aggtcaaaac tgttgcaata agttgcgtcg tcttcatcgt ttcctacctt atcaatcttc 29340
tgcctcgtgg tgacgggcca tgaattcgct gagccagcca gatgagttgc cttcttgtgc 29400
ctcgcgtagt cgagttgcaa agcgcaccgt gttggcacgc cccgaaagca cggcgacata 29460
ttcacgcata tcccgcagat caaattcgca gatgacgctt ccactttctc gtttaagaag 29520
aaacttacgg ctgccgaccg tcatgtcttc acggatcgcc tgaaattcct tttcggtaca 29580
tttcagtcca tcgacataag ccgatcgatc tgcggttggt gatggataga aaatcttcgt 29640
catacattgc gcaaccaagc tggctcctag cggcgattcc agaacatgct ctggttgctg 29700
cgttgccagt attagcatcc cgttgttttt tcgaacggtc aggaggaatt tgtcgacgac 29760
agtcgaaaat ttagggttta acaaataggc gcgaaactca tcgcagctca tcacaaaacg 29820
gcggccgtcg atcatggctc caatccgatg caggagatat gctgcagcgg gagcgcatac 29880
ttcctcgtat tcgagaagat gcgtcatgtc gaagccggta atcgacggat ctaactttac 29940
ttcgtcaact tcgccgtcaa atgcccagcc aagcgcatgg ccccggcacc agcgttggag 30000
ccgcgctcct gcgccttcgg cgggcccatg caacaaaaat tcacgtaacc ccgcgattga 30060
acgcatttgt ggatcaaacg agagctgacg atggatacca cggaccagac ggcggttctc 30120
ttccggagaa atcccacccc gaccatcact ctcgatgaga gccacgatcc attcgcgcag 30180
aaaatcgtgt gaggctgctg tgttttctag gccacgcaac ggcgccaacc cgctgggtgt 30240
gcctctgtga agtgccaaat atgttcctcc tgtggcgcga accagcaatt cgccaccccg 30300
gtccttgtca aagaacacga ccgtacctgc acggtcgacc atgctctgtt cgagcatggc 30360
tagaacaaac atcatgagcg tcgtcttacc cctcccgata ggcccgaata ttgccgtcat 30420
gccaacatcg tgctcatgcg ggatatagtc gaaaggcgtt ccgccattgg tacgaaatcg 30480
ggcaatcgcg ttgccccagt ggcctgagct ggcgccctct ggaaagtttt cgaaagagac 30540
aaaccctgcg aaattgcgtg aagtgattgc gccagggcgt gtgcgccact taaaattccc 30600
cggcaattgg gaccaatagg ccgcttccat accaatacct tcttggacaa ccacggcacc 30660
tgcatccgcc attcgtgtcc gagcccgcgc gcccctgtcc ccaagactat tgagatcgtc 30720
tgcatagacg caaaggctca aatgatgtga gcccataacg aattcgttgc tcgcaagtgc 30780
gtcctcagcc tcggataatt tgccgatttg agtcacggct ttatcgccgg aactcagcat 30840
ctggctcgat ttgaggctaa gtttcgcgtg cgcttgcggg cgagtcagga acgaaaaact 30900
ctgcgtgaga acaagtggaa aatcgaggga tagcagcgcg ttgagcatgc ccggccgtgt 30960
ttttgcaggg tattcgcgaa acgaatagat ggatccaacg taactgtctt ttggcgttct 31020
gatctcgagt cctcgcttgc cgcaaatgac tctgtcggta taaatcgaag cgccgagtga 31080
gccgctgacg accggaaccg gtgtgaaccg accagtcatg atcaaccgta gcgcttcgcc 31140
aatttcggtg aagagcacac cctgcttctc gcggatgcca agacgatgca ggccatacgc 31200
tttaagagag ccagcgacaa catgccaaag atcttccatg ttcctgatct ggcccgtgag 31260
atcgttttcc ctttttccgc ttagcttggt gaacctcctc tttaccttcc ctaaagccgc 31320
ctgtgggtag acaatcaacg taaggaagtg ttcattgcgg aggagttggc cggagagcac 31380
gcgctgttca aaagcttcgt tcaggctagc ggcgaaaaca ctacggaagt gtcgcggcgc 31440
cgatgatggc acgtcggcat gacgtacgag gtgagcatat attgacacat gatcatcagc 31500
gatattgcgc aacagcgtgt tgaacgcacg acaacgcgca ttgcgcattt cagtttcctc 31560
aagctcgaat gcaacgccat caattctcgc aatggtcatg atcgatccgt cttcaagaag 31620
gacgatatgg tcgctgaggt ggccaatata agggagatag atctcaccgg atctttcggt 31680
cgttccactc gcgccgagca tcacaccatt cctctccctc gtgggggaac cctaattgga 31740
tttgggctaa cagtagcgcc cccccaaact gcactatcaa tgcttcttcc cgcggtccgc 31800
aaaaatagca ggacgacgct cgccgcattg tagtctcgct ccacgatgag ccgggctgca 31860
aaccataacg gcacgagaac gacttcgtag agcgggttct gaacgataac gatgacaaag 31920
ccggcgaaca tcatgaataa ccctgccaat gtcagtggca ccccaagaaa caatgcgggc 31980
cgtgtggctg cgaggtaaag ggtcgattct tccaaacgat cagccatcaa ctaccgccag 32040
tgagcgtttg gccgaggaag ctcgccccaa acatgataac aatgccgccg acgacgccgg 32100
caaccagccc aagcgaagcc cgcccgaaca tccaggagat cccgatagcg acaatgccga 32160
gaacagcgag tgactggccg aacggaccaa ggataaacgt gcatatattg ttaaccattg 32220
tggcggggtc agtgccgcca cccgcagatt gcgctgcggc gggtccggat gaggaaatgc 32280
tccatgcaat tgcaccgcac aagcttgggg cgcagctcga tatcacgcgc atcatcgcat 32340
tcgagagcga gaggcgattt agatgtaaac ggtatctctc aaagcatcgc atcaatgcgc 32400
acctccttag tataagtcga ataagacttg attgtcgtct gcggatttgc cgttgtcctg 32460
gtgtggcggt ggcggagcga ttaaaccgcc agcgccatcc tcctgcgagc ggcgctgata 32520
tgacccccaa acatcccacg tctcttcgga ttttagcgcc tcgtgatcgt cttttggagg 32580
ctcgattaac gcgggcacca gcgattgagc agctgtttca acttttcgca cgtagccgtt 32640
tgcaaaaccg ccgatgaaat taccggtgtt gtaagcggag atcgcccgac gaagcgcaaa 32700
ttgcttctcg tcaatcgttt cgccgcctgc ataacgactt ttcagcatgt ttgcagcggc 32760
agataatgat gtgcacgcct ggagcgcacc gtcaggtgtc agaccgagca tagaaaaatt 32820
tcgagagttt atttgcatga ggccaacatc cagcgaatgc cgtgcatcga gacggtgcct 32880
gacgacttgg gttgcttggc tgtgatcttg ccagtgaagc gtttcgccgg tcgtgttgtc 32940
atgaatcgct aaaggatcaa agcgactctc caccttagct atcgccgcaa gcgtagatgt 33000
cgcaactgat ggggcacact tgcgagcaac atggtcaaac tcagcagatg agagtggcgt 33060
ggcaaggctc gacgaacaga aggagaccat caaggcaaga gaaagcgacc ccgatctctt 33120
aagcatacct tatctcctta gctcgcaact aacaccgcct ctcccgttgg aagaagtgcg 33180
ttgttttatg ttgaagatta tcgggagggt cggttactcg aaaattttca attgcttctt 33240
tatgatttca attgaagcga gaaacctcgc ccggcgtctt ggaacgcaac atggaccgag 33300
aaccgcgcat ccatgactaa gcaaccggat cgacctattc aggccgcagt tggtcaggtc 33360
aggctcagaa cgaaaatgct cggcgaggtt acgctgtctg taaacccatt cgatgaacgg 33420
gaagcttcct tccgattgct cttggcagga atattggccc atgcctgctt gcgctttgca 33480
aatgctctta tcgcgttggt atcatatgcc ttgtccgcca gcagaaacgc actctaagcg 33540
attatttgta aaaatgtttc ggtcatgcgg cggtcatggg cttgacccgc tgtcagcgca 33600
agacggatcg gtcaaccgtc ggcatcgaca acagcgtgaa tcttggtggt caaaccgcca 33660
cgggaacgtc ccatacagcc atcgtcttga tcccgctgtt tcccgtcgcc gcatgttggt 33720
ggacgcggac acaggaactg tcaatcatga cgacattcta tcgaaagcct tggaaatcac 33780
actcagaata tgatcccaga cgtctgcctc acgccatcgt acaaagcgat tgtagcaggt 33840
tgtacaggaa ccgtatcgat caggaacgtc tgcccagggc gggcccgtcc ggaagcgcca 33900
caagatgaca ttgatcaccc gcgtcaacgc gcggcacgcg acgcggctta tttgggaaca 33960
aaggactgaa caacagtcca ttcgaaatcg gtgacatcaa agcggggacg ggttatcagt 34020
ggcctccaag tcaagcctca atgaatcaaa atcagaccga tttgcaaacc tgatttatga 34080
gtgtgcggcc taaatgatga aatcgtcctt ctagatcgcc tccgtggtgt agcaacacct 34140
cgcagtatcg ccgtgctgac cttggccagg gaattgactg gcaagggtgc tttcacatga 34200
ccgctctttt ggccgcgata gatgatttcg ttgctgcttt gggcacgtag aaggagagaa 34260
gtcatatcgg agaaattcct cctggcgcga gagcctgctc tatcgcgacg gcatccccact 34320
gtcgggaaca gaccggatca ttcacgaggc gaaagtcgtc aacacatgcg ttataggcat 34380
cttcccttga aggatgatct tgttgctgcc aatctggagg tgcggcagcc gcaggcagat 34440
gcgatctcag cgcaacttgc ggcaaaacat ctcactcacc tgaaaaccac tagcgagtct 34500
cgcgatcaga cgaaggcctt ttacttaacg acacaatatc cgatgtctgc atcacaggcg 34560
tcgctatccc agtcaatact aaagcggtgc aggaactaaa gattactgat gacttaggcg 34620
tgccacgagg cctgagacga cgcgcgtaga cagtttttg aaatcattat caaagtgatg 34680
gcctccgctg aagcctatca cctctgcgcc ggtctgtcgg agagatgggc aagcattatt 34740
acggtcttcg cgcccgtaca tgcattggac gattgcaggg tcaatggatc tgagatcatc 34800
cagaggattg ccgcccttac cttccgtttc gagttggagc cagcccctaa atgagacgac 34860
atagtcgact tgatgtgaca atgccaagag agagatttgc ttaacccgat ttttttgctc 34920
aagcgtaagc ctattgaagc ttgccggcat gacgtccgcg ccgaaagaat atcctacaag 34980
taaaacattc tgcacaccga aatgcttggt gtagacatcg attatgtgac caagatcctt 35040
agcagtttcg cttggggacc gctccgacca gaaataccga agtgaactga cgccaatgac 35100
aggaatccct tccgtctgca gataggtacc atcgatagat ctgctgcctc gcgcgtttcg 35160
gtgatgacgg tgaaaacctc tgacacatgc agctcccgga gacggtcaca gcttgtctgt 35220
aagcggatgc cgggagcaga caagcccgtc agggcgcgtc agcgggtgtt ggcgggtgtc 35280
ggggcgcagc catgacccag tcacgtagcg atagcggagt gtatactggc ttaactatgc 35340
ggcatcagag cagattgtac tgagagtgca ccatatgcgg tgtgaaatac cgcacagatg 35400
cgtaaggaga aaataccgca tcaggcgctc ttccgcttcc tcgctcactg actcgctgcg 35460
ctcggtcgtt cggctgcggc gagcggtatc agctcactca aaggcggtaa tacggttatc 35520
cacagaatca ggggataacg caggaaagaa catgtgagca aaaggccagc aaaaggccag 35580
gaaccgtaaa aaggccgcgt tgctggcgtt tttccatagg ctccgccccc ctgacgagca 35640
tcacaaaaat cgacgctcaa gtcagaggtg gcgaaacccg acaggactat aaagatacca 35700
ggcgtttccc cctggaagct ccctcgtgcg ctctcctgtt ccgaccctgc cgcttaccgg 35760
atacctgtcc gcctttctcc cttcgggaag cgtggcgctt tctcatagct cacgctgtag 35820
gtatctcagt tcggtgtagg tcgttcgctc caagctgggc tgtgtgcacg aaccccccgt 35880
tcagcccgac cgctgcgcct tatccggtaa ctatcgtctt gagtccaacc cggtaagaca 35940
cgacttatcg ccactggcag cagccactgg taacaggatt agcagagcga ggtatgtagg 36000
cggtgctaca gagttcttga agtggtggcc taactacggc tacactagaa ggacagtatt 36060
tggtatctgc gctctgctga agccagttac cttcggaaaa agagttggta gctcttgatc 36120
cggcaaacaa accaccgctg gtagcggtgg tttttttgtt tgcaagcagc agattacgcg 36180
cagaaaaaaa ggatctcaag aagatccttt gatcttttct acggggtctg acgctcagtg 36240
gaacgaaaac tcacgttaag ggattttggt catgagatta tcaaaaagga tcttcaccta 36300
gatcctttta aattaaaaat gaagttttaa atcaatctaa agtatatatg agtaaacttg 36360
gtctgacagt taccaatgct taatcagtga ggcacctatc tcagcgatct gtctatttcg 36420
ttcatccata gttgcctgac tccccgtcgt gtagataact acgatacggg agggcttacc 36480
atctggcccc agtgctgcaa tgataccgcg agacccacgc tcaccggctc cagatttatc 36540
agcaataaac cagccagccg gaagggccga gcgcagaagt ggtcctgcaa ctttatccgc 36600
ctccatccag tctattaatt gttgccggga agctagagta agtagttcgc cagttaatag 36660
tttgcgcaac gttgttgcca ttgctgcagg gggggggggg gggggggttcc attgttcatt 36720
ccacggacaa aaacagagaa aggaaacgac agaggccaaa aagctcgctt tcagcacctg 36780
tcgtttcctt tcttttcaga gggtatttta aataaaaaca ttaagttatg acgaagaaga 36840
acggaaacgc cttaaaccgg aaaattttca taaatagcga aaacccgcga ggtcgccgcc 36900
ccgtaacctg tcggatcacc ggaaaggacc cgtaaagtga taatgattat catctacata 36960
tcacaacgtg cgtggaggcc atcaaaccac gtcaaataat caattatgac gcaggtatcg 37020
tattaattga tctgcatcaa cttaacgtaa aaacaacttc agacaataca aatcagcgac 37080
actgaatacg gggcaacctc atgtcccccc cccccccccc cctgcaggca tcgtggtgtc 37140
acgctcgtcg tttggtatgg cttcattcag ctccggttcc caacgatcaa ggcgagttac 37200
atgatccccc atgttgtgca aaaaagcggt tagctccttc ggtcctccga tcgttgtcag 37260
aagtaagttg gccgcagtgt tatcactcat ggttatggca gcactgcata attctcttac 37320
tgtcatgcca tccgtaagat gcttttctgt gactggtgag tactcaacca agtcattctg 37380
agaatagtgt atgcggcgac cgagttgctc ttgcccggcg tcaacacggg ataataccgc 37440
gccacatagc agaactttaa aagtgctcat cattggaaaa cgttcttcgg ggcgaaaact 37500
ctcaaggatc ttaccgctgt tgagatccag ttcgatgtaa cccactcgtg cacccaactg 37560
atcttcagca tcttttactt tcaccagcgt ttctgggtga gcaaaaacag gaaggcaaaa 37620
tgccgcaaaa aagggaataa gggcgacacg gaaatgttga atactcatac tcttcctttt 37680
tcaatattat tgaagcattt atcagggtta ttgtctcatg agcggataca tatttgaatg 37740
tatttagaaa aataaacaaa taggggttcc gcgcacattt ccccgaaaag tgccacctga 37800
cgtctaagaa accattatta tcatgacatt aacctataaa aataggcgta tcacgaggcc 37860
ctttcgtctt caagaattgg tcgacgatct tgctgcgttc ggatattttc gtggagttcc 37920
cgccacagac ccggattgaa ggcgagatcc agcaactcgc gccagatcat cctgtgacgg 37980
aactttggcg cgtgatgact ggccaggacg tcggccgaaa gagcgacaag cagatcacgc 38040
ttttcgacag cgtcggattt gcgatcgagg atttttcggc gctgcgctac gtccgcgacc 38100
gcgttgaggg atcaagccac agcagcccac tcgaccttct agccgaccca gacgagccaa 38160
gggatctttt tggaatgctg ctccgtcgtc aggctttccg acgtttgggt ggttgaacag 38220
aagtcattat cgtacggaat gccaagcact cccgagggga accctgtggt tggcatgcac 38280
atacaaatgg acgaacggat aaaccttttc acgccctttt aaatatccgt tattctaata 38340
aacgctcttt tctcttaggt ttacccgcca atatatcctg tcaaacactg atagtttaaa 38400
ctgaaggcgg gaaacgacaa tctgatcatg agcggagaat taagggagtc acgttatgac 38460
ccccgccgat gacgcgggac aagccgtttt acgtttggaa ctgacagaac cgcaacgttg 38520

```
aaggagccac tcagcccaag ctggtacgat tgtaatacga ctcactatag ggcgaattga  38580
gcgctgttta aacgctcttc aactggaaga gcggttacca gaggccagaa tggccatctc  38640
ggaccgatat cgctatcaac tttgtataga aaagttgggc cgaattcgag ctcggtacgg  38700
ccagaatggc ccggaccggg ttaccgaatt cgagctcggt accctgggat ccgatatcga  38760
tgggccctgg ccgaagcttg catgcctgca gtgcagcgtg acccggtcgt gcccctctct  38820
agagataatg agcattgcat gtctaagtta taaaaaatta ccacatattt tttttgtcac  38880
acttgtttga agtgcagttt atctatcttt atacatatat ttaaacttta ctctacgaat  38940
aatataatct atagtactac aataatatca gtgttttaga gaatcatata aatgaacagt  39000
tagacatggt ctaaaggaca attgagtatt ttgacaacag gactctacag ttttatcttt  39060
ttagtgtgca tgtgttctcc tttttttttg caaatagctt cacctatata atacttcatc  39120
cattttatta gtacatccat ttagggttta gggttaatgg tttttataga ctaatttttt  39180
tagtacatct attttattct attttagcct ctaaattaag aaaactaaaa ctctatttta  39240
gtttttttat ttaataattt agatataaaa tagaataaaa taaagtgact aaaaattaaa  39300
caaataccct ttaagaaatt aaaaaaacta aggaaacatt tttcttgttt cgagtagata  39360
atgccagcct gttaaacgcc gtcgacgagt ctaacggaca ccaaccagcg aaccagcagc  39420
gtcgcgtcgg gccaagcgaa gcagacggca cggcatctct gtcgctgcct ctggacccct  39480
ctcgagagtt ccgctccacc gttggacttg ctccgctgtc ggcatccaga aattgcgtgg  39540
cggagcggca gacgtgagcc ggcacggcag gcggcctcct cctcctctca cggcaccggc  39600
agctacgggg gattcctttc ccaccgctcc ttcgctttcc cttcctcgcc cgccgtaata  39660
aatagacacc ccctccacac cctctttccc caacctcgtg ttgttcggag cgcacacaca  39720
cacaaccaga tctcccccaa atccacccgt cggcacctcc gcttcaaggt acgccgctcg  39780
tcctcccccc cccccctctc taccttctct agatcggcgt tccggtccat gcatggttag  39840
ggcccggtag ttctacttct gttcatgttt gtgttagatc cgtgtttgtg ttagatccgt  39900
gctgctagcg ttcgtacacg gatgcgacct gtacgtcaga cacgttctga ttgctaactt  39960
gccagtgttt ctctttgggg aatcctggga tggctctagc cgttccgcag acgggatcga  40020
tttcatgatt ttttttgttt cgttgcatag ggtttggttt gcccttttcc tttatttcaa  40080
tatatgccgt gcacttgttt gtcgggtcat cttttcatgc ttttttttgt cttggttgtg  40140
atgatgtggt ctggttgggc ggtcgttcta gatcggagta gaattctgtt tcaaactacc  40200
tggtggattt attaattttg gatctgtatg tgtgtgccat acatattcat agttacgaat  40260
tgaagatgat ggatggaaat atcgatctag gataggtata catgttgatg cgggttttac  40320
tgatgcatat acagagatgc tttttgttcg cttggttgtg atgatgtggt gtggttgggc  40380
ggtcgttcat tcgttctaga tcggagtaga atactgtttc aaactacctg gtgtatttat  40440
taattttgga actgtatgtg tgtgtcatac atcttcatag ttacgagttt aagatggatg  40500
gaaatatcga tctaggatag gtatacatgt tgatgtgggt tttactgatg catatacatg  40560
atggcatatg cagcatctat tcatatgctc taaccttgag tacctatcta ttataataaa  40620
caagtatgtt ttataattat tttgatcttg atatacttgg atgatggcat atgcagcagc  40680
tatatgtgga tttttttagc cctgccttca tacgctattt atttgcttgg tactgtttct  40740
tttgtcgatg ctcaccctgt tgtttggtgt tacttctgca ggtcgactct agaggatcca  40800
tggcaccgaa gaagaagcgc aaggtgatgg acaagaagta cagcatcggc ctcgacatcg  40860
```

gcaccaactc ggtgggctgg gccgtcatca cggacgaata taaggtcccg tcgaagaagt 40920
tcaaggtcct cggcaataca gaccgccaca gcatcaagaa aaacttgatc ggcgccctcc 40980
tgttcgatag cggcgagacc gcggaggcga ccaggctcaa gaggaccgcc aggagacggt 41040
acactaggcg caagaacagg atctgctacc tgcaggagat cttcagcaac gagatggcga 41100
aggtggacga ctccttcttc caccgcctgg aggaatcatt cctggtggag gaggacaaga 41160
agcatgagcg gcacccaatc ttcggcaaca tcgtcgacga ggtaagtttc tgcttctacc 41220
tttgatatat atataataat tatcattaat tagtagtaat ataatatttc aaatattttt 41280
ttcaaaataa aagaatgtag tatatagcaa ttgcttttct gtagtttata agtgtgtata 41340
ttttaattta taacttttct aatatatgac caaaacatgg tgatgtgcag gtggcctacc 41400
acgagaagta cccgacaatc taccacctcc ggaagaaact ggtggacagc acagacaagg 41460
cggacctccg gctcatctac cttgccctcg cgcatatgat caagttccgc ggccacttcc 41520
tcatcgaggg cgacctgaac ccggacaact ccgacgtgga caagctgttc atccagctcg 41580
tgcagacgta caatcaactg ttcgaggaga accccataaa cgctagcggc gtggacgcca 41640
aggccatcct ctcggccagg ctctcgaaat caagaaggct ggagaacctt atcgcgcagt 41700
tgccaggcga aaagaagaac ggcctcttcg gcaaccttat tgcgctcagc ctcggcctga 41760
cgccgaactt caaatcaaac ttcgacctcg cggaggacgc caagctccag ctctcaaagg 41820
acacctacga cgacgacctc gacaacctcc tggcccagat aggagaccag tacgcggacc 41880
tcttcctcgc cgccaagaac ctctccgacg ctatcctgct cagcgacatc cttcgggtca 41940
acaccgaaat taccaaggca ccgctgtccg ccagcatgat taaacgctac gacgagcacc 42000
atcaggacct cacgctgctc aaggcactcg tccgccagca gctccccgag aagtacaagg 42060
agatcttctt cgaccaatca aaaaacggct acgcgggata tatcgacggc ggtgccagcc 42120
aggaagagtt ctacaagttc atcaaaccaa tcctggagaa gatggacggc accgaggagt 42180
tgctggtcaa gctcaacagg gaggacctcc tcaggaagca gaggaccttc gacaacggct 42240
ccatcccgca tcagatccac ctgggcgaac tgcatgccat cctgcggcgc caggaggact 42300
tctacccgtt cctgaaggat aaccgggaga agatcgagaa gatcttgacg ttccgcatcc 42360
catactacgt gggcccgctg gctcgcggca actcccggtt cgcctggatg acccggaagt 42420
cggaggagac catcacaccc tggaactttg aggaggtggt cgataagggc gctagcgctc 42480
agagcttcat cgagcgcatg accaacttcg ataaaaacct gcccaatgaa aaagtcctcc 42540
ccaagcactc gctgctctac gagtacttca ccgtgtacaa cgagctcacc aaggtcaaat 42600
acgtcaccga gggcatgcgg aagccggcgt tcctgagcgg cgagcagaag aaggcgatag 42660
tggacctcct cttcaagacc aacaggaagg tgaccgtgaa gcaattaaaa gaggactact 42720
tcaagaaaat agagtgcttc gactccgtgg agatctcggg cgtggaggat cggttcaacg 42780
cctcactcgg cacgtatcac gacctcctca agatcattaa agacaaggac ttcctcgaca 42840
acgaggagaa cgaggacatc ctcgaggaca tcgtcctcac cctgaccctg ttcgaggacc 42900
gcgaaatgat cgaggagagg ctgaagacct acgcgcacct gttcgacgac aaggtcatga 42960
aacagctcaa gaggcgccgc tacactggtt ggggaaggct gtcccgcaag ctcattaatg 43020
gcatcaggga caagcagagc ggcaagacca tcctggactt cctcaagtcc gacgggttcg 43080
ccaaccgcaa cttcatgcag ctcattcacg acgactcgct cacgttcaag gaagacatcc 43140
agaaggcaca ggtgagcggg cagggtgact ccctccacga acacatcgcc aacctggccg 43200
gctcgccggc cattaaaaag ggcatcctgc agacggtcaa ggtcgtcgac gagctcgtga 43260
aggtgatggg ccggcacaag cccgaaaata tcgtcataga gatggccagg gagaaccaga 43320
ccacccaaaa agggcagaag aactcgcgcg agcggatgaa acggatcgag gagggcatta 43380
aagagctcgg gtcccagatc ctgaaggagc accccgtgga aaatacccag ctccagaatg 43440
aaaagctcta cctctactac ctgcagaacg gccgcgacat gtacgtggac caggagctgg 43500
acattaatcg gctatcggac tacgacgtcg accacatcgt gccgcagtcg ttcctcaagg 43560
acgatagcat cgacaacaag gtgctcaccc ggtcggataa aaatcggggc aagagcgaca 43620
acgtgcccag cgaggaggtc gtgaagaaga tgaaaaacta ctggcgccag ctcctcaacg 43680
cgaaactgat cacccagcgc aagttcgaca acctgacgaa ggcggaacgc ggtggcttga 43740
gcgaactcga taaggcgggc ttcataaaaa ggcagctggt cgagacgcgc cagatcacga 43800
agcatgtcgc ccagatcctg gacagccgca tgaatactaa gtacgatgaa aacgacaagc 43860
tgatccggga ggtgaaggtg atcacgctga agtccaagct cgtgtcggac ttccgcaagg 43920
acttccagtt ctacaaggtc cgcgagatca acaactacca ccacgcccac gacgcctacc 43980
tgaatgcggt ggtcgggacc gccctgatca agaagtaccc gaagctggag tcggagttcg 44040
tgtacggcga ctacaaggtc tacgacgtgc gcaaaatgat cgccaagtcc gagcaggaga 44100
tcggcaaggc cacggcaaaa tacttcttct actcgaacat catgaacttc ttcaagaccg 44160
agatcaccct cgcgaacggc gagatccgca agcgcccgct catcgaaacc aacggcgaga 44220
cgggcgagat cgtctgggat aagggccggg atttcgcgac ggtccgcaag gtgctctcca 44280
tgccgcaagt caatatcgtg aaaaagacgg aggtccagac gggcgggttc agcaaggagt 44340
ccatcctccc gaagcgcaac tccgacaagc tcatcgcgag gaagaaggat tgggacccga 44400
aaaaatatgg cggcttcgac agcccgaccg tcgcatacag cgtcctcgtc gtggcgaagg 44460
tggagaaggg caagtcaaag aagctcaagt ccgtgaagga gctgctcggg atcacgatta 44520
tggagcggtc ctccttcgag aagaacccga tcgacttcct agaggccaag ggatataagg 44580
aggtcaagaa ggacctgatt attaaactgc cgaagtactc gctcttcgag ctggaaaacg 44640
gccgcaagag gatgctcgcc tccgcaggcg agttgcagaa gggcaacgag ctcgccctcc 44700
cgagcaaata cgtcaatttc ctgtacctcg ctagccacta tgaaaagctc aagggcagcc 44760
cggaggacaa cgagcagaag cagctcttcg tggagcagca caagcattac ctggacgaga 44820
tcatcgagca gatcagcgag ttctcgaagc gggtgatcct cgccgacgcg aacctggaca 44880
aggtgctgtc ggcatataac aagcaccgcg acaaaccaat acgcgagcag gccgaaaata 44940
tcatccacct cttcaccctc accaacctcg gcgctccggc agccttcaag tacttcgaca 45000
ccacgattga ccggaagcgg tacacgagca cgaaggaggt gctcgatgcg acgctgatcc 45060
accagagcat cacagggctc tatgaaacac gcatcgacct gagccagctg ggcggagaca 45120
agagaccacg ggaccgccac gatggcgagc tgggaggccg caagcgggca aggtaggtac 45180
cgttaaccta gacttgtcca tcttctggat tggccaactt aattaatgta tgaaataaaa 45240
ggatgcacac atagtgacat gctaatcact ataatgtggg catcaaagtt gtgtgttatg 45300
tgtaattact agttatctga ataaaagaga aagagatcat ccatatttct tatcctaaat 45360
gaatgtcacg tgtctttata attctttgat gaaccagatg catttcatta accaaatcca 45420
tatacatata aatattaatc atatataatt aatatcaatt gggttagcaa aacaaatcta 45480
gtctaggtgt gttttgcgaa tgcggccgcc accgcggtgg agctcgaatt cgagctcggt 45540
accctgggat ccagcttcgc ttagttttta gtttttggca gaaaaaatga tcaatgtttc 45600

-continued acaaaccaaa tatttttata acttttgatg aaagaagatc accacggtca tatctagggg 45660
tggtaacaaa ttgcgatcta aatgtttctt cataaaaaat aaggcttctt aataaatttt 45720
agttcaaaat aaatacgaat aaagtctgat tctaatctga ttcgatcctt aaattttata 45780
atgcaaaatt tagagctcat taccacctct agtcatatgt ctagtctgag gtatatccaa 45840
aaagcccttt ctctaaattc cacacccaac tcagatgttt gcaaataaat actccgactc 45900
caaaatgtag gtgaagtgca actttctcca ttttatatca acatttgtta tttttgttt 45960 aacatttcac actcaaaact aattaataaa atacgtggtt gttgaacgtg cgcacatgtc 46020
tcccttacat tatgtttttt tatttatgta ttattgttgt tttcctccga acaacttgtc 46080
aacatatcat cattggtctt taatatttat gaatatggaa gcctagttat ttacacttgg 46140
ctacacacta gttgtagttt tgccacttgt ctaacatgca actctagtag ttttgccact 46200
tgcctggcat gcaactctag tattgacact tgtatagcat ataatgccaa tacgacacct 46260
gccttacatg aaacattatt tttgacactt gtataccatg caacattacc attgacattt 46320
gtccatacac attatatcaa atatattgag cgcatgtcac aaactcgata caaagctgga 46380
tgaccctccc tcaccacatc tataaaaacc cgagcgctac tgtaaatcac tcacaacaca 46440
acacatatct tttagtaacc tttcaatagg cgtcccccaa gaactagtaa ccatggccct 46500
gtccaacaag ttcatcggcg acgacatgaa gatgacctac cacatggacg gctgcgtgaa 46560
cggccactac ttcaccgtga agggcgaggg cagcggcaag ccctacgagg gcacccagac 46620
ctccaccttc aaggtgacca tggccaacgg cggccccctg gccttctcct tcgacatcct 46680
gtccaccgtg ttcatgtacg gcaaccgctg cttcaccgcc taccccacca gcatgcccga 46740
ctacttcaag caggccttcc ccgacggcat gtcctacgag agaaccttca cctacgagga 46800
cggcggcgtg gccaccgcca gctgggagat cagcctgaag ggcaactgct tcgagcacaa 46860
gtccaccttc cacggcgtga acttccccgc cgacggcccc gtgatggcca agaagaccac 46920
cggctgggac ccctccttcg agaagatgac cgtgtgcgac ggcatcttga agggcgacgt 46980
gaccgccttc ctgatgctgc agggcggcgg caactacaga tgccagttcc acacctccta 47040
caagaccaag aagcccgtga ccatgccccc caaccacgtg gtggagcacc gcatcgccag 47100
aaccgacctg gacaagggcg gcaacagcgt gcagctgacc gagcacgccg tggcccacat 47160
cacctccgtg gtgcccttct gaagcggccc atggatattc gaacgcgtag gtaccacatg 47220
gttaacctag acttgtccat cttctggatt ggccaactta attaatgtat gaaataaaag 47280
gatgcacaca tagtgacatg ctaatcacta taatgtgggc atcaaagttg tgtgttatgt 47340
gtaattacta gttatctgaa taaaagagaa agagatcatc catatttctt atcctaaatg 47400
aatgtcacgt gtctttataa ttctttgatg aaccagatgc atttcattaa ccaaatccat 47460
atacatataa atattaatca tatataatta atatcaattg ggttagcaaa acaaatctag 47520
tctaggtgtg ttttgcgaat tcccatggac ctcgaggggg ggcccgggca cccagctttc 47580
ttgtacaaag tggccgttaa cggatcggcc agaatggccc ggaccgggtt accgaattcg 47640
agctcggtac cctgggatcg gccgctctag aactagtgga tcccccgggc tgcaggaatt 47700
cccatggagt caaagattca aatagaggac ctaacagaac tcgccgtaaa gactggcgaa 47760
cagttcatac agagtctctt acgactcaat gacaagaaga aaatcttcgt caacatggtg 47820
gagcacgaca cgcttgtcta ctccaaaaat atcaaagata cagtctcaga agaccaaagg 47880
gcaattgaga cttttcaaca aagggtaata tccggaaacc tcctcggatt ccattgccca 47940
gctatctgtc actttattgt gaagatagtg gaaaaggaag gtggctccta caaatgccat 48000
cattgcgata aaggaaaggc catcgttgaa gatgcctctg ccgacagtgg tcccaaagat 48060
ggacccccac ccacgaggag catcgtggaa aaagaagacg ttccaaccac gtcttcaaag 48120
caagtggatt gatgtgatat ctccactgac gtaagggatg acgcacaatc ccactaagct 48180
tcggccgggg cccatcgatc tggcgaaagg gggatgtgct gcaaggcgat taagttgggt 48240
aacgccaggg ttttcccagt cacgacgttg taaaacgacg gccagtgcca agctcagatc 48300
agcttggggc tggtatcgat aaatgtttcc acatagattt tgcatatcat aatgatgttt 48360
gtcgttccgt atctatgttt catacaaaat ttttacgcat atcgcaacac atgggcacat 48420
acctagtgac tgtataactc tgcatgtatg agtgtatgac tatatgatgt agtaactaat 48480
aagaagggta gacatttgag tgattctttt attcctggac ttgtaagact tgacatttct 48540
gccttgagtg cgatacatca tatggacagg ggttatgcat acactgcttg tttgttgttt 48600
atgttctaag agcatctcca acaacgtgac atatgaaaat gccctacaat ttaaaaatgg 48660
ttatatttta taaaatttag ggcataaata aaacatcccg ctccaacatt aaagccttaa 48720
atctattata gggaagccca ctatgatata gtatatttga ggcactttag agggtgccct 48780
ataatttttt gaccattttt ttatgaaatg agacactatt ggagtatttt ttttccgtag 48840
agcaccatat ttcaatttga gacaccaatt taaggcattg ttggagatgt tctaaatgtt 48900
ggtttatttt gtctgtatcg ttgtggtttt gatagtggtg cctttgcaat gtacatctta 48960
cattgacaat aataataggt aaaactctac aaatttttta tctaatggac tcttgtatga 49020
aacattgtac ttgcacacat ctgatgtaaa cactgcatac ttttaacagt gacaagattc 49080
tgtttcattt tagggctagt ttgggaacca aattttatta gggtttttat tttctaagaa 49140
aaagtaattt attttacctt gagaaaatat aaattacttg agaaaataga gttccaaact 49200
agctcttatc tttgtcgaat cctcctctat tcaaatgtga catttctggc acgtgacaac 49260
tggtgatgtt gtagactgtg ttaagtaata cgtgtcatta ttactaaatg ccattttagt 49320
aaatgttgag tatgtactct actacagtaa gtattattgg tgtatttaca ctagacagtt 49380
ggcggcctgg cgggtaaagt tatcctgtag aaagttgggc caggccaaaa ccaaccgcca 49440
aaggaaaggc cttccggccc gcccaccttt gcgcgccgaa ggtcagttcc ttcagtctcc 49500
tcccgcttca gactctgacc acgtcgacaa tccgggccga aacacatctg caccgtccac 49560
ttgcgacaga ttgaacacac cacttctatc cacgtcagcg atccgtggca ctagcccttc 49620
caccaatcag cccaagttgc ccctttcctt taaattcgcc gcacccattg ctcttctcac 49680
ggccatagaa atcgaccgag cgaatccctc gcatcgcatt cgcagccttt gctgcatcac 49740
accaccgcga aaccccagca gccgcatctg caggtcgact ctagaggatc catggcctcc 49800
tccgaggacg tcatcaagga gttcatgcgc ttcaaggtgc gcatggaggg ctccgtgaac 49860
ggccacgagt tcgagatcga gggcgagggc gagggccgcc cctacgaggg cacccagacc 49920
gccaagctga aggtgaccaa gggcggcccc ctgcccttcg cctgggacat cctgtccccc 49980
cagttccagt acggctccaa ggtgtacgtg aagcaccccg ccgacatccc cgactacaag 50040
aagctgtcct tccccgaggg cttcaagtgg gagcgcgtga tgaacttcga ggacggcggc 50100
gtggtgacag tgacccagga ctcctccctg caggacggct ccttcatcta caaggtgaag 50160
ttcatcggcg tgaacttccc ctccgacggc cccgtaatgc agaagaagac tatgggctgg 50220
gaggcctcca ccgagcgcct gtacccccgc gacggcgtgc tgaagggcga gatccacaag 50280
gccctgaagc tgaaggacgg cggccacgct agcccatcca cccactcact cactcatatc 50340

-continued

```
tgtgctgtac gtacgagaat ttctcgacca accgtcgtga gacctgccca ccggagatcg  50400
gacgcaagag ggtttaggca agaatgtcgt gcgacagggt gagcgctgac tagtatacgt  50460
gagagacctt gagatatacc tcacacgtac gcgtacttta catgacgtag gacattacga  50520
ctcaaacaga ttcacgtcag atttcggagt ttctcacgcg tgagagcctt ggagggcggt  50580
atgtatgtca tactatatgt tggatggag ggagtgagtg agtgatatgt ggctagcaag  50640
ggcggccccc tgcccttcgc ctgggacatc ctgtcccccc agttccagta cggctccaag  50700
gtgtacgtga agcaccccgc cgacatcccc gactacaaga agctgtcctt ccccgagggc  50760
ttcaagtggg agcgcgtgat gaacttcgag gacggcggcg tggtgacagt gacccaggac  50820
tcctccctgc aggacggctc cttcatctac aaggtgaagt tcatcggcgt gaacttcccc  50880
tccgacggcc ccgtaatgca gaagaagact atgggctggg aggcctccac cgagcgcctg  50940
tacccccgcg acggcgtgct gaagggcgag atccacaagg ccctgaagct gaaggacggc  51000
ggccactacc tggtggagtt caagtccatc tacatggcca agaagcccgt gcagctgccc  51060
ggctactact acgtggactc caagctggac atcacctccc acaacgagga ctacaccatc  51120
gtggagcagt acgagcgcgc cgagggccgc caccacctgt tcctgtagtc aggatctgag  51180
tcgaaaccta gacttgtcca tcttctggat tggccaactt aattaatgta tgaaataaaa  51240
ggatgcacac atagtgacat gctaatcact ataatgtggg catcaaagtt gtgtgttatg  51300
tgtaattact agttatctga ataaaagaga aagagatcat ccatatttct tatcctaaat  51360
gaatgtcacg tgtctttata attctttgat gaaccagatg catttcatta accaaatcca  51420
tatacatata aatattaatc atatataatt aatatcaatt gggttagcaa aacaaatcta  51480
gtctaggtgt gttttgcgaa tgcggccgcc accgcggtgg agctcgaatt ccggtccggg  51540
tcacccggtc cgggcctaga aggccagctt gcggccgccc cgggcaactt tattatacaa  51600
agttgataga tatcggtccg agcggcctag aaggcctttg gtcacctttg tccaccaaga  51660
tggaactgcg gccgctcatt aattaagtca ggcgcgcctc tagttgaaga cacgttcatg  51720
tcttcatcgt aagaagacac tcagtagtct tcggccagaa tggcctaact caaggccatc  51780
gtggcctctt gctcttcagg atgaagagct atgtttaaac gtgcaagcgc tactagacaa  51840
ttcagtacat taaaaacgtc cgcaatgtgt tattaagttg tctaagcgtc aatttgttta  51900
caccacaata tatcctgcca ccagccagcc aacagctccc cgaccggcag ctcggcacaa  51960
aatcaccact cgatacaggc agcccatcag tccgggacgg cgtcagcggg agagccgttg  52020
taaggcggca gactttgctc atgttaccga tgctattcgg aagaacggca actaagctgc  52080
cgggtttgaa acacggatga tctcgcggag ggtagcatgt tgattgtaac gatgacagag  52140
cgttgctgcc tgtgatcaaa tatcatctcc ctcgcagaga tccgaattat cagccttctt  52200
attcatttct cgcttaaccg tgacaggctg tcgatcttga gaactatgcc gacataatag  52260
gaaatcgctg gataaagccg ctgaggaagc tgagtggcgc tatttcttta gaagtgaacg  52320
ttgacgatcg tcgaccgtac cccgatgaat taattcggac gtacgttctg aacacagctg  52380
gatacttact tgggcgattg tcatacatga catcaacaat gtacccgttt gtgtaaccgt  52440
ctcttggagg ttcgtatgac actagtggtt cccctcagct tgcgactaga tgttgaggcc  52500
taacatttta ttagagagca ggctagttgc ttagatacat gatcttcagg ccgttatctg  52560
tcagggcaag cgaaaattgg ccatttatga cgaccaatgc cccgcagaag ctcccatctt  52620
tgccgccata gacgccgcgc ccccttttg gggtgtagaa catccttttg ccagatgtgg  52680
aaaagaagtt cgttgtccca ttgttggcaa tgacgtagta gccggcgaaa gtgcgagacc  52740
```

catttgcgct atatataagc ctacgatttc cgttgcgact attgtcgtaa ttggatgaac 52800
tattatcgta gttgctctca gagttgtcgt aatttgatgg actattgtcg taattgctta 52860
tggagttgtc gtagttgctt ggagaaatgt cgtagttgga tggggagtag tcatagggaa 52920
gacgagcttc atccactaaa acaattggca ggtcagcaag tgcctgcccc gatgccatcg 52980
caagtacgag gcttagaacc accttcaaca gatcgcgcat agtcttcccc agctctctaa 53040
cgcttgagtt aagccgcgcc gcgaagcggc gtcggcttga acgaattgtt agacattatt 53100
tgccgactac cttggtgatc tcgcctttca cgtagtgaac aaattcttcc aactgatctg 53160
cgcgcgaggc caagcgatct tcttgtccaa gataagcctg cctagcttca agtatgacgg 53220
gctgatactg ggccggcagg cgctccattg cccagtcggc agcgacatcc ttcggcgcga 53280
ttttgccggt tactgcgctg taccaaatgc gggacaacgt aagcactaca tttcgctcat 53340
cgccagccca gtcgggcggc gagttccata gcgttaaggt ttcatttagc gcctcaaata 53400
gatcctgttc aggaaccgga tcaaagagtt cctccgccgc tggacctacc aaggcaacgc 53460
tatgttctct tgcttttgtc agcaagatag ccagatcaat gtcgatcgtg gctggctcga 53520
agatacctgc aagaatgtca ttgcgctgcc attctccaaa ttgcagttcg cgcttagctg 53580
gataacgcca cggaatgatg tcgtcgtgca caacaatggt gacttctaca gcgcggagaa 53640
tctcgctctc tccaggggaa gccgaagttt ccaaaaggtc gttgatcaaa gctcgccgcg 53700
ttgtttcatc aagccttaca gtcaccgtaa ccagcaaatc aatatcactg tgtggcttca 53760
ggccgccatc cactgcggag ccgtacaaat gtacggccag caacgtcggt tcgagatggc 53820
gctcgatgac gccaactacc tctgatagtt gagtcgatac ttcggcgatc accgcttccc 53880
tcatgatgtt taactcctga attaagccgc gccgcgaagc ggtgtcggct tgaatgaatt 53940
gttaggcgtc atcctgtgct cccgagaacc agtaccagta catcgctgtt tcgttcgaga 54000
cttgaggtct agttttatac gtgaacaggt caatgccgcc gagagtaaag ccacattttg 54060
cgtacaaatt gcaggcaggt acattgttcg tttgtgtctc taatcgtatg ccaaggagct 54120
gtctgcttag tgcccacttt ttcgcaaatt cgatgagact gtgcgcgact cctttgcctc 54180
ggtgcgtgtg cgacacaaca atgtgttcga tagaggctag atcgttccat gttgagttga 54240
gttcaatctt cccgacaagc tcttggtcga tgaatgcgcc atagcaagca gagtcttcat 54300
cagagtcatc atccgagatg taatccttcc ggtaggggct cacacttctg gtagatagtt 54360
caaagccttg gtcggatagg tgcacatcga acacttcacg aacaatgaaa tggttctcag 54420
catccaatgt ttccgccacc tgctcaggga tcaccgaaat cttcatatga cgcctaacgc 54480
ctggcacagc ggatcgcaaa cctggcgcgg cttttggcac aaaaggcgtg acaggtttgc 54540
gaatccgttg ctgccacttg ttaacccttt tgccagattt ggtaactata atttatgtta 54600
gaggcgaagt cttgggtaaa aactggccta aaattgctgg ggatttcagg aaagtaaaca 54660
tcaccttccg gctcgatgtc tattgtagat atatgtagtg tatctacttg atcgggggat 54720
ctgctgcctc gcgcgtttcg gtgatgacgg tgaaaacctc tgacacatgc agctcccgga 54780
gacggtcaca gcttgtctgt aagcggatgc cgggagcaga caagcccgtc agggcgcgtc 54840
agcgggtgtt ggcgggtgtc ggggcgcagc catgacccag tcacgtagcg atagcggagt 54900
gtatactggc ttaactatgc ggcatcagag cagattgtac tgagagtgca ccatatgcgg 54960
tgtgaaatac cgcacagatg cgtaaggaga aaataccgca tcaggcgctc ttccgcttcc 55020
tcgctcactg actcgctgcg ctcggtcgtt cggctgcggc gagcggtatc agctcactca 55080

```
aaggcggtaa tacggttatc cacagaatca ggggataacg caggaaagaa catgtgagca  55140
aaaggccagc aaaaggccag gaaccgtaaa aaggccgcgt tgctggcgtt tttccatagg  55200
ctccgccccc ctgacgagca tcacaaaaat cgacgctcaa gtcagaggtg gcgaaacccg  55260
acaggactat aaagatacca ggcgtttccc cctggaagct ccctcgtgcg ctctcctgtt  55320
ccgaccctgc cgcttaccgg atacctgtcc gcctttctcc cttcgggaag cgtggcgctt  55380
tctcatagct cacgctgtag gtatctcagt tcggtgtagg tcgttcgctc caagctgggc  55440
tgtgtgcacg aaccccccgt tcagcccgac cgctgcgcct tatccggtaa ctatcgtctt  55500
gagtccaacc cggtaagaca cgacttatcg ccactggcag cagccactgg taacaggatt  55560
agcagagcga ggtatgtagg cggtgctaca gagttcttga agtggtggcc taactacggc  55620
tacactagaa ggacagtatt tggtatctgc gctctgctga agccagttac cttcggaaaa  55680
agagttggta gctcttgatc cggcaaacaa accaccgctg gtagcggtgg tttttttgtt  55740
tgcaagcagc agattacgcg cagaaaaaaa ggatctcaag aagatccttt gatcttttct  55800
acggggtctg acgctcagtg gaacgaaaac tcacgttaag ggattttggt catgagatta  55860
tcaaaaagga tcttcaccta gatcctttta aattaaaaat gaagttttaa atcaatctaa  55920
agtatatatg agtaaacttg gtctgacagt taccaatgct taatcagtga ggcacctatc  55980
tcagcgatct gtctatttcg ttcatccata gttgcctgac tccccgtcgt gtagataact  56040
acgatacggg agggcttacc atctggcccc agtgctgcaa tgataccgcg agacccacgc  56100
tcaccggctc cagatttatc agcaataaac cagccagccg gaagggccga gcgcagaagt  56160
ggtcctgcaa ctttatccgc ctccatccag tctattaatt gttgccggga agctagagta  56220
agtagttcgc cagttaatag tttgcgcaac gttgttgcca ttgctgcagg gggggggggg  56280
gggggggact tccattgttc attccacgga caaaaacaga gaaaggaaac gacagaggcc  56340
aaaaagcctc gctttcagca cctgtcgttt cctttctttt cagagggtat tttaaataaa  56400
aacattaagt tatgacgaag aagaacggaa acgccttaaa ccggaaaatt ttcataaata  56460
gcgaaaaccc gcgaggtcgc cgccccgtaa cct                               56493
```

<210> SEQ ID NO 47
<211> LENGTH: 55518
<212> TYPE: DNA
<213> ORGANISM: Artificial sequence
<220> FEATURE:
<223> OTHER INFORMATION: Agrobacterium vector containing maize codon optimized Cas9 and maize MDH promoter

<400> SEQUENCE: 47

```
gtcggatcac cggaaaggac ccgtaaagtg ataatgatta tcatctacat atcacaacgt     60
gcgtggaggc catcaaacca cgtcaaataa tcaattatga cgcaggtatc gtattaattg    120
atctgcatca acttaacgta aaaacaactt cagacaatac aaatcagcga cactgaatac    180
ggggcaacct catgtccccc cccccccccc ccctgcaggc atcgtggtgt cacgctcgtc    240
gtttggtatg gcttcattca gctccggttc ccaacgatca aggcgagtta catgatcccc    300
catgttgtgc aaaaaagcgg ttagctcctt cggtcctccg atcgttgtca gaagtaagtt    360
ggccgcagtg ttatcactca tggttatggc agcactgcat aattctctta ctgtcatgcc    420
atccgtaaga tgcttttctg tgactggtga gtactcaacc aagtcattct gagaatagtg    480
tatgcggcga ccgagttgct cttgcccggc gtcaacacgg gataataccg cgccacatag    540
cagaacttta aaagtgctca tcattggaaa acgttcttcg ggcgaaaac tctcaaggat    600
```

-continued

```
cttaccgctg ttgagatcca gttcgatgta acccactcgt gcacccaact gatcttcagc    660
atcttttact ttcaccagcg tttctgggtg agcaaaaaca ggaaggcaaa atgccgcaaa    720
aaagggaata agggcgacac ggaaatgttg aatactcata ctcttccttt ttcaatatta    780
ttgaagcatt tatcagggtt attgtctcat gagcggatac atatttgaat gtatttagaa    840
aaataaacaa ataggggttc cgcgcacatt tccccgaaaa gtgccacctg acgtctaaga    900
aaccattatt atcatgacat taacctataa aaataggcgt atcacgaggc cctttcgtct    960
tcaagaattg gtcgacgatc ttgctgcgtt cggatatttt cgtggagttc ccgccacaga   1020
cccggattga aggcgagatc cagcaactcg cgccagatca tcctgtgacg gaactttggc   1080
gcgtgatgac tggccaggac gtcggccgaa agagcgacaa gcagatcacg cttttcgaca   1140
gcgtcggatt tgcgatcgag gatttttcgg cgctgcgcta cgtccgcgac cgcgttgagg   1200
gatcaagcca cagcagccca ctcgaccttc tagccgaccc agacgagcca agggatcttt   1260
ttggaatgct gctccgtcgt caggctttcc gacgtttggg tggttgaaca gaagtcatta   1320
tcgtacggaa tgccaagcac tcccgagggg aaccctgtgg ttggcatgca catacaaatg   1380
gacgaacgga taaacctttt cacgcccttt taaatatccg ttattctaat aaacgctctt   1440
ttctcttagg tttacccgcc aatatatcct gtcaaacact gatagtttaa actgaaggcg   1500
ggaaacgaca atctgatcat gagcggagaa ttaagggagt cacgttatga cccccgccga   1560
tgacgcggga caagccgttt tacgtttgga actgacagaa ccgcaacgtt gaaggagcca   1620
ctcagcccaa gctggtacga ttgtaatacg actcactata gggcgaattg agcgctgttt   1680
aaacgctctt caactggaag agcggttacc agaggccaga atggccatct cggaccgata   1740
tcgctatcaa ctttgtatag aaaagttggg ccgaattcga gctcggtacg gccagaatgg   1800
cccggaccgg gttaccgaat tcgagctcgg taccctggga tccgatatcg atgggccctg   1860
gccgaagctt tttggaaggc taaggagagg aagccggcga gaaggagggg gcgttttacg   1920
tgtcactgtc ctgtcgtgtt ggctgttgac acgaatcatt tcttccgcgc gtgggaagaa   1980
gaagatgcac attagcggcc tgaagtagag atgtcaatgg ggaattcccc agcggggatt   2040
aactccccag acccgtaccc atgaacatag accggccccc atccccgaac ccgaacccga   2100
cctcgggtac gaaaatcctc ccatacccat tcccgaccgg gtactaaata cccatgggta   2160
tccatacccg acccgattat tcaaaaatta atgggctttt tatttgttaa ccggcggacg   2220
caatgcttgg gactctaggt ttttttactt tgttgaccgg ctggcggctg ggcttttttcc  2280
tacaggccca aagttggtcg gcagccacta ggccacacgt cacaggcagc ccacaagtaa   2340
atgtcgttgg attgctggat ggtggaataa aaatcctaga tgctagattg ttctggttcc   2400
gggtattttt ctccatggct aatcgggttt gggtttagcc ctcccaaacc cgaacccgcc   2460
atacccgatg ggtaagggat ttattccaaa tctataccca tggggatttg ttttaaccca   2520
taccttaacc ctaatagagg aattccccac gggtaatcgg gtttcggggc ccattgacat   2580
ctctagactg aaggcgtcca actcaaatca ttaaaaagtg ttgacgcacg cgctgatgcg   2640
ccggccgcac agcacaggct gcacagcccg tttaatcagc gatggagccc cggccgtcag   2700
ccagccaggt ccggcgtccg ggtctgcgcc ctgcggcgtc actgctgtcg ccaccgtctc   2760
cgatggtccc acatccatcc agcgggccgc gcgtggtaca aaaggctctt cctcgccgtc   2820
aggtgcagct gcccaaacac cagacacaga ctccaccacc ccgcttcgat cttctgttgc   2880
agctgaaatc tgtcagattc tgcagttcat tcctcatggc accgaagaag aagcgcaagg   2940
tgatggacaa gaagtacagc atcggcctcg acatcggcac caactcggtg ggctgggccg   3000
```

tcatcacgga cgaatataag gtcccgtcga agaagttcaa ggtcctcggc aatacagacc 3060
gccacagcat caagaaaaac ttgatcggcg ccctcctgtt cgatagcggc gagaccgcgg 3120
aggcgaccag gctcaagagg accgccagga gacggtacac taggcgcaag aacaggatct 3180
gctacctgca ggagatcttc agcaacgaga tggcgaaggt ggacgactcc ttcttccacc 3240
gcctggagga atcattcctg gtggaggagg acaagaagca tgagcggcac ccaatcttcg 3300
gcaacatcgt cgacgaggta agtttctgct tctacctttg atatatatat aataattatc 3360
attaattagt agtaatataa tatttcaaat atttttttca aaataaaaga atgtagtata 3420
tagcaattgc ttttctgtag tttataagtg tgtatatttt aatttataac ttttctaata 3480
tatgaccaaa acatggtgat gtgcaggtgg cctaccacga gaagtacccg acaatctacc 3540
acctccggaa gaaactggtg gacagcacag acaaggcgga cctccggctc atctaccttg 3600
ccctcgcgca tatgatcaag ttccgcggcc acttcctcat cgagggcgac ctgaacccgg 3660
acaactccga cgtggacaag ctgttcatcc agctcgtgca gacgtacaat caactgttcg 3720
aggagaaccc cataaacgct agcggcgtgg acgccaaggc catcctctcg gccaggctct 3780
cgaaatcaag aaggctggag aaccttatcg cgcagttgcc aggcgaaaag aagaacggcc 3840
tcttcggcaa ccttattgcg ctcagcctcg gcctgacgcc gaacttcaaa tcaaacttcg 3900
acctcgcgga ggacgccaag ctccagctct caaaggacac ctacgacgac gacctcgaca 3960
acctcctggc ccagatagga gaccagtacg cggacctctt cctcgccgcc aagaacctct 4020
ccgacgctat cctgctcagc gacatccttc gggtcaacac cgaaattacc aaggcaccgc 4080
tgtccgccag catgattaaa cgctacgacg agcaccatca ggacctcacg ctgctcaagg 4140
cactcgtccg ccagcagctc cccgagaagt acaaggagat cttcttcgac caatcaaaaa 4200
acggctacgc gggatatatc gacggcggtg ccagccagga agagttctac aagttcatca 4260
aaccaatcct ggagaagatg gacggcaccg aggagttgct ggtcaagctc aacagggagg 4320
acctcctcag gaagcagagg accttcgaca acggctccat cccgcatcag atccacctgg 4380
gcgaactgca tgccatcctg cggcgccagg aggacttcta cccgttcctg aaggataacc 4440
gggagaagat cgagaagatc ttgacgttcc gcatcccata ctacgtgggc ccgctggctc 4500
gcggcaactc ccggttcgcc tggatgaccc ggaagtcgga ggagaccatc acaccctgga 4560
actttgagga ggtggtcgat aagggcgcta gcgctcagag cttcatcgag cgcatgacca 4620
acttcgataa aaacctgccc aatgaaaaag tcctccccaa gcactcgctg ctctacgagt 4680
acttcaccgt gtacaacgag ctcaccaagg tcaaatacgt caccgagggc atgcggaagc 4740
cggcgttcct gagcggcgag cagaagaagg cgatagtgga cctcctcttc aagaccaaca 4800
ggaaggtgac cgtgaagcaa ttaaaagagg actacttcaa gaaaatagag tgcttcgact 4860
ccgtggagat ctcgggcgtg gaggatcggt tcaacgcctc actcggcacg tatcacgacc 4920
tcctcaagat cattaaagac aaggacttcc tcgacaacga ggagaacgag gacatcctcg 4980
aggacatcgt cctcaccctg accctgttcg aggaccgcga aatgatcgag gagaggctga 5040
agacctacgc gcacctgttc gacgacaagg tcatgaaaca gctcaagagg cgccgctaca 5100
ctggttgggg aaggctgtcc cgcaagctca ttaatggcat cagggacaag cagagcggca 5160
agaccatcct ggacttcctc aagtccgacg ggttcgccaa ccgcaacttc atgcagctca 5220
ttcacgacga ctcgctcacg ttcaaggaag acatccagaa ggcacaggtg agcgggcagg 5280
gtgactccct ccacgaacac atcgccaacc tggccggctc gccggccatt aaaaagggca 5340

```
tcctgcagac ggtcaaggtc gtcgacgagc tcgtgaaggt gatgggccgg cacaagcccg   5400
aaaatatcgt catagagatg gccagggaga accagaccac ccaaaaaggg cagaagaact   5460
cgcgcgagcg gatgaaacgg atcgaggagg gcattaaaga gctcgggtcc cagatcctga   5520
aggagcaccc cgtggaaaat acccagctcc agaatgaaaa gctctacctc tactacctgc   5580
agaacggccg cgacatgtac gtggaccagg agctggacat taatcggcta tcggactacg   5640
acgtcgacca catcgtgccg cagtcgttcc tcaaggacga tagcatcgac aacaaggtgc   5700
tcacccggtc ggataaaaat cggggcaaga gcgacaacgt gcccagcgag gaggtcgtga   5760
agaagatgaa aaactactgg cgccagctcc tcaacgcgaa actgatcacc cagcgcaagt   5820
tcgacaacct gacgaaggcg gaacgcggtg gcttgagcga actcgataag gcgggcttca   5880
taaaaaggca gctggtcgag acgcgccaga tcacgaagca tgtcgcccag atcctggaca   5940
gccgcatgaa tactaagtac gatgaaaacg acaagctgat ccgggaggtg aaggtgatca   6000
cgctgaagtc caagctcgtg tcggacttcc gcaaggactt ccagttctac aaggtccgcg   6060
agatcaacaa ctaccaccac gcccacgacg cctacctgaa tgcggtggtc gggaccgccc   6120
tgatcaagaa gtacccgaag ctggagtcgg agttcgtgta cggcgactac aaggtctacg   6180
acgtgcgcaa aatgatcgcc aagtccgagc aggagatcgg caaggccacg gcaaaatact   6240
tcttctactc gaacatcatg aacttcttca agaccgagat caccctcgcg aacggcgaga   6300
tccgcaagcg cccgctcatc gaaaccaacg gcgagacggg cgagatcgtc tgggataagg   6360
gccgggattt cgcgacggtc cgcaaggtgc tctccatgcc gcaagtcaat atcgtgaaaa   6420
agacggaggt ccagacgggc gggttcagca aggagtccat cctcccgaag cgcaactccg   6480
acaagctcat cgcgaggaag aaggattggg acccgaaaaa atatggcggc ttcgacagcc   6540
cgaccgtcgc atacagcgtc ctcgtcgtgg cgaaggtgga gaagggcaag tcaaagaagc   6600
tcaagtccgt gaaggagctg ctcgggatca cgattatgga gcggtcctcc ttcgagaaga   6660
acccgatcga cttcctagag gccaagggat ataaggaggt caagaaggac ctgattatta   6720
aactgccgaa gtactcgctc ttcgagctgg aaaacggccg caagaggatg ctcgcctccg   6780
caggcgagtt gcagaagggc aacgagctcg ccctcccgag caaatacgtc aatttcctgt   6840
acctcgctag ccactatgaa aagctcaagg gcagcccgga ggacaacgag cagaagcagc   6900
tcttcgtgga gcagcacaag cattacctgg acgagatcat cgagcagatc agcgagttct   6960
cgaagcgggt gatcctcgcc gacgcgaacc tggacaaggt gctgtcggca tataacaagc   7020
accgcgacaa accaatacgc gagcaggccg aaaatatcat ccacctcttc accctcacca   7080
acctcggcgc tccggcagcc ttcaagtact tcgacaccac gattgaccgg aagcggtaca   7140
cgagcacgaa ggaggtgctc gatgcgacgc tgatccacca gagcatcaca gggctctatg   7200
aaacacgcat cgacctgagc cagctgggcg gagacaagag accacgggac cgccacgatg   7260
gcgagctggg aggccgcaag cgggcaaggt aggtaccgtt aacctagact tgtccatctt   7320
ctggattggc caacttaatt aatgtatgaa ataaaaggat gcacacatag tgacatgcta   7380
atcactataa tgtgggcatc aaagttgtgt gttatgtgta attactagtt atctgaataa   7440
aagagaaaga gatcatccat atttcttatc ctaaatgaat gtcacgtgtc tttataattc   7500
tttgatgaac cagatgcatt tcattaacca aatccatata catataaata ttaatcatat   7560
ataattaata tcaattgggt tagcaaaaca aatctagtct aggtgtgttt tgcgaatgcg   7620
gccgccaccg cggtggagct cgaattcgag ctcggtaccc tgggatccag cttcgcttag   7680
tttttagttt ttggcagaaa aaatgatcaa tgtttcacaa accaaatatt tttataactt   7740
```

ttgatgaaag aagatcacca cggtcatatc taggggtggt aacaaattgc gatctaaatg 7800
tttcttcata aaaaataagg cttcttaata aattttagtt caaaataaat acgaataaag 7860
tctgattcta atctgattcg atccttaaat tttataatgc aaaatttaga gctcattacc 7920
acctctagtc atatgtctag tctgaggtat atccaaaaag ccctttctct aaattccaca 7980
cccaactcag atgtttgcaa ataaatactc cgactccaaa atgtaggtga agtgcaactt 8040
tctccatttt atatcaacat ttgttatttt ttgtttaaca tttcacactc aaaactaatt 8100
aataaaatac gtggttgttg aacgtgcgca catgtctccc ttacattatg ttttttttatt 8160 tatgtattat tgttgttttc ctccgaacaa cttgtcaaca tatcatcatt ggtctttaat 8220
atttatgaat atggaagcct agttatttac acttggctac acactagttg tagttttgcc 8280
acttgtctaa catgcaactc tagtagtttt gccacttgcc tggcatgcaa ctctagtatt 8340
gacacttgta tagcatataa tgccaatacg acacctgcct tacatgaaac attatttttg 8400
acacttgtat accatgcaac attaccattg acatttgtcc atacacatta tatcaaatat 8460
attgagcgca tgtcacaaac tcgatacaaa gctggatgac cctccctcac cacatctata 8520
aaaacccgag cgctactgta aatcactcac aacacaacac atatctttta gtaacctttc 8580
aataggcgtc ccccaagaac tagtaaccat ggccctgtcc aacaagttca tcggcgacga 8640
catgaagatg acctaccaca tggacggctg cgtgaacggc cactacttca ccgtgaaggg 8700
cgagggcagc ggcaagccct acgagggcac ccagacctcc accttcaagg tgaccatggc 8760
caacggcggc cccctggcct tctccttcga catcctgtcc accgtgttca tgtacggcaa 8820
ccgctgcttc accgcctacc ccaccagcat gcccgactac ttcaagcagg ccttccccga 8880
cggcatgtcc tacgagagaa ccttcaccta cgaggacggc ggcgtggcca ccgccagctg 8940
ggagatcagc ctgaagggca actgcttcga gcacaagtcc accttccacg gcgtgaactt 9000
ccccgccgac ggccccgtga tggccaagaa gaccaccggc tgggacccct ccttcgagaa 9060
gatgaccgtg tgcgacggca tcttgaaggg cgacgtgacc gccttcctga tgctgcaggg 9120
cggcggcaac tacagatgcc agttccacac ctcctacaag accaagaagc ccgtgaccat 9180
gccccccaac cacgtggtgg agcaccgcat cgccagaacc gacctggaca agggcggcaa 9240
cagcgtgcag ctgaccgagc acgccgtggc ccacatcacc tccgtggtgc ccttctgaag 9300
cggcccatgg atattcgaac gcgtaggtac cacatggtta acctagactt gtccatcttc 9360
tggattggcc aacttaatta atgtatgaaa taaaaggatg cacacatagt gacatgctaa 9420
tcactataat gtgggcatca aagttgtgtg ttatgtgtaa ttactagtta tctgaataaa 9480
agagaaagag atcatccata tttcttatcc taaatgaatg tcacgtgtct ttataattct 9540
ttgatgaacc agatgcattt cattaaccaa atccatatac atataaatat taatcatata 9600
taattaatat caattgggtt agcaaaacaa atctagtcta ggtgtgtttt gcgaattccc 9660
atggacctcg aggggggggcc cggcacccaa gctttcttgt acaaagtggc cgttaacgga 9720
tcggccagaa tggcccggac cgggttaccg aattcgagct cggtaccctg ggatcggccg 9780
ctctagaact agtggatccc ccgggctgca ggaattccca tggagtcaaa gattcaaata 9840
gaggacctaa cagaactcgc cgtaaagact ggcgaacagt tcatacagag tctcttacga 9900
ctcaatgaca agaagaaaat cttcgtcaac atggtggagc acgacacgct tgtctactcc 9960
aaaaatatca aagatacagt ctcagaagac caaagggcaa ttgagacttt tcaacaaagg 10020
gtaatatccg gaaacctcct cggattccat tgcccagcta tctgtcactt tattgtgaag 10080
atagtggaaa aggaaggtgg ctcctacaaa tgccatcatt gcgataaagg aaaggccatc 10140
gttgaagatg cctctgccga cagtggtccc aaagatggac ccccacccac gaggagcatc 10200
gtggaaaaag aagacgttcc aaccacgtct tcaaagcaag tggattgatg tgatatctcc 10260
actgacgtaa gggatgacgc acaatcccac taagcttcgg ccggggccca tcgatctggc 10320
gaaaggggga tgtgctgcaa ggcgattaag ttgggtaacg ccagggtttt cccagtcacg 10380
acgttgtaaa acgacggcca gtgccaagct cagatcagct tggggctggt atcgataaat 10440
gtttccacat agattttgca tatcataatg atgtttgtcg ttccgtatct atgtttcata 10500
caaaattttt acgcatatcg caacacatgg gcacatacct agtgactgta taactctgca 10560
tgtatgagtg tatgactata tgatgtagta actaataaga agggtagaca tttgagtgat 10620
tcttttattc ctggacttgt aagacttgac atttctgcct tgagtgcgat acatcatatg 10680
gacaggggtt atgcatacac tgcttgtttg ttgtttatgt tctaagagca tctccaacaa 10740
cgtgacatat gaaaatgccc tacaatttaa aaatggttat attttataaa atttagggca 10800
taaataaaac atcccgctcc aacattaaag ccttaaatct attataggga agcccactat 10860
gatatagtat atttgaggca ctttagaggg tgccctataa ttttttgacc atttttttat 10920
gaaatgagac actattggag tatttttttt ccgtagagca ccatatttca atttgagaca 10980
ccaatttaag gcattgttgg agatgttcta aatgttggtt tattttgtct gtatcgttgt 11040
ggttttgata gtggtgcctt tgcaatgtac atcttacatt gacaataata ataggtaaaa 11100
ctctacaaat tttttatcta atggactctt gtatgaaaca ttgtacttgc acacatctga 11160
tgtaaacact gcatactttt aacagtgaca agattctgtt tcattttagg gctagtttgg 11220
gaaccaaatt ttattagggt ttttattttc taagaaaaag taatttattt taccttgaga 11280
aaatataaat tacttgagaa aatagagttc caaactagct cttatctttg tcgaatcctc 11340
ctctattcaa atgtgacatt tctggcacgt gacaactggt gatgttgtag actgtgttaa 11400
gtaatacgtg tcattattac taaatgccat tttagtaaat gttgagtatg tactctacta 11460
cagtaagtat tattggtgta tttacactag acagttggcg gcctggcggg taaagttatc 11520
ctgtagaaag ttgggccagg ccaaaaccaa ccgccaaagg aaaggccttc cggcccgccc 11580
acctttgcgc gccgaaggtc agttccttca gtctcctccc gcttcagact ctgaccacgt 11640
cgacaatccg ggccgaaaca catctgcacc gtccacttgc gacagattga acacaccact 11700
tctatccacg tcagcgatcc gtggcactag ccccttccacc aatcagccca agttgcccct 11760
ttcctttaaa ttcgccgcac ccattgctct tctcacggcc atagaaatcg accgagcgaa 11820
tccctcgcat cgcattcgca gcctttgctg catcacacca ccgcgaaacc ccagcagccg 11880
catctgcagg tcgactctag aggatccatg gcctcctccg aggacgtcat caaggagttc 11940
atgcgcttca aggtgcgcat ggagggctcc gtgaacggcc acgagttcga gatcgagggc 12000
gagggcgagg gccgccccta cgagggcacc cagaccgcca agctgaaggt gaccaagggc 12060
ggcccccctgc ccttcgcctg ggacatcctg tccccccagt tccagtacgg ctccaaggtg 12120
tacgtgaagc accccgccga catccccgac tacaagaagc tgtccttccc cgagggcttc 12180
aagtgggagc gcgtgatgaa cttcgaggac ggcggcgtgg tgacagtgac ccaggactcc 12240
tccctgcagg acggctcctt catctacaag gtgaagttca tcggcgtgaa cttcccctcc 12300
gacggccccg taatgcagaa gaagactatg ggctgggagg cctccaccga gcgcctgtac 12360
ccccgcgacg gcgtgctgaa gggcgagatc cacaaggccc tgaagctgaa ggacggcggc 12420
cacgctagcc catccaccca ctcactcact catatctgtg ctgtacgtac gagaatttct 12480
cgaccaaccg tcgtgagacc tgcccaccgg agatcggacg caagagggtt taggcaagaa 12540
tgtcgtgcga cagggtgagc gctgactagt atacgtgaga gaccttgaga tatacctcac 12600
acgtacgcgt actttacatg acgtaggaca ttacgactca aacagattca cgtcagattt 12660
cggagtttct cacgcgtgag agccttggag ggcggtatgt atgtcatact atatgttggg 12720
atggagggag tgagtgagtg atatgtggct agcaagggcg gccccctgcc cttcgcctgg 12780
gacatcctgt ccccccagtt ccagtacggc tccaaggtgt acgtgaagca ccccgccgac 12840
atccccgact acaagaagct gtccttcccc gagggcttca agtgggagcg cgtgatgaac 12900
ttcgaggacg gcggcgtggt gacagtgacc caggactcct ccctgcagga cggctccttc 12960
atctacaagg tgaagttcat cggcgtgaac ttcccctccg acggccccgt aatgcagaag 13020
aagactatgg gctgggaggc ctccaccgag cgcctgtacc cccgcgacgg cgtgctgaag 13080
ggcgagatcc acaaggccct gaagctgaag gacggcggcc actacctggt ggagttcaag 13140
tccatctaca tggccaagaa gcccgtgcag ctgcccggct actactacgt ggactccaag 13200
ctggacatca cctcccacaa cgaggactac accatcgtgg agcagtacga gcgcgccgag 13260
ggccgccacc acctgttcct gtagtcagga tctgagtcga aacctagact tgtccatctt 13320
ctggattggc caacttaatt aatgtatgaa ataaaaggat gcacacatag tgacatgcta 13380
atcactataa tgtgggcatc aaagttgtgt gttatgtgta attactagtt atctgaataa 13440
aagagaaaga gatcatccat atttcttatc ctaaatgaat gtcacgtgtc tttataattc 13500
tttgatgaac cagatgcatt tcattaacca aatccatata catataaata ttaatcatat 13560
ataattaata tcaattgggt tagcaaaaca aatctagtct aggtgtgttt tgcgaatgcg 13620
gccgccaccg cggtggagct cgaattccgg tccgggtcac ccggtccggg cctagaaggc 13680
cagcttgcgg ccgccccggg caactttatt atacaaagtt gatagatatc ggtccgagcg 13740
gcctagaagg cctttggtca cctttgtcca ccaagatgga actgcggccg ctcattaatt 13800
aagtcaggcg cgcctctagt tgaagacacg ttcatgtctt catcgtaaga agacactcag 13860
tagtcttcgg ccagaatggc ctaactcaag gccatcgtgg cctcttgctc ttcaggatga 13920
agagctatgt ttaaacgtgc aagcgctact agacaattca gtacattaaa aacgtccgca 13980
atgtgttatt aagttgtcta agcgtcaatt tgtttacacc acaatatatc ctgccaccag 14040
ccagccaaca gctccccgac cggcagctcg gcacaaaatc accactcgat acaggcagcc 14100
catcagtccg ggacggcgtc agcgggagag ccgttgtaag gcggcagact ttgctcatgt 14160
taccgatgct attcggaaga acggcaacta agctgccggg tttgaaacac ggatgatctc 14220
gcggagggta gcatgttgat tgtaacgatg acagagcgtt gctgcctgtg atcaaatatc 14280
atctccctcg cagagatccg aattatcagc cttcttattc atttctcgct taaccgtgac 14340
aggctgtcga tcttgagaac tatgccgaca taataggaaa tcgctggata aagccgctga 14400
ggaagctgag tggcgctatt tctttagaag tgaacgttga cgatcgtcga ccgtaccccg 14460
atgaattaat tcggacgtac gttctgaaca cagctggata cttacttggg cgattgtcat 14520
acatgacatc aacaatgtac ccgtttgtgt aaccgtctct tggaggttcg tatgacacta 14580
gtggttcccc tcagcttgcg actagatgtt gaggcctaac attttattag agagcaggct 14640
agttgcttag atacatgatc ttcaggccgt tatctgtcag ggcaagcgaa aattggccat 14700
ttatgacgac caatgccccg cagaagctcc catctttgcc gccatagacg ccgcgccccc 14760
cttttggggt gtagaacatc cttttgccag atgtggaaaa gaagttcgtt gtcccattgt 14820
tggcaatgac gtagtagccg gcgaaagtgc gagacccatt tgcgctatat ataagcctac 14880
gatttccgtt gcgactattg tcgtaattgg atgaactatt atcgtagttg ctctcagagt 14940
tgtcgtaatt tgatggacta ttgtcgtaat tgcttatgga gttgtcgtag ttgcttggag 15000
aaatgtcgta gttggatggg gagtagtcat agggaagacg agcttcatcc actaaaacaa 15060
ttggcaggtc agcaagtgcc tgccccgatg ccatcgcaag tacgaggctt agaaccacct 15120
tcaacagatc gcgcatagtc ttccccagct ctctaacgct tgagttaagc cgcgccgcga 15180
agcggcgtcg gcttgaacga attgttagac attatttgcc gactaccttg gtgatctcgc 15240
ctttcacgta gtgaacaaat tcttccaact gatctgcgcg cgaggccaag cgatcttctt 15300
gtccaagata agcctgccta gcttcaagta tgacgggctg atactgggcc ggcaggcgct 15360
ccattgccca gtcggcagcg acatccttcg gcgcgatttt gccggttact gcgctgtacc 15420
aaatgcggga caacgtaagc actacatttc gctcatcgcc agcccagtcg ggcggcgagt 15480
tccatagcgt taaggtttca tttagcgcct caaatagatc ctgttcagga accggatcaa 15540
agagttcctc cgccgctgga cctaccaagg caacgctatg ttctcttgct tttgtcagca 15600
agatagccag atcaatgtcg atcgtggctg gctcgaagat acctgcaaga atgtcattgc 15660
gctgccattc tccaaattgc agttcgcgct tagctggata acgccacgga atgatgtcgt 15720
cgtgcacaac aatggtgact tctacagcgc ggagaatctc gctctctcca ggggaagccg 15780
aagtttccaa aaggtcgttg atcaaagctc gccgcgttgt ttcatcaagc cttacagtca 15840
ccgtaaccag caaatcaata tcactgtgtg gcttcaggcc gccatccact gcggagccgt 15900
acaaatgtac ggccagcaac gtcggttcga gatggcgctc gatgacgcca actacctctg 15960
atagttgagt cgatacttcg gcgatcaccg cttccctcat gatgtttaac tcctgaatta 16020
agccgcgccg cgaagcggtg tcggcttgaa tgaattgtta ggcgtcatcc tgtgctcccg 16080
agaaccagta ccagtacatc gctgtttcgt tcgagacttg aggtctagtt ttatacgtga 16140
acaggtcaat gccgccgaga gtaaagccac attttgcgta caaattgcag gcaggtacat 16200
tgttcgtttg tgtctctaat cgtatgccaa ggagctgtct gcttagtgcc cacttttcg 16260
caaattcgat gagactgtgc gcgactcctt tgcctcggtg cgtgtgcgac acaacaatgt 16320
gttcgataga ggctagatcg ttccatgttg agttgagttc aatcttcccg acaagctctt 16380
ggtcgatgaa tgcgccatag caagcagagt cttcatcaga gtcatcatcc gagatgtaat 16440
ccttccggta ggggctcaca cttctggtag atagttcaaa gccttggtcg gataggtgca 16500
catcgaacac ttcacgaaca atgaaatggt tctcagcatc caatgtttcc gccacctgct 16560
cagggatcac cgaaatcttc atatgacgcc taacgcctgg cacagcggat cgcaaacctg 16620
gcgcggcttt tggcacaaaa ggcgtgacag gtttgcgaat ccgttgctgc cacttgttaa 16680
ccctttgcc agatttggta actataattt atgttagagg cgaagtcttg ggtaaaaact 16740
ggcctaaaat tgctggggat ttcaggaaag taaacatcac cttccggctc gatgtctatt 16800
gtagatatat gtagtgtatc tacttgatcg gggatctgc tgcctcgcgc gtttcggtga 16860
tgacggtgaa aacctctgac acatgcagct cccggagacg gtcacagctt gtctgtaagc 16920
ggatgccggg agcagacaag cccgtcaggg cgcgtcagcg ggtgttggcg ggtgtcgggg 16980
cgcagccatg acccagtcac gtagcgatag cggagtgtat actggcttaa ctatgcggca 17040
tcagagcaga ttgtactgag agtgcaccat atgcggtgtg aaataccgca cagatgcgta 17100
aggagaaaat accgcatcag gcgctcttcc gcttcctcgc tcactgactc gctgcgctcg 17160
gtcgttcggc tgcggcgagc ggtatcagct cactcaaagg cggtaatacg gttatccaca 17220
gaatcagggg ataacgcagg aaagaacatg tgagcaaaag gccagcaaaa ggccaggaac 17280
cgtaaaaagg ccgcgttgct ggcgtttttc cataggctcc gcccccctga cgagcatcac 17340
aaaaatcgac gctcaagtca gaggtggcga aacccgacag gactataaag ataccaggcg 17400
tttccccctg gaagctccct cgtgcgctct cctgttccga ccctgccgct taccggatac 17460
ctgtccgcct ttctcccttc gggaagcgtg gcgctttctc atagctcacg ctgtaggtat 17520
ctcagttcgg tgtaggtcgt tcgctccaag ctgggctgtg tgcacgaacc ccccgttcag 17580
cccgaccgct gcgccttatc cggtaactat cgtcttgagt ccaacccggt aagacacgac 17640
ttatcgccac tggcagcagc cactggtaac aggattagca gagcgaggta tgtaggcggt 17700
gctacagagt tcttgaagtg gtggcctaac tacggctaca ctagaaggac agtatttggt 17760
atctgcgctc tgctgaagcc agttaccttc ggaaaaagag ttggtagctc ttgatccggc 17820
aaacaaacca ccgctggtag cggtggtttt tttgtttgca agcagcagat tacgcgcaga 17880
aaaaaaggat ctcaagaaga tcctttgatc ttttctacgg ggtctgacgc tcagtggaac 17940
gaaaactcac gttaagggat tttggtcatg agattatcaa aaaggatctt cacctagatc 18000
cttttaaatt aaaaatgaag ttttaaatca atctaaagta tatatgagta aacttggtct 18060
gacagttacc aatgcttaat cagtgaggca cctatctcag cgatctgtct atttcgttca 18120
tccatagttg cctgactccc cgtcgtgtag ataactacga tacgggaggg cttaccatct 18180
ggccccagtg ctgcaatgat accgcgagac ccacgctcac cggctccaga tttatcagca 18240
ataaaccagc cagccggaag ggccgagcgc agaagtggtc ctgcaacttt atccgcctcc 18300
atccagtcta ttaattgttg ccgggaagct agagtaagta gttcgccagt taatagtttg 18360
cgcaacgttg ttgccattgc tgcagggggg gggggggggg gggacttcca ttgttcattc 18420
cacggacaaa aacagagaaa ggaaacgaca gaggccaaaa agcctcgctt tcagcacctg 18480
tcgtttcctt tcttttcaga gggtatttta aataaaaaca ttaagttatg acgaagaaga 18540
acggaaacgc cttaaaccgg aaaattttca taaatagcga aaacccgcga ggtcgccgcc 18600
ccgtaacctg tcggatcacc ggaaaggacc cgtaaagtga taatgattat catctacata 18660
tcacaacgtg cgtggaggcc atcaaaccac gtcaaataat caattatgac gcaggtatcg 18720
tattaattga tctgcatcaa cttaacgtaa aaacaacttc agacaataca aatcagcgac 18780
actgaatacg gggcaacctc atgtcccccc cccccccccc cctgcaggca tcgtggtgtc 18840
acgctcgtcg tttggtatgg cttcattcag ctccggttcc caacgatcaa ggcgagttac 18900
atgatccccc atgttgtgca aaaaagcggt tagctccttc ggtcctccga tcgttgtcag 18960
aagtaagttg gccgcagtgt tatcactcat ggttatggca gcactgcata attctcttac 19020
tgtcatgcca tccgtaagat gcttttctgt gactggtgag tactcaacca agtcattctg 19080
agaatagtgt atgcggcgac cgagttgctc ttgcccggcg tcaacacggg ataataccgc 19140
gccacatagc agaactttaa aagtgctcat cattggaaaa cgttcttcgg ggcgaaaact 19200
ctcaaggatc ttaccgctgt tgagatccag ttcgatgtaa cccactcgtg cacccaactg 19260
atcttcagca tcttttactt tcaccagcgt ttctgggtga gcaaaaacag gaaggcaaaa 19320
tgccgcaaaa aagggaataa gggcgacacg gaaatgttga atactcatac tcttcctttt 19380
tcaatattat tgaagcattt atcagggtta ttgtctcatg agcggataca tatttgaatg 19440
tatttagaaa aataaacaaa taggggttcc gcgcacattt ccccgaaaag tgccacctga 19500
cgtctaagaa accattatta tcatgacatt aacctataaa aataggcgta tcacgaggcc 19560

-continued

```
ctttcgtctt caagaattcg gagcttttgc cattctcacc ggattcagtc gtcactcatg  19620
gtgatttctc acttgataac cttatttttg acgaggggaa attaataggt tgtattgatg  19680
ttggacgagt cggaatcgca gaccgatacc aggatcttgc catcctatgg aactgcctcg  19740
gtgagttttc tccttcatta cagaaacggc tttttcaaaa atatggtatt gataatcctg  19800
atatgaataa attgcagttt catttgatgc tcgatgagtt tttctaatca gaattggtta  19860
attggttgta acactggcag agcattacgc tgacttgacg ggacggcggc tttgttgaat  19920
aaatcgaact tttgctgagt tgaaggatca gatcacgcat cttcccgaca acgcagaccg  19980
ttccgtggca aagcaaaagt tcaaaatcac caactggtcc acctacaaca aagctctcat  20040
caaccgtggc tccctcactt tctggctgga tgatggggcg attcaggcct ggtatgagtc  20100
agcaacacct tcttcacgag gcagacctca gcgccagaag gccgccagag aggccgagcg  20160
cggccgtgag gcttggacgc tagggcaggg catgaaaaag cccgtagcgg gctgctacgg  20220
gcgtctgacg cggtggaaag ggggaggggga tgttgtctac atggctctgc tgtagtgagt  20280
gggttgcgct ccggcagcgg tcctgatcaa tcgtcaccct ttctcggtcc ttcaacgttc  20340
ctgacaacga gcctcctttt cgccaatcca tcgacaatca ccgcgagtcc ctgctcgaac  20400
gctgcgtccg gaccggcttc gtcgaaggcg tctatcgcgg cccgcaacag cggcgagagc  20460
ggagcctgtt caacggtgcc gccgcgctcg ccggcatcgc tgtcgccggc ctgctcctca  20520
agcacggccc caacagtgaa gtagctgatt gtcatcagcg cattgacggc gtccccggcc  20580
gaaaaacccg cctcgcagag gaagcgaagc tgcgcgtcgg ccgtttccat ctgcggtgcg  20640
cccggtcgcg tgccggcatg gatgcgcgcg ccatcgcggt aggcgagcag cgcctgcctg  20700
aagctgcggg cattcccgat cagaaatgag cgccagtcgt cgtcggctct cggcaccgaa  20760
tgcgtatgat tctccgccag catggcttcg gccagtgcgt cgagcagcgc ccgcttgttc  20820
ctgaagtgcc agtaaagcgc cggctgctga acccccaacc gttccgccag tttgcgtgtc  20880
gtcagaccgt ctacgccgac ctcgttcaac aggtccaggg cggcacggat cactgtattc  20940
ggctgcaact ttgtcatgct tgacacttta tcactgataa acataaatatg tccaccaact  21000
tatcagtgat aaagaatccg cgcgttcaat cggaccagcg gaggctggtc cggaggccag  21060
acgtgaaacc caacataccc ctgatcgtaa ttctgagcac tgtcgcgctc gacgctgtcg  21120
gcatcggcct gattatgccg gtgctgccgg gcctcctgcg cgatctggtt cactcgaacg  21180
acgtcaccgc ccactatggc attctgctgg cgctgtatgc gttggtgcaa tttgcctgcg  21240
cacctgtgct gggcgcgctg tcggatcgtt tcgggcggcg gccaatcttg ctcgtctcgc  21300
tggccggcgc cactgtcgac tacgccatca tggcgacagc gcctttcctt tgggttctct  21360
atatcgggcg gatcgtggcc ggcatcaccg gggcgactgg ggcggtagcc ggcgcttata  21420
ttgccgatat cactgatggc gatgagcgcg cgcggcactt cggcttcatg agcgcctgtt  21480
tcgggttcgg gatggtcgcg ggacctgtgc tcggtgggct gatgggcggt ttctcccccc  21540
acgctccgtt cttcgccgcg gcagccttga acggcctcaa tttcctgacg ggctgtttcc  21600
ttttgccgga gtcgcacaaa ggcgaacgcc ggccgttacg ccgggaggct ctcaacccgc  21660
tcgcttcgtt ccggtgggcc cggggcatga ccgtcgtcgc cgccctgatg gcggtcttct  21720
tcatcatgca acttgtcgga caggtgccgg ccgcgctttg ggtcattttc ggcgaggatc  21780
gctttcactg ggacgcgacc acgatcggca tttcgcttgc cgcatttggc attctgcatt  21840
cactcgccca ggcaatgatc accggccctg tagccgcccg gctcggcgaa aggcgggcac  21900
tcatgctcgg aatgattgcc gacggcacag gctacatcct gcttgccttc gcgacacggg  21960
```

gatggatggc gttcccgatc atggtcctgc ttgcttcggg tggcatcgga atgccggcgc 22020
tgcaagcaat gttgtccagg caggtggatg aggaacgtca ggggcagctg caaggctcac 22080
tggcggcgct caccagcctg acctcgatcg tcggacccct cctcttcacg gcgatctatg 22140
cggcttctat aacaacgtgg aacgggtggg catggattgc aggcgctgcc ctctacttgc 22200
tctgcctgcc ggcgctgcgt cgcgggcttt ggagcggcgc agggcaacga gccgatcgct 22260
gatcgtggaa acgataggcc tatgccatgc gggtcaaggc gacttccggc aagctatacg 22320
cgccctagga gtgcggttgg aacgttggcc cagccagata ctcccgatca cgagcaggac 22380
gccgatgatt tgaagcgcac tcagcgtctg atccaagaac aaccatccta gcaacacggc 22440
ggtccccggg ctgagaaagc ccagtaagga aacaactgta ggttcgagtc gcgagatccc 22500
ccggaaccaa aggaagtagg ttaaacccgc tccgatcagg ccgagccacg ccaggccgag 22560
aacattggtt cctgtaggca tcgggattgg cggatcaaac actaaagcta ctggaacgag 22620
cagaagtcct ccggccgcca gttgccaggc ggtaaaggtg agcagaggca cgggaggttg 22680
ccacttgcgg gtcagcacgg ttccgaacgc catggaaacc gcccccgcca ggcccgctgc 22740
gacgccgaca ggatctagcg ctgcgtttgg tgtcaacacc aacagcgcca cgcccgcagt 22800
tccgcaaata gcccccagga ccgccatcaa tcgtatcggg ctacctagca gagcggcaga 22860
gatgaacacg accatcagcg gctgcacagc gcctaccgtc gccgcgaccc cgcccggcag 22920
gcggtagacc gaaataaaca acaagctcca gaatagcgaa atattaagtg cgccgaggat 22980
gaagatgcgc atccaccaga ttcccgttgg aatctgtcgg acgatcatca cgagcaataa 23040
acccgccggc aacgcccgca gcagcatacc ggcgacccct cggcctcgct gttcgggctc 23100
cacgaaaacg ccggacagat gcgccttgtg agcgtccttg gggccgtcct cctgtttgaa 23160
gaccgacagc ccaatgatct cgccgtcgat gtaggcgccg aatgccacgg catctcgcaa 23220
ccgttcagcg aacgcctcca tgggcttttt ctcctcgtgc tcgtaaacgg acccgaacat 23280
ctctggagct ttcttcaggg ccgacaatcg gatctcgcgg aaatcctgca cgtcggccgc 23340
tccaagccgt cgaatctgag ccttaatcac aattgtcaat tttaatcctc tgtttatcgg 23400
cagttcgtag agcgcgccgt gcgtcccgag cgatactgag cgaagcaagt gcgtcgagca 23460
gtgcccgctt gttcctgaaa tgccagtaaa gcgctggctg ctgaaccccc agccggaact 23520
gaccccacaa ggccctagcg tttgcaatgc accaggtcat cattgaccca ggcgtgttcc 23580
accaggccgc tgcctcgcaa ctcttcgcag gcttcgccga cctgctcgcg ccacttcttc 23640
acgcgggtgg aatccgatcc gcacatgagg cggaaggttt ccagcttgag cgggtacggc 23700
tcccggtgcg agctgaaata gtcgaacatc cgtcgggccg tcggcgacag cttgcggtac 23760
ttctcccata tgaatttcgt gtagtggtcg ccagcaaaca gcacgacgat ttcctcgtcg 23820
atcaggacct ggcaacggga cgttttcttg ccacggtcca ggacgcggaa gcggtgcagc 23880
agcgacaccg attccaggtg cccaacgcgg tcggacgtga agcccatcgc cgtcgcctgt 23940
aggcgcgaca ggcattcctc ggccttcgtg taataccggc cattgatcga ccagcccagg 24000
tcctggcaaa gctcgtagaa cgtgaaggtg atcggctcgc cgataggggt gcgcttcgcg 24060
tactccaaca cctgctgcca caccagttcg tcatcgtcgg cccgcagctc gacgccggtg 24120
taggtgatct tcacgtcctt gttgacgtgg aaaatgacct tgttttgcag cgcctcgcgc 24180
gggattttct tgttgcgcgt ggtgaacagg gcagagcggg ccgtgtcgtt tggcatcgct 24240
cgcatcgtgt ccggccacgg cgcaatatcg aacaaggaaa gctgcatttc cttgatctgc 24300
tgcttcgtgt gtttcagcaa cgcggcctgc ttggcctcgc tgacctgttt tgccaggtcc 24360
tcgccggcgg tttttcgctt cttggtcgtc atagttcctc gcgtgtcgat ggtcatcgac 24420
ttcgccaaac ctgccgcctc ctgttcgaga cgacgcgaac gctccacggc ggccgatggc 24480
gcgggcaggg cagggggagc cagttgcacg ctgtcgcgct cgatcttggc cgtagcttgc 24540
tggaccatcg agccgacgga ctggaaggtt tcgcggggcg cacgcatgac ggtgcggctt 24600
gcgatggttt cggcatcctc ggcggaaaac cccgcgtcga tcagttcttg cctgtatgcc 24660
ttccggtcaa acgtccgatt cattcaccct ccttgcggga ttgccccgac tcacgccggg 24720
gcaatgtgcc cttattcctg atttgacccg cctggtgcct tggtgtccag ataatccacc 24780
ttatcggcaa tgaagtcggt cccgtagacc gtctggccgt ccttctcgta cttggtattc 24840
cgaatcttgc cctgcacgaa taccagcgac cccttgccca aatacttgcc gtgggcctcg 24900
gcctgagagc caaaacactt gatgcggaag aagtcggtgc gctcctgctt gtcgccggca 24960
tcgttgcgcc actcttcatt aaccgctata tcgaaaattg cttgcggctt gttagaattg 25020
ccatgacgta cctcggtgtc acgggtaaga ttaccgataa actggaactg attatggctc 25080
atatcgaaag tctccttgag aaaggagact ctagtttagc taaacattgg ttccgctgtc 25140
aagaacttta gcggctaaaa ttttgcgggc cgcgaccaaa ggtgcgaggg gcggcttccg 25200
ctgtgtacaa ccagatattt ttcaccaaca tccttcgtct gctcgatgag cggggcatga 25260
cgaaacatga gctgtcggag agggcagggg tttcaatttc gtttttatca gacttaacca 25320
acggtaaggc caacccctcg ttgaaggtga tggaggccat tgccgacgcc ctggaaactc 25380
ccctacctct tctcctggag tccaccgacc ttgaccgcga ggcactcgcg gagattgcgg 25440
gtcatccttt caagagcagc gtgccgcccg gatacgaacg catcagtgtg gttttgccgt 25500
cacataaggc gtttatcgta aagaaatggg gcgacgacac ccgaaaaaag ctgcgtggaa 25560
ggctctgacg ccaagggtta gggcttgcac ttccttcttt agccgctaaa acggcccctt 25620
ctctgcgggc cgtcggctcg cgcatcatat cgacatcctc aacggaagcc gtgccgcgaa 25680
tggcatcggg cgggtgcgct ttgacagttg ttttctatca gaacccctac gtcgtgcggt 25740
tcgattagct gtttgtcttg caggctaaac actttcggta tatcgtttgc ctgtgcgata 25800
atgttgctaa tgatttgttg cgtaggggtt actgaaaagt gagcgggaaa gaagagtttc 25860
agaccatcaa ggagcgggcc aagcgcaagc tggaacgcga catgggtgcg gacctgttgg 25920
ccgcgctcaa cgacccgaaa accgttgaag tcatgctcaa cgcggacggc aaggtgtggc 25980
acgaacgcct tggcgagccg atgcggtaca tctgcgacat gcggcccagc cagtcgcagg 26040
cgattataga aacggtggcc ggattccacg gcaaagaggt cacgcggcat tcgcccatcc 26100
tggaaggcga gttccccttg gatggcagcc gctttgccgg ccaattgccg ccggtcgtgg 26160
ccgcgccaac ctttgcgatc cgcaagcgcg cggtcgccat cttcacgctg gaacagtacg 26220
tcgaggcggg catcatgacc cgcgagcaat acgaggtcat taaaagcgcc gtcgcggcgc 26280
atcgaaacat cctcgtcatt ggcggtactg gctcgggcaa gaccacgctc gtcaacgcga 26340
tcatcaatga aatggtcgcc ttcaacccgt ctgagcgcgt cgtcatcatc gaggacaccg 26400
gcgaaatcca gtgcgccgca gagaacgccg tccaatacca caccagcatc gacgtctcga 26460
tgacgctgct gctcaagaca acgctgcgta tgcgccccga ccgcatcctg gtcggtgagg 26520
tacgtggccc cgaagccctt gatctgttga tggcctggaa caccgggcat gaaggaggtg 26580
ccgccaccct gcacgcaaac aaccccaaag cgggcctgag ccggctcgcc atgcttatca 26640
gcatgcaccc ggattcaccg aaacccattg agccgctgat tggcgaggcg gttcatgtgg 26700

```
tcgtccatat cgccaggacc cctagcggcc gtcgagtgca agaaattctc gaagttcttg  26760
gttacgagaa cggccagtac atcaccaaaa ccctgtaagg agtatttcca atgacaacgg  26820
ctgttccgtt ccgtctgacc atgaatcgcg gcattttgtt ctaccttgcc gtgttcttcg  26880
ttctcgctct cgcgttatcc gcgcatccgg cgatggcctc ggaaggcacc ggcggcagct  26940
tgccatatga gagctggctg acgaacctgc gcaactccgt aaccggcccg gtggccttcg  27000
cgctgtccat catcggcatc gtcgtcgccg gcggcgtgct gatcttcggc ggcgaactca  27060
acgccttctt ccgaaccctg atcttcctgg ttctggtgat ggcgctgctg gtcggcgcgc  27120
agaacgtgat gagcaccttc ttcggtcgtg gtgccgaaat cgcggccctc ggcaacgggg  27180
cgctgcacca ggtgcaagtc gcggcggcgg atgccgtgcg tgcggtagcg gctggacggc  27240
tcgcctaatc atggctctgc gcacgatccc catccgtcgc gcaggcaacc gagaaaacct  27300
gttcatgggt ggtgatcgtg aactggtgat gttctcgggc ctgatggcgt ttgcgctgat  27360
tttcagcgcc caagagctgc gggccaccgt ggtcggtctg atcctgtggt tcggggcgct  27420
ctatgcgttc cgaatcatgg cgaaggccga tccgaagatg cggttcgtgt acctgcgtca  27480
ccgccggtac aagccgtatt acccggcccg ctcgaccccg ttccgcgaga acaccaatag  27540
ccaagggaag caataccgat gatccaagca attgcgattg caatcgcggg cctcggcgcg  27600
cttctgttgt tcatcctctt tgcccgcatc cgcgcggtcg atgccgaact gaaactgaaa  27660
aagcatcgtt ccaaggacgc cggcctggcc gatctgctca actacgccgc tgtcgtcgat  27720
gacggcgtaa tcgtgggcaa gaacggcagc tttatggctg cctggctgta caagggcgat  27780
gacaacgcaa gcagcaccga ccagcagcgc gaagtagtgt ccgcccgcat caaccaggcc  27840
ctcgcgggcc tgggaagtgg gtggatgatc catgtggacg ccgtgcggcg tcctgctccg  27900
aactacgcgg agcggggcct gtcggcgttc cctgaccgtc tgacggcagc gattgaagaa  27960
gagcgctcgg tcttgccttg ctcgtcggtg atgtacttca ccagctccgc gaagtcgctc  28020
ttcttgatgg agcgcatggg gacgtgcttg gcaatcacgc gcacccccgg gccgttttag  28080
cggctaaaaa agtcatggct ctgccctcgg gcggaccacg cccatcatga ccttgccaag  28140
ctcgtcctgc ttctcttcga tcttcgccag cagggcgagg atcgtggcat caccgaaccg  28200
cgccgtgcgc gggtcgtcgg tgagccagag tttcagcagg ccgcccaggc ggcccaggtc  28260
gccattgatg cgggccagct cgcggacgtg ctcatagtcc acgacgcccg tgattttgta  28320
gccctggccg acggccagca ggtaggccga caggctcatg ccggccgccg ccgccttttc  28380
ctcaatcgct cttcgttcgt ctggaaggca gtacaccttg ataggtgggc tgcccttcct  28440
ggttggcttg gtttcatcag ccatccgctt gccctcatct gttacgccgg cggtagccgg  28500
ccagcctcgc agagcaggat tcccgttgag caccgccagg tgcgaataag ggacagtgaa  28560
gaaggaacac ccgctcgcgg gtgggcctac ttcacctatc ctgcccggct gacgccgttg  28620
gatacaccaa ggaaagtcta cacgaaccct ttggcaaaat cctgtatatc gtgcgaaaaa  28680
ggatggatat accgaaaaaa tcgctataat gaccccgaag cagggttatg cagcggaaaa  28740
gcgctgcttc cctgctgttt tgtggaatat ctaccgactg gaaacaggca aatgcaggaa  28800
attactgaac tgaggggaca ggcgagagac gatgccaaag agctacaccg acgagctggc  28860
cgagtgggtt gaatcccgcg cggccaagaa gcgccggcgt gatgaggctg cggttgcgtt  28920
cctggcggtg agggcggatg tcgaggcggc gttagcgtcc ggctatgcgc tcgtcaccat  28980
ttgggagcac atgcgggaaa cggggaaggt caagttctcc tacgagacgt tccgctcgca  29040
```

cgccaggcgg cacatcaagg ccaagcccgc cgatgtgccc gcaccgcagg ccaaggctgc 29100
ggaacccgcg ccggcaccca agacgccgga gccacggcgg ccgaagcagg ggggcaaggc 29160
tgaaaagccg gcccccgctg cggccccgac cggcttcacc ttcaacccaa caccggacaa 29220
aaaggatcta ctgtaatggc gaaaattcac atggttttgc agggcaaggg cggggtcggc 29280
aagtcggcca tcgccgcgat cattgcgcag tacaagatgg acaaggggca gacacccttg 29340
tgcatcgaca ccgacccggt gaacgcgacg ttcgagggct acaaggccct gaacgtccgc 29400
cggctgaaca tcatggccgg cgacgaaatt aactcgcgca acttcgacac cctggtcgag 29460
ctgattgcgc cgaccaagga tgacgtggtg atcgacaacg gtgccagctc gttcgtgcct 29520
ctgtcgcatt acctcatcag caaccaggtg ccggctctgc tgcaagaaat ggggcatgag 29580
ctggtcatcc ataccgtcgt caccggcggc caggctctcc tggacacggt gagcggcttc 29640
gcccagctcg ccagccagtt cccggccgaa gcgcttttcg tggtctggct gaacccgtat 29700 tggggggccta tcgagcatga gggcaagagc tttgagcaga tgaaggcgta cacggccaac 29760
aaggcccgcg tgtcgtccat catccagatt ccggccctca aggaagaaac ctacggccgc 29820
gatttcagcg acatgctgca agagcggctg acgttcgacc aggcgctggc cgatgaatcg 29880
ctcacgatca tgacgcggca acgcctcaag atcgtgcggc gcggcctgtt tgaacagctc 29940
gacgcggcgg ccgtgctatg agcgaccaga ttgaagagct gatccgggag attgcggcca 30000
agcacggcat cgccgtcggc cgcgacgacc cggtgctgat cctgcatacc atcaacgccc 30060
ggctcatggc cgacagtgcg gccaagcaag aggaaatcct tgccgcgttc aaggaagagc 30120
tggaagggat cgcccatcgt tggggcgagg acgccaaggc caaagcggag cggatgctga 30180
acgcggccct ggcggccagc aaggacgcaa tggcgaaggt aatgaaggac agcgccgcgc 30240
aggcggccga agcgatccgc agggaaatcg acgacggcct tggccgccag ctcgcggcca 30300
aggtcgcgga cgcgcggcgc gtggcgatga tgaacatgat cgccggcggc atggtgttgt 30360
tcgcggccgc cctggtggtg tgggcctcgt tatgaatcgc agaggcgcag atgaaaaagc 30420
ccggcgttgc cgggctttgt ttttgcgtta gctgggcttg tttgacaggc ccaagctctg 30480
actgcgcccg cgctcgcgct cctgggcctg tttcttctcc tgctcctgct tgcgcatcag 30540
ggcctggtgc cgtcgggctg cttcacgcat cgaatcccag tcgccggcca gctcgggatg 30600
ctccgcgcgc atcttgcgcg tcgccagttc ctcgatcttg ggcgcgtgaa tgcccatgcc 30660
ttccttgatt tcgcgcacca tgtccagccg cgtgtgcagg gtctgcaagc gggcttgctg 30720
ttgggcctgc tgctgctgcc aggcggcctt tgtacgcggc agggacagca agccgggggc 30780
attggactgt agctgctgca aacgcgcctg ctgacggtct acgagctgtt ctaggcggtc 30840
ctcgatgcgc tccacctggt catgctttgc ctgcacgtag agcgcaaggg tctgctggta 30900
ggtctgctcg atgggcgcgg attctaagag ggcctgctgt tccgtctcgg cctcctgggc 30960
cgcctgtagc aaatcctcgc cgctgttgcc gctggactgc tttactgccg gggactgctg 31020
ttgccctgct cgcgccgtcg tcgcagttcg gcttgccccc actcgattga ctgcttcatt 31080
tcgagccgca gcgatgcgat ctcggattgc gtcaacggac ggggcagcgc ggaggtgtcc 31140
ggcttctcct tgggtgagtc ggtcgatgcc atagccaaag gtttccttcc aaaatgcgtc 31200
cattgctgga ccgtgtttct cattgatgcc cgcaagcatc ttcggcttga ccgccaggtc 31260
aagcgcgcct tcatgggcgg tcatgacgga cgccgccatg accttgccgc cgttgttctc 31320
gatgtagccg cgtaatgagg caatggtgcc gcccatcgtc agcgtgtcat cgacaacgat 31380
gtacttctgg ccggggatca cctccccctc gaaagtcggg ttgaacgcca ggcgatgatc 31440
tgaaccggct ccggttcggg cgaccttctc ccgctgcaca atgtccgttt cgacctcaag 31500
gccaaggcgg tcggccagaa cgaccgccat catggccgga atcttgttgt tccccgccgc 31560
ctcgacggcg aggactggaa cgatgcgggg cttgtcgtcg ccgatcagcg tcttgagctg 31620
ggcaacagtg tcgtccgaaa tcaggcgctc gaccaaatta agcgccgctt ccgcgtcgcc 31680
ctgcttcgca gcctggtatt caggctcgtt ggtcaaagaa ccaaggtcgc cgttgcgaac 31740
caccttcggg aagtctcccc acggtgcgcg ctcggctctg ctgtagctgc tcaagacgcc 31800
tccctttta gccgctaaaa ctctaacgag tgcgcccgcg actcaacttg acgctttcgg 31860
cacttacctg tgccttgcca cttgcgtcat aggtgatgct tttcgcactc ccgatttcag 31920
gtactttatc gaaatctgac cgggcgtgca ttacaaagtt cttccccacc tgttggtaaa 31980
tgctgccgct atctgcgtgg acgatgctgc cgtcgtggcg ctgcgactta tcggcctttt 32040
gggccatata gatgttgtaa atgccaggtt tcagggcccc ggctttatct accttctggt 32100
tcgtccatgc gccttggttc tcggtctgga caattctttg cccattcatg accaggaggc 32160
ggtgtttcat tgggtgactc ctgacggttg cctctggtgt taaacgtgtc ctggtcgctt 32220
gccggctaaa aaaaagccga cctcggcagt tcgaggccgg ctttccctag agccgggcgc 32280
gtcaaggttg ttccatctat tttagtgaac tgcgttcgat ttatcagtta ctttcctccc 32340
gctttgtgtt tcctcccact cgtttccgcg tctagccgac ccctcaacat agcggcctct 32400
tcttgggctg cctttgcctc ttgccgcgct tcgtcacgct cggcttgcac cgtcgtaaag 32460
cgctcggcct gcctggccgc ctcttgcgcc gccaacttcc tttgctcctg gtgggcctcg 32520
gcgtcggcct gcgccttcgc tttcaccgct gccaactccg tgcgcaaact ctccgcttcg 32580
cgcctggtgg cgtcgcgctc gccgcgaagc gcctgcattt cctggttggc cgcgtccagg 32640
gtcttgcggc tctcttcttt gaatgcgcgg gcgtcctggt gagcgtagtc cagctcggcg 32700
cgcagctcct gcgctcgacg ctccacctcg tcggcccgct gcgtcgccag cgcggcccgc 32760
tgctcggctc ctgccagggc ggtgcgtgct tcggccaggg cttgccgctg gcgtgcggcc 32820
agctcggccg cctcggcggc ctgctgctct agcaatgtaa cgcgcgcctg ggcttcttcc 32880
agctcgcggg cctgcgcctc gaaggcgtcg gccagctccc cgcgcacggc ttccaactcg 32940
ttgcgctcac gatcccagcc ggcttgcgct gcctgcaacg attcattggc aagggcctgg 33000
gcggcttgcc agagggcggc cacggcctgg ttgccggcct gctgcaccgc gtccggcacc 33060
tggactgcca gcggggcggc ctgcgccgtg cgctggcgtc gccattcgcg catgccggcg 33120
ctggcgtcgt tcatgttgac gcgggcggcc ttacgcactg catccacggt cgggaagttc 33180
tcccggtcgc cttgctcgaa cagctcgtcc gcagccgcaa aaatgcggtc gcgcgtctct 33240
ttgttcagtt ccatgttggc tccggtaatt ggtaagaata ataatactct tacctacctt 33300
atcagcgcaa gagtttagct gaacagttct cgacttaacg gcaggttttt tagcggctga 33360
agggcaggca aaaaaagccc cgcacggtcg gcgggggcaa agggtcagcg ggaaggggat 33420
tagcgggcgt cgggcttctt catgcgtcgg ggccgcgctt cttgggatgg agcacgacga 33480
agcgcgcacg cgcatcgtcc tcggccctat cggcccgcgt cgcggtcagg aacttgtcgc 33540
gcgctaggtc ctccctggtg ggcaccaggg gcatgaactc ggcctgctcg atgtaggtcc 33600
actccatgac cgcatcgcag tcgaggccgc gttccttcac cgtctcttgc aggtcgcggt 33660
acgcccgctc gttgagcggc tggtaacggg ccaattggtc gtaaatggct gtcggccatg 33720
agcggccttt cctgttgagc cagcagccga cgacgaagcc ggcaatgcag gcccctggca 33780
caaccaggcc gacgccgggg gcaggggatg gcagcagctc gccaaccagg aaccccgccg 33840
cgatgatgcc gatgccggtc aaccagccct tgaaactatc cggccccgaa acacccctgc 33900
gcattgcctg gatgctgcgc cggatagctt gcaacatcag gagccgtttc ttttgttcgt 33960
cagtcatggt ccgccctcac cagttgttcg tatcggtgtc ggacgaactg aaatcgcaag 34020
agctgccggt atcggtccag ccgctgtccg tgtcgctgct gccgaagcac ggcgaggggt 34080
ccgcgaacgc cgcagacggc gtatccggcc gcagcgcatc gcccagcatg gccccggtca 34140
gcgagccgcc ggccaggtag cccagcatgg tgctgttggt cgccccggcc accagggccg 34200
acgtgacgaa atcgccgtca ttccctctgg attgttcgct gctcggcggg gcagtgcgcc 34260
gcgccggcgg cgtcgtggat ggctcgggtt ggctggcctg cgacggccgg cgaaaggtgc 34320
gcagcagctc gttatcgacc ggctgcggcg tcggggccgc cgccttgcgc tgcggtcggt 34380
gttccttctt cggctcgcgc agcttgaaca gcatgatcgc ggaaaccagc agcaacgccg 34440
cgcctacgcc tcccgcgatg tagaacagca tcggattcat tcttcggtcc tccttgtagc 34500
ggaaccgttg tctgtgcggc gcgggtggcc cgcgccgctg tctttgggga tcagccctcg 34560
atgagcgcga ccagtttcac gtcggcaagg ttcgcctcga actcctggcc gtcgtcctcg 34620
tacttcaacc aggcatagcc ttccgccggc ggccgacggt tgaggataag gcgggcaggg 34680
cgctcgtcgt gctcgacctg gacgatggcc tttttcagct tgtccgggtc cggctccttc 34740
gcgccctttt ccttggcgtc cttaccgtcc tggtcgccgt cctcgccgtc ctggccgtcg 34800
ccggcctccg cgtcacgctc ggcatcagtc tggccgttga aggcatcgac ggtgttggga 34860
tcgcggccct tctcgtccag gaactcgcgc agcagcttga ccgtgccgcg cgtgatttcc 34920
tgggtgtcgt cgtcaagcca cgcctcgact tcctccgggc gcttcttgaa ggccgtcacc 34980
agctcgttca ccacggtcac gtcgcgcacg cggccggtgt tgaacgcatc ggcgatcttc 35040
tccggcaggt ccagcagcgt gacgtgctgg gtgatgaacg ccggcgactt gccgatttcc 35100
ttggcgatat cgcctttctt cttgcccttc gccagctcgc ggccaatgaa gtcggcaatt 35160
tcgcgcgggg tcagctcgtt gcgttgcagg ttctcgataa cctggtcggc ttcgttgtag 35220
tcgttgtcga tgaacgccgg gatggacttc ttgccggccc acttcgagcc acggtagcgg 35280
cgggcgccgt gattgatgat atagcggccc ggctgctcct ggttctcgcg caccgaaatg 35340
ggtgacttca ccccgcgctc tttgatcgtg gcaccgattt ccgcgatgct ctccggggaa 35400
aagccggggt tgtcggccgt ccgcggctga tgcggatctt cgtcgatcag gtccaggtcc 35460
agctcgatag ggccggaacc gccctgagac gccgcaggag cgtccaggag gctcgacagg 35520
tcgccgatgc tatccaaccc caggccggac ggctgcgccg cgcctgcggc ttcctgagcg 35580
gccgcagcgg tgtttttctt ggtggtcttg gcttgagccg cagtcattgg gaaatctcca 35640
tcttcgtgaa cacgtaatca gccagggcgc gaacctcttt cgatgccttg cgcgcggccg 35700
ttttcttgat cttccagacc ggcacaccgg atgcgagggc atcggcgatg ctgctgcgca 35760
ggccaacggt ggccggaatc atcatcttgg ggtacgcggc cagcagctcg gcttggtggc 35820
gcgcgtggcg cggattccgc gcatcgacct tgctgggcac catgccaagg aattgcagct 35880
tggcgttctt ctggcgcacg ttcgcaatgg tcgtgaccat cttcttgatg ccctggatgc 35940
tgtacgcctc aagctcgatg ggggacagca catagtcggc cgcgaagagg gcggccgcca 36000
ggccgacgcc aagggtcggg gccgtgtcga tcaggcacac gtcgaagcct tggttcgcca 36060
gggccttgat gttcgccccg aacagctcgc gggcgtcgtc cagcgacagc cgttcggcgt 36120
tcgccagtac cgggttggac tcgatgaggg cgaggcgcgc ggcctggccg tcgccggctg 36180
cgggtgcggt ttcggtccag ccgccggcag ggacagcgcc gaacagcttg cttgcatgca 36240
ggccggtagc aaagtccttg agcgtgtagg acgcattgcc ctgggggtcc aggtcgatca 36300
cggcaacccg caagccgcgc tcgaaaaagt cgaaggcaag atgcacaagg gtcgaagtct 36360
tgccgacgcc gcctttctgg ttggccgtga ccaaagtttt catcgtttgg tttcctgttt 36420
tttcttggcg tccgcttccc acttccggac gatgtacgcc tgatgttccg gcagaaccgc 36480
cgttacccgc gcgtacccct cgggcaagtt cttgtcctcg aacgcggccc acacgcgatg 36540
caccgcttgc gacactgcgc ccctggtcag tcccagcgac gttgcgaacg tcgcctgtgg 36600
cttcccatcg actaagacgc cccgcgctat ctcgatggtc tgctgcccca cttccagccc 36660
ctggatcgcc tcctggaact ggctttcggt aagccgtttc ttcatggata acacccataa 36720
tttgctccgc gccttggttg aacatagcgg tgacagccgc cagcacatga gagaagttta 36780
gctaaacatt tctcgcacgt caacaccttt agccgctaaa actcgtcctt ggcgtaacaa 36840
aacaaaagcc cggaaaccgg gctttcgtct cttgccgctt atggctctgc acccggctcc 36900
atcaccaaca ggtcgcgcac gcgcttcact cggttgcgga tcgacactgc cagcccaaca 36960
aagccggttg ccgccgccgc caggatcgcg ccgatgatgc cggccacacc ggccatcgcc 37020
caccaggtcg ccgccttccg gttccattcc tgctggtact gcttcgcaat gctggacctc 37080
ggctcaccat aggctgaccg ctcgatggcg tatgccgctt ctccccttgg cgtaaaaccc 37140
agcgccgcag gcggcattgc catgctgccc gccgctttcc cgaccacgac gcgcgcacca 37200
ggcttgcggt ccagaccttc ggccacggcg agctgcgcaa ggacataatc agccgccgac 37260
ttggctccac gcgcctcgat cagctcttgc actcgcgcga aatccttggc ctccacggcc 37320
gccatgaatc gcgcacgcgg cgaaggctcc gcagggccgg cgtcgtgatc gccgccgaga 37380
atgcccttca ccaagttcga cgacacgaaa atcatgctga cggctatcac catcatgcag 37440
acggatcgca cgaacccgct gaattgaaca cgagcacggc acccgcgacc actatgccaa 37500
gaatgcccaa ggtaaaaatt gccggccccg ccatgaagtc cgtgaatgcc ccgacggccg 37560
aagtgaaggg caggccgcca cccaggccgc cgccctcact gcccggcacc tggtcgctga 37620
atgtcgatgc cagcacctgc ggcacgtcaa tgcttccggg cgtcgcgctc gggctgatcg 37680
cccatcccgt tactgccccg atcccggcaa tggcaaggac tgccagcgct gccatttttg 37740
gggtgaggcc gttcgcggcc gaggggcgca gcccctgggg ggatgggagg cccgcgttag 37800
cgggccggga gggttcgaga aggggggggca ccccccttcg gcgtgcgcgg tcacgcgcac 37860
agggcgcagc cctggttaaa aacaaggttt ataaatattg gtttaaaagc aggttaaaag 37920
acaggttagc ggtggccgaa aaacgggcgg aaacccttgc aaatgctgga ttttctgcct 37980
gtggacagcc cctcaaatgt caataggtgc gcccctcatc tgtcagcact ctgcccctca 38040
agtgtcaagg atcgcgcccc tcatctgtca gtagtcgcgc ccctcaagtg tcaataccgc 38100
agggcactta tccccaggct tgtccacatc atctgtggga aactcgcgta aaatcaggcg 38160
ttttcgccga tttgcgaggc tggccagctc cacgtcgccg gccgaaatcg agcctgcccc 38220
tcatctgtca acgccgcgcc gggtgagtcg gcccctcaag tgtcaacgtc cgcccctcat 38280
ctgtcagtga gggccaagtt ttccgcgagg tatccacaac gccggcggcc gcggtgtctc 38340
gcacacggct tcgacggcgt ttctggcgcg tttgcagggc catagacggc cgccagccca 38400
gcggcgaggg caaccagccc ggtgagcgtc ggaaaggcgc tggaagcccc gtagcgacgc 38460
ggagaggggc gagacaagcc aagggcgcag gctcgatgcg cagcacgaca tagccggttc 38520

```
tcgcaaggac gagaatttcc ctgcggtgcc cctcaagtgt caatgaaagt ttccaacgcg  38580
agccattcgc gagagccttg agtccacgct agatgagagc tttgttgtag gtggaccagt  38640
tggtgatttt gaacttttgc tttgccacgg aacggtctgc gttgtcggga agatgcgtga  38700
tctgatcctt caactcagca aaagttcgat ttattcaaca aagccacgtt gtgtctcaaa  38760
atctctgatg ttacattgca caagataaaa atatatcatc atgaacaata aaactgtctg  38820
cttacataaa cagtaataca aggggtgtta tgagccatat tcaacgggaa acgtcttgct  38880
cgactctaga gctcgttcct cgaggcctcg aggcctcgag gaacggtacc tgcggggaag  38940
cttacaataa tgtgtgttgt taagtcttgt tgcctgtcat cgtctgactg actttcgtca  39000
taaatcccgg cctccgtaac ccagctttgg gcaagctcac ggatttgatc cggcggaacg  39060
ggaatatcga gatgccgggc tgaacgctgc agttccagct ttccctttcg ggacaggtac  39120
tccagctgat tgattatctg ctgaagggtc ttggttccac ctcctggcac aatgcgaatg  39180
attacttgag cgcgatcggg catccaattt tctcccgtca ggtgcgtggt caagtgctac  39240
aaggcacctt tcagtaacga gcgaccgtcg atccgtcgcc gggatacgga caaaatggag  39300
cgcagtagtc catcgagggc ggcgaaagcc tcgccaaaag caatacgttc atctcgcaca  39360
gcctccagat ccgatcgagg gtcttcggcg taggcagata gaagcatgga tacattgctt  39420
gagagtattc cgatggactg aagtatggct tccatctttt ctcgtgtgtc tgcatctatt  39480
tcgagaaagc ccccgatgcg gcgcaccgca acgcgaattg ccatactatc cgaaagtccc  39540
agcaggcgcg cttgatagga aaaggtttca tactcggccg atcgcagacg ggcactcacg  39600
accttgaacc cttcaacttt cagggatcga tgctggttga tggtagtctc actcgacgtg  39660
gctctggtgt gttttgacat agcttcctcc aaagaaagcg gaaggtctgg atactccagc  39720
acgaaatgtg cccgggtaga cggatggaag tctagccctg ctcaatatga aatcaacagt  39780
acatttacag tcaatactga atatacttgc tacatttgca attgtcttat aacgaatgtg  39840
aaataaaaat agtgtaacaa cgcttttact catcgataat cacaaaaaca tttatacgaa  39900
caaaaataca aatgcactcc ggtttcacag gataggcggg atcagaatat gcaacttttg  39960
acgttttgtt ctttcaaagg gggtgctggc aaaaccaccg cactcatggg cctttgcgct  40020
gctttggcaa atgacggtaa acgagtggcc ctctttgatg ccgacgaaaa ccggcctctg  40080
acgcgatgga gagaaaacgc cttacaaagc agtactggga tcctcgctgt gaagtctatt  40140
ccgccgacga aatgcccctt cttgaagcag cctatgaaaa tgccgagctc gaaggatttg  40200
attatgcgtt ggccgatacg cgtggcggct cgagcgagct caacaacaca atcatcgcta  40260
gctcaaacct gcttctgatc cccaccatgc taacgccgct cgacatcgat gaggcactat  40320
ctacctaccg ctacgtcatc gagctgctgt tgagtgaaaa tttggcaatt cctacagctg  40380
ttttgcgcca acgcgtcccg gtcggccgat tgacaacatc gcaacgcagg atgtcagaga  40440
cgctagagag ccttccagtt gtaccgtctc ccatgcatga aagagatgca tttgccgcga  40500
tgaaagaacg cggcatgttg catcttacat tactaaacac gggaactgat ccgacgatgc  40560
gcctcataga gaggaatctt cggattgcga tggaggaagt cgtggtcatt tcgaaactga  40620
tcagcaaaat cttggaggct tgaagatggc aattcgcaag cccgcattgt cggtcggcga  40680
agcacggcgg cttgctggtg ctcgacccga gatccaccat cccaacccga cacttgttcc  40740
ccagaagctg gacctccagc acttgcctga aaaagccgac gagaaagacc agcaacgtga  40800
gcctctcgtc gccgatcaca tttacagtcc cgatcgacaa cttaagctaa ctgtggatgc  40860
ccttagtcca cctccgtccc cgaaaaagct ccaggttttt ctttcagcgc gaccgcccgc  40920
```

```
gcctcaagtg tcgaaaacat atgacaacct cgttcggcaa tacagtccct cgaagtcgct  40980
acaaatgatt ttaaggcgcg cgttggacga tttcgaaagc atgctggcag atggatcatt  41040
tcgcgtggcc ccgaaaagtt atccgatccc ttcaactaca gaaaaatccg ttctcgttca  41100
gacctcacgc atgttcccgg ttgcgttgct cgaggtcgct cgaagtcatt ttgatccgtt  41160
ggggttggag accgctcgag ctttcggcca caagctggct accgccgcgc tcgcgtcatt  41220
ctttgctgga gagaagccat cgagcaattg gtgaagaggg acctatcgga acccctcacc  41280
aaatattgag tgtaggtttg aggccgctgg ccgcgtcctc agtcaccttt tgagccagat  41340
aattaagagc caaatgcaat tggctcaggc tgccatcgtc cccccgtgcg aaacctgcac  41400
gtccgcgtca aagaaataac cggcacctct tgctgttttt atcagttgag ggcttgacgg  41460
atccgcctca agtttgcggc gcagccgcaa aatgagaaca tctatactcc tgtcgtaaac  41520
ctcctcgtcg cgtactcgac tggcaatgag aagttgctcg cgcgatagaa cgtcgcgggg  41580
tttctctaaa aacgcgagga gaagattgaa ctcacctgcc gtaagtttca cctcaccgcc  41640
agcttcggac atcaagcgac gttgcctgag attaagtgtc cagtcagtaa aacaaaaaga  41700
ccgtcggtct ttggagcgga caacgttggg gcgcacgcgc aaggcaaccc gaatgcgtgc  41760
aagaaactct ctcgtactaa acggcttagc gataaaatca cttgctccta gctcgagtgc  41820
aacaacttta tccgtctcct caaggcggtc gccactgata attatgattg gaatatcaga  41880
ctttgccgcc agatttcgaa cgatctcaag cccatcttca cgacctaaat ttagatcaac  41940
aaccacgaca tcgaccgtcg cggaagagag tactctagtg aactgggtgc tgtcggctac  42000
cgcggtcact ttgaaggcgt ggatcgtaag gtattcgata ataagatgcc gcatagcgac  42060
atcgtcatcg ataagaagaa cgtgtttcaa cggctcacct ttcaatctaa aatctgaacc  42120
cttgttcaca gcgcttgaga aattttcacg tgaaggatgt acaatcatct ccagctaaat  42180
gggcagttcg tcagaattgc ggctgaccgc ggatgacgaa aatgcgaacc aagtatttca  42240
attttatgac aaaagttctc aatcgttgtt acaagtgaaa cgcttcgagg ttacagctac  42300
tattgattaa ggagatcgcc tatggtctcg ccccggcgtc gtgcgtccgc cgcgagccag  42360
atctcgccta cttcataaac gtcctcatag gcacggaatg gaatgatgac atcgatcgcc  42420
gtagagagca tgtcaatcag tgtgcgatct tccaagctag caccttgggc gctacttttg  42480
acaagggaaa acagtttctt gaatccttgg attggattcg cgccgtgtat tgttgaaatc  42540
gatcccggat gtcccgagac gacttcactc agataagccc atgctgcatc gtcgcgcatc  42600
tcgccaagca atatccggtc cggccgcata cgcagacttg cttggagcaa gtgctcggcg  42660
ctcacagcac ccagcccagc accgttcttg gagtagagta gtctaacatg attatcgtgt  42720
ggaatgacga gttcgagcgt atcttctatg gtgattagcc tttcctgggg ggggatggcg  42780
ctgatcaagg tcttgctcat tgttgtcttg ccgcttccgg tagggccaca tagcaacatc  42840
gtcagtcggc tgacgacgca tgcgtgcaga aacgcttcca aatccccgtt gtcaaaatgc  42900
tgaaggatag cttcatcatc ctgattttgg cgtttccttc gtgtctgcca ctggttccac  42960
ctcgaagcat cataacggga ggagacttct ttaagaccag aaacacgcga gcttggccgt  43020
cgaatggtca agctgacggt gcccgaggga acggtcggcg gcagacagat ttgtagtcgt  43080
tcaccaccag gaagttcagt ggcgcagagg gggttacgtg gtccgacatc ctgctttctc  43140
agcgcgcccg ctaaaatagc gatatcttca agatcatcat aagagacggg caaaggcatc  43200
ttggtaaaaa tgccggcttg gcgcacaaat gcctctccag gtcgattgat cgcaatttct  43260
```

tcagtcttcg ggtcatcgag ccattccaaa atcggcttca gaagaaagcg tagttgcgga 43320
tccacttcca tttacaatgt atcctatctc taagcggaaa tttgaattca ttaagagcgg 43380
cggttcctcc cccgcgtggc gccgccagtc aggcggagct ggtaaacacc aaagaaatcg 43440
aggtcccgtg ctacgaaaat ggaaacggtg tcaccctgat tcttcttcag ggttggcggt 43500
atgttgatgg ttgccttaag ggctgtctca gttgtctgct caccgttatt ttgaaagctg 43560
ttgaagctca tcccgccacc cgagctgccg gcgtaggtgc tagctgcctg gaaggcgcct 43620
tgaacaacac tcaagagcat agctccgcta aaacgctgcc agaagtggct gtcgaccgag 43680
cccggcaatc ctgagcgacc gagttcgtcc gcgcttggcg atgttaacga gatcatcgca 43740
tggtcaggtg tctcggcgcg atcccacaac acaaaaacgc gcccatctcc ctgttgcaag 43800
ccacgctgta tttcgccaac aacggtggtg ccacgatcaa gaagcacgat attgttcgtt 43860
gttccacgaa tatcctgagg caagacacac tttacatagc ctgccaaatt tgtgtcgatt 43920
gcggtttgca agatgcacgg aattattgtc ccttgcgtta ccataaaatc ggggtgcggc 43980
aagagcgtgg cgctgctggg ctgcagctcg gtgggtttca tacgtatcga caaatcgttc 44040
tcgccggaca cttcgccatt cggcaaggag ttgtcgtcac gcttgccttc ttgtcttcgg 44100
cccgtgtcgc cctgaatggc gcgtttgctg acccccttgat cgccgctgct atatgcaaaa 44160
atcggtgttt cttccggccg tggctcatgc cgctccggtt cgcccctcgg cggtagagga 44220
gcagcaggct gaacagcctc ttgaaccgct ggaggatccg gcggcacctc aatcggagct 44280
ggatgaaatg gcttggtgtt tgttgcgatc aaagttgacg gcgatgcgtt ctcattcacc 44340
ttcttttggc gcccacctag ccaaatgagg cttaatgata acgcgagaac gacacctccg 44400
acgatcaatt tctgagaccc cgaaagacgc cggcgatgtt tgtcggagac cagggatcca 44460
gatgcatcaa cctcatgtgc cgcttgctga ctatcgttat tcatcccttc gccccccttca 44520 ggacgcgttt cacatcgggc ctcaccgtgc ccgtttgcgg cctttggcca acgggatcgt 44580
aagcggtgtt ccagatacat agtactgtgt ggccatccct cagacgccaa cctcgggaaa 44640
ccgaagaaat ctcgacatcg ctccctttaa ctgaatagtt ggcaacagct tccttgccat 44700
caggattgat ggtgtagatg gagggtatgc gtacattgcc cggaaagtgg aataccgtcg 44760
taaatccatt gtcgaagact tcgagtggca acagcgaacg atcgccttgg gcgacgtagt 44820
gccaattact gtccgccgca ccaagggctg tgacaggctg atccaataaa ttctcagctt 44880
tccgttgata ttgtgcttcc gcgtgtagtc tgtccacaac agccttctgt tgtgcctccc 44940
ttcgccgagc cgccgcatcg tcggcggggt aggcgaattg gacgctgtaa tagagatcgg 45000
gctgctcttt atcgaggtgg gacagagtct tggaacttat actgaaaaca taacggcgca 45060
tcccggagtc gcttgcggtt agcacgatta ctggctgagg cgtgaggacc tggcttgcct 45120
tgaaaaatag ataatttccc cgcggtaggg ctgctagatc tttgctattt gaaacggcaa 45180
ccgctgtcac cgtttcgttc gtggcgaatg ttacgaccaa agtagctcca accgccgtcg 45240
agaggcgcac cacttgatcg ggattgtaag ccaaataacg catgcgcgga tctagcttgc 45300
ccgccattgg agtgtcttca gcctccgcac cagtcgcagc ggcaaataaa catgctaaaa 45360
tgaaaagtgc ttttctgatc atggttcgct gtggcctacg tttgaaacgg tatcttccga 45420
tgtctgatag gaggtgacaa ccagacctgc cgggttggtt agtctcaatc tgccgggcaa 45480
gctggtcacc ttttcgtagc gaactgtcgc ggtccacgta ctcaccacag gcattttgcc 45540
gtcaacgacg agggtccttt tatagcgaat ttgctgcgtg cttggagtta catcatttga 45600
agcgatgtgc tcgacctcca ccctgccgcg tttgccaaga atgacttgag gcgaactggg 45660
attgggatag ttgaagaatt gctggtaatc ctggcgcact gttggggcac tgaagttcga 45720
taccaggtcg taggcgtact gagcggtgtc ggcatcataa ctctcgcgca ggcgaacgta 45780
ctcccacaat gaggcgttaa cgacggcctc ctcttgagtt gcaggcaatc gcgagacaga 45840
cacctcgctg tcaacggtgc cgtccggccg tatccataga tatacgggca caagcctgct 45900
caacggcacc attgtggcta tagcgaacgc ttgagcaaca tttcccaaaa tcgcgatagc 45960
tgcgacagct gcaatgagtt tggagagacg tcgcgccgat ttcgctcgcg cggtttgaaa 46020
ggcttctact tccttatagt gctcggcaag gctttcgcgc gccactagca tggcatattc 46080
aggccccgtc atagcgtcca cccgaattgc cgagctgaag atctgacgga gtaggctgcc 46140
atcgccccac attcagcggg aagatcgggc ctttgcagct cgctaatgtg tcgtttgtct 46200
ggcagccgct caaagcgaca actaggcaca gcaggcaata cttcatagaa ttctccattg 46260
aggcgaattt ttgcgcgacc tagcctcgct caacctgagc gaagcgacgg tacaagctgc 46320
tggcagattg ggttgcgccg ctccagtaac tgcctccaat gttgccggcg atcgccggca 46380
aagcgacaat gagcgcatcc cctgtcagaa aaaacatatc gagttcgtaa agaccaatga 46440
tcttggccgc ggtcgtaccg gcgaaggtga ttacaccaag cataagggtg agcgcagtcg 46500
cttcggttag gatgacgatc gttgccacga ggtttaagag gagaagcaag agaccgtagg 46560
tgataagttg cccgatccac ttagctgcga tgtcccgcgt gcgatcaaaa atatatccga 46620
cgaggatcag aggcccgatc gcgagaagca ctttcgtgag aattccaacg gcgtcgtaaa 46680
ctccgaaggc agaccagagc gtgccgtaaa ggacccactg tgccccttgg aaagcaagga 46740
tgtcctggtc gttcatcgga ccgatttcgg atgcgatttt ctgaaaaacg gcctgggtca 46800
cggcgaacat tgtatccaac tgtgccggaa cagtctgcag aggcaagccg gttacactaa 46860
actgctgaac aaagtttggg accgtctttt cgaagatgga aaccacatag tcttggtagt 46920
tagcctgccc aacaattaga gcaacaacga tggtgaccgt gatcacccga gtgataccgc 46980
tacgggtatc gacttcgccg cgtatgacta aaataccctg aacaataatc caaagagtga 47040
cacaggcgat caatggcgca ctcaccgcct cctggatagt ctcaagcatc gagtccaagc 47100
ctgtcgtgaa ggctacatcg aagatcgtat gaatggccgt aaacggcgcc ggaatcgtga 47160
aattcatcga ttggacctga acttgactgg tttgtcgcat aatgttggat aaaatgagct 47220
cgcattcggc gaggatgcgg gcggatgaac aaatcgccca gccttagggg agggcaccaa 47280
agatgacagc ggtcttttga tgctccttgc gttgagcggc cgcctcttcc gcctcgtgaa 47340
ggccggcctg cgcggtagtc atcgttaata ggcttgtcgc ctgtacattt tgaatcattg 47400
cgtcatggat ctgcttgaga agcaaaccat tggtcacggt tgcctgcatg atattgcgag 47460
atcgggaaag ctgagcagac gtatcagcat tcgccgtcaa gcgtttgtcc atcgtttcca 47520
gattgtcagc cgcaatgcca gcgctgtttg cggaaccggt gatctgcgat cgcaacaggt 47580
ccgcttcagc atcactaccc acgactgcac gatctgtatc gctggtgatc gcacgtgccg 47640
tggtcgacat tggcattcgc ggcgaaaaca tttcattgtc taggtccttc gtcgaaggat 47700
actgattttt ctggttgagc gaagtcagta gtccagtaac gccgtaggcc gacgtcaaca 47760
tcgtaaccat cgctatagtc tgagtgagat tctccgcagt cgcgagcgca gtcgcgagcg 47820
tctcagcctc cgttgccggg tcgctaacaa caaactgcgc ccgcgcgggc tgaatatata 47880
gaaagctgca ggtcaaaact gttgcaataa gttgcgtcgt cttcatcgtt tcctacctta 47940
tcaatcttct gcctcgtggt gacgggccat gaattcgctg agccagccag atgagttgcc 48000
ttcttgtgcc tcgcgtagtc gagttgcaaa gcgcaccgtg ttggcacgcc ccgaaagcac 48060
ggcgacatat tcacgcatat cccgcagatc aaattcgcag atgacgcttc cactttctcg 48120
tttaagaaga aacttacggc tgccgaccgt catgtcttca cggatcgcct gaaattcctt 48180
ttcggtacat ttcagtccat cgacataagc cgatcgatct gcggttggtg atggatagaa 48240
aatcttcgtc atacattgcg caaccaagct ggctcctagc ggcgattcca gaacatgctc 48300
tggttgctgc gttgccagta ttagcatccc gttgtttttt cgaacggtca ggaggaattt 48360
gtcgacgaca gtcgaaaatt tagggtttaa caaataggcg cgaaactcat cgcagctcat 48420
cacaaaacgg cggccgtcga tcatggctcc aatccgatgc aggagatatg ctgcagcggg 48480
agcgcatact tcctcgtatt cgagaagatg cgtcatgtcg aagccggtaa tcgacggatc 48540
taactttact tcgtcaactt cgccgtcaaa tgcccagcca agcgcatggc cccggcacca 48600
gcgttggagc cgcgctcctg cgccttcggc gggcccatgc aacaaaaatt cacgtaaccc 48660
cgcgattgaa cgcatttgtg gatcaaacga gagctgacga tggataccac ggaccagacg 48720
gcggttctct tccggagaaa tcccaccccg accatcactc tcgatgagag ccacgatcca 48780
ttcgcgcaga aaatcgtgtg aggctgctgt gttttctagg ccacgcaacg gcgccaaccc 48840
gctgggtgtg cctctgtgaa gtgccaaata tgttcctcct gtggcgcgaa ccagcaattc 48900
gccaccccgg tccttgtcaa agaacacgac cgtacctgca cggtcgacca tgctctgttc 48960
gagcatggct agaacaaaca tcatgagcgt cgtcttaccc ctcccgatag gcccgaatat 49020
tgccgtcatg ccaacatcgt gctcatgcgg gatatagtcg aaaggcgttc cgccattggt 49080
acgaaatcgg gcaatcgcgt tgccccagtg gcctgagctg gcgccctctg gaaagttttc 49140
gaaagagaca aaccctgcga aattgcgtga agtgattgcg ccagggcgtg tgcgccactt 49200
aaaattcccc ggcaattggg accaataggc cgcttccata ccaatacctt cttggacaac 49260
cacggcacct gcatccgcca ttcgtgtccg agcccgcgcg cccctgtccc caagactatt 49320
gagatcgtct gcatagacgc aaaggctcaa atgatgtgag cccataacga attcgttgct 49380
cgcaagtgcg tcctcagcct cggataattt gccgatttga gtcacggctt tatcgccgga 49440
actcagcatc tggctcgatt tgaggctaag tttcgcgtgc gcttgcgggc gagtcaggaa 49500
cgaaaaactc tgcgtgagaa caagtggaaa atcgagggat agcagcgcgt tgagcatgcc 49560
cggccgtgtt tttgcagggt attcgcgaaa cgaatagatg gatccaacgt aactgtcttt 49620
tggcgttctg atctcgagtc ctcgcttgcc gcaaatgact ctgtcggtat aaatcgaagc 49680
gccgagtgag ccgctgacga ccggaaccgg tgtgaaccga ccagtcatga tcaaccgtag 49740
cgcttcgcca atttcggtga agagcacacc ctgcttctcg cggatgccaa gacgatgcag 49800
gccatacgct ttaagagagc cagcgacaac atgccaaaga tcttccatgt tcctgatctg 49860
gcccgtgaga tcgttttccc tttttccgct tagcttggtg aacctcctct ttaccttccc 49920
taaagccgcc tgtgggtaga caatcaacgt aaggaagtgt tcattgcgga ggagttggcc 49980
ggagagcacg cgctgttcaa aagcttcgtt caggctagcg gcgaaaacac tacggaagtg 50040
tcgcggcgcc gatgatggca cgtcggcatg acgtacgagg tgagcatata ttgacacatg 50100
atcatcagcg atattgcgca acagcgtgtt gaacgcacga caacgcgcat tgcgcatttc 50160
agtttcctca agctcgaatg caacgccatc aattctcgca atggtcatga tcgatccgtc 50220
ttcaagaagg acgatatggt cgctgaggtg gccaatataa gggagataga tctcaccgga 50280
tctttcggtc gttccactcg cgccgagcat cacaccattc ctctccctcg tgggggaacc 50340
ctaattggat ttgggctaac agtagcgccc ccccaaactg cactatcaat gcttcttccc 50400

```
gcggtccgca aaaatagcag gacgacgctc gccgcattgt agtctcgctc cacgatgagc  50460
cgggctgcaa accataacgg cacgagaacg acttcgtaga gcgggttctg aacgataacg  50520
atgacaaagc cggcgaacat catgaataac cctgccaatg tcagtggcac cccaagaaac  50580
aatgcgggcc gtgtggctgc gaggtaaagg gtcgattctt ccaaacgatc agccatcaac  50640
taccgccagt gagcgtttgg ccgaggaagc tcgccccaaa catgataaca atgccgccga  50700
cgacgccggc aaccagccca agcgaagccc gcccgaacat ccaggagatc ccgatagcga  50760
caatgccgag aacagcgagt gactggccga acggaccaag gataaacgtg catatattgt  50820
taaccattgt ggcggggtca gtgccgccac ccgcagattg cgctgcggcg ggtccggatg  50880
aggaaatgct ccatgcaatt gcaccgcaca agcttggggc gcagctcgat atcacgcgca  50940
tcatcgcatt cgagagcgag aggcgattta gatgtaaacg gtatctctca aagcatcgca  51000
tcaatgcgca cctccttagt ataagtcgaa taagacttga ttgtcgtctg cggatttgcc  51060
gttgtcctgg tgtggcggtg gcggagcgat taaaccgcca gcgccatcct cctgcgagcg  51120
gcgctgatat gacccccaaa catcccacgt ctcttcggat tttagcgcct cgtgatcgtc  51180
ttttggaggc tcgattaacg cgggcaccag cgattgagca gctgtttcaa cttttcgcac  51240
gtagccgttt gcaaaaccgc cgatgaaatt accggtgttg taagcggaga tcgcccgacg  51300
aagcgcaaat tgcttctcgt caatcgtttc gccgcctgca taacgacttt tcagcatgtt  51360
tgcagcggca gataatgatg tgcacgcctg gagcgcaccg tcaggtgtca gaccgagcat  51420
agaaaaattt cgagagttta tttgcatgag gccaacatcc agcgaatgcc gtgcatcgag  51480
acggtgcctg acgacttggg ttgcttggct gtgatcttgc cagtgaagcg tttcgccggt  51540
cgtgttgtca tgaatcgcta aaggatcaaa gcgactctcc accttagcta tcgccgcaag  51600
cgtagatgtc gcaactgatg gggcacactt gcgagcaaca tggtcaaact cagcagatga  51660
gagtggcgtg gcaaggctcg acgaacagaa ggagaccatc aaggcaagag aaagcgaccc  51720
cgatctctta agcatacctt atctccttag ctcgcaacta acaccgcctc tcccgttgga  51780
agaagtgcgt tgttttatgt tgaagattat cgggagggtc ggttactcga aaattttcaa  51840
ttgcttcttt atgatttcaa ttgaagcgag aaacctcgcc cggcgtcttg gaacgcaaca  51900
tggaccgaga accgcgcatc catgactaag caaccggatc gacctattca ggccgcagtt  51960
ggtcaggtca ggctcagaac gaaaatgctc ggcgaggtta cgctgtctgt aaacccattc  52020
gatgaacggg aagcttcctt ccgattgctc ttggcaggaa tattggccca tgcctgcttg  52080
cgctttgcaa atgctcttat cgcgttggta tcatatgcct tgtccgccag cagaaacgca  52140
ctctaagcga ttatttgtaa aaatgtttcg gtcatgcggc ggtcatgggc ttgacccgct  52200
gtcagcgcaa gacggatcgg tcaaccgtcg gcatcgacaa cagcgtgaat cttggtggtc  52260
aaaccgccac gggaacgtcc catacagcca tcgtcttgat cccgctgttt cccgtcgccg  52320
catgttggtg gacgcggaca caggaactgt caatcatgac gacattctat cgaaagcctt  52380
ggaaatcaca ctcagaatat gatcccagac gtctgcctca cgccatcgta caaagcgatt  52440
gtagcaggtt gtacaggaac cgtatcgatc aggaacgtct gcccagggcg ggcccgtccg  52500
gaagcgccac aagatgacat tgatcacccg cgtcaacgcg cggcacgcga cgcggcttat  52560
ttgggaacaa aggactgaac aacagtccat tcgaaatcgg tgacatcaaa gcggggacgg  52620
gttatcagtg gcctccaagt caagcctcaa tgaatcaaaa tcagaccgat ttgcaaacct  52680
gatttatgag tgtgcggcct aaatgatgaa atcgtccttc tagatcgcct ccgtggtgta  52740
```

gcaacacctc gcagtatcgc cgtgctgacc ttggccaggg aattgactgg caagggtgct 52800
ttcacatgac cgctcttttg gccgcgatag atgatttcgt tgctgctttg ggcacgtaga 52860
aggagagaag tcatatcgga gaaattcctc ctggcgcgag agcctgctct atcgcgacgg 52920
catcccactg tcgggaacag accggatcat tcacgaggcg aaagtcgtca acacatgcgt 52980
tataggcatc ttcccttgaa ggatgatctt gttgctgcca atctggaggt gcggcagccg 53040
caggcagatg cgatctcagc gcaacttgcg gcaaaacatc tcactcacct gaaaaccact 53100
agcgagtctc gcgatcagac gaaggccttt tacttaacga cacaatatcc gatgtctgca 53160
tcacaggcgt cgctatccca gtcaatacta aagcggtgca ggaactaaag attactgatg 53220
acttaggcgt gccacgaggc ctgagacgac gcgcgtagac agtttttga aatcattatc 53280
aaagtgatgg cctccgctga agcctatcac ctctgcgccg gtctgtcgga gagatgggca 53340
agcattatta cggtcttcgc gcccgtacat gcattggacg attgcagggt caatggatct 53400
gagatcatcc agaggattgc cgcccttacc ttccgtttcg agttggagcc agcccctaaa 53460
tgagacgaca tagtcgactt gatgtgacaa tgccaagaga gagatttgct taacccgatt 53520
tttttgctca agcgtaagcc tattgaagct tgccggcatg acgtccgcgc cgaaagaata 53580
tcctacaagt aaaacattct gcacaccgaa atgcttggtg tagacatcga ttatgtgacc 53640
aagatcctta gcagtttcgc ttggggaccg ctccgaccag aaataccgaa gtgaactgac 53700
gccaatgaca ggaatccctt ccgtctgcag ataggtacca tcgatagatc tgctgcctcg 53760
cgcgtttcgg tgatgacggt gaaaacctct gacacatgca gctcccggag acggtcacag 53820
cttgtctgta agcggatgcc gggagcagac aagcccgtca gggcgcgtca gcgggtgttg 53880
gcgggtgtcg gggcgcagcc atgacccagt cacgtagcga tagcggagtg tatactggct 53940
taactatgcg gcatcagagc agattgtact gagagtgcac catatgcggt gtgaaatacc 54000
gcacagatgc gtaaggagaa aataccgcat caggcgctct tccgcttcct cgctcactga 54060
ctcgctgcgc tcggtcgttc ggctgcggcg agcggtatca gctcactcaa aggcggtaat 54120
acggttatcc acagaatcag gggataacgc aggaaagaac atgtgagcaa aaggccagca 54180
aaaggccagg aaccgtaaaa aggccgcgtt gctggcgttt ttccataggc tccgcccccc 54240
tgacgagcat cacaaaaatc gacgctcaag tcagaggtgg cgaaacccga caggactata 54300
aagataccag gcgtttcccc ctggaagctc cctcgtgcgc tctcctgttc cgaccctgcc 54360
gcttaccgga tacctgtccg cctttctccc ttcgggaagc gtggcgcttt ctcatagctc 54420
acgctgtagg tatctcagtt cggtgtaggt cgttcgctcc aagctgggct gtgtgcacga 54480
accccccgtt cagcccgacc gctgcgcctt atccggtaac tatcgtcttg agtccaaccc 54540
ggtaagacac gacttatcgc cactggcagc agccactggt aacaggatta gcagagcgag 54600
gtatgtaggc ggtgctacag agttcttgaa gtggtggcct aactacggct acactagaag 54660
gacagtattt ggtatctgcg ctctgctgaa gccagttacc ttcggaaaaa gagttggtag 54720
ctcttgatcc ggcaaacaaa ccaccgctgg tagcggtggt ttttttgttt gcaagcagca 54780
gattacgcgc agaaaaaaag gatctcaaga agatcctttg atcttttcta cggggtctga 54840
cgctcagtgg aacgaaaact cacgttaagg gattttggtc atgagattat caaaaaggat 54900
cttcacctag atccttttaa attaaaaatg aagttttaaa tcaatctaaa gtatatatga 54960
gtaaacttgg tctgacagtt accaatgctt aatcagtgag gcacctatct cagcgatctg 55020
tctatttcgt tcatccatag ttgcctgact ccccgtcgtg tagataacta cgatacggga 55080
gggcttacca tctggcccca gtgctgcaat gataccgcga gacccacgct caccggctcc 55140
agatttatca gcaataaacc agccagccgg aagggccgag cgcagaagtg gtcctgcaac 55200
tttatccgcc tccatccagt ctattaattg ttgccgggaa gctagagtaa gtagttcgcc 55260
agttaatagt ttgcgcaacg ttgttgccat tgctgcaggg gggggggggg gggggttcca 55320
ttgttcattc cacggacaaa aacagagaaa ggaaacgaca gaggccaaaa agctcgcttt 55380
cagcacctgt cgtttccttt cttttcagag ggtattttaa ataaaaacat taagttatga 55440
cgaagaagaa cggaaacgcc ttaaaccgga aaattttcat aaatagcgaa aacccgcgag 55500
gtcgccgccc cgtaacct 55518

<210> SEQ ID NO 48
<211> LENGTH: 61
<212> TYPE: DNA
<213> ORGANISM: artificial sequence
<220> FEATURE:
<223> OTHER INFORMATION: reference sequence

<400> SEQUENCE: 48
cacgtatata tacgcgtacg cgtacgtgtg aggtatatat atcctccgcc ggggcacgta 60
c 61

<210> SEQ ID NO 49
<211> LENGTH: 62
<212> TYPE: DNA
<213> ORGANISM: artificial sequence
<220> FEATURE:
<223> OTHER INFORMATION: synthetic

<400> SEQUENCE: 49
cacgtatata tacgcgtacg cgtacgttgt gaggtatata tatcctccgc cggggcacgt 60
ac 62

<210> SEQ ID NO 50
<211> LENGTH: 60
<212> TYPE: DNA
<213> ORGANISM: artificial sequence
<220> FEATURE:
<223> OTHER INFORMATION: synthetic

<400> SEQUENCE: 50
cacgtatata tacgcgtacg cgtacggtga ggtatatata tcctccgccg gggcacgtac 60

<210> SEQ ID NO 51
<211> LENGTH: 60
<212> TYPE: DNA
<213> ORGANISM: artificial sequence
<220> FEATURE:
<223> OTHER INFORMATION: synthetic

<400> SEQUENCE: 51
cacgtatata tacgcgtacg cgtactgtga ggtatatata tcctccgccg gggcacgtac 60

<210> SEQ ID NO 52
<211> LENGTH: 59
<212> TYPE: DNA
<213> ORGANISM: artificial sequence
<220> FEATURE:
<223> OTHER INFORMATION: synthetic

<400> SEQUENCE: 52
cacgtatata tacgcgtacg cgtacgtgag gtatatatat cctccgccgg ggcacgtac 59

<210> SEQ ID NO 53
<211> LENGTH: 32
<212> TYPE: DNA
<213> ORGANISM: artificial sequence
<220> FEATURE:
<223> OTHER INFORMATION: synthetic

<400> SEQUENCE: 53
cacgtatata tatcctccgc cggggcacgt ac 32

<210> SEQ ID NO 54
<211> LENGTH: 19
<212> TYPE: DNA
<213> ORGANISM: artificial sequence
<220> FEATURE:
<223> OTHER INFORMATION: synthetic

<400> SEQUENCE: 54
cacgtatata tacgcgtac 19

<210> SEQ ID NO 55
<211> LENGTH: 57
<212> TYPE: DNA
<213> ORGANISM: artificial sequence
<220> FEATURE:
<223> OTHER INFORMATION: synthetic

<400> SEQUENCE: 55
cacgtatata tacgcgtacg cgtgtgaggt atatatatcc tccgccgggg cacgtac 57

<210> SEQ ID NO 56
<211> LENGTH: 33
<212> TYPE: DNA
<213> ORGANISM: artificial sequence
<220> FEATURE:
<223> OTHER INFORMATION: synthetic

<400> SEQUENCE: 56
cacgtatata tacgcgtacg ccggggcacg tac 33

<210> SEQ ID NO 57
<211> LENGTH: 30
<212> TYPE: DNA
<213> ORGANISM: artificial sequence
<220> FEATURE:
<223> OTHER INFORMATION: synthetic

<400> SEQUENCE: 57
cacgtatata tcctccgccg gggcacgtac 30

<210> SEQ ID NO 58
<211> LENGTH: 59
<212> TYPE: DNA
<213> ORGANISM: artificial sequence
<220> FEATURE:
<223> OTHER INFORMATION: synthetic

<400> SEQUENCE: 58
cacgtatata tacgcgtacg cgtatgtgag gtatatatat cctccgccgg ggcacgtac 59

<210> SEQ ID NO 59
<211> LENGTH: 54
<212> TYPE: DNA
<213> ORGANISM: artificial sequence
<220> FEATURE:
<223> OTHER INFORMATION: synthetic

<400> SEQUENCE: 59
gcgctgctcg attccgtccc catggtcgcc atcacgggac aggtgccgcg acgc 54

<210> SEQ ID NO 60
<211> LENGTH: 18
<212> TYPE: PRT
<213> ORGANISM: artificial sequence
<220> FEATURE:
<223> OTHER INFORMATION: synthetic

<400> SEQUENCE: 60

Ala Leu Leu Asp Ser Val Pro Met Val Ala Ile Thr Gly Gln Val Pro
1 5 10 15

Arg Arg

<210> SEQ ID NO 61
<211> LENGTH: 54
<212> TYPE: DNA
<213> ORGANISM: artificial sequence
<220> FEATURE:
<223> OTHER INFORMATION: synthetic

<400> SEQUENCE: 61
gcgttgctcg actccgtccc cattgtcgcc atcacgggac aggtgtcgcg acgc 54

<210> SEQ ID NO 62
<211> LENGTH: 18
<212> TYPE: PRT
<213> ORGANISM: artificial sequence
<220> FEATURE:
<223> OTHER INFORMATION: synthetic

<400> SEQUENCE: 62

Ala Leu Leu Asp Ser Val Pro Ile Val Ala Ile Thr Gly Gln Val Ser
1 5 10 15

Arg Arg

<210> SEQ ID NO 63
<211> LENGTH: 54
<212> TYPE: DNA
<213> ORGANISM: artificial sequence
<220> FEATURE:
<223> OTHER INFORMATION: sequence on Fig. 2

<400> SEQUENCE: 63
gcgttgctgg actccgtgcc gatggtcgcc atcacgggac aggtgtcccg acgc 54

<210> SEQ ID NO 64
<211> LENGTH: 18
<212> TYPE: PRT
<213> ORGANISM: artificial sequence
<220> FEATURE:
<223> OTHER INFORMATION: synthetic

<400> SEQUENCE: 64

Ala Leu Leu Asp Ser Val Pro Met Val Ala Ile Thr Gly Gln Val Ser
1 5 10 15

Arg Arg

<210> SEQ ID NO 65
<211> LENGTH: 31
<212> TYPE: DNA
<213> ORGANISM: artificial sequence
<220> FEATURE:
<223> OTHER INFORMATION: synthetic

<400> SEQUENCE: 65
atggctcccc cggccacccc gctccggccg t 31

<210> SEQ ID NO 66
<211> LENGTH: 10
<212> TYPE: PRT
<213> ORGANISM: artificial sequence
<220> FEATURE:
<223> OTHER INFORMATION: synthetic

<400> SEQUENCE: 66

Met Ala Pro Pro Ala Thr Pro Leu Arg Pro
1 5 10

<210> SEQ ID NO 67
<211> LENGTH: 30
<212> TYPE: DNA
<213> ORGANISM: artificial sequence
<220> FEATURE:
<223> OTHER INFORMATION: synthetic

<400> SEQUENCE: 67
atggctcccc cggccacccc ctccggccgt 30

<210> SEQ ID NO 68
<211> LENGTH: 10
<212> TYPE: PRT
<213> ORGANISM: artificial sequence
<220> FEATURE:
<223> OTHER INFORMATION: synthetic

<400> SEQUENCE: 68

Met Ala Pro Pro Ala Thr Pro Ser Gly Arg
1 5 10

<210> SEQ ID NO 69
<211> LENGTH: 31
<212> TYPE: DNA
<213> ORGANISM: artificial sequence
<220> FEATURE:
<223> OTHER INFORMATION: synthetic
<220> FEATURE:
<221> NAME/KEY: misc_feature
<222> LOCATION: (21)..(21)
<223> OTHER INFORMATION: n is a, c, g, or t

<400> SEQUENCE: 69
atggctcccc cggccacccc nctccggccg t 31

<210> SEQ ID NO 70
<211> LENGTH: 40
<212> TYPE: DNA
<213> ORGANISM: artificial sequence
<220> FEATURE:
<223> OTHER INFORMATION: synthetic

<400> SEQUENCE: 70
tcgactcgct caccatgtcc ggcccatgac caccgccgcc 40

<210> SEQ ID NO 71
<211> LENGTH: 41
<212> TYPE: DNA
<213> ORGANISM: artificial sequence
<220> FEATURE:

<223> OTHER INFORMATION: synthetic
<220> FEATURE:
<221> NAME/KEY: misc_feature
<222> LOCATION: (17)..(17)
<223> OTHER INFORMATION: n is a, c, g, or t

<400> SEQUENCE: 71
tcgactcgct caccatngtc cggcccatga ctccccccggc c 41

<210> SEQ ID NO 72
<211> LENGTH: 24
<212> TYPE: DNA
<213> ORGANISM: artificial sequence
<220> FEATURE:
<223> OTHER INFORMATION: synthetic

<400> SEQUENCE: 72
attcccccgg ccaccccgtc ggcc 24

<210> SEQ ID NO 73
<211> LENGTH: 8
<212> TYPE: PRT
<213> ORGANISM: artificial sequence
<220> FEATURE:
<223> OTHER INFORMATION: synthetic

<400> SEQUENCE: 73

Ile Pro Pro Ala Thr Pro Ser Ala
1               5

<210> SEQ ID NO 74
<211> LENGTH: 23
<212> TYPE: DNA
<213> ORGANISM: artificial sequence
<220> FEATURE:
<223> OTHER INFORMATION: synthetic

<400> SEQUENCE: 74
attcccccgg ccacccgtcg gcc 23

<210> SEQ ID NO 75
<211> LENGTH: 7
<212> TYPE: PRT
<213> ORGANISM: artificial sequence
<220> FEATURE:
<223> OTHER INFORMATION: synthetic

<400> SEQUENCE: 75

Ile Pro Pro Ala Thr Arg Arg
1               5

<210> SEQ ID NO 76
<211> LENGTH: 24
<212> TYPE: DNA
<213> ORGANISM: artificial sequence
<220> FEATURE:
<223> OTHER INFORMATION: synthetic

<400> SEQUENCE: 76
attcccccgg ccacctcgtc ggcc 24

<210> SEQ ID NO 77
<211> LENGTH: 8
<212> TYPE: PRT
<213> ORGANISM: artificial sequence
<220> FEATURE:
<223> OTHER INFORMATION: synthetic

<400> SEQUENCE: 77

Ile Pro Pro Ala Thr Ser Ser Ala
1 5

<210> SEQ ID NO 78
<211> LENGTH: 441
<212> TYPE: DNA
<213> ORGANISM: Artificial Sequence
<220> FEATURE:
<223> OTHER INFORMATION: IN2 promoter

<400> SEQUENCE: 78
atccctggcc accaaacatc cctaatcatc cccaaatttt ataggaacta ctaatttctc 60
taacttaaaa aaaatctaaa atagtatact ttagcagcct ctcaatctga tttgttcccc 120
aaatttgaat cctggcttcg ctctgtcacc tgttgtactc tacatggtgc gcagggggag 180
agcctaatct ttcacgactt tgtttgtaac tgttagccag accggcgtat ttgtcaatgt 240
ataaacacgt aataaaattt acgtaccata tagtaagact ttgtatataa gacgtcacct 300
cttacgtgca tggttatatg cgacatgtgc agtgacgtta tcagatatag ctcaccctat 360
atatatagct ctgtccggtg tcagtagcaa tcaccattca tcagcacccc ggcaggtcga 420
ccccgagctc cctgcacctg c 441

<210> SEQ ID NO 79
<211> LENGTH: 21
<212> TYPE: DNA
<213> ORGANISM: Zea mays

<400> SEQUENCE: 79
gctcccccgg ccacccccgct c 21

<210> SEQ ID NO 80
<211> LENGTH: 20
<212> TYPE: DNA
<213> ORGANISM: Zea mays

<400> SEQUENCE: 80
gctcccccgg ccaccccctc 20

<210> SEQ ID NO 81
<211> LENGTH: 20
<212> TYPE: DNA
<213> ORGANISM: Zea mays

<400> SEQUENCE: 81
cgccgagggc gactaccggc 20

<210> SEQ ID NO 82
<211> LENGTH: 23
<212> TYPE: DNA
<213> ORGANISM: Zea mays

<400> SEQUENCE: 82
cgccgagggc gactaccggc agg 23